(12) United States Patent
Chen et al.

(10) Patent No.: US 10,457,717 B2
(45) Date of Patent: Oct. 29, 2019

(54) ENGINEERED POLYPEPTIDES

(71) Applicant: Denali Therapeutics Inc., South San Francisco, CA (US)

(72) Inventors: Xiaocheng Chen, South San Francisco, CA (US); Mihalis Kariolis, South San Francisco, CA (US); Robert C. Wells, South San Francisco, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 60 days.

(21) Appl. No.: 15/934,744

(22) Filed: Mar. 23, 2018

(65) Prior Publication Data

US 2018/0237496 A1 Aug. 23, 2018

Related U.S. Application Data

(63) Continuation of application No. PCT/US2018/018445, filed on Feb. 15, 2018.

(60) Provisional application No. 62/460,692, filed on Feb. 17, 2017, provisional application No. 62/543,658, filed on Aug. 10, 2017, provisional application No. 62/543,819, filed on Aug. 10, 2017, provisional application No. 62/583,314, filed on Nov. 8, 2017, provisional application No. 62/583,426, filed on Nov. 8, 2017.

(51) Int. Cl.
*C07K 14/705* (2006.01)
*G01N 33/68* (2006.01)

(52) U.S. Cl.
CPC ... *C07K 14/70582* (2013.01); *G01N 33/6854* (2013.01); *C07K 2319/30* (2013.01); *C07K 2319/70* (2013.01)

(58) Field of Classification Search
CPC ............. C07K 14/70582; G01N 33/6854
See application file for complete search history.

(56) References Cited

U.S. PATENT DOCUMENTS

| | | | |
|---|---|---|---|
| 5,254,342 A | 10/1993 | Shen et al. | |
| 5,527,527 A | 6/1996 | Friden | |
| 6,743,893 B2 | 6/2004 | Engler et al. | |
| 7,241,449 B1 | 7/2007 | Myers et al. | |
| 7,741,446 B2 | 6/2010 | Pardridge et al. | |
| 7,744,879 B2 | 6/2010 | Shusta et al. | |
| 8,053,567 B2 | 11/2011 | Pardridge et al. | |
| 8,084,254 B2 | 12/2011 | Couraud et al. | |
| 8,293,495 B2 | 10/2012 | Shusta et al. | |
| 8,417,465 B2 | 4/2013 | Prabhakarpandian et al. | |
| 8,609,065 B2 | 12/2013 | Kuik-Romeijn et al. | |
| 8,900,865 B2 | 12/2014 | Harlow et al. | |
| 9,005,973 B2 | 4/2015 | Cost et al. | |
| 9,156,889 B2 | 10/2015 | Nomoto et al. | |
| 9,513,280 B2 | 12/2016 | Kim et al. | |
| 2003/0074141 A1 | 4/2003 | Russell | |
| 2005/0170394 A1 | 8/2005 | Zerangue | |
| 2006/0193776 A1 | 8/2006 | Goldsmith et al. | |
| 2010/0273200 A1 | 10/2010 | Niwa et al. | |
| 2013/0318641 A1 | 11/2013 | Bradley et al. | |
| 2014/0142370 A1 | 5/2014 | Wong et al. | |
| 2014/0295547 A1 | 10/2014 | Kuo et al. | |
| 2015/0044140 A1 | 2/2015 | Giralt Lledó et al. | |
| 2015/0110791 A1 | 4/2015 | Zhang et al. | |
| 2015/0196663 A1 | 7/2015 | Shusta et al. | |
| 2016/0040125 A1 | 2/2016 | Da Silva Ferreira et al. | |
| 2016/0168253 A1 | 6/2016 | Bohrmann et al. | |

FOREIGN PATENT DOCUMENTS

| | | | |
|---|---|---|---|
| EP | 2568051 A1 * | 3/2013 | ........... C12Q 1/6881 |
| WO | 1991/005038 A1 | 4/1991 | |
| WO | 1994/028121 A1 | 12/1994 | |
| WO | 1999/000150 A2 | 1/1999 | |
| WO | 2001/059459 A2 | 8/2001 | |
| WO | 2001/064849 A1 | 9/2001 | |
| WO | 2003/003007 A2 | 1/2003 | |
| WO | 2004/094647 A2 | 11/2004 | |
| WO | WO-2004094647 A2 * | 11/2004 | ........... A61K 31/352 |
| WO | 2010/014622 A2 | 2/2010 | |
| WO | 2012/075037 A1 | 6/2012 | |
| WO | 2012/143379 A1 | 10/2012 | |
| WO | 2013/091637 A1 | 6/2013 | |
| WO | 2013/177062 A2 | 11/2013 | |
| WO | 2014/033074 A1 | 3/2014 | |
| WO | 2014/074695 A1 | 5/2014 | |
| WO | 2014/189973 A2 | 11/2014 | |

(Continued)

OTHER PUBLICATIONS

Lawrence, et al. (Crystal Structure of the Ectodomain of Human Transferrin Receptor, Science 1999, 286:779-782) (Year: 1999).*
Mizutani, et al. (Transferrin Receptor 1 Facilitates Poliovirus Permeation of Mouse Brain Capillary Endothelial Cells, JBC 2015, 291: 2829-2836) (Year: 2015).*
Mizutani, et al. (Transferrin Receptor 1 Facilitates Poliovirus Permeation of Mouse Brain Capillary Endothelial Cells, JBC 2015, 291: 2829-2836, of record) (Year: 2015).*
Atwal, J. et al., "A Therapeutic Antibody Targeting BACE1 Inhibits Amyloid-β Production in Vivo," Sci Transl. Med. 3:84ra43, 2014.
Banks, W., "Mouse Models of Neurological Disorders: A View From the Blood-brain Barrier," Biochim Biophys Acta, 1802(10):881-888, 2010.
Buchegger, F. et al., "Functional analysis of human/chicken transferrin receptor chimeras indicates that the carboxy-terminal region is important for ligand binding," Eur. J. Biochem., 235, 9-17, 1996.

(Continued)

*Primary Examiner* — Karlheinz R. Skowronek
*Assistant Examiner* — Khalid Kader
(74) *Attorney, Agent, or Firm* — Kilpatrick Townsend & Stockton LLP

(57) ABSTRACT

Provided herein are polypeptides that bind to a blood-brain barrier (BBB) receptor, methods of generating such polypeptides, and methods of using the polypeptides to target a composition to a BBB receptor-expressing cell, e.g., for transport across the BBB. Also provided herein are transferrin receptor (TfR) constructs that comprise a monomeric TfR apical domain or one or more portions of the TfR apical domain which have been circularly permuted relative to the full-length TfR sequence.

29 Claims, 65 Drawing Sheets

Specification includes a Sequence Listing.

(56) References Cited

FOREIGN PATENT DOCUMENTS

| WO | 2015/014884 A1 | 2/2015 |
| WO | 2015/101586 A1 | 7/2015 |
| WO | 2016/038123 A1 | 3/2016 |
| WO | 2016/081640 A1 | 5/2016 |
| WO | 2016/081643 A1 | 5/2016 |
| WO | 2016/090486 A1 | 6/2016 |
| WO | 2016/202343 A1 | 12/2016 |
| WO | 2016/207240 A1 | 12/2016 |
| WO | 2016/208695 A1 | 12/2016 |
| WO | 2017/035119 A1 | 3/2017 |

OTHER PUBLICATIONS

Dominguez, A. et al., "Beyond editing: repurposing CRISPR-Cas9 for precision genome regulation and interrogation," Nature Rev. Molec Cell. Biol., 17:5-15, 2016.

Denali Therapeutics Inc., Form S-1 Registration Statement, as filed with the U.S. Securities and Exchange Commission on Nov. 13, 2017, retrieved online at <https://www.sec.gov/Archives/edgar/data/1714899/000119312517340997/d445892ds1.htm> on Mar. 20, 2018, 292 pages.

Lawrence, C. et al., "Crystal Structure of the Ectodomain of Human Transferrin Receptor," Science, 286:779-782, 1999.

McGraw, T. et al., "Functional Expression of the Human Transferrin Receptor cDNA in Chinese Hamster Ovary Cells Deficient in Endogenous Transferrin Receptor," J. Cell Biology, 105:207-214, 1987.

Milstone, L. et al., "Stratum-Specific Expression of Human Transferrin Receptor Increases Iron in Mouse Epidermas," J. Invest. Dermatol, 126:648-652, 2006.

Sohet, F. and Daneman, R., "Genetic mouse models to study blood-brain barrier development and function," Fluids and Barriers of the CNS 10:3, 2013.

Wen, J. et al. "Soluble Form of Canine Transferrin Receptor Inhibits Canine Parvovirus Infection In Vitro and In Vivo," BioMed Research Intl., 2013:8, 2013.

Winnard, P. et al., "Development of novel chimeric transmembrane proteins for multimodality imaging of cancer cells," Cancer Biol. & Ther., 6:12, 1889-1899, 2007.

Yu, Y. et al., "Therapeutic bispecific antibodies cross the blood-brain barrier in nonhuman primates," Sci Transl. Med., 6:261ra154, 2014.

Partial International Search Report for PCT/US2018/018445, dated May 2, 2018, 5 pages.

Abraham, J. et al., "Structural basis for receptor recognition by New World hemorrhagic fever arenaviruses," Nat. Struct. Mol. Biol., 17(4):438-444, 2010.

Ji, D. et al., "Efficient creation of an APOE knockout rabbit," Transgenic Res., 24:227-235, 2015.

Mizutani, T. et al., "Transferrin Receptor 1 Facilitates Poliovirus Permeation of Mouse Brain Capillary Endothelial Cells," Journal of Biological Chemistry, 291(6): 2829-2836, 2016.

Naito, M. et al., "Expression of Exogenous DNA in the gonads of chimaeric chicken embryos produced by transfer of primordial germ cells transfected in vitro and subsequent fate of the introduced DNA," J Reprod Fert 113:137-143, 1998.

Palermo, L. M. et al., "Residues in the apical domain of the feline and canine transferrin receptors control host-specific binding and cell infection of canine and feline parvoviruses," Journal of Virology, The American Society for Microbiology, 77(16):8915-8923, 2003.

Pardridge, W.M., "Blood-brain barrier drug delivery of IgG fusion proteins with a transferrin receptor monoclonal antibody," Expert Opinion on Drug Deli, Informa Healthcare, UK, 12(2):207-222, 2015.

Raina, A. et al., "Testis mediated gene transfer: In vitro transfection in goat testis by electroporation," Gene, 96-100, 2015.

Yu, Y. Joy et al., "Therapeutic bispecific antibodies cross the blood-brain barrier in nonhuman primates," Science Translational Medicine, 6(261), 261ra154, 11 pages, 2014.

International Search Report for PCT/US2018/018445, dated Aug. 16, 2018, 9 pages.

Eckenroth, B.E. et al., "How the binding of human transferrin primes the transferrin receptor potentiating iron release at endosomal pH," Proceedings of the National Academy of Sciences, 108(32):13089-13094, 2011.

Li, R. et al., "Production of Genetically Engineered Golden Syrian Hamsters by Pronuclear Injection of the CRISPR/Cas9 Complex," J Vis Exp., (131): 1-2, 2018.

Ma, Y. et al., "Generation of eGFP and Cre knockin rats by CRISPR/Cas9," FEBS Journal (281): 3779-3790, 2014.

Alvarez, E. et al., "Intermolecular disulfide bonds are not required for the expression of the dimeric state and functional activity of the transferrin receptor," The EMBO Journal, 8(8):2231-2240, 1989.

International Search Report for PCT/US2018/018302, dated May 4, 2018, 6 pages.

* cited by examiner

CH2C. 7

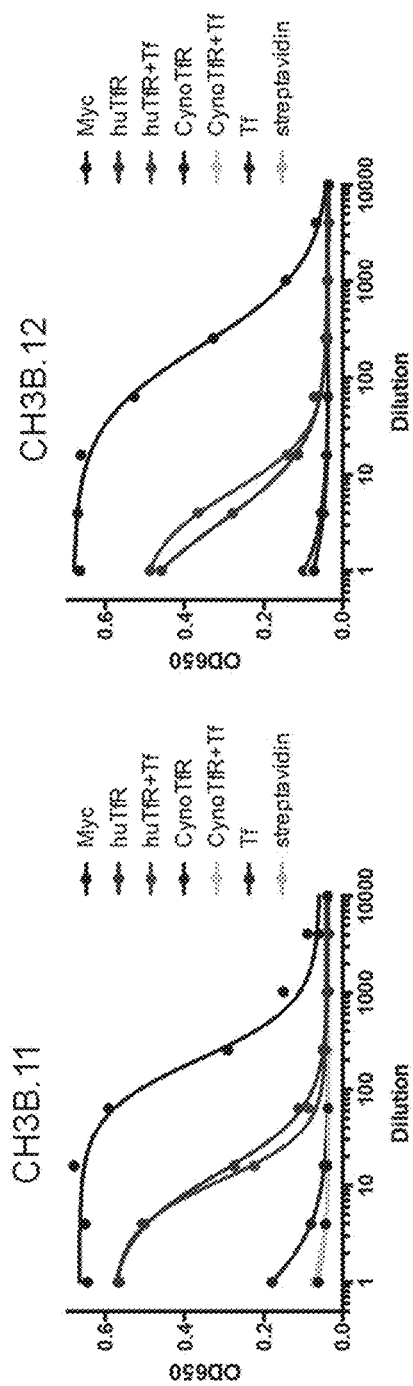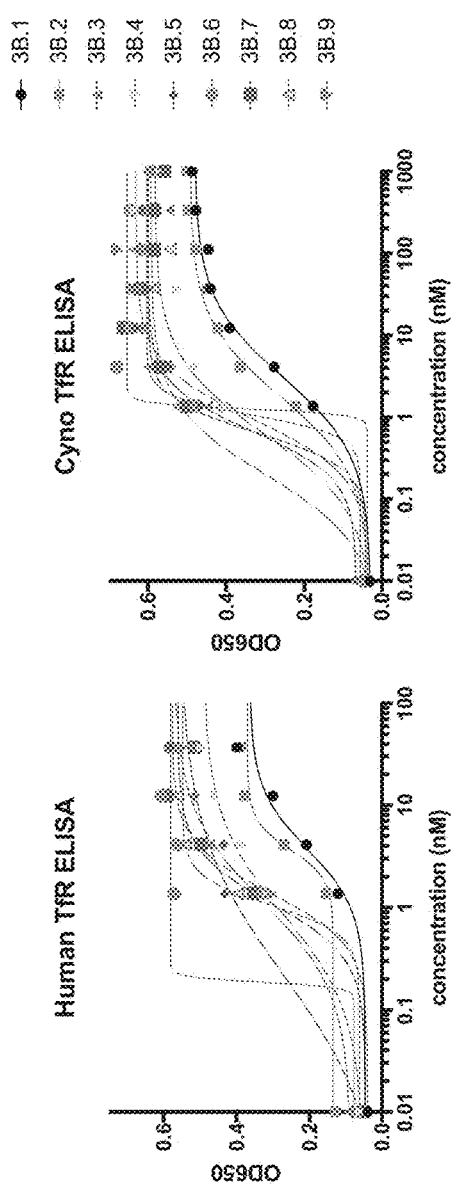
FIG. 4A
FIG. 4B

FIG. 14A CHO-K1 huTfR

FIG. 14B CHO-K1 cyTfR

FIG. 14C CHO-K1 parent (no TfR)

FIG. 18A

Consensus1-35

| Wildtype | E | W | E | S | N | G | Q | P | E | N | N | Y | K | V | D | K | S | R | W | Q | Q | G | N |
|---|---|---|---|---|---|---|---|---|---|---|---|---|---|---|---|---|---|---|---|---|---|---|---|
| Clone 3 | | | | | Y | | T | E | W | S | Q | | | | E | | | D | | | | | H |
| 1-35 | | | | | Y | | T | E | W | S | S | | | | T | | | E | | | | | F |
| 1-44 | | | | | Y | | T | E | W | S | N | | | | S | | | E | | | | | F |
| Library 3.1 | | | | | ▓ | | ▓ | E | W | ▓ | ▓ | | | | X | | | ▓ | | | | | X |

FIG. 18B

Consensus1-18

| Wildtype | E | W | E | S | N | G | Q | P | E | N | N | Y | K | V | D | K | S | R | W | Q | Q | G | N |
|---|---|---|---|---|---|---|---|---|---|---|---|---|---|---|---|---|---|---|---|---|---|---|---|
| Clone 4 | | | | | L | | L | V | W | V | G | Y | | | A | | | T | | | | | W |
| 1-21 | | | | | L | | L | V | W | V | G | | | | P | | | T | | | | | W |
| 1-18 | | | | | L | | H | V | W | A | V | | | | P | | | T | | | | | W |
| 1-25 | | | | | M | | H | V | W | V | G | | | | D | | | T | | | | | W |
| 1-34 | | | | | L | | L | V | G | V | F | S | | | P | | | T | | | | | W |
| 1-51 | | | | | L | | H | V | W | V | G | | | | S | | | E | | | | | W |
| Library 3.2 | | | | | ▓ | | ▓ | V | W | ▓ | ▓ | | | | P:50 | | | ▓ | | | | | W:50 |
| | | | | | | | | G | | ▓ | | | | | X:50 | | | | | | | | F:25 |
| | | | | | | | | | | | | | | | | | | | | | | | H:25 |
| | | | | | | | | | | | | | | | | | | | | | | | Y:25 |
| | | | | | | | | | | | | | | | | | | | | | | | (L):25 |

FIG. 18C

Gap

| Wildtype | E | W | E | S | N | G | Q | P | E | N | N | Y | K | V | D | K | S | R | W | Q | Q | G | N |
|---|---|---|---|---|---|---|---|---|---|---|---|---|---|---|---|---|---|---|---|---|---|---|---|
| WT | x | W | x | | N | G | Q | P | E | N | N | x | | | D | | x | R | | | x | | N |
| 1-18 GAP | x | | x | | L | | H | V | W | A | V | x | | | P | | x | T | | | x | | W |
| 1-34 GAP | x | | x | | L | | L | V | G | V | F | x | | | P | | x | T | | | x | | W |
| 1-35 GAP | x | | x | | Y | | T | E | W | S | S | x | | | T | | x | E | | | x | | F |

FIG. 18D

Aromatic

| Wildtype | E | W | E | S | N | G | Q | P | E | N | N | Y | K | V | D | K | S | R | W | Q | Q | G | N |
|---|---|---|---|---|---|---|---|---|---|---|---|---|---|---|---|---|---|---|---|---|---|---|---|
| 1-18 | | | | | L | | H | V | W | A | V | | | | P | | | T | | | | | W |
| Library 3.4 | | | | | ▓ | | ▓ | V | W | ▓ | ▓ | | | | P | | | ▓ | | | | | W:50 |
| | | | | | | | | | | | | | | | | | | | | | | | F:25 |
| | | | | | | | | | | | | | | | | | | | | | | | H:25 |
| | | | | | | | | | | | | | | | | | | | | | | | Y:25 |
| | | | | | | | | | | | | | | | | | | | | | | | (L):25 |

CH3C.3.2-1

CH3C.3.2-19

CH3C.3.2-5

CH3C.18

CH3C.35

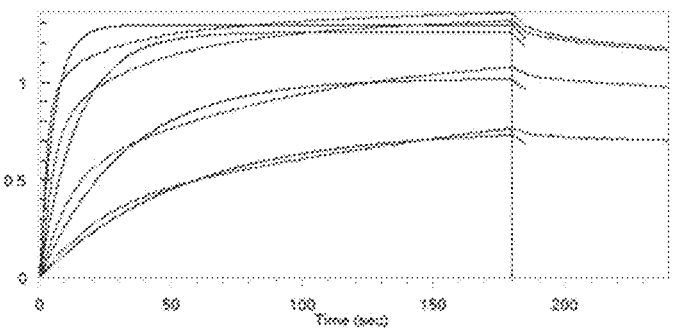
FIG. 27A  CH3C.35.N163 human TfR
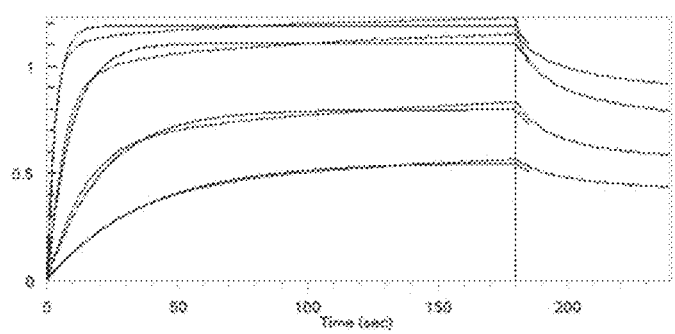
FIG. 27B  CH3C.35 human TfR
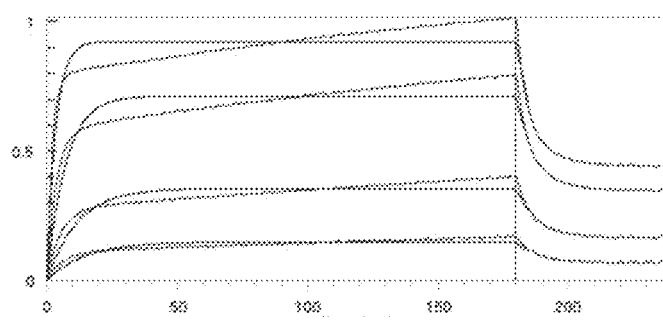
FIG. 27C  CH3C.35.N163.mono human TfR
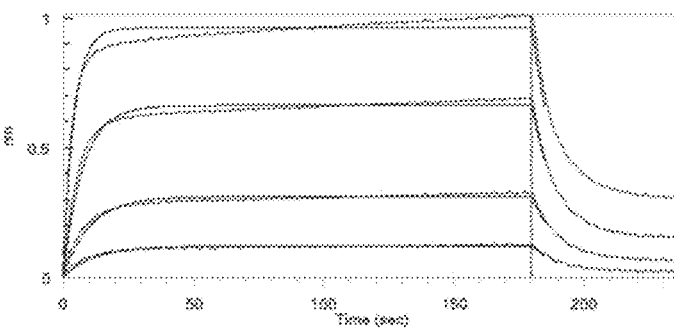
FIG. 27D  CH3C.35.mono human TfR FIG. 29A
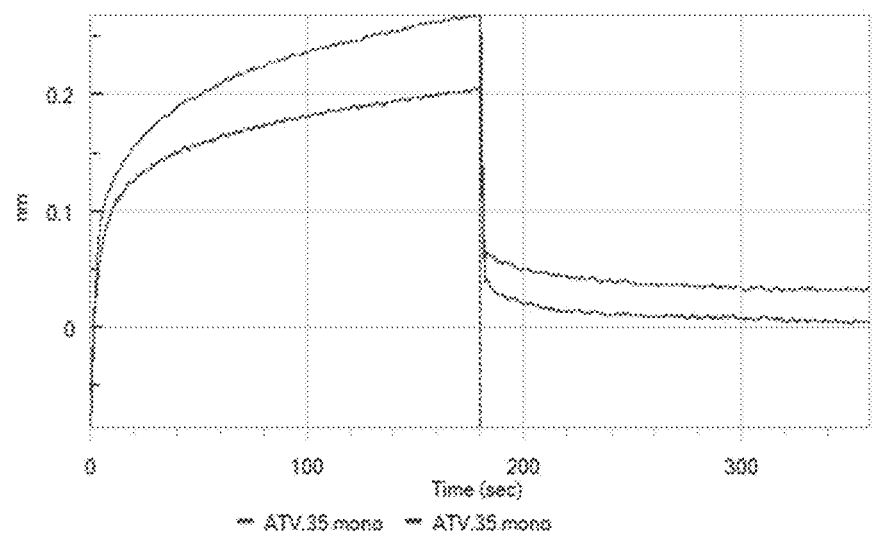
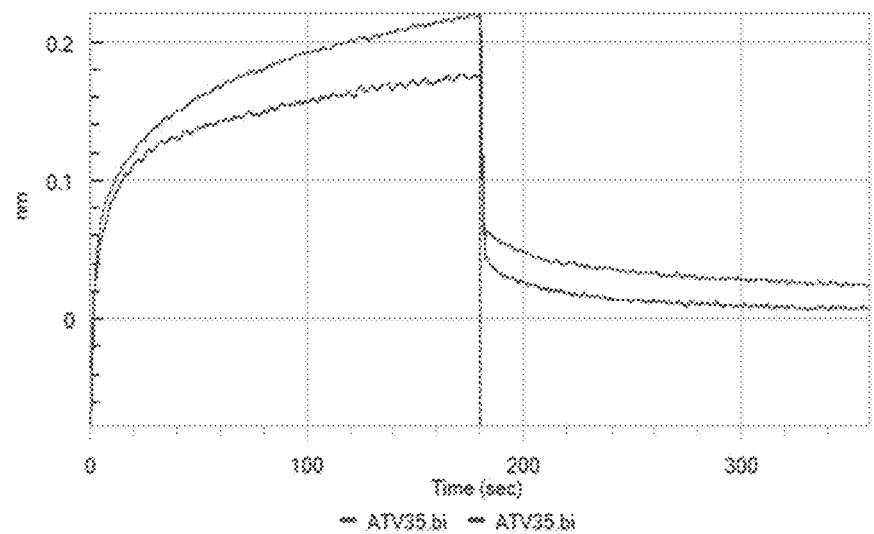

FIG. 29B
CH3C.35.19.mono
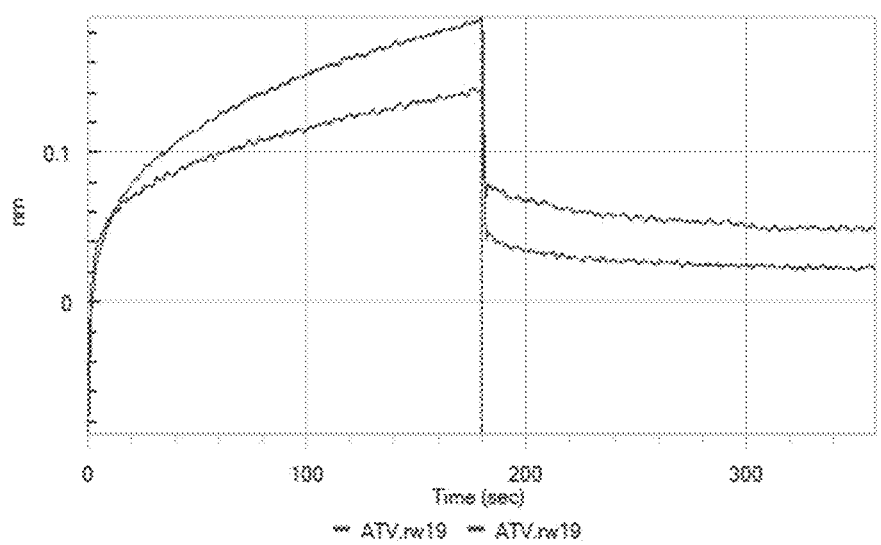
CH3C.35.19.bi
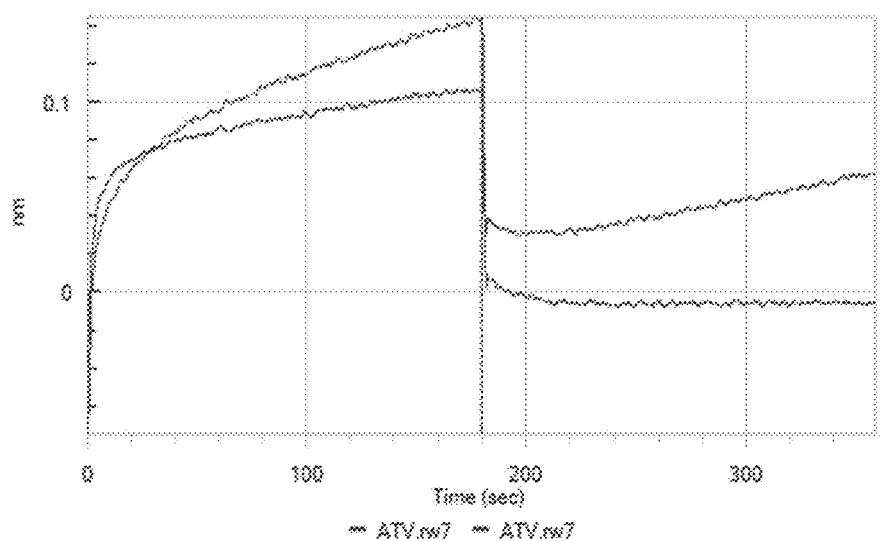

*FIG. 29C*
CH3C.35.20.mono
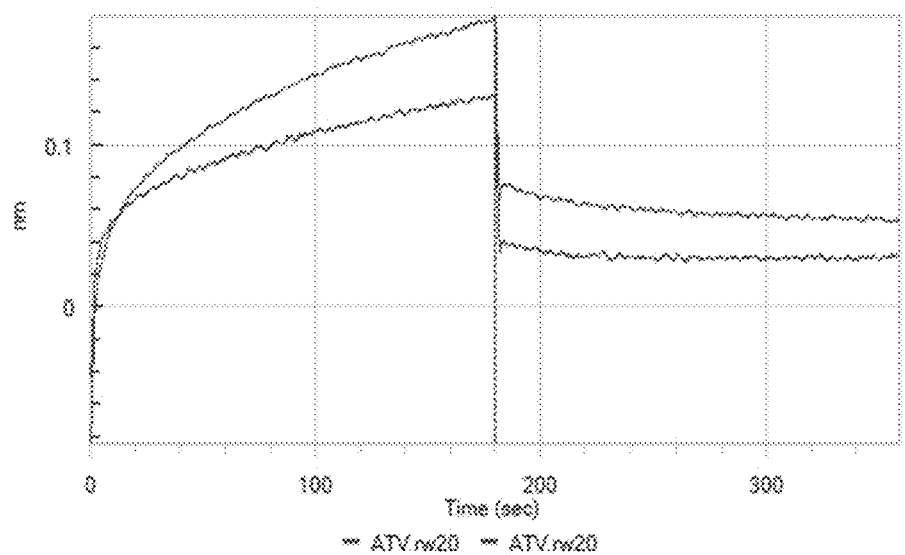
CH3C.35.20.bi
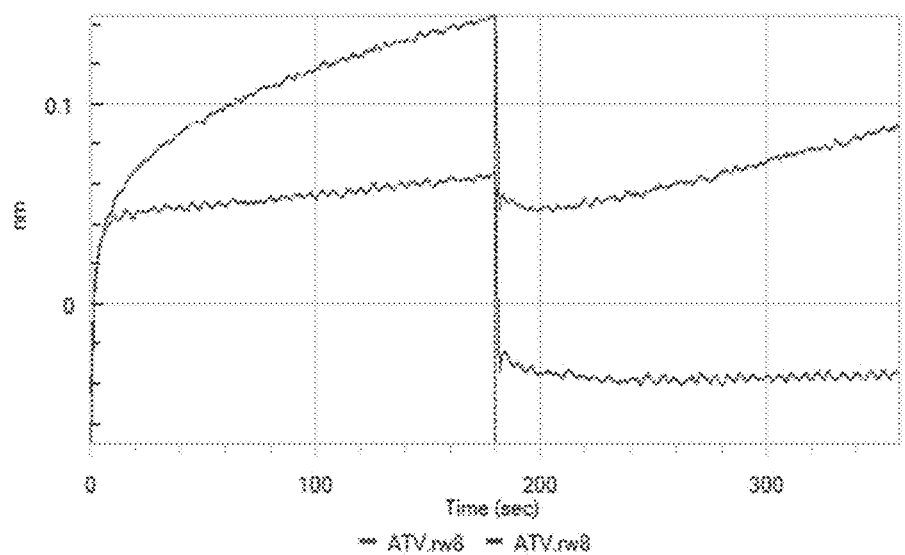

FIG. 29D
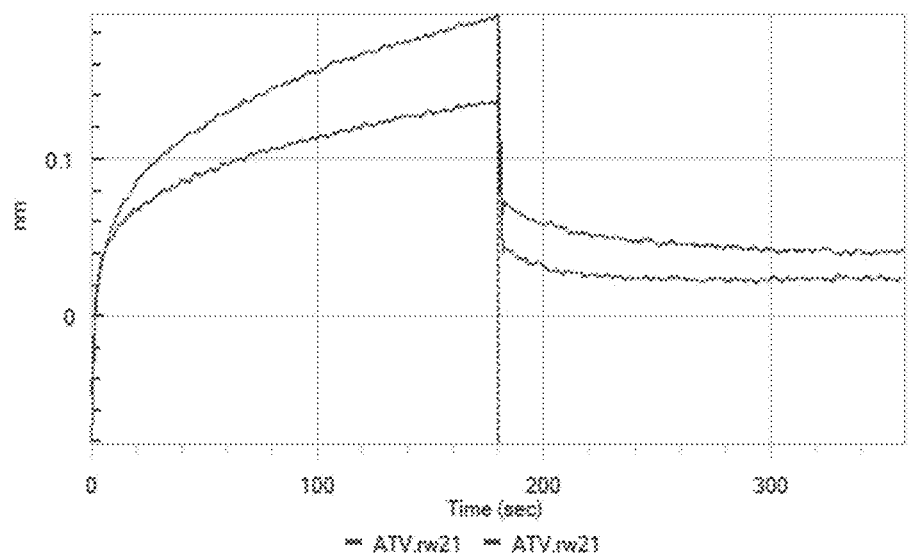
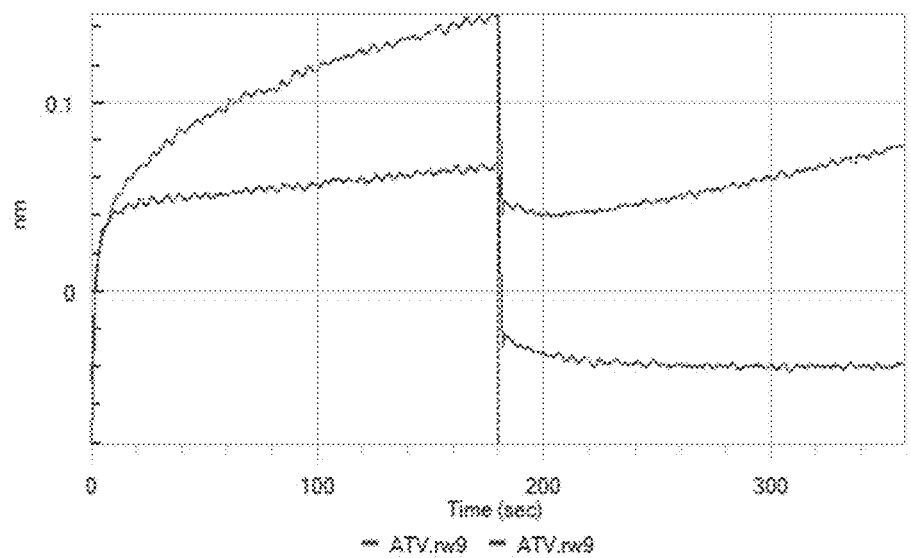

FIG. 29E
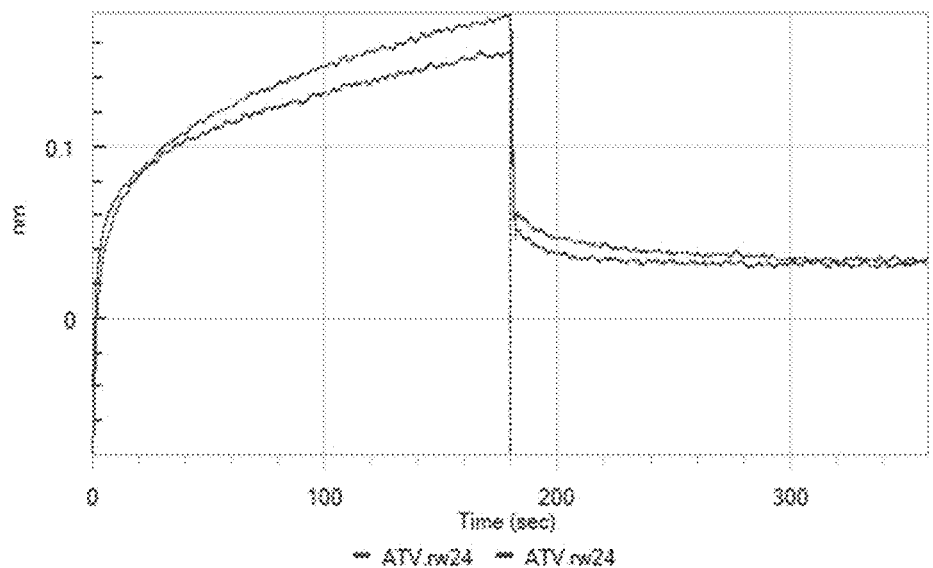
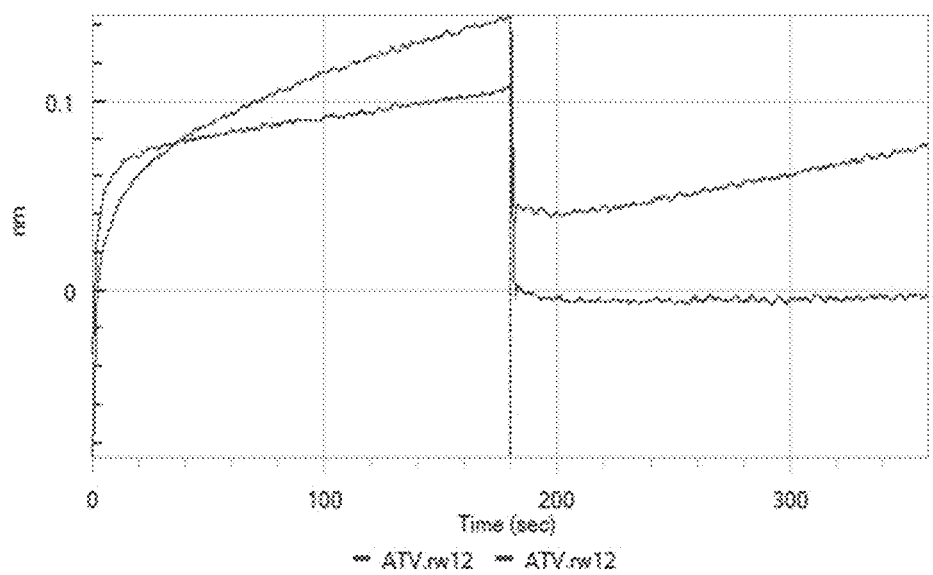

FIG. 36A
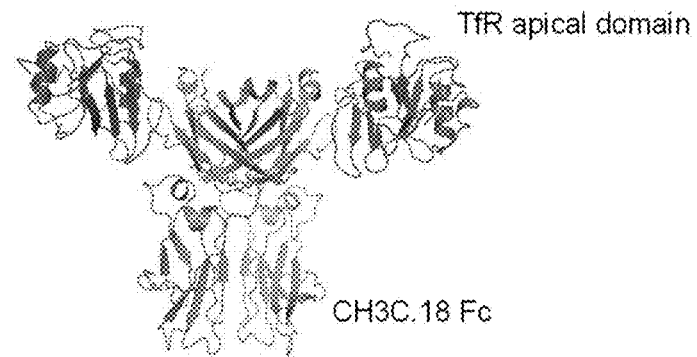
Structural architecture
TfR apical domain
CH3C.18 Fc
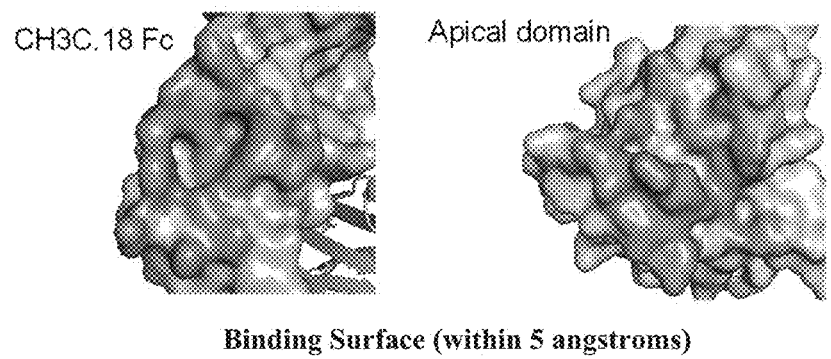
CH3C.18 Fc     Apical domain
Binding Surface (within 5 angstroms)
FIG. 36B
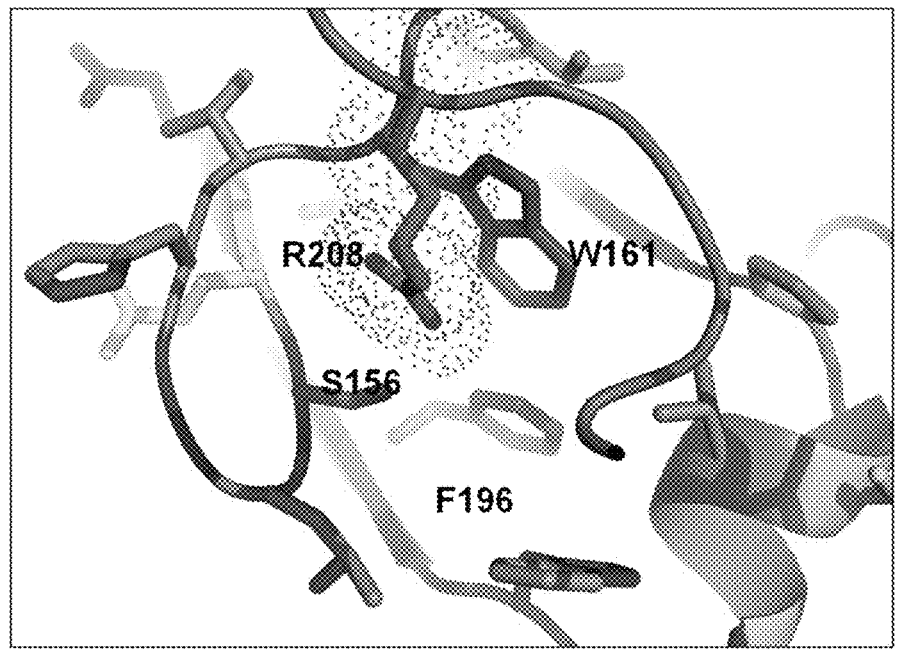

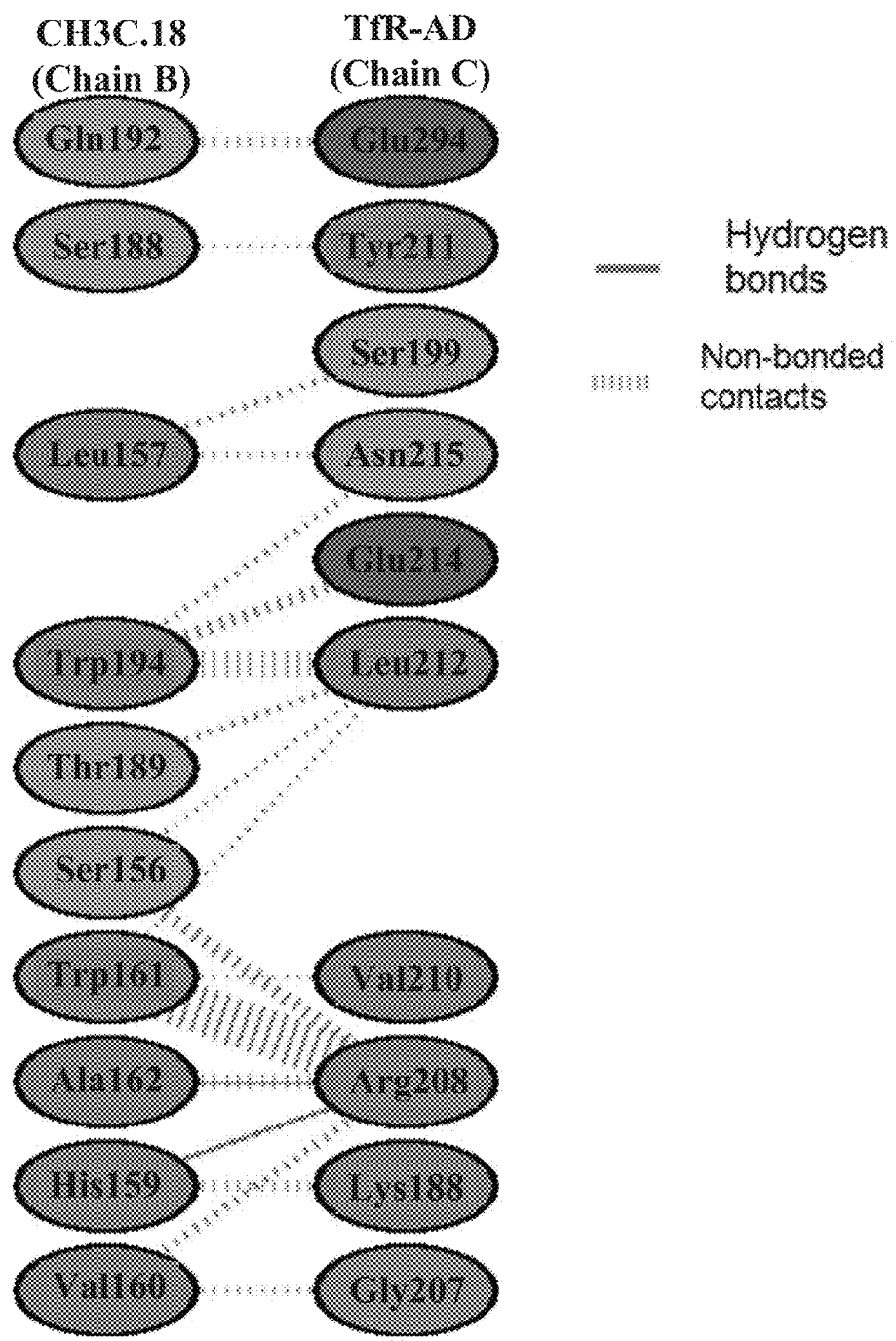

FIG. 38

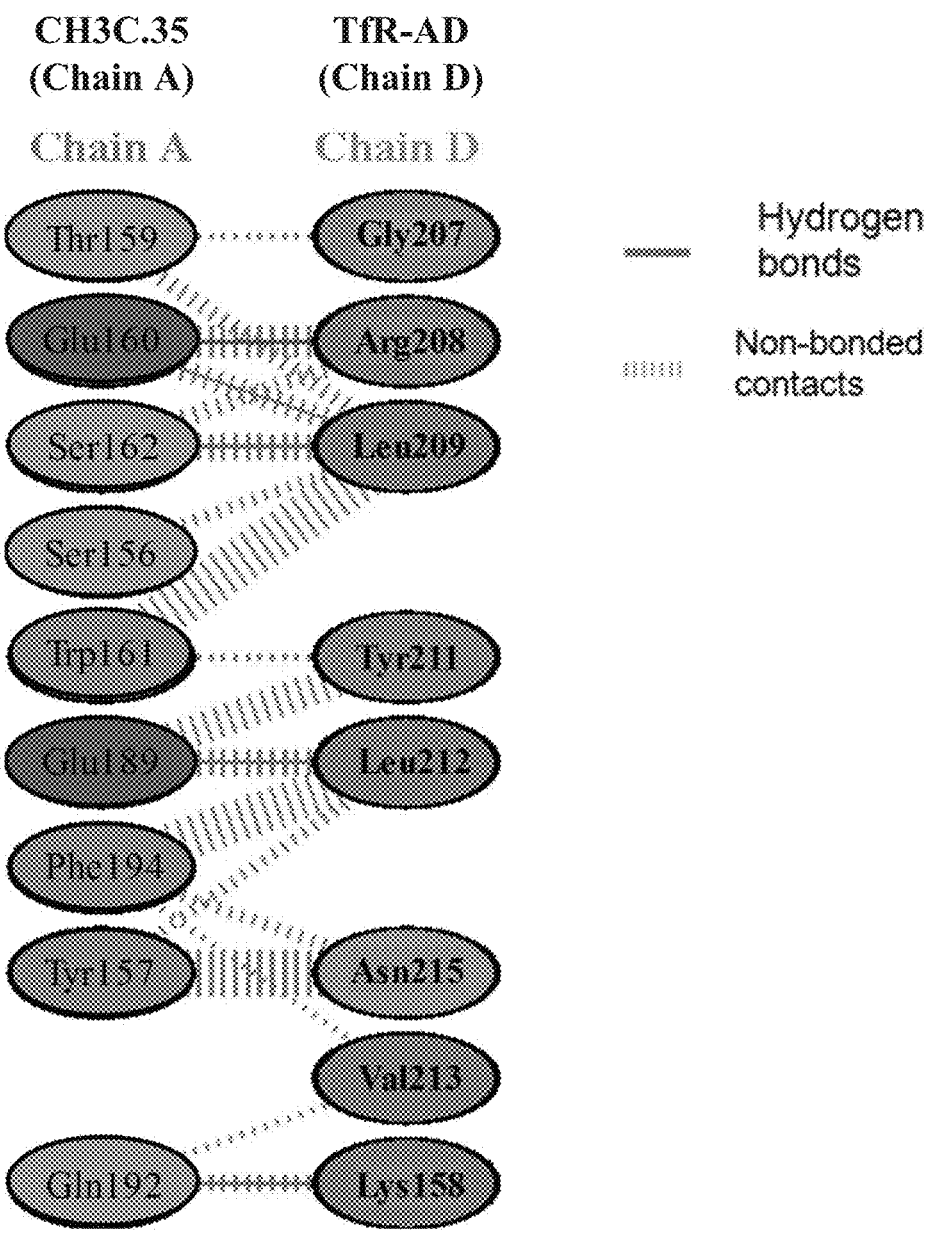

Brain Aβ

Brain TfR

SEQUENCE LISTING

<160> NUMBER OF SEQ ID NOS: 474

<210> SEQ ID NO 1
<211> LENGTH: 220
<212> TYPE: PRT
<213> ORGANISM: Homo sapiens

<400> SEQUENCE: 1

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 2
<211> LENGTH: 113
<212> TYPE: PRT
<213> ORGANISM: Artificial Sequence
<220> FEATURE:
<223> OTHER INFORMATION: Synthetic construct

<400> SEQUENCE: 2

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

```
Ser Asn Lys Ala Leu Pro Ala Pro Ile Glu Lys Thr Ile Ser Lys Ala
            100                 105                 110
Lys

<210> SEQ ID NO 3
<211> LENGTH: 107
<212> TYPE: PRT
<213> ORGANISM: Artificial Sequence
<220> FEATURE:
<223> OTHER INFORMATION: Synthetic construct

<400> SEQUENCE: 3

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 4
<211> LENGTH: 220
<212> TYPE: PRT
<213> ORGANISM: Artificial Sequence
<220> FEATURE:
<223> OTHER INFORMATION: Synthetic construct

<400> SEQUENCE: 4

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Leu Gly Leu Val
145                 150                 155                 160

Trp Val Gly Tyr Lys Thr Thr Pro Pro Val Leu Asp Ser Asp Gly Ser
                165                 170                 175
```

```
Phe Phe Leu Tyr Ser Lys Leu Thr Val Ala Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 5
<211> LENGTH: 220
<212> TYPE: PRT
<213> ORGANISM: Artificial Sequence
<220> FEATURE:
<223> OTHER INFORMATION: Synthetic construct

<400> SEQUENCE: 5

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Val
145                 150                 155                 160

Trp Ser His Tyr Lys Thr Thr Pro Pro Val Leu Asp Ser Asp Gly Ser
                165                 170                 175

Phe Phe Leu Tyr Ser Lys Leu Thr Val Ser Lys Ser Glu Trp Gln Gln
            180                 185                 190

Gly Tyr Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 6
<211> LENGTH: 220
<212> TYPE: PRT
<213> ORGANISM: Artificial Sequence
<220> FEATURE:
<223> OTHER INFORMATION: Synthetic construct

<400> SEQUENCE: 6

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
```

```
                    35                  40                  45
Asn Trp Tyr Val Asp Gly Val Glu Val His Asn Ala Lys Thr Lys Pro
 50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Pro Ala Pro Ile Glu Lys Thr Ile Ser Lys Ala
                100                 105                 110
Lys Gly Gln Pro Arg Glu Pro Gln Val Tyr Thr Leu Pro Pro Ser Arg
                115                 120                 125
Asp Glu Leu Thr Lys Asn Gln Val Ser Leu Thr Cys Leu Val Lys Gly
                130                 135                 140
Phe Tyr Pro Ser Asp Ile Ala Val Glu Trp Ser Tyr Gly Thr Glu
145                 150                 155                 160
Trp Ser Gln Tyr Lys Thr Thr Pro Pro Val Leu Asp Ser Asp Gly Ser
                165                 170                 175
Phe Phe Leu Tyr Ser Lys Leu Thr Val Glu Lys Ser Asp Trp Gln Gln
                180                 185                 190
Gly His Val Phe Ser Cys Ser Val Met His Glu Ala Leu His Asn His
                195                 200                 205
Tyr Thr Gln Lys Ser Leu Ser Leu Ser Pro Gly Lys
                210                 215                 220

<210> SEQ ID NO 7
<211> LENGTH: 220
<212> TYPE: PRT
<213> ORGANISM: Artificial Sequence
<220> FEATURE:
<223> OTHER INFORMATION: Synthetic construct

<400> SEQUENCE: 7

Pro Cys Pro Ala Pro Glu Leu Leu Gly Gly Pro Ser Val Phe Leu Phe
  1               5                  10                  15
Pro Pro Lys Pro Lys Asp Thr Leu Met Ile Ser Arg Thr Pro Glu Val
                 20                  25                  30
Thr Cys Val Val Val Asp Val Ser His Glu Asp Pro Glu Val Lys Phe
                 35                  40                  45
Asn Trp Tyr Val Asp Gly Val Glu Val His Asn Ala Lys Thr Lys Pro
 50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Pro Ala Pro Ile Glu Lys Thr Ile Ser Lys Ala
                100                 105                 110
Lys Gly Gln Pro Arg Glu Pro Gln Val Tyr Thr Leu Pro Pro Ser Arg
                115                 120                 125
Asp Glu Leu Thr Lys Asn Gln Val Ser Leu Thr Cys Leu Val Lys Gly
                130                 135                 140
Phe Tyr Pro Ser Asp Ile Ala Val Glu Trp Ser Val Gly Thr Pro
145                 150                 155                 160
Trp Ala Leu Tyr Lys Thr Thr Pro Pro Val Leu Asp Ser Asp Gly Ser
                165                 170                 175
Phe Phe Leu Tyr Ser Lys Leu Thr Val Leu Lys Ser Glu Trp Gln Gln
```

```
            180             185             190
Gly Trp Val Phe Ser Cys Ser Val Met His Glu Ala Leu His Asn His
            195             200             205

Tyr Thr Gln Lys Ser Leu Ser Leu Ser Pro Gly Lys
            210             215             220

<210> SEQ ID NO 8
<211> LENGTH: 220
<212> TYPE: PRT
<213> ORGANISM: Artificial Sequence
<220> FEATURE:
<223> OTHER INFORMATION: Synthetic construct

<400> SEQUENCE: 8

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Val
145                 150                 155                 160

Trp Ser Lys Tyr Lys Thr Thr Pro Pro Val Leu Asp Ser Asp Gly Ser
                165                 170                 175

Phe Phe Leu Tyr Ser Lys Leu Thr Val Ser Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 9
<211> LENGTH: 220
<212> TYPE: PRT
<213> ORGANISM: Artificial Sequence
<220> FEATURE:
<223> OTHER INFORMATION: Synthetic construct

<400> SEQUENCE: 9

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45
```

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Leu Gly His Val
145                 150                 155                 160

Trp Ala Val Tyr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
                180                 185                 190

Gly Trp Val Phe Ser Cys Ser Val Met His Glu Ala Leu His Asn His
                195                 200                 205

Tyr Thr Gln Lys Ser Leu Ser Leu Ser Pro Gly Lys
210                 215                 220

<210> SEQ ID NO 10
<211> LENGTH: 220
<212> TYPE: PRT
<213> ORGANISM: Artificial Sequence
<220> FEATURE:
<223> OTHER INFORMATION: Synthetic construct

<400> SEQUENCE: 10

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Leu Gly Leu Val
145                 150                 155                 160

Trp Val Gly Tyr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
                180                 185                 190

Gly Trp Val Phe Ser Cys Ser Val Met His Glu Ala Leu His Asn His
            195                 200                 205
Tyr Thr Gln Lys Ser Leu Ser Leu Ser Pro Gly Lys
    210                 215                 220

<210> SEQ ID NO 11
<211> LENGTH: 220
<212> TYPE: PRT
<213> ORGANISM: Artificial Sequence
<220> FEATURE:
<223> OTHER INFORMATION: Synthetic construct

<400> SEQUENCE: 11

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Glu Trp Glu Ser Met Gly His Val
145                 150                 155                 160
Trp Val Gly Tyr Lys Thr Thr Pro Pro Val Leu Asp Ser Asp Gly Ser
                165                 170                 175
Phe Phe Leu Tyr Ser Lys Leu Thr Val Asp Lys Ser Trp Gln Gln
            180                 185                 190
Gly Trp Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 12
<211> LENGTH: 220
<212> TYPE: PRT
<213> ORGANISM: Artificial Sequence
<220> FEATURE:
<223> OTHER INFORMATION: Synthetic construct

<400> SEQUENCE: 12

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60

```
Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Ser Leu Gly Leu Val
145                 150                 155                 160

Trp Val Phe Ser Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 13
<211> LENGTH: 220
<212> TYPE: PRT
<213> ORGANISM: Artificial Sequence
<220> FEATURE:
<223> OTHER INFORMATION: Synthetic construct

<400> SEQUENCE: 13

Pro Cys Pro Ala Pro Glu Leu Leu Gly Gly Pro Ser Val Phe Leu Phe
1               5                  10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
            195                 200                 205
```

```
Tyr Thr Gln Lys Ser Leu Ser Leu Ser Pro Gly Lys
    210                 215                 220

<210> SEQ ID NO 14
<211> LENGTH: 220
<212> TYPE: PRT
<213> ORGANISM: Artificial Sequence
<220> FEATURE:
<223> OTHER INFORMATION: Synthetic construct

<400> SEQUENCE: 14

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 15
<211> LENGTH: 220
<212> TYPE: PRT
<213> ORGANISM: Artificial Sequence
<220> FEATURE:
<223> OTHER INFORMATION: Synthetic construct

<400> SEQUENCE: 15

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
```

```
                65                  70                  75                  80
Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Leu Gly His Val
145                 150                 155                 160

Trp Val Gly Tyr Lys Thr Thr Pro Pro Val Leu Asp Ser Asp Gly Ser
                165                 170                 175

Phe Phe Leu Tyr Ser Lys Leu Thr Val Ser Lys Ser Glu Trp Gln Gln
                180                 185                 190

Gly Trp Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 16
<211> LENGTH: 220
<212> TYPE: PRT
<213> ORGANISM: Artificial Sequence
<220> FEATURE:
<223> OTHER INFORMATION: Synthetic construct

<400> SEQUENCE: 16

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Leu Gly His Val
145                 150                 155                 160

Trp Val Ala Thr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
                180                 185                 190

Gly Trp Val Phe Ser Cys Ser Val Met His Glu Ala Leu His Asn His
                195                 200                 205

Tyr Thr Gln Lys Ser Leu Ser Leu Ser Pro Gly Lys
```

-continued

```
                210                 215                 220
```

<210> SEQ ID NO 17
<211> LENGTH: 220
<212> TYPE: PRT
<213> ORGANISM: Artificial Sequence
<220> FEATURE:
<223> OTHER INFORMATION: Synthetic construct

<400> SEQUENCE: 17

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Leu Gly Pro Val
145                 150                 155                 160

Trp Val His Thr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 18
<211> LENGTH: 220
<212> TYPE: PRT
<213> ORGANISM: Artificial Sequence
<220> FEATURE:
<223> OTHER INFORMATION: Synthetic construct

<400> SEQUENCE: 18

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

```
Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Leu Gly His Val
145                 150                 155                 160

Trp Val Asp Gln Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 19
<211> LENGTH: 220
<212> TYPE: PRT
<213> ORGANISM: Artificial Sequence
<220> FEATURE:
<223> OTHER INFORMATION: Synthetic construct

<400> SEQUENCE: 19

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Leu Gly His Val
145                 150                 155                 160

Trp Val Asn Gln Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
            210                 215                 220
```

<210> SEQ ID NO 20
<211> LENGTH: 220
<212> TYPE: PRT
<213> ORGANISM: Artificial Sequence
<220> FEATURE:
<223> OTHER INFORMATION: Synthetic construct

<400> SEQUENCE: 20

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Leu Gly His Val
145                 150                 155                 160

Trp Val Asn Phe Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 21
<211> LENGTH: 220
<212> TYPE: PRT
<213> ORGANISM: Artificial Sequence
<220> FEATURE:
<223> OTHER INFORMATION: Synthetic construct

<400> SEQUENCE: 21

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Trp Trp Glu Ser Leu Gly His Val
145                 150                 155                 160

Trp Ala Val Tyr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 22
<211> LENGTH: 220
<212> TYPE: PRT
<213> ORGANISM: Artificial Sequence
<220> FEATURE:
<223> OTHER INFORMATION: Synthetic construct

<400> SEQUENCE: 22

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Ser Leu Gly His Val
145                 150                 155                 160

Trp Ala Val Tyr Gln Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 23
```

```
<211> LENGTH: 220
<212> TYPE: PRT
<213> ORGANISM: Artificial Sequence
<220> FEATURE:
<223> OTHER INFORMATION: Synthetic construct

<400> SEQUENCE: 23

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Leu Gly His Val
145                 150                 155                 160

Trp Ala Val Tyr Gln Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 24
<211> LENGTH: 220
<212> TYPE: PRT
<213> ORGANISM: Artificial Sequence
<220> FEATURE:
<223> OTHER INFORMATION: Synthetic construct

<400> SEQUENCE: 24

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

```
                    100                 105                 110
Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Trp Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 25
<211> LENGTH: 220
<212> TYPE: PRT
<213> ORGANISM: Artificial Sequence
<220> FEATURE:
<223> OTHER INFORMATION: Synthetic construct

<400> SEQUENCE: 25

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 26
<211> LENGTH: 220
<212> TYPE: PRT
```

<213> ORGANISM: Artificial Sequence
<220> FEATURE:
<223> OTHER INFORMATION: Synthetic construct

<400> SEQUENCE: 26

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 27
<211> LENGTH: 220
<212> TYPE: PRT
<213> ORGANISM: Artificial Sequence
<220> FEATURE:
<223> OTHER INFORMATION: Synthetic construct

<400> SEQUENCE: 27

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

Lys Gly Gln Pro Arg Glu Pro Gln Val Tyr Thr Leu Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 28
<211> LENGTH: 220
<212> TYPE: PRT
<213> ORGANISM: Artificial Sequence
<220> FEATURE:
<223> OTHER INFORMATION: Synthetic construct

<400> SEQUENCE: 28

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Ser Tyr Gln Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 29
<211> LENGTH: 220
<212> TYPE: PRT
<213> ORGANISM: Artificial Sequence
<220> FEATURE:

<223> OTHER INFORMATION: Synthetic construct

<400> SEQUENCE: 29

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Tyr Gly Thr Glu
145                 150                 155                 160

Trp Ser Asn Tyr Gln Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 30
<211> LENGTH: 220
<212> TYPE: PRT
<213> ORGANISM: Artificial Sequence
<220> FEATURE:
<223> OTHER INFORMATION: Synthetic construct

<400> SEQUENCE: 30

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Asp Tyr Val Thr Thr Leu Pro Pro Ser Arg
            115                 120                 125

```
Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220

<210> SEQ ID NO 31
<211> LENGTH: 220
<212> TYPE: PRT
<213> ORGANISM: Artificial Sequence
<220> FEATURE:
<223> OTHER INFORMATION: Synthetic construct

<400> SEQUENCE: 31

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Phe Asp Met Val Thr Thr Leu Pro Pro Ser Arg
    115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220

<210> SEQ ID NO 32
<211> LENGTH: 220
<212> TYPE: PRT
<213> ORGANISM: Artificial Sequence
<220> FEATURE:
<223> OTHER INFORMATION: Synthetic construct
```

<400> SEQUENCE: 32

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Glu Tyr Val Thr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220
```

<210> SEQ ID NO 33
<211> LENGTH: 220
<212> TYPE: PRT
<213> ORGANISM: Artificial Sequence
<220> FEATURE:
<223> OTHER INFORMATION: Synthetic construct

<400> SEQUENCE: 33

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Glu Met Val Thr Thr Leu Pro Pro Ser Arg
        115                 120                 125

Asp Glu Leu Thr Lys Asn Gln Val Ser Leu Thr Cys Leu Val Lys Gly
```

```
                130                 135                 140
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220
```

<210> SEQ ID NO 34
<211> LENGTH: 220
<212> TYPE: PRT
<213> ORGANISM: Artificial Sequence
<220> FEATURE:
<223> OTHER INFORMATION: Synthetic construct

<400> SEQUENCE: 34

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Glu Leu Val Thr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220
```

<210> SEQ ID NO 35
<211> LENGTH: 220
<212> TYPE: PRT
<213> ORGANISM: Artificial Sequence
<220> FEATURE:
<223> OTHER INFORMATION: Synthetic construct

<400> SEQUENCE: 35

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Glu Ile Val Thr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Gly Phe His Asp Leu Ser Leu Ser Pro Gly Lys
        210                 215                 220

<210> SEQ ID NO 36
<211> LENGTH: 220
<212> TYPE: PRT
<213> ORGANISM: Artificial Sequence
<220> FEATURE:
<223> OTHER INFORMATION: Synthetic construct

<400> SEQUENCE: 36

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Asp Ile Val Thr Thr Leu Pro Pro Ser Arg
            115                 120                 125

Asp Glu Leu Thr Lys Asn Gln Val Ser Leu Thr Cys Leu Val Lys Gly
        130                 135                 140
```

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Gly Phe His Asp Leu Ser Leu Ser Pro Gly Lys
            210                 215                 220
```

<210> SEQ ID NO 37
<211> LENGTH: 220
<212> TYPE: PRT
<213> ORGANISM: Artificial Sequence
<220> FEATURE:
<223> OTHER INFORMATION: Synthetic construct

<400> SEQUENCE: 37

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Phe Asp Tyr Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Gly Phe His Asp Leu Ser Leu Ser Pro Gly Lys
            210                 215                 220
```

<210> SEQ ID NO 38
<211> LENGTH: 220
<212> TYPE: PRT
<213> ORGANISM: Artificial Sequence
<220> FEATURE:
<223> OTHER INFORMATION: Synthetic construct

<400> SEQUENCE: 38

```
Pro Cys Pro Ala Pro Glu Leu Leu Gly Gly Pro Ser Val Phe Leu Phe
1               5                   10                  15
```

```
Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Phe Gly Met Val Thr Thr Leu Pro Pro Ser Arg
                115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Gly Phe His Asp Leu Ser Leu Ser Pro Gly Lys
                210                 215                 220

<210> SEQ ID NO 39
<211> LENGTH: 220
<212> TYPE: PRT
<213> ORGANISM: Artificial Sequence
<220> FEATURE:
<223> OTHER INFORMATION: Synthetic construct

<400> SEQUENCE: 39

Pro Cys Pro Ala Pro Glu Leu Leu Gly Gly Pro Ser Val Phe Leu Phe
 1               5                   10                  15

Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Phe Ala Asp Val Thr Ile Leu Pro Pro Ser Arg
                115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160
```

```
Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Gly Phe Tyr Asp Leu Ser Leu Ser Pro Gly Lys
    210                 215                 220

<210> SEQ ID NO 40
<211> LENGTH: 220
<212> TYPE: PRT
<213> ORGANISM: Artificial Sequence
<220> FEATURE:
<223> OTHER INFORMATION: Synthetic construct

<400> SEQUENCE: 40

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Phe Gly Leu Val Thr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Gly Phe His Asp Leu Ser Leu Ser Pro Gly Lys
    210                 215                 220

<210> SEQ ID NO 41
<211> LENGTH: 220
<212> TYPE: PRT
<213> ORGANISM: Artificial Sequence
<220> FEATURE:
<223> OTHER INFORMATION: Synthetic construct

<400> SEQUENCE: 41

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
```

```
                20                  25                  30
Thr Cys Val Val Val Asp Val Ser His Glu Asp Pro Glu Val Lys Phe
            35                  40                  45
Asn Trp Tyr Val Asp Gly Val Glu Val His Asn Ala Lys Thr Lys Pro
        50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Phe Asp Tyr Val Thr Thr Leu Pro Pro Ser Arg
        115                 120                 125
Asp Glu Leu Thr Lys Asn Gln Val Ser Leu Thr Cys Leu Val Lys Gly
            130                 135                 140
Phe Tyr Pro Ser Asp Ile Ala Val Glu Trp Glu Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
            180                 185                 190
Gly Asn Val Phe Ser Cys Ser Val Met His Glu Ala Leu His Asn His
        195                 200                 205
Tyr Gly Phe Ser Asp Leu Ser Leu Ser Pro Gly Lys
    210                 215                 220

<210> SEQ ID NO 42
<211> LENGTH: 220
<212> TYPE: PRT
<213> ORGANISM: Artificial Sequence
<220> FEATURE:
<223> OTHER INFORMATION: Synthetic construct

<400> SEQUENCE: 42

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Ile Asp Tyr Val Thr Thr Leu Pro Pro Ser Arg
        115                 120                 125
Asp Glu Leu Thr Lys Asn Gln Val Ser Leu Thr Cys Leu Val Lys Gly
            130                 135                 140
Phe Tyr Pro Ser Asp Ile Ala Val Glu Trp Glu Ser Asn Gly Gln Pro
145                 150                 155                 160
Glu Asn Asn Tyr Lys Thr Thr Pro Pro Val Leu Asp Ser Asp Gly Ser
```

```
                    165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe Ser Asp Leu Ser Leu Ser Pro Gly Lys
    210                 215                 220

<210> SEQ ID NO 43
<211> LENGTH: 220
<212> TYPE: PRT
<213> ORGANISM: Artificial Sequence
<220> FEATURE:
<223> OTHER INFORMATION: Synthetic construct

<400> SEQUENCE: 43

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Lys Asp Val Thr Ile Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe Phe Asp Leu Ser Leu Ser Pro Gly Lys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic construct

<400> SEQUENCE: 44

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

Thr Cys Val Val Asp Val Ser His Glu Asp Pro Glu Val Lys Phe
                35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Phe Asp Leu Val Thr Ile Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Gly Phe Tyr Asp Leu Ser Leu Ser Pro Gly Lys
                210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic construct

<400> SEQUENCE: 45

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Asp Val Ser His Glu Asp Pro Glu Val Lys Phe
                35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Ile Asp Tyr Val Thr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Gly Phe Ser Asp Leu Ser Leu Ser Pro Gly Lys
        210                 215                 220

<210> SEQ ID NO 46
<211> LENGTH: 220
<212> TYPE: PRT
<213> ORGANISM: Artificial Sequence
<220> FEATURE:
<223> OTHER INFORMATION: Synthetic construct

<400> SEQUENCE: 46

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Glu Leu Val Ala Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe His Asp Leu Ser Leu Ser Pro Gly Lys
    210                 215                 220

<210> SEQ ID NO 47
<211> LENGTH: 220
<212> TYPE: PRT
<213> ORGANISM: Artificial Sequence
<220> FEATURE:
<223> OTHER INFORMATION: Synthetic construct

<400> SEQUENCE: 47

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Glu Phe
        35                  40                  45

```
Ile Trp Tyr Val Asp Gly Val Asp Val Arg Tyr Glu Trp Gln Leu Pro
    50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
    210                 215                 220

<210> SEQ ID NO 48
<211> LENGTH: 220
<212> TYPE: PRT
<213> ORGANISM: Artificial Sequence
<220> FEATURE:
<223> OTHER INFORMATION: Synthetic construct

<400> SEQUENCE: 48

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Gly Phe
                35                  40                  45

Val Trp Tyr Val Asp Gly Val Pro Val Ser Trp Glu Trp Tyr Trp Pro
    50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190
```

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 49
<211> LENGTH: 220
<212> TYPE: PRT
<213> ORGANISM: Artificial Sequence
<220> FEATURE:
<223> OTHER INFORMATION: Synthetic construct

<400> SEQUENCE: 49

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
        35                  40                  45

Asp Trp Tyr Val Asp Gly Val Met Val Arg Arg Glu Trp His Arg Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 50
<211> LENGTH: 220
<212> TYPE: PRT
<213> ORGANISM: Artificial Sequence
<220> FEATURE:
<223> OTHER INFORMATION: Synthetic construct

<400> SEQUENCE: 50

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Ser Phe
        35                  40                  45

Glu Trp Tyr Val Asp Gly Val Pro Val Arg Trp Glu Trp Gln Trp Pro

```
                  50                  55                  60
Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                     85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 51
<211> LENGTH: 220
<212> TYPE: PRT
<213> ORGANISM: Artificial Sequence
<220> FEATURE:
<223> OTHER INFORMATION: Synthetic construct

<400> SEQUENCE: 51

Pro Cys Pro Ala Pro Glu Leu Leu Gly Gly Pro Ser Val Phe Leu Phe
  1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Ala Phe
                 35                  40                  45

Thr Trp Tyr Val Asp Gly Val Pro Val Arg Trp Glu Trp Gln Asn Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                     85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
```

```
                  195                 200                 205

Tyr Thr Gln Lys Ser Leu Ser Leu Ser Pro Gly Lys
    210                 215                 220

<210> SEQ ID NO 52
<211> LENGTH: 220
<212> TYPE: PRT
<213> ORGANISM: Artificial Sequence
<220> FEATURE:
<223> OTHER INFORMATION: Synthetic construct

<400> SEQUENCE: 52

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Asn Phe
        35                  40                  45

Asp Trp Tyr Val Asp Gly Val Leu Val Arg Arg Glu Trp His Arg Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 53
<211> LENGTH: 220
<212> TYPE: PRT
<213> ORGANISM: Artificial Sequence
<220> FEATURE:
<223> OTHER INFORMATION: Synthetic construct

<400> SEQUENCE: 53

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
        35                  40                  45

Val Trp Tyr Val Asp Gly Val Ala Val Arg Trp Glu Trp Ile Arg Pro
    50                  55                  60
```

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 54
<211> LENGTH: 220
<212> TYPE: PRT
<213> ORGANISM: Artificial Sequence
<220> FEATURE:
<223> OTHER INFORMATION: Synthetic construct

<400> SEQUENCE: 54

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Glu Phe
        35                  40                  45

Ile Trp Tyr Val Asp Gly Val Glu Val Ala Trp Glu Trp Phe Trp Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 55
<211> LENGTH: 220
<212> TYPE: PRT
<213> ORGANISM: Artificial Sequence
<220> FEATURE:
<223> OTHER INFORMATION: Synthetic construct

<400> SEQUENCE: 55

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gly Phe
        35                  40                  45

Ala Trp Tyr Val Asp Gly Val Asn Val Arg Val Glu Trp Gln Tyr Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 56
<211> LENGTH: 220
<212> TYPE: PRT
<213> ORGANISM: Artificial Sequence
<220> FEATURE:
<223> OTHER INFORMATION: Synthetic construct

<400> SEQUENCE: 56

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gly Phe
        35                  40                  45

Val Trp Tyr Val Asp Gly Val Glu Val Arg Arg Glu Trp Val Arg Pro
    50                  55                  60

Arg Glu Glu Gln Tyr Asn Ser Thr Tyr Arg Val Val Ser Val Leu Thr
65                  70                  75                  80

```
Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 57
<211> LENGTH: 220
<212> TYPE: PRT
<213> ORGANISM: Artificial Sequence
<220> FEATURE:
<223> OTHER INFORMATION: Synthetic construct

<400> SEQUENCE: 57

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Ser Phe
            35                  40                  45

Asp Trp Tyr Val Asp Gly Val Leu Val Arg Arg Glu Trp Gln Arg Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220
```

```
<210> SEQ ID NO 58
<211> LENGTH: 220
<212> TYPE: PRT
<213> ORGANISM: Artificial Sequence
<220> FEATURE:
<223> OTHER INFORMATION: Synthetic construct

<400> SEQUENCE: 58
```

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Glu Phe
        35                  40                  45

Thr Trp Tyr Val Asp Gly Val Asp Val Arg Tyr Glu Trp Tyr Tyr Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

```
<210> SEQ ID NO 59
<211> LENGTH: 220
<212> TYPE: PRT
<213> ORGANISM: Artificial Sequence
<220> FEATURE:
<223> OTHER INFORMATION: Synthetic construct

<400> SEQUENCE: 59
```

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
        35                  40                  45

Thr Trp Tyr Val Asp Gly Val Asp Val Arg Tyr Glu Trp Val Arg Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val

```
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Thr Cys Leu Val Lys Gly
            130                 135                 140
Phe Tyr Pro Ser Asp Ile Ala Val Glu Trp Glu Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
                180                 185                 190
Gly Asn Val Phe Ser Cys Ser Val Met His Glu Ala Leu His Asn His
                195                 200                 205
Tyr Thr Gln Lys Ser Leu Ser Leu Ser Pro Gly Lys
            210                 215                 220

<210> SEQ ID NO 60
<211> LENGTH: 220
<212> TYPE: PRT
<213> ORGANISM: Artificial Sequence
<220> FEATURE:
<223> OTHER INFORMATION: Synthetic construct

<400> SEQUENCE: 60

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Gln Phe
        35                  40                  45
Tyr Trp Tyr Val Asp Gly Val Asn Val Arg Arg Glu Trp His Arg Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Thr Cys Leu Val Lys Gly
            130                 135                 140
Phe Tyr Pro Ser Asp Ile Ala Val Glu Trp Glu Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
                180                 185                 190
Gly Asn Val Phe Ser Cys Ser Val Met His Glu Ala Leu His Asn His
                195                 200                 205
Tyr Thr Gln Lys Ser Leu Ser Leu Ser Pro Gly Lys
            210                 215                 220
```

<210> SEQ ID NO 61
<211> LENGTH: 220
<212> TYPE: PRT
<213> ORGANISM: Artificial Sequence
<220> FEATURE:
<223> OTHER INFORMATION: Synthetic construct

<400> SEQUENCE: 61

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Tyr Phe
        35                  40                  45

Asp Trp Tyr Val Asp Gly Val Met Val Arg Arg Glu Trp His Arg Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 62
<211> LENGTH: 220
<212> TYPE: PRT
<213> ORGANISM: Artificial Sequence
<220> FEATURE:
<223> OTHER INFORMATION: Synthetic construct

<400> SEQUENCE: 62

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Trp Phe
        35                  40                  45

Glu Trp Tyr Val Asp Gly Val Phe Val Gly Val Ala Tyr Asp Val Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 63
<211> LENGTH: 220
<212> TYPE: PRT
<213> ORGANISM: Artificial Sequence
<220> FEATURE:
<223> OTHER INFORMATION: Synthetic construct

<400> SEQUENCE: 63

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Gln Thr Pro Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 64
<211> LENGTH: 220

```
<212> TYPE: PRT
<213> ORGANISM: Artificial Sequence
<220> FEATURE:
<223> OTHER INFORMATION: Synthetic construct

<400> SEQUENCE: 64

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Ser Pro Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 65
<211> LENGTH: 220
<212> TYPE: PRT
<213> ORGANISM: Artificial Sequence
<220> FEATURE:
<223> OTHER INFORMATION: Synthetic construct

<400> SEQUENCE: 65

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Gln Thr Pro Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 66
<211> LENGTH: 220
<212> TYPE: PRT
<213> ORGANISM: Artificial Sequence
<220> FEATURE:
<223> OTHER INFORMATION: Synthetic construct

<400> SEQUENCE: 66

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Phe Arg Gly Pro Pro Trp Glu Val Lys Phe
        35                  40                  45

Asn Trp Tyr Val Asp Gly Val Glu Val His Asn Ala Lys Thr Lys Pro
50                  55                  60

Arg Glu Glu Glu Tyr Tyr His Asp Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 67
<211> LENGTH: 220
<212> TYPE: PRT
<213> ORGANISM: Artificial Sequence
<220> FEATURE:
<223> OTHER INFORMATION: Synthetic construct

<400> SEQUENCE: 67

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Gln Thr Val Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 68
<211> LENGTH: 220
<212> TYPE: PRT
<213> ORGANISM: Artificial Sequence
<220> FEATURE:
<223> OTHER INFORMATION: Synthetic construct

<400> SEQUENCE: 68

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Lys Met Pro Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
```

```
                115             120             125
Asp Glu Leu Thr Lys Asn Gln Val Ser Leu Thr Cys Leu Val Lys Gly
            130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
                195             200             205

Tyr Thr Gln Lys Ser Leu Ser Leu Ser Pro Gly Lys
            210             215             220

<210> SEQ ID NO 69
<211> LENGTH: 220
<212> TYPE: PRT
<213> ORGANISM: Artificial Sequence
<220> FEATURE:
<223> OTHER INFORMATION: Synthetic construct

<400> SEQUENCE: 69

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Thr Pro Glu Val
            20              25              30

Thr Cys Val Val Val Asp Pro Pro Val Pro Pro Trp Glu Val Lys Phe
        35              40              45

Asn Trp Tyr Val Asp Gly Val Glu Val His Asn Ala Lys Thr Lys Pro
    50              55              60

Arg Glu Glu Glu Tyr Tyr Ser Asn Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
        195             200             205

Tyr Thr Gln Lys Ser Leu Ser Leu Ser Pro Gly Lys
    210             215             220

<210> SEQ ID NO 70
<211> LENGTH: 220
<212> TYPE: PRT
<213> ORGANISM: Artificial Sequence
<220> FEATURE:
<223> OTHER INFORMATION: Synthetic construct
```

<400> SEQUENCE: 70

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Ala Phe Pro Pro Trp Glu Val Lys Phe
            35                  40                  45

Asn Trp Tyr Val Asp Gly Val Glu Val His Asn Ala Lys Thr Lys Pro
50                  55                  60

Arg Glu Glu Glu Tyr Tyr Gln Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220
```

<210> SEQ ID NO 71
<211> LENGTH: 220
<212> TYPE: PRT
<213> ORGANISM: Artificial Sequence
<220> FEATURE:
<223> OTHER INFORMATION: Synthetic construct

<400> SEQUENCE: 71

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Ala Ile Trp Pro Pro Trp Glu Val Lys Phe
            35                  40                  45

Asn Trp Tyr Val Asp Gly Val Glu Val His Asn Ala Lys Thr Lys Pro
50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125
```

```
Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 72
<211> LENGTH: 220
<212> TYPE: PRT
<213> ORGANISM: Artificial Sequence
<220> FEATURE:
<223> OTHER INFORMATION: Synthetic construct

<400> SEQUENCE: 72

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Pro Val Ala Pro Trp Glu Val Lys Phe
        35                  40                  45

Asn Trp Tyr Val Asp Gly Val Glu Val His Asn Ala Lys Thr Lys Pro
50                  55                  60

Arg Glu Glu Glu Tyr Tyr Ser Ser Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 73
<211> LENGTH: 220
<212> TYPE: PRT
<213> ORGANISM: Artificial Sequence
<220> FEATURE:
<223> OTHER INFORMATION: Synthetic construct

<400> SEQUENCE: 73
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Gln Met Pro Gln Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 74
<211> LENGTH: 220
<212> TYPE: PRT
<213> ORGANISM: Artificial Sequence
<220> FEATURE:
<223> OTHER INFORMATION: Synthetic construct

<400> SEQUENCE: 74

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Pro Gln Thr Ala Pro Trp Glu Val Lys Phe
        35                  40                  45

Asn Trp Tyr Val Asp Gly Val Glu Val His Asn Ala Lys Thr Lys Pro
    50                  55                  60

Arg Glu Glu Glu Tyr Tyr Thr Tyr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140
```

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220
```

<210> SEQ ID NO 75
<211> LENGTH: 220
<212> TYPE: PRT
<213> ORGANISM: Artificial Sequence
<220> FEATURE:
<223> OTHER INFORMATION: Synthetic construct

<400> SEQUENCE: 75

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Pro Gln Thr Pro Gln Glu Val Lys Phe
            35                  40                  45

Asn Trp Tyr Val Asp Gly Val Glu Val His Asn Ala Lys Thr Lys Pro
            50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220
```

<210> SEQ ID NO 76
<211> LENGTH: 220
<212> TYPE: PRT
<213> ORGANISM: Artificial Sequence
<220> FEATURE:
<223> OTHER INFORMATION: Synthetic construct

<400> SEQUENCE: 76

```
Pro Cys Pro Ala Pro Glu Leu Leu Gly Gly Pro Ser Val Phe Leu Phe
```

-continued

```
1               5                   10                  15
Pro Pro Lys Pro Lys Asp Thr Leu Met Ile Ser Arg Thr Pro Glu Val
                20                  25                  30

Thr Cys Val Val Val Asp Pro Gln Thr Pro Trp Glu Val Lys Phe
            35                  40                  45

Asn Trp Tyr Val Asp Gly Val Glu Val His Asn Ala Lys Thr Lys Pro
 50                  55                  60

Arg Glu Glu Glu Tyr Tyr Thr Tyr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
                210                 215                 220
```

<210> SEQ ID NO 77
<211> LENGTH: 220
<212> TYPE: PRT
<213> ORGANISM: Artificial Sequence
<220> FEATURE:
<223> OTHER INFORMATION: Synthetic construct

<400> SEQUENCE: 77

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Pro Arg Val Pro Pro Trp Glu Val Lys Phe
            35                  40                  45

Asn Trp Tyr Val Asp Gly Val Glu Val His Asn Ala Lys Thr Lys Pro
 50                  55                  60

Arg Glu Glu Glu Tyr Tyr Gln Asn Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
```

```
                145                 150                 155                 160
Glu Asn Asn Tyr Lys Thr Thr Pro Pro Val Leu Asp Ser Asp Gly Ser
                    165                 170                 175

Phe Phe Leu Tyr Ser Lys Leu Thr Val Asp Lys Ser Arg Trp Gln Gln
                    180                 185                 190

Gly Asn Val Phe Ser Cys Ser Val Met His Glu Ala Leu His Asn His
                    195                 200                 205

Tyr Thr Gln Lys Ser Leu Ser Leu Ser Pro Gly Lys
                    210                 215                 220

<210> SEQ ID NO 78
<211> LENGTH: 220
<212> TYPE: PRT
<213> ORGANISM: Artificial Sequence
<220> FEATURE:
<223> OTHER INFORMATION: Synthetic construct

<400> SEQUENCE: 78

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Pro Ser Val Pro Pro Trp Glu Val Lys Phe
            35                  40                  45

Asn Trp Tyr Val Asp Gly Val Glu Val His Asn Ala Lys Thr Lys Pro
        50                  55                  60

Arg Glu Glu Glu Tyr Tyr Ser Asn Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                    165                 170                 175

Phe Phe Leu Tyr Ser Lys Leu Thr Val Asp Lys Ser Arg Trp Gln Gln
                    180                 185                 190

Gly Asn Val Phe Ser Cys Ser Val Met His Glu Ala Leu His Asn His
                    195                 200                 205

Tyr Thr Gln Lys Ser Leu Ser Leu Ser Pro Gly Lys
                    210                 215                 220

<210> SEQ ID NO 79
<211> LENGTH: 220
<212> TYPE: PRT
<213> ORGANISM: Artificial Sequence
<220> FEATURE:
<223> OTHER INFORMATION: Synthetic construct

<400> SEQUENCE: 79

Pro Cys Pro Ala Pro Glu Leu Leu Gly Gly Pro Ser Val Phe Leu Phe
1               5                   10                  15
```

```
Pro Pro Lys Pro Lys Asp Thr Leu Met Ile Ser Arg Thr Pro Glu Val
            20                  25                  30

Thr Cys Val Val Val Asp Met Leu Trp Pro Val Pro Glu Val Lys Phe
        35                  40                  45

Asn Trp Tyr Val Asp Gly Val Glu Val His Asn Ala Lys Thr Lys Pro
 50                  55                  60

Arg Glu Glu Val Tyr His Arg Pro Tyr Arg Val Val Ser Val Leu Thr
 65                  70                  75                  80

Val Leu His Gln Asp Trp Leu Asn Gly Lys Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 80
<211> LENGTH: 220
<212> TYPE: PRT
<213> ORGANISM: Artificial Sequence
<220> FEATURE:
<223> OTHER INFORMATION: Synthetic construct

<400> SEQUENCE: 80

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Met Leu Trp Pro Val Pro Glu Val Lys Phe
        35                  40                  45

Asn Trp Tyr Val Asp Gly Val Glu Val His Asn Ala Lys Thr Lys Pro
 50                  55                  60

Arg Glu Glu Thr Tyr His Asn Pro Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160
```

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 81
<211> LENGTH: 220
<212> TYPE: PRT
<213> ORGANISM: Artificial Sequence
<220> FEATURE:
<223> OTHER INFORMATION: Synthetic construct

<400> SEQUENCE: 81

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Met Glu Trp Pro Val Thr Glu Val Lys Phe
        35                  40                  45

Asn Trp Tyr Val Asp Gly Val Glu Val His Asn Ala Lys Thr Lys Pro
    50                  55                  60

Arg Glu Glu Thr Tyr His Asn Pro Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 82
<211> LENGTH: 220
<212> TYPE: PRT
<213> ORGANISM: Artificial Sequence
<220> FEATURE:
<223> OTHER INFORMATION: Synthetic construct

<400> SEQUENCE: 82

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Met Leu Trp Pro Val Pro Glu Val Lys Phe
              35                  40                  45

Asn Trp Tyr Val Asp Gly Val Glu Val His Asn Ala Lys Thr Lys Pro
 50                  55                  60

Arg Glu Glu Thr Tyr His His Pro Tyr Arg Val Val Ser Val Leu Thr
 65                  70                  75                  80

Val Leu His Gln Asp Trp Leu Asn Gly Lys Glu Tyr Lys Cys Lys Val
              85                  90                  95

Ser Asn Lys Ala Leu Pro Ala Pro Ile Glu Lys Thr Ile Ser Lys Ala
             100                 105                 110

Lys Gly Gln Pro Arg Glu Pro Gln Val Tyr Thr Leu Pro Pro Ser Arg
             115                 120                 125

Asp Glu Leu Thr Lys Asn Gln Val Ser Leu Thr Cys Leu Val Lys Gly
             130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                 165                 170                 175

Phe Phe Leu Tyr Ser Lys Leu Thr Val Asp Lys Ser Arg Trp Gln Gln
             180                 185                 190

Gly Asn Val Phe Ser Cys Ser Val Met His Glu Ala Leu His Asn His
             195                 200                 205

Tyr Thr Gln Lys Ser Leu Ser Leu Ser Pro Gly Lys
             210                 215                 220

<210> SEQ ID NO 83
<211> LENGTH: 220
<212> TYPE: PRT
<213> ORGANISM: Artificial Sequence
<220> FEATURE:
<223> OTHER INFORMATION: Synthetic construct

<400> SEQUENCE: 83

Pro Cys Pro Ala Pro Glu Leu Leu Gly Gly Pro Ser Val Phe Leu Phe
1               5                  10                  15

Pro Pro Lys Pro Lys Asp Thr Leu Met Ile Ser Arg Thr Pro Glu Val
             20                  25                  30

Thr Cys Val Val Val Asp Asp Asp Leu Thr Phe Gln Glu Val Lys Phe
              35                  40                  45

Asn Trp Tyr Val Asp Gly Val Glu Val His Asn Ala Lys Thr Lys Pro
 50                  55                  60

Arg Glu Glu Val Tyr Val Thr Pro Tyr Arg Val Val Ser Val Leu Thr
 65                  70                  75                  80

Val Leu His Gln Asp Trp Leu Asn Gly Lys Glu Tyr Lys Cys Lys Val
              85                  90                  95

Ser Asn Lys Ala Leu Pro Ala Pro Ile Glu Lys Thr Ile Ser Lys Ala
             100                 105                 110

Lys Gly Gln Pro Arg Glu Pro Gln Val Tyr Thr Leu Pro Pro Ser Arg
             115                 120                 125

Asp Glu Leu Thr Lys Asn Gln Val Ser Leu Thr Cys Leu Val Lys Gly
             130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                 165                 170                 175

```
Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 84
<211> LENGTH: 220
<212> TYPE: PRT
<213> ORGANISM: Artificial Sequence
<220> FEATURE:
<223> OTHER INFORMATION: Synthetic construct

<400> SEQUENCE: 84

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Asp Asp Leu Thr Phe Gln Glu Val Lys Phe
            35                  40                  45

Asn Trp Tyr Val Asp Gly Val Glu Val His Asn Ala Lys Thr Lys Pro
        50                  55                  60

Arg Glu Glu Leu Tyr Val Thr Pro Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 85
<211> LENGTH: 220
<212> TYPE: PRT
<213> ORGANISM: Artificial Sequence
<220> FEATURE:
<223> OTHER INFORMATION: Synthetic construct

<400> SEQUENCE: 85

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Ala Tyr Gly Asp Pro Glu Glu Val Lys Phe
```

```
            35                  40                  45
Asn Trp Tyr Val Asp Gly Val Glu Val His Asn Ala Lys Thr Lys Pro
 50                  55                  60
Arg Glu Glu Trp Tyr Asp Val Pro Tyr Arg Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Glu Trp Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
            180                 185                 190
Gly Asn Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 86
<211> LENGTH: 220
<212> TYPE: PRT
<213> ORGANISM: Artificial Sequence
<220> FEATURE:
<223> OTHER INFORMATION: Synthetic construct

<400> SEQUENCE: 86

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser Pro Pro Arg Met Val Lys Phe
            35                  40                  45
Asn Trp Tyr Val Asp Gly Val Glu Val His Asn Ala Lys Thr Lys Ser
 50                  55                  60
Leu Thr Ser Gln His Asn Ser Thr Val Arg Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Glu Trp Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
```

```
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 87
<211> LENGTH: 220
<212> TYPE: PRT
<213> ORGANISM: Artificial Sequence
<220> FEATURE:
<223> OTHER INFORMATION: Synthetic construct

<400> SEQUENCE: 87

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser Val Pro Pro Trp Met Val Lys Phe
        35                  40                  45

Asn Trp Tyr Val Asp Gly Val Glu Val His Asn Ala Lys Thr Lys Ser
    50                  55                  60

Leu Thr Ser Gln His Asn Ser Thr Val Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 88
<211> LENGTH: 220
<212> TYPE: PRT
<213> ORGANISM: Artificial Sequence
<220> FEATURE:
<223> OTHER INFORMATION: Synthetic construct

<400> SEQUENCE: 88

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser Asp Met Trp Glu Tyr Val Lys Phe
        35                  40                  45
```

Asn Trp Tyr Val Asp Gly Val Glu Val His Asn Ala Lys Thr Lys Pro
            50                  55                  60

Trp Val Lys Gln Leu Asn Ser Thr Trp Arg Val Val Ser Val Leu Thr
 65                  70                  75                  80

Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
            210                 215                 220

<210> SEQ ID NO 89
<211> LENGTH: 220
<212> TYPE: PRT
<213> ORGANISM: Artificial Sequence
<220> FEATURE:
<223> OTHER INFORMATION: Synthetic construct

<400> SEQUENCE: 89

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                20                  25                  30

Thr Cys Val Val Val Asp Val Ser Asp Asp Trp Thr Trp Val Lys Phe
            35                  40                  45

Asn Trp Tyr Val Asp Gly Val Glu Val His Asn Ala Lys Thr Lys Pro
 50                  55                  60

Trp Ile Ala Gln Pro Asn Ser Thr Trp Arg Val Val Ser Val Leu Thr
 65                  70                  75                  80

Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
         195                 200                 205

Tyr Thr Gln Lys Ser Leu Ser Leu Ser Pro Gly Lys
    210                 215                 220

<210> SEQ ID NO 90
<211> LENGTH: 220
<212> TYPE: PRT
<213> ORGANISM: Artificial Sequence
<220> FEATURE:
<223> OTHER INFORMATION: Synthetic construct

<400> SEQUENCE: 90

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser Asp Asp Trp Glu Trp Val Lys Phe
        35                  40                  45

Asn Trp Tyr Val Asp Gly Val Glu Val His Asn Ala Lys Thr Lys Pro
    50                  55                  60

Trp Lys Leu Gln Leu Asn Ser Thr Trp Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 91
<211> LENGTH: 220
<212> TYPE: PRT
<213> ORGANISM: Artificial Sequence
<220> FEATURE:
<223> OTHER INFORMATION: Synthetic construct

<400> SEQUENCE: 91

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Val Trp Phe
        35                  40                  45

Tyr Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Ser Val
                85                  90                  95

Val Asn Ile Ala Leu Trp Trp Ser Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 92
<211> LENGTH: 220
<212> TYPE: PRT
<213> ORGANISM: Artificial Sequence
<220> FEATURE:
<223> OTHER INFORMATION: Synthetic construct

<400> SEQUENCE: 92

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Val Val Gly Phe
            35                  40                  45

Arg Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Arg Val
                85                  90                  95

Ser Asn Ser Ala Leu Thr Trp Lys Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 93
<211> LENGTH: 220
<212> TYPE: PRT
<213> ORGANISM: Artificial Sequence
<220> FEATURE:
<223> OTHER INFORMATION: Synthetic construct

<400> SEQUENCE: 93

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Val Gly Phe
        35                  40                  45

Arg Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Arg Val
                85                  90                  95

Ser Asn Ser Ala Leu Ser Trp Arg Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 94
<211> LENGTH: 220
<212> TYPE: PRT
<213> ORGANISM: Artificial Sequence
<220> FEATURE:
<223> OTHER INFORMATION: Synthetic construct

<400> SEQUENCE: 94

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Ile Val Gly Phe
        35                  40                  45

Arg Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr

```
                65                  70                  75                  80
Val Leu His Gln Asp Trp Leu Asn Gly Lys Glu Tyr Lys Cys Arg Val
                    85                  90                  95

Ser Asn Ser Ala Leu Arg Trp Arg Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 95
<211> LENGTH: 220
<212> TYPE: PRT
<213> ORGANISM: Artificial Sequence
<220> FEATURE:
<223> OTHER INFORMATION: Synthetic construct

<400> SEQUENCE: 95

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Ala Val Gly Phe
            35                  40                  45

Glu Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Gln Val
                85                  90                  95

Phe Asn Trp Ala Leu Asp Trp Val Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
```

<210> SEQ ID NO 96
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(63)
<223> OTHER INFORMATION: Xaa can be any naturally occurring amino acid

<400> SEQUENCE: 96

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Xaa Phe
        35                  40                  45

Xaa Trp Tyr Val Asp Gly Val Xaa Val Xaa Xaa Xaa Xaa Xaa Xaa Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 97
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature

```
<222> LOCATION: (39)..(44)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(72)
<223> OTHER INFORMATION: Xaa can be any naturally occurring amino acid

<400> SEQUENCE: 97

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Xaa Xaa Xaa Xaa Xaa Xaa Glu Val Lys Phe
        35                  40                  45

Asn Trp Tyr Val Asp Gly Val Glu Val His Asn Ala Lys Thr Lys Pro
    50                  55                  60

Arg Glu Glu Xaa Tyr Xaa Xaa Xaa Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 98
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (41)..(45)
<223> OTHER INFORMATION: Xaa can be any naturally occurring amino acid
<220> FEATURE:
<221> NAME/KEY: misc_feature
<222> LOCATION: (65)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
```

<400> SEQUENCE: 98

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser Xaa Xaa Xaa Xaa Val Lys Phe
        35                  40                  45

Asn Trp Tyr Val Asp Gly Val Glu Val His Asn Ala Lys Thr Lys Pro
    50                  55                  60

Xaa Xaa Xaa Gln Xaa Asn Ser Thr Xaa Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 99
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (102)..(104)
<223> OTHER INFORMATION: Xaa can be any naturally occurring amino acid

<400> SEQUENCE: 99

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Xaa Val Xaa Phe
        35                  40                  45

Xaa Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Xaa Val
                85                  90                  95

Xaa Asn Xaa Ala Leu Xaa Xaa Xaa Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
210                 215                 220

<210> SEQ ID NO 100
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (118)..(120)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (210)..(213)
<223> OTHER INFORMATION: Xaa can be any naturally occurring amino acid

<400> SEQUENCE: 100

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
50                  55                  60

```
Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Xaa Xaa Xaa Val Xaa Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Xaa Xaa Xaa Xaa Leu Ser Leu Ser Pro Gly Lys
    210                 215                 220

<210> SEQ ID NO 101
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (127)..(129)
<223> OTHER INFORMATION: Xaa can be any naturally occurring amino acid
<220> FEATURE:
<221> NAME/KEY: misc_feature
<222> LOCATION: (131)..(134)
<223> OTHER INFORMATION: Xaa can be any naturally occurring amino acid

<400> SEQUENCE: 101

Pro Cys Pro Ala Pro Glu Leu Leu Gly Gly Pro Ser Val Phe Leu Phe
  1               5                  10                  15

Pro Pro Lys Pro Lys Asp Thr Leu Met Ile Ser Arg Thr Pro Glu Val
             20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Phe Asp Tyr Val Thr Thr Leu Pro Pro Xaa Xaa
        115                 120                 125

Xaa Glu Xaa Xaa Xaa Xaa Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
```

```
                  165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe Ser Asp Leu Ser Leu Ser Pro Gly Lys
    210                 215                 220

<210> SEQ ID NO 102
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid

<400> SEQUENCE: 102

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Asp Tyr Xaa Thr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Xaa Xaa His
        195                 200                 205

Xaa Gly Phe Ser Asp Leu Ser Leu Ser Pro Gly Lys
    210                 215                 220

<210> SEQ ID NO 103
<211> LENGTH: 220
<212> TYPE: PRT
```

<213> ORGANISM: Artificial Sequence
<220> FEATURE:
<223> OTHER INFORMATION: Synthetic construct
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (217)..(220)
<223> OTHER INFORMATION: Xaa can be any naturally occurring amino acid

<400> SEQUENCE: 103

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Asp Tyr Val Thr Thr Leu Xaa Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Gly Phe Ser Asp Xaa Ser Leu Xaa Xaa Xaa Xaa
    210                 215                 220

<210> SEQ ID NO 104
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid

```
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid

<400> SEQUENCE: 104
```

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65              70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Xaa Pro Xaa Phe Asp Tyr Val Thr Thr Leu Pro Pro Ser Arg
            115                 120                 125

Asp Glu Leu Thr Lys Asn Gln Val Ser Leu Thr Cys Leu Val Xaa Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Xaa Gly Xaa
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Gly Phe Ser Asp Leu Ser Leu Ser Pro Gly Lys
    210                 215                 220

```
<210> SEQ ID NO 105
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (157)..(158)
<223> OTHER INFORMATION: Xaa can be any naturally occurring amino acid
<220> FEATURE:
<221> NAME/KEY: misc_feature
<222> LOCATION: (193)..(195)
<223> OTHER INFORMATION: Xaa can be any naturally occurring amino acid

<400> SEQUENCE: 105
```

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val

```
                20                  25                  30
Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Phe Asp Tyr Val Thr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Xaa Ser Xaa Xaa Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Xaa Xaa Xaa Phe Ser Cys Ser Val Met His Glu Ala Leu His Asn His
        195                 200                 205

Tyr Gly Phe Ser Asp Leu Ser Leu Ser Pro Gly Lys
    210                 215                 220

<210> SEQ ID NO 106
<211> LENGTH: 220
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(163)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid

<400> SEQUENCE: 106

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60
```

```
Arg Glu Glu Gln Tyr Asn Ser Thr Tyr Arg Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Ser Xaa Gly Xaa Xaa
145                 150                 155                 160

Xaa Xaa Xaa Tyr Lys Thr Thr Pro Pro Val Leu Asp Ser Asp Gly Ser
                165                 170                 175

Phe Phe Leu Tyr Ser Lys Leu Thr Val Xaa Lys Ser Xaa Trp Gln Gln
            180                 185                 190

Gly Xaa Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 107
<211> LENGTH: 181
<212> TYPE: PRT
<213> ORGANISM: Homo sapiens

<400> SEQUENCE: 107

Asn Ser Val Ile Ile Val Asp Lys Asn Gly Arg Leu Val Tyr Leu Val
 1               5                  10                  15

Glu Asn Pro Gly Gly Tyr Val Ala Tyr Ser Lys Ala Ala Thr Val Thr
                20                  25                  30

Gly Lys Leu Val His Ala Asn Phe Gly Thr Lys Lys Asp Phe Glu Asp
            35                  40                  45

Leu Tyr Thr Pro Val Asn Gly Ser Ile Val Ile Val Arg Ala Gly Lys
 50                  55                  60

Ile Thr Phe Ala Glu Lys Val Ala Asn Ala Glu Ser Leu Asn Ala Ile
 65                  70                  75                  80

Gly Val Leu Ile Tyr Met Asp Gln Thr Lys Phe Pro Ile Val Asn Ala
                85                  90                  95

Glu Leu Ser Phe Phe Gly His Ala His Leu Gly Thr Gly Asp Pro Tyr
            100                 105                 110

Thr Pro Gly Phe Pro Ser Phe Asn His Thr Gln Phe Pro Pro Ser Arg
            115                 120                 125

Ser Ser Gly Leu Pro Asn Ile Pro Val Gln Thr Ile Ser Arg Ala Ala
        130                 135                 140

Ala Glu Lys Leu Phe Gly Asn Met Glu Gly Asp Cys Pro Ser Asp Trp
145                 150                 155                 160

Lys Thr Asp Ser Thr Cys Arg Met Val Thr Ser Glu Ser Lys Asn Val
                165                 170                 175

Lys Leu Thr Val Ser
            180

<210> SEQ ID NO 108
<211> LENGTH: 181
<212> TYPE: PRT
```

<213> ORGANISM: Macaca fascicularis

<400> SEQUENCE: 108

Asn Ser Val Ile Ile Val Asp Lys Asn Gly Leu Val Tyr Leu Val
1               5                   10                  15

Glu Asn Pro Gly Gly Tyr Val Ala Tyr Ser Lys Ala Ala Thr Val Thr
            20                  25                  30

Gly Lys Leu Val His Ala Asn Phe Gly Thr Lys Lys Asp Phe Glu Asp
        35                  40                  45

Leu Asp Ser Pro Val Asn Gly Ser Ile Val Ile Val Arg Ala Gly Lys
    50                  55                  60

Ile Thr Phe Ala Glu Lys Val Ala Asn Ala Glu Ser Leu Asn Ala Ile
65                  70                  75                  80

Gly Val Leu Ile Tyr Met Asp Gln Thr Lys Phe Pro Ile Val Lys Ala
                85                  90                  95

Asp Leu Ser Phe Phe Gly His Ala His Leu Gly Thr Gly Asp Pro Tyr
            100                 105                 110

Thr Pro Gly Phe Pro Ser Phe Asn His Thr Gln Phe Pro Pro Ser Gln
        115                 120                 125

Ser Ser Gly Leu Pro Asn Ile Pro Val Gln Thr Ile Ser Arg Ala Ala
    130                 135                 140

Ala Glu Lys Leu Phe Gly Asn Met Glu Gly Asp Cys Pro Ser Asp Trp
145                 150                 155                 160

Lys Thr Asp Ser Thr Cys Lys Met Val Thr Ser Glu Asn Lys Ser Val
                165                 170                 175

Lys Leu Thr Val Ser
            180

<210> SEQ ID NO 109
<211> LENGTH: 159
<212> TYPE: PRT
<213> ORGANISM: Artificial Sequence
<220> FEATURE:
<223> OTHER INFORMATION: Synthetic construct

<400> SEQUENCE: 109

Ser Ser Gly Leu Pro Asn Ile Pro Val Gln Thr Ile Ser Arg Ala Ala
1               5                   10                  15

Ala Glu Lys Leu Phe Gly Asn Met Glu Gly Asp Cys Pro Ser Asp Trp
            20                  25                  30

Lys Thr Asp Ser Thr Cys Arg Met Val Thr Ser Glu Ser Lys Asn Val
        35                  40                  45

Lys Leu Thr Val Ser Asn Asp Ser Ala Gln Asn Ser Val Ile Ile Val
    50                  55                  60

Asp Lys Asn Gly Arg Leu Val Tyr Leu Val Asn Pro Gly Gly Tyr
65                  70                  75                  80

Val Ala Tyr Ser Lys Ala Ala Thr Val Thr Gly Lys Leu Val His Ala
                85                  90                  95

Asn Phe Gly Thr Lys Lys Asp Phe Glu Asp Leu Tyr Thr Pro Val Asn
            100                 105                 110

Gly Ser Ile Val Ile Val Arg Ala Gly Lys Ile Thr Phe Ala Glu Lys
        115                 120                 125

Val Ala Asn Ala Glu Ser Leu Asn Ala Ile Gly Val Leu Ile Tyr Met
    130                 135                 140

Asp Gln Thr Lys Phe Pro Ile Val Asn Ala Glu Leu Ser Gly Pro
145                 150                 155

<210> SEQ ID NO 110
<211> LENGTH: 159
<212> TYPE: PRT
<213> ORGANISM: Artificial Sequence
<220> FEATURE:
<223> OTHER INFORMATION: Synthetic construct

<400> SEQUENCE: 110

```
Ser Ser Gly Leu Pro Asn Ile Pro Val Gln Thr Ile Ser Arg Ala Ala
1               5                   10                  15

Ala Glu Lys Leu Phe Gly Asn Met Glu Gly Asp Cys Pro Ser Asp Trp
            20                  25                  30

Lys Thr Asp Ser Thr Cys Lys Met Val Thr Ser Glu Asn Lys Ser Val
        35                  40                  45

Lys Leu Thr Val Ser Asn Asp Ser Ala Gln Asn Ser Val Ile Ile Val
    50                  55                  60

Asp Lys Asn Gly Gly Leu Val Tyr Leu Val Glu Asn Pro Gly Gly Tyr
65                  70                  75                  80

Val Ala Tyr Ser Lys Ala Ala Thr Val Thr Gly Lys Leu Val His Ala
                85                  90                  95

Asn Phe Gly Thr Lys Lys Asp Phe Glu Asp Leu Asp Ser Pro Val Asn
            100                 105                 110

Gly Ser Ile Val Ile Val Arg Ala Gly Lys Ile Thr Phe Ala Glu Lys
        115                 120                 125

Val Ala Asn Ala Glu Ser Leu Asn Ala Ile Gly Val Leu Ile Tyr Met
    130                 135                 140

Asp Gln Thr Lys Phe Pro Ile Val Lys Ala Asp Leu Ser Gly Pro
145                 150                 155
```

<210> SEQ ID NO 111
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 111

```
Val Pro Pro Xaa Met
1               5
```

<210> SEQ ID NO 112
<211> LENGTH: 4
<212> TYPE: PRT
<213> ORGANISM: Artificial Sequence
<220> FEATURE:
<223> OTHER INFORMATION: Synthetic construct

<400> SEQUENCE: 112

```
Ser Leu Thr Ser
1
```

<210> SEQ ID NO 113
<211> LENGTH: 12
<212> TYPE: PRT
<213> ORGANISM: Artificial Sequence
<220> FEATURE:
<223> OTHER INFORMATION: Synthetic construct
<220> FEATURE:

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 113

Trp Glu Ser Xaa Gly Xaa Xaa Xaa Xaa Xaa Tyr Lys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 114

Thr Val Xaa Lys Ser Xaa Trp Gln Gln Gly Xaa Val
1               5                   10

<210> SEQ ID NO 115
<211> LENGTH: 5
<212> TYPE: PRT
<213> ORGANISM: Artificial Sequence
<220> FEATURE:
<223> OTHER INFORMATION: Synthetic construct

<400> SEQUENCE: 115

Tyr Gly Thr Glu Trp
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic construct

<400> SEQUENCE: 116

Leu Gly Leu Val Trp Val Gly
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic construct

<400> SEQUENCE: 117

Tyr Gly Thr Val Trp Ser His
1               5

<210> SEQ ID NO 118
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 118

Tyr Gly Thr Glu Trp Ser Gln
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic construct

<400> SEQUENCE: 119

Val Gly Thr Pro Trp Ala Leu
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic construct

<400> SEQUENCE: 120

Tyr Gly Thr Val Trp Ser Lys
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic construct

<400> SEQUENCE: 121

Leu Gly His Val Trp Ala Val
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct

<400> SEQUENCE: 122

Met Gly His Val Trp Val Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct

<400> SEQUENCE: 123

Leu Gly Leu Val Gly Val Phe
1               5

<210> SEQ ID NO 124
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 124

Tyr Gly Thr Glu Trp Ser Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Tyr Gly Thr Glu Trp Ser Asn
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic construct

<400> SEQUENCE: 126

Leu Gly His Val Trp Val Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct

<400> SEQUENCE: 127

Leu Gly His Val Trp Val Ala
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic construct

<400> SEQUENCE: 128

Leu Gly Pro Val Trp Val His
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic construct

<400> SEQUENCE: 129

Leu Gly His Val Trp Val Asp
1               5

<210> SEQ ID NO 130
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 130

Leu Gly His Val Trp Val Asn
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic construct

<400> SEQUENCE: 131

Ala Lys Ser Thr Trp Gln Gln Gly Trp
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic construct

<400> SEQUENCE: 132

Ser Lys Ser Glu Trp Gln Gln Gly Tyr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic construct

<400> SEQUENCE: 133

Glu Lys Ser Asp Trp Gln Gln Gly His
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic construct

<400> SEQUENCE: 134

Leu Lys Ser Glu Trp Gln Gln Gly Trp
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic construct

<400> SEQUENCE: 135

Ser Lys Ser Glu Trp Gln Gln Gly Phe
1               5

<210> SEQ ID NO 136
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 136

Pro Lys Ser Thr Trp Gln Gln Gly Trp
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic construct

<400> SEQUENCE: 137

Asp Lys Ser Thr Trp Gln Gln Gly Trp
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic construct

<400> SEQUENCE: 138

Thr Lys Ser Glu Trp Gln Gln Gly Phe
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic construct

<400> SEQUENCE: 139

Ser Lys Ser Glu Trp Gln Gln Gly Trp
1               5

<210> SEQ ID NO 140
<211> LENGTH: 5
<212> TYPE: PRT
<213> ORGANISM: Artificial Sequence
<220> FEATURE:
<223> OTHER INFORMATION: Synthetic construct

<400> SEQUENCE: 140

Phe Asp Tyr Val Thr
1               5

<210> SEQ ID NO 141
<211> LENGTH: 5
<212> TYPE: PRT
<213> ORGANISM: Artificial Sequence
<220> FEATURE:
<223> OTHER INFORMATION: Synthetic construct

<400> SEQUENCE: 141

Phe Asp Met Val Thr
1               5

<210> SEQ ID NO 142
<211> LENGTH: 5
<212> TYPE: PRT
<213> ORGANISM: Artificial Sequence
<220> FEATURE:
```

<223> OTHER INFORMATION: Synthetic construct

<400> SEQUENCE: 142

Phe Glu Tyr Val Thr
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic construct

<400> SEQUENCE: 143

Phe Glu Met Val Thr
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic construct

<400> SEQUENCE: 144

Phe Glu Leu Val Thr
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic construct

<400> SEQUENCE: 145

Phe Glu Ile Val Thr
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic construct

<400> SEQUENCE: 146

Phe Asp Ile Val Thr
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic construct

<400> SEQUENCE: 147

Phe Gly Met Val Thr
1               5

<210> SEQ ID NO 148
<211> LENGTH: 5
<212> TYPE: PRT
<213> ORGANISM: Artificial Sequence
<220> FEATURE:
<223> OTHER INFORMATION: Synthetic construct

```
<400> SEQUENCE: 148

Phe Ala Asp Val Thr
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic construct

<400> SEQUENCE: 149

Phe Gly Leu Val Thr
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic construct

<400> SEQUENCE: 150

Ile Asp Tyr Val Thr
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic construct

<400> SEQUENCE: 151

Phe Lys Asp Val Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic construct

<400> SEQUENCE: 152

Phe Asp Leu Val Thr
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic construct

<400> SEQUENCE: 153

Phe Glu Leu Val Ala
1               5

<210> SEQ ID NO 154
<211> LENGTH: 4
<212> TYPE: PRT
<213> ORGANISM: Artificial Sequence
<220> FEATURE:
<223> OTHER INFORMATION: Synthetic construct
```

```
<400> SEQUENCE: 154

Gly His Phe Asp
1

<210> SEQ ID NO 155
<211> LENGTH: 4
<212> TYPE: PRT
<213> ORGANISM: Artificial Sequence
<220> FEATURE:
<223> OTHER INFORMATION: Synthetic construct

<400> SEQUENCE: 155

Gly Phe Tyr Asp
1

<210> SEQ ID NO 156
<211> LENGTH: 4
<212> TYPE: PRT
<213> ORGANISM: Artificial Sequence
<220> FEATURE:
<223> OTHER INFORMATION: Synthetic construct

<400> SEQUENCE: 156

Gly Phe Ser Asp
1

<210> SEQ ID NO 157
<211> LENGTH: 4
<212> TYPE: PRT
<213> ORGANISM: Artificial Sequence
<220> FEATURE:
<223> OTHER INFORMATION: Synthetic construct

<400> SEQUENCE: 157

Gly Phe Phe Asp
1

<210> SEQ ID NO 158
<211> LENGTH: 3
<212> TYPE: PRT
<213> ORGANISM: Artificial Sequence
<220> FEATURE:
<223> OTHER INFORMATION: Synthetic construct

<400> SEQUENCE: 158

Glu Phe Ile
1

<210> SEQ ID NO 159
<211> LENGTH: 3
<212> TYPE: PRT
<213> ORGANISM: Artificial Sequence
<220> FEATURE:
<223> OTHER INFORMATION: Synthetic construct

<400> SEQUENCE: 159

Gly Phe Val
1

<210> SEQ ID NO 160
<211> LENGTH: 3
<212> TYPE: PRT
<213> ORGANISM: Artificial Sequence
<220> FEATURE:
<223> OTHER INFORMATION: Synthetic construct

<400> SEQUENCE: 160
```

Gln Phe Asp
1

<210> SEQ ID NO 161
<211> LENGTH: 3
<212> TYPE: PRT
<213> ORGANISM: Artificial Sequence
<220> FEATURE:
<223> OTHER INFORMATION: Synthetic construct

<400> SEQUENCE: 161

Ser Phe Glu
1

<210> SEQ ID NO 162
<211> LENGTH: 3
<212> TYPE: PRT
<213> ORGANISM: Artificial Sequence
<220> FEATURE:
<223> OTHER INFORMATION: Synthetic construct

<400> SEQUENCE: 162

Ala Phe Thr
1

<210> SEQ ID NO 163
<211> LENGTH: 3
<212> TYPE: PRT
<213> ORGANISM: Artificial Sequence
<220> FEATURE:
<223> OTHER INFORMATION: Synthetic construct

<400> SEQUENCE: 163

Asn Phe Asp
1

<210> SEQ ID NO 164
<211> LENGTH: 3
<212> TYPE: PRT
<213> ORGANISM: Artificial Sequence
<220> FEATURE:
<223> OTHER INFORMATION: Synthetic construct

<400> SEQUENCE: 164

Gln Phe Val
1

<210> SEQ ID NO 165
<211> LENGTH: 3
<212> TYPE: PRT
<213> ORGANISM: Artificial Sequence
<220> FEATURE:
<223> OTHER INFORMATION: Synthetic construct

<400> SEQUENCE: 165

Gly Phe Ala
1

<210> SEQ ID NO 166
<211> LENGTH: 3
<212> TYPE: PRT
<213> ORGANISM: Artificial Sequence
<220> FEATURE:
<223> OTHER INFORMATION: Synthetic construct

<400> SEQUENCE: 166

Ser Phe Asp
1

<210> SEQ ID NO 167
<211> LENGTH: 3
<212> TYPE: PRT
<213> ORGANISM: Artificial Sequence
<220> FEATURE:
<223> OTHER INFORMATION: Synthetic construct

<400> SEQUENCE: 167

Glu Phe Thr
1

<210> SEQ ID NO 168
<211> LENGTH: 3
<212> TYPE: PRT
<213> ORGANISM: Artificial Sequence
<220> FEATURE:
<223> OTHER INFORMATION: Synthetic construct

<400> SEQUENCE: 168

Gln Phe Thr
1

<210> SEQ ID NO 169
<211> LENGTH: 3
<212> TYPE: PRT
<213> ORGANISM: Artificial Sequence
<220> FEATURE:
<223> OTHER INFORMATION: Synthetic construct

<400> SEQUENCE: 169

Gln Phe Tyr
1

<210> SEQ ID NO 170
<211> LENGTH: 3
<212> TYPE: PRT
<213> ORGANISM: Artificial Sequence
<220> FEATURE:
<223> OTHER INFORMATION: Synthetic construct

<400> SEQUENCE: 170

Tyr Phe Asp
1

<210> SEQ ID NO 171
<211> LENGTH: 3
<212> TYPE: PRT
<213> ORGANISM: Artificial Sequence
<220> FEATURE:
<223> OTHER INFORMATION: Synthetic construct

<400> SEQUENCE: 171

Trp Phe Glu
1

<210> SEQ ID NO 172
<211> LENGTH: 8
<212> TYPE: PRT
<213> ORGANISM: Artificial Sequence
<220> FEATURE:
<223> OTHER INFORMATION: Synthetic construct

<400> SEQUENCE: 172

Asp Val Arg Tyr Glu Trp Gln Leu

```
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic construct

<400> SEQUENCE: 173

Pro Val Ser Trp Glu Trp Tyr Trp
1               5

<210> SEQ ID NO 174
<211> LENGTH: 8
<212> TYPE: PRT
<213> ORGANISM: Artificial Sequence
<220> FEATURE:
<223> OTHER INFORMATION: Synthetic construct

<400> SEQUENCE: 174

Met Val Arg Arg Glu Trp His Arg
1               5

<210> SEQ ID NO 175
<211> LENGTH: 8
<212> TYPE: PRT
<213> ORGANISM: Artificial Sequence
<220> FEATURE:
<223> OTHER INFORMATION: Synthetic construct

<400> SEQUENCE: 175

Pro Val Arg Trp Glu Trp Gln Trp
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic construct

<400> SEQUENCE: 176

Pro Val Arg Trp Glu Trp Gln Asn
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic construct

<400> SEQUENCE: 177

Leu Val Arg Arg Glu Trp His Arg
1               5

<210> SEQ ID NO 178
<211> LENGTH: 8
<212> TYPE: PRT
<213> ORGANISM: Artificial Sequence
<220> FEATURE:
<223> OTHER INFORMATION: Synthetic construct

<400> SEQUENCE: 178

Ala Val Arg Trp Glu Trp Ile Arg
1               5
```

```
<210> SEQ ID NO 179
<211> LENGTH: 8
<212> TYPE: PRT
<213> ORGANISM: Artificial Sequence
<220> FEATURE:
<223> OTHER INFORMATION: Synthetic construct

<400> SEQUENCE: 179

Glu Val Ala Trp Glu Trp Phe Trp
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic construct

<400> SEQUENCE: 180

Asn Val Arg Val Glu Trp Gln Tyr
1               5

<210> SEQ ID NO 181
<211> LENGTH: 8
<212> TYPE: PRT
<213> ORGANISM: Artificial Sequence
<220> FEATURE:
<223> OTHER INFORMATION: Synthetic construct

<400> SEQUENCE: 181

Glu Val Arg Arg Glu Trp Val Arg
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic construct

<400> SEQUENCE: 182

Leu Val Arg Arg Glu Trp Gln Arg
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic construct

<400> SEQUENCE: 183

Asp Val Arg Tyr Glu Trp Tyr Tyr
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic construct

<400> SEQUENCE: 184

Asp Val Arg Tyr Glu Trp Val Arg
1               5
```

<210> SEQ ID NO 185
<211> LENGTH: 8
<212> TYPE: PRT
<213> ORGANISM: Artificial Sequence
<220> FEATURE:
<223> OTHER INFORMATION: Synthetic construct

<400> SEQUENCE: 185

Asn Val Arg Arg Glu Trp His Arg
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic construct

<400> SEQUENCE: 186

Phe Val Gly Val Ala Tyr Asp Val
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic construct

<400> SEQUENCE: 187

Pro Gln Thr Pro Pro Trp
1               5

<210> SEQ ID NO 188
<211> LENGTH: 6
<212> TYPE: PRT
<213> ORGANISM: Artificial Sequence
<220> FEATURE:
<223> OTHER INFORMATION: Synthetic construct

<400> SEQUENCE: 188

Pro Pro Ser Pro Pro Trp
1               5

<210> SEQ ID NO 189
<211> LENGTH: 6
<212> TYPE: PRT
<213> ORGANISM: Artificial Sequence
<220> FEATURE:
<223> OTHER INFORMATION: Synthetic construct

<400> SEQUENCE: 189

Phe Arg Gly Pro Pro Trp
1               5

<210> SEQ ID NO 190
<211> LENGTH: 6
<212> TYPE: PRT
<213> ORGANISM: Artificial Sequence
<220> FEATURE:
<223> OTHER INFORMATION: Synthetic construct

<400> SEQUENCE: 190

Pro Gln Thr Val Pro Trp
1               5

```
<210> SEQ ID NO 191
<211> LENGTH: 6
<212> TYPE: PRT
<213> ORGANISM: Artificial Sequence
<220> FEATURE:
<223> OTHER INFORMATION: Synthetic construct

<400> SEQUENCE: 191

Pro Lys Met Pro Pro Trp
1               5

<210> SEQ ID NO 192
<211> LENGTH: 6
<212> TYPE: PRT
<213> ORGANISM: Artificial Sequence
<220> FEATURE:
<223> OTHER INFORMATION: Synthetic construct

<400> SEQUENCE: 192

Pro Pro Val Pro Pro Trp
1               5

<210> SEQ ID NO 193
<211> LENGTH: 6
<212> TYPE: PRT
<213> ORGANISM: Artificial Sequence
<220> FEATURE:
<223> OTHER INFORMATION: Synthetic construct

<400> SEQUENCE: 193

Pro Ala Phe Pro Pro Trp
1               5

<210> SEQ ID NO 194
<211> LENGTH: 6
<212> TYPE: PRT
<213> ORGANISM: Artificial Sequence
<220> FEATURE:
<223> OTHER INFORMATION: Synthetic construct

<400> SEQUENCE: 194

Ala Ile Trp Pro Pro Trp
1               5

<210> SEQ ID NO 195
<211> LENGTH: 6
<212> TYPE: PRT
<213> ORGANISM: Artificial Sequence
<220> FEATURE:
<223> OTHER INFORMATION: Synthetic construct

<400> SEQUENCE: 195

Pro Pro Val Ala Pro Trp
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic construct

<400> SEQUENCE: 196

Pro Gln Met Pro Pro Gln
1               5

<210> SEQ ID NO 197
```

```
<211> LENGTH: 6
<212> TYPE: PRT
<213> ORGANISM: Artificial Sequence
<220> FEATURE:
<223> OTHER INFORMATION: Synthetic construct

<400> SEQUENCE: 197

Pro Gln Thr Ala Pro Trp
1               5

<210> SEQ ID NO 198
<211> LENGTH: 6
<212> TYPE: PRT
<213> ORGANISM: Artificial Sequence
<220> FEATURE:
<223> OTHER INFORMATION: Synthetic construct

<400> SEQUENCE: 198

Pro Gln Thr Pro Pro Gln
1               5

<210> SEQ ID NO 199
<211> LENGTH: 6
<212> TYPE: PRT
<213> ORGANISM: Artificial Sequence
<220> FEATURE:
<223> OTHER INFORMATION: Synthetic construct

<400> SEQUENCE: 199

Pro Arg Val Pro Pro Trp
1               5

<210> SEQ ID NO 200
<211> LENGTH: 6
<212> TYPE: PRT
<213> ORGANISM: Artificial Sequence
<220> FEATURE:
<223> OTHER INFORMATION: Synthetic construct

<400> SEQUENCE: 200

Pro Ser Val Pro Pro Trp
1               5

<210> SEQ ID NO 201
<211> LENGTH: 6
<212> TYPE: PRT
<213> ORGANISM: Artificial Sequence
<220> FEATURE:
<223> OTHER INFORMATION: Synthetic construct

<400> SEQUENCE: 201

Met Leu Trp Pro Val Pro
1               5

<210> SEQ ID NO 202
<211> LENGTH: 6
<212> TYPE: PRT
<213> ORGANISM: Artificial Sequence
<220> FEATURE:
<223> OTHER INFORMATION: Synthetic construct

<400> SEQUENCE: 202

Met Glu Trp Pro Val Thr
1               5

<210> SEQ ID NO 203
<211> LENGTH: 6
```

```
<212> TYPE: PRT
<213> ORGANISM: Artificial Sequence
<220> FEATURE:
<223> OTHER INFORMATION: Synthetic construct

<400> SEQUENCE: 203

Asp Asp Leu Thr Phe Gln
1               5

<210> SEQ ID NO 204
<211> LENGTH: 6
<212> TYPE: PRT
<213> ORGANISM: Artificial Sequence
<220> FEATURE:
<223> OTHER INFORMATION: Synthetic construct

<400> SEQUENCE: 204

Ala Tyr Gly Asp Pro Glu
1               5

<210> SEQ ID NO 205
<211> LENGTH: 5
<212> TYPE: PRT
<213> ORGANISM: Artificial Sequence
<220> FEATURE:
<223> OTHER INFORMATION: Synthetic construct

<400> SEQUENCE: 205

Glu Tyr Tyr Thr Tyr
1               5

<210> SEQ ID NO 206
<211> LENGTH: 5
<212> TYPE: PRT
<213> ORGANISM: Artificial Sequence
<220> FEATURE:
<223> OTHER INFORMATION: Synthetic construct

<400> SEQUENCE: 206

Glu Tyr Tyr Ser Asn
1               5

<210> SEQ ID NO 207
<211> LENGTH: 5
<212> TYPE: PRT
<213> ORGANISM: Artificial Sequence
<220> FEATURE:
<223> OTHER INFORMATION: Synthetic construct

<400> SEQUENCE: 207

Glu Tyr Tyr His Asp
1               5

<210> SEQ ID NO 208
<211> LENGTH: 5
<212> TYPE: PRT
<213> ORGANISM: Artificial Sequence
<220> FEATURE:
<223> OTHER INFORMATION: Synthetic construct

<400> SEQUENCE: 208

Glu Tyr Tyr Gln Asn
1               5

<210> SEQ ID NO 209
<211> LENGTH: 5
<212> TYPE: PRT
```

```
<213> ORGANISM: Artificial Sequence
<220> FEATURE:
<223> OTHER INFORMATION: Synthetic construct

<400> SEQUENCE: 209

Glu Tyr Tyr Ser Ser
1               5

<210> SEQ ID NO 210
<211> LENGTH: 5
<212> TYPE: PRT
<213> ORGANISM: Artificial Sequence
<220> FEATURE:
<223> OTHER INFORMATION: Synthetic construct

<400> SEQUENCE: 210

Val Tyr His Arg Pro
1               5

<210> SEQ ID NO 211
<211> LENGTH: 5
<212> TYPE: PRT
<213> ORGANISM: Artificial Sequence
<220> FEATURE:
<223> OTHER INFORMATION: Synthetic construct

<400> SEQUENCE: 211

Thr Tyr His Asn Pro
1               5

<210> SEQ ID NO 212
<211> LENGTH: 5
<212> TYPE: PRT
<213> ORGANISM: Artificial Sequence
<220> FEATURE:
<223> OTHER INFORMATION: Synthetic construct

<400> SEQUENCE: 212

Thr Tyr His His Pro
1               5

<210> SEQ ID NO 213
<211> LENGTH: 5
<212> TYPE: PRT
<213> ORGANISM: Artificial Sequence
<220> FEATURE:
<223> OTHER INFORMATION: Synthetic construct

<400> SEQUENCE: 213

Val Tyr Val Thr Pro
1               5

<210> SEQ ID NO 214
<211> LENGTH: 5
<212> TYPE: PRT
<213> ORGANISM: Artificial Sequence
<220> FEATURE:
<223> OTHER INFORMATION: Synthetic construct

<400> SEQUENCE: 214

Leu Tyr Val Thr Pro
1               5

<210> SEQ ID NO 215
<211> LENGTH: 5
<212> TYPE: PRT
<213> ORGANISM: Artificial Sequence
```

```
<220> FEATURE:
<223> OTHER INFORMATION: Synthetic construct

<400> SEQUENCE: 215

Trp Tyr Asp Val Pro
1               5

<210> SEQ ID NO 216
<211> LENGTH: 5
<212> TYPE: PRT
<213> ORGANISM: Artificial Sequence
<220> FEATURE:
<223> OTHER INFORMATION: Synthetic construct

<400> SEQUENCE: 216

Val Pro Pro Arg Met
1               5

<210> SEQ ID NO 217
<211> LENGTH: 5
<212> TYPE: PRT
<213> ORGANISM: Artificial Sequence
<220> FEATURE:
<223> OTHER INFORMATION: Synthetic construct

<400> SEQUENCE: 217

Val Pro Pro Trp Met
1               5

<210> SEQ ID NO 218
<211> LENGTH: 5
<212> TYPE: PRT
<213> ORGANISM: Artificial Sequence
<220> FEATURE:
<223> OTHER INFORMATION: Synthetic construct

<400> SEQUENCE: 218

Asp Met Trp Glu Tyr
1               5

<210> SEQ ID NO 219
<211> LENGTH: 5
<212> TYPE: PRT
<213> ORGANISM: Artificial Sequence
<220> FEATURE:
<223> OTHER INFORMATION: Synthetic construct

<400> SEQUENCE: 219

Asp Asp Trp Thr Trp
1               5

<210> SEQ ID NO 220
<211> LENGTH: 5
<212> TYPE: PRT
<213> ORGANISM: Artificial Sequence
<220> FEATURE:
<223> OTHER INFORMATION: Synthetic construct

<400> SEQUENCE: 220

Asp Asp Trp Glu Trp
1               5

<210> SEQ ID NO 221
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 221

Leu Thr Ser Gln His Asn Ser Thr Val
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic construct

<400> SEQUENCE: 222

Trp Val Lys Gln Leu Asn Ser Thr Trp
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic construct

<400> SEQUENCE: 223

Trp Ile Ala Gln Pro Asn Ser Thr Trp
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic construct

<400> SEQUENCE: 224

Trp Lys Leu Gln Leu Asn Ser Thr Trp
1               5

<210> SEQ ID NO 225
<211> LENGTH: 5
<212> TYPE: PRT
<213> ORGANISM: Artificial Sequence
<220> FEATURE:
<223> OTHER INFORMATION: Synthetic construct

<400> SEQUENCE: 225

Trp Val Trp Phe Tyr
1               5

<210> SEQ ID NO 226
<211> LENGTH: 5
<212> TYPE: PRT
<213> ORGANISM: Artificial Sequence
<220> FEATURE:
<223> OTHER INFORMATION: Synthetic construct

<400> SEQUENCE: 226

Val Val Gly Phe Arg
1               5

<210> SEQ ID NO 227
<211> LENGTH: 5
<212> TYPE: PRT
<213> ORGANISM: Artificial Sequence
<220> FEATURE:
<223> OTHER INFORMATION: Synthetic construct

```
<400> SEQUENCE: 227

Ile Val Gly Phe Arg
1               5

<210> SEQ ID NO 228
<211> LENGTH: 5
<212> TYPE: PRT
<213> ORGANISM: Artificial Sequence
<220> FEATURE:
<223> OTHER INFORMATION: Synthetic construct

<400> SEQUENCE: 228

Ala Val Gly Phe Glu
1               5

<210> SEQ ID NO 229
<211> LENGTH: 10
<212> TYPE: PRT
<213> ORGANISM: Artificial Sequence
<220> FEATURE:
<223> OTHER INFORMATION: Synthetic construct

<400> SEQUENCE: 229

Ser Val Val Asn Ile Ala Leu Trp Trp Ser
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Synthetic construct

<400> SEQUENCE: 230

Arg Val Ser Asn Ser Ala Leu Thr Trp Lys
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Synthetic construct

<400> SEQUENCE: 231

Arg Val Ser Asn Ser Ala Leu Ser Trp Arg
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Synthetic construct

<400> SEQUENCE: 232

Arg Val Ser Asn Ser Ala Leu Arg Trp Arg
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Synthetic construct
```

<400> SEQUENCE: 233

Gln Val Phe Asn Trp Ala Leu Asp Trp Val
1               5                   10

<210> SEQ ID NO 234
<211> LENGTH: 15
<212> TYPE: PRT
<213> ORGANISM: Homo sapiens

<400> SEQUENCE: 234

Glu Pro Lys Ser Cys Asp Lys Thr His Thr Cys Pro Pro Cys Pro
1               5                   10                  15

<210> SEQ ID NO 235
<211> LENGTH: 760
<212> TYPE: PRT
<213> ORGANISM: Homo sapiens

<400> SEQUENCE: 235

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65              70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
130             135                 140

Lys Leu Leu Asn Glu Asn Ser Tyr Val Pro Arg Glu Ala Gly Ser Gln
145             150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
210             215                 220

Ala Ala Thr Val Thr Gly Lys Leu Val His Ala Asn Phe Gly Thr Lys
225             230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly

-continued

```
                290                 295                 300
Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
        370                 375                 380

Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
            405                 410                 415

Ala Lys Ser Gly Val Gly Thr Ala Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
        450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
            485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720
```

```
Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```

<210> SEQ ID NO 236
<211> LENGTH: 220
<212> TYPE: PRT
<213> ORGANISM: Artificial Sequence
<220> FEATURE:
<223> OTHER INFORMATION: Synthetic construct

<400> SEQUENCE: 236

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 237
<211> LENGTH: 220
<212> TYPE: PRT
<213> ORGANISM: Artificial Sequence
<220> FEATURE:
<223> OTHER INFORMATION: Synthetic construct

<400> SEQUENCE: 237

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
```

```
                 35                  40                  45
Asn Trp Tyr Val Asp Gly Val Glu Val His Asn Ala Lys Thr Lys Pro
             50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Thr Cys Leu Val Lys Gly
            130                 135                 140
Phe Tyr Pro Ser Asp Ile Ala Val Glu Trp Ser Tyr Gly Thr Glu
145                 150                 155                 160
Trp Ser Ser Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
            180                 185                 190
Gly Phe Val Phe Ser Cys Ser Val Met His Glu Ala Leu His Asn His
            195                 200                 205
Tyr Thr Gln Lys Ser Leu Ser Leu Ser Pro Gly Lys
            210                 215                 220

<210> SEQ ID NO 238
<211> LENGTH: 220
<212> TYPE: PRT
<213> ORGANISM: Artificial Sequence
<220> FEATURE:
<223> OTHER INFORMATION: Synthetic construct

<400> SEQUENCE: 238

Pro Cys Pro Ala Pro Glu Leu Leu Gly Gly Pro Ser Val Phe Leu Phe
 1               5                  10                  15
Pro Pro Lys Pro Lys Asp Thr Leu Met Ile Ser Arg Thr Pro Glu Val
             20                  25                  30
Thr Cys Val Val Val Asp Val Ser His Glu Asp Pro Glu Val Lys Phe
                 35                  40                  45
Asn Trp Tyr Val Asp Gly Val Glu Val His Asn Ala Lys Thr Lys Pro
             50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Thr Cys Leu Val Lys Gly
            130                 135                 140
Phe Tyr Pro Ser Asp Ile Ala Val Trp Trp Glu Ser Tyr Gly Thr Glu
145                 150                 155                 160
Trp Ser Ser Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
```

```
                180             185                 190
Gly Phe Val Phe Ser Cys Ser Val Met His Glu Ala Leu His Asn His
            195                 200                 205
Tyr Thr Gln Lys Ser Leu Ser Leu Ser Pro Gly Lys
        210                 215                 220

<210> SEQ ID NO 239
<211> LENGTH: 220
<212> TYPE: PRT
<213> ORGANISM: Artificial Sequence
<220> FEATURE:
<223> OTHER INFORMATION: Synthetic construct

<400> SEQUENCE: 239

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Trp Trp Glu Ser Tyr Gly Thr Glu
145                 150                 155                 160
Trp Ser Asn Tyr Lys Thr Thr Pro Pro Val Leu Asp Ser Asp Gly Ser
                165                 170                 175
Phe Phe Leu Tyr Ser Lys Leu Thr Val Thr Lys Ser Glu Trp Gln Gln
            180                 185                 190
Gly Phe Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 240
<211> LENGTH: 220
<212> TYPE: PRT
<213> ORGANISM: Artificial Sequence
<220> FEATURE:
<223> OTHER INFORMATION: Synthetic construct

<400> SEQUENCE: 240

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
```

```
Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 241
<211> LENGTH: 220
<212> TYPE: PRT
<213> ORGANISM: Artificial Sequence
<220> FEATURE:
<223> OTHER INFORMATION: Synthetic construct

<400> SEQUENCE: 241

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Trp Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190
```

```
Gly Phe Val Phe Ser Cys Ser Val Met His Glu Ala Leu His Asn His
            195                 200                 205
Tyr Thr Gln Lys Ser Leu Ser Leu Ser Pro Gly Lys
    210                 215                 220

<210> SEQ ID NO 242
<211> LENGTH: 220
<212> TYPE: PRT
<213> ORGANISM: Artificial Sequence
<220> FEATURE:
<223> OTHER INFORMATION: Synthetic construct

<400> SEQUENCE: 242

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Trp Trp Glu Ser Leu Gly His Val
145                 150                 155                 160
Trp Ala Val Tyr Lys Thr Thr Pro Pro Val Leu Asp Ser Asp Gly Ser
                165                 170                 175
Phe Phe Leu Tyr Ser Lys Leu Thr Val Pro Lys Ser Thr Trp Gln Gln
            180                 185                 190
Gly Trp Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 243
<211> LENGTH: 220
<212> TYPE: PRT
<213> ORGANISM: Artificial Sequence
<220> FEATURE:
<223> OTHER INFORMATION: Synthetic construct

<400> SEQUENCE: 243

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
```

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Leu Trp Glu Ser Leu Gly His Val
145                 150                 155                 160

Trp Ala Val Tyr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
                180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 244
<211> LENGTH: 220
<212> TYPE: PRT
<213> ORGANISM: Artificial Sequence
<220> FEATURE:
<223> OTHER INFORMATION: Synthetic construct

<400> SEQUENCE: 244

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Tyr Trp Glu Ser Leu Gly His Val
145                 150                 155                 160

Trp Ala Val Tyr Lys Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
                180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 245
<211> LENGTH: 220
<212> TYPE: PRT
<213> ORGANISM: Artificial Sequence
<220> FEATURE:
<223> OTHER INFORMATION: Synthetic construct

<400> SEQUENCE: 245

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Leu Gly His Val
145                 150                 155                 160

Trp Ala Val Tyr Gln Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 246
<211> LENGTH: 220
<212> TYPE: PRT
<213> ORGANISM: Artificial Sequence
<220> FEATURE:
<223> OTHER INFORMATION: Synthetic construct

<400> SEQUENCE: 246

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr

```
                65                  70                  75                  80
Val Leu His Gln Asp Trp Leu Asn Gly Lys Glu Tyr Lys Cys Lys Val
                        85                  90                  95

Ser Asn Lys Ala Leu Pro Ala Pro Ile Glu Lys Thr Ile Ser Lys Ala
                    100                 105                 110

Lys Gly Gln Pro Arg Glu Pro Gln Val Tyr Thr Leu Pro Pro Ser Arg
                    115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Leu Gly His Val
145                 150                 155                 160

Trp Ala Val Tyr Phe Thr Thr Pro Pro Val Leu Asp Ser Asp Gly Ser
                    165                 170                 175

Phe Phe Leu Tyr Ser Lys Leu Thr Val Pro Lys Ser Thr Trp Gln Gln
                    180                 185                 190

Gly Trp Val Phe Ser Cys Ser Val Met His Glu Ala Leu His Asn His
                    195                 200                 205

Tyr Thr Gln Lys Ser Leu Ser Leu Ser Pro Gly Lys
                    210                 215                 220

<210> SEQ ID NO 247
<211> LENGTH: 220
<212> TYPE: PRT
<213> ORGANISM: Artificial Sequence
<220> FEATURE:
<223> OTHER INFORMATION: Synthetic construct

<400> SEQUENCE: 247

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                    20                  25                  30

Thr Cys Val Val Val Asp Val Ser His Glu Asp Pro Glu Val Lys Phe
                    35                  40                  45

Asn Trp Tyr Val Asp Gly Val Glu Val His Asn Ala Lys Thr Lys Pro
            50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                        85                  90                  95

Ser Asn Lys Ala Leu Pro Ala Pro Ile Glu Lys Thr Ile Ser Lys Ala
                    100                 105                 110

Lys Gly Gln Pro Arg Glu Pro Gln Val Tyr Thr Leu Pro Pro Ser Arg
                    115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Leu Gly His Val
145                 150                 155                 160

Trp Ala Val Tyr His Thr Thr Pro Pro Val Leu Asp Ser Asp Gly Ser
                    165                 170                 175

Phe Phe Leu Tyr Ser Lys Leu Thr Val Pro Lys Ser Thr Trp Gln Gln
                    180                 185                 190

Gly Trp Val Phe Ser Cys Ser Val Met His Glu Ala Leu His Asn His
                    195                 200                 205

Tyr Thr Gln Lys Ser Leu Ser Leu Ser Pro Gly Lys
                    210                 215                 220
```

<210> SEQ ID NO 248
<211> LENGTH: 220
<212> TYPE: PRT
<213> ORGANISM: Artificial Sequence
<220> FEATURE:
<223> OTHER INFORMATION: Synthetic construct

<400> SEQUENCE: 248

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 249
<211> LENGTH: 220
<212> TYPE: PRT
<213> ORGANISM: Artificial Sequence
<220> FEATURE:
<223> OTHER INFORMATION: Synthetic construct

<400> SEQUENCE: 249

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 250
<211> LENGTH: 220
<212> TYPE: PRT
<213> ORGANISM: Artificial Sequence
<220> FEATURE:
<223> OTHER INFORMATION: Synthetic construct

<400> SEQUENCE: 250

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 251
<211> LENGTH: 220
<212> TYPE: PRT
<213> ORGANISM: Artificial Sequence
<220> FEATURE:
<223> OTHER INFORMATION: Synthetic construct

<400> SEQUENCE: 251

```
Pro Cys Pro Ala Pro Glu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Gly Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 252
<211> LENGTH: 220
<212> TYPE: PRT
<213> ORGANISM: Artificial Sequence
<220> FEATURE:
<223> OTHER INFORMATION: Synthetic construct

<400> SEQUENCE: 252

```
Pro Cys Pro Ala Pro Glu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Ser Cys Trp Val Met His Glu Ala Leu His Asn His
        195                 200                 205

Tyr Thr Gln Lys Ser Leu Ser Leu Ser Pro Gly Lys
        210                 215                 220

<210> SEQ ID NO 253
<211> LENGTH: 220
<212> TYPE: PRT
<213> ORGANISM: Artificial Sequence
<220> FEATURE:
<223> OTHER INFORMATION: Synthetic construct

<400> SEQUENCE: 253

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Trp Val Met His Glu Ala Leu His Asn His
        195                 200                 205

Tyr Thr Gln Lys Ser Leu Ser Leu Ser Pro Gly Lys
        210                 215                 220

<210> SEQ ID NO 254

```
<211> LENGTH: 220
<212> TYPE: PRT
<213> ORGANISM: Artificial Sequence
<220> FEATURE:
<223> OTHER INFORMATION: Synthetic construct

<400> SEQUENCE: 254

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Thr Cys Trp Val Met His Glu Ala Leu His Asn His
        195                 200                 205

Tyr Thr Gln Lys Ser Leu Ser Leu Ser Pro Gly Lys
    210                 215                 220

<210> SEQ ID NO 255
<211> LENGTH: 220
<212> TYPE: PRT
<213> ORGANISM: Artificial Sequence
<220> FEATURE:
<223> OTHER INFORMATION: Synthetic construct

<400> SEQUENCE: 255

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
```

```
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Thr Cys Gly Val Met His Glu Ala Leu His Asn His
            195                 200                 205

Tyr Thr Gln Lys Ser Leu Ser Leu Ser Pro Gly Lys
            210                 215                 220

<210> SEQ ID NO 256
<211> LENGTH: 220
<212> TYPE: PRT
<213> ORGANISM: Artificial Sequence
<220> FEATURE:
<223> OTHER INFORMATION: Synthetic construct

<400> SEQUENCE: 256

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Glu Cys Trp Val Met His Glu Ala Leu His Asn His
            195                 200                 205

Tyr Thr Gln Lys Ser Leu Ser Leu Ser Pro Gly Lys
            210                 215                 220

<210> SEQ ID NO 257
<211> LENGTH: 220
<212> TYPE: PRT
```

<213> ORGANISM: Artificial Sequence
<220> FEATURE:
<223> OTHER INFORMATION: Synthetic construct

<400> SEQUENCE: 257

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Lys Cys Trp Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 258
<211> LENGTH: 220
<212> TYPE: PRT
<213> ORGANISM: Artificial Sequence
<220> FEATURE:
<223> OTHER INFORMATION: Synthetic construct

<400> SEQUENCE: 258

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

Lys Gly Gln Pro Arg Glu Pro Gln Val Tyr Thr Leu Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Pro Glu Glu Trp Gln Gln
                180                 185                 190

Gly Phe Val Phe Lys Cys Trp Val Met His Glu Ala Leu His Asn His
                195                 200                 205

Tyr Thr Gln Lys Ser Leu Ser Leu Ser Pro Gly Lys
            210                 215                 220

<210> SEQ ID NO 259
<211> LENGTH: 220
<212> TYPE: PRT
<213> ORGANISM: Artificial Sequence
<220> FEATURE:
<223> OTHER INFORMATION: Synthetic construct

<400> SEQUENCE: 259

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
130                 135                 140

Phe Tyr Pro Ser Asp Ile Ala Val Trp Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
            210                 215                 220

<210> SEQ ID NO 260
<211> LENGTH: 220
<212> TYPE: PRT
<213> ORGANISM: Artificial Sequence
<220> FEATURE:

<223> OTHER INFORMATION: Synthetic construct

<400> SEQUENCE: 260

| Pro | Cys | Pro | Ala | Pro | Glu | Leu | Leu | Gly | Gly | Pro | Ser | Val | Phe | Leu | Phe |
|---|---|---|---|---|---|---|---|---|---|---|---|---|---|---|---|
| 1 | | | | 5 | | | | | 10 | | | | | 15 | |

Pro Pro Lys Pro Lys Asp Thr Leu Met Ile Ser Arg Thr Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65                70              75              80

Val Leu His Gln Asp Trp Leu Asn Gly Lys Glu Tyr Lys Cys Lys Val
        85              90              95

Ser Asn Lys Ala Leu Pro Ala Pro Ile Glu Lys Thr Ile Ser Lys Ala
        100            105            110

Lys Gly Gln Pro Arg Glu Pro Gln Val Tyr Thr Leu Pro Pro Ser Arg
        115            120            125

Asp Glu Leu Thr Lys Asn Gln Val Ser Leu Thr Cys Leu Val Lys Gly
    130              135            140

Phe Tyr Pro Ser Asp Ile Ala Val Trp Trp Glu Ser Tyr Gly Thr Glu
145                150              155            160

Trp Ser Ser Tyr Arg Thr Thr Pro Pro Val Leu Asp Ser Asp Gly Ser
        165            170            175

Phe Phe Leu Tyr Ser Lys Leu Thr Val Thr Gly Glu Glu Trp Gln Gln
        180            185            190

Gly Phe Val Phe Ser Cys Ser Val Met His Glu Ala Leu His Asn His
        195            200            205

Tyr Thr Gln Lys Ser Leu Ser Leu Ser Pro Gly Lys
    210              215              220

<210> SEQ ID NO 261
<211> LENGTH: 220
<212> TYPE: PRT
<213> ORGANISM: Artificial Sequence
<220> FEATURE:
<223> OTHER INFORMATION: Synthetic construct

<400> SEQUENCE: 261

Pro Cys Pro Ala Pro Glu Leu Leu Gly Gly Pro Ser Val Phe Leu Phe
1                5              10              15

Pro Pro Lys Pro Lys Asp Thr Leu Met Ile Ser Arg Thr Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65                70              75              80

Val Leu His Gln Asp Trp Leu Asn Gly Lys Glu Tyr Lys Cys Lys Val
        85              90              95

Ser Asn Lys Ala Leu Pro Ala Pro Ile Glu Lys Thr Ile Ser Lys Ala
        100            105            110

Lys Gly Gln Pro Arg Glu Pro Gln Val Tyr Thr Leu Pro Pro Ser Arg
        115            120            125

Asp Glu Leu Thr Lys Asn Gln Val Ser Leu Thr Cys Leu Val Lys Gly
            130                 135                 140

Phe Tyr Pro Ser Asp Ile Ala Val Trp Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Thr Cys Trp Val Met His Glu Ala Leu His Asn His
            195                 200                 205

Tyr Thr Gln Lys Ser Leu Ser Leu Ser Pro Gly Lys
            210                 215                 220

<210> SEQ ID NO 262
<211> LENGTH: 220
<212> TYPE: PRT
<213> ORGANISM: Artificial Sequence
<220> FEATURE:
<223> OTHER INFORMATION: Synthetic construct

<400> SEQUENCE: 262

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Trp Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Gly Glu Glu Trp Gln Gln
            180                 185                 190

Gly Phe Val Phe Thr Cys Trp Val Met His Glu Ala Leu His Asn His
            195                 200                 205

Tyr Thr Gln Lys Ser Leu Ser Leu Ser Pro Gly Lys
            210                 215                 220

<210> SEQ ID NO 263
<211> LENGTH: 220
<212> TYPE: PRT
<213> ORGANISM: Artificial Sequence
<220> FEATURE:
<223> OTHER INFORMATION: Synthetic construct

<400> SEQUENCE: 263

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Arg Glu Glu Trp Gln Gln
            180                 185                 190

Gly Phe Val Phe Thr Cys Gly Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 264
<211> LENGTH: 220
<212> TYPE: PRT
<213> ORGANISM: Artificial Sequence
<220> FEATURE:
<223> OTHER INFORMATION: Synthetic construct

<400> SEQUENCE: 264

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
```

-continued

Phe Tyr Pro Ser Asp Ile Ala Val Leu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
                180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 265
<211> LENGTH: 220
<212> TYPE: PRT
<213> ORGANISM: Artificial Sequence
<220> FEATURE:
<223> OTHER INFORMATION: Synthetic construct

<400> SEQUENCE: 265

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
130                 135                 140

Phe Tyr Pro Ser Asp Ile Ala Val Leu Trp Glu Ser Tyr Gly Thr Glu
145                 150                 155                 160

Trp Ser Ser Tyr Arg Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
                180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 266
<211> LENGTH: 220
<212> TYPE: PRT
<213> ORGANISM: Artificial Sequence
<220> FEATURE:
<223> OTHER INFORMATION: Synthetic construct

<400> SEQUENCE: 266

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 267
<211> LENGTH: 220
<212> TYPE: PRT
<213> ORGANISM: Artificial Sequence
<220> FEATURE:
<223> OTHER INFORMATION: Synthetic construct

<400> SEQUENCE: 267

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

```
Phe Tyr Pro Ser Asp Ile Ala Val Glu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220
```

<210> SEQ ID NO 268
<211> LENGTH: 220
<212> TYPE: PRT
<213> ORGANISM: Artificial Sequence
<220> FEATURE:
<223> OTHER INFORMATION: Synthetic construct

<400> SEQUENCE: 268

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Val Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220
```

<210> SEQ ID NO 269
<211> LENGTH: 220
<212> TYPE: PRT
<213> ORGANISM: Artificial Sequence
<220> FEATURE:
<223> OTHER INFORMATION: Synthetic construct

<400> SEQUENCE: 269

```
Pro Cys Pro Ala Pro Glu Leu Leu Gly Gly Pro Ser Val Phe Leu Phe
1               5                   10                  15
```

```
Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
            210                 215                 220

<210> SEQ ID NO 270
<211> LENGTH: 220
<212> TYPE: PRT
<213> ORGANISM: Artificial Sequence
<220> FEATURE:
<223> OTHER INFORMATION: Synthetic construct

<400> SEQUENCE: 270

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Phe Gly Thr Glu
145                 150                 155                 160
```

Trp Ala Ser Tyr Lys Thr Thr Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 271
<211> LENGTH: 220
<212> TYPE: PRT
<213> ORGANISM: Artificial Sequence
<220> FEATURE:
<223> OTHER INFORMATION: Synthetic construct

<400> SEQUENCE: 271

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Phe Gly Thr Glu
145                 150                 155                 160

Trp Val Ser Tyr Lys Thr Thr Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 272
<211> LENGTH: 220
<212> TYPE: PRT
<213> ORGANISM: Artificial Sequence
<220> FEATURE:
<223> OTHER INFORMATION: Synthetic construct

<400> SEQUENCE: 272

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val

```
                20                  25                  30
Thr Cys Val Val Val Asp Val Ser His Glu Asp Pro Glu Val Lys Phe
            35                  40                  45
Asn Trp Tyr Val Asp Gly Val Glu Val His Asn Ala Lys Thr Lys Pro
        50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Trp Trp Glu Ser Phe Gly Thr Glu
145                 150                 155                 160
Trp Ser Ser Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
            180                 185                 190
Gly Phe Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 273
<211> LENGTH: 220
<212> TYPE: PRT
<213> ORGANISM: Artificial Sequence
<220> FEATURE:
<223> OTHER INFORMATION: Synthetic construct

<400> SEQUENCE: 273

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Thr Cys Leu Val Lys Gly
    130                 135                 140
Phe Tyr Pro Ser Asp Ile Ala Val Trp Trp Glu Ser Tyr Gly Thr Glu
145                 150                 155                 160
Trp Ala Ser Tyr Lys Thr Thr Pro Pro Val Leu Asp Ser Asp Gly Ser
```

165                 170                 175
Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 274
<211> LENGTH: 220
<212> TYPE: PRT
<213> ORGANISM: Artificial Sequence
<220> FEATURE:
<223> OTHER INFORMATION: Synthetic construct

<400> SEQUENCE: 274

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Val Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 275
<211> LENGTH: 220
<212> TYPE: PRT
<213> ORGANISM: Artificial Sequence
<220> FEATURE:
<223> OTHER INFORMATION: Synthetic construct

<400> SEQUENCE: 275

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

```
Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Trp Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
        210                 215                 220

<210> SEQ ID NO 276
<211> LENGTH: 220
<212> TYPE: PRT
<213> ORGANISM: Artificial Sequence
<220> FEATURE:
<223> OTHER INFORMATION: Synthetic construct

<400> SEQUENCE: 276

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Trp Trp Glu Ser Phe Gly Thr Glu
145                 150                 155                 160

Trp Ala Ser Tyr Lys Thr Thr Pro Pro Val Leu Asp Ser Asp Gly Ser
                165                 170                 175
```

```
Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 277
<211> LENGTH: 220
<212> TYPE: PRT
<213> ORGANISM: Artificial Sequence
<220> FEATURE:
<223> OTHER INFORMATION: Synthetic construct

<400> SEQUENCE: 277

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Trp Trp Glu Ser Phe Gly Thr Glu
145                 150                 155                 160

Trp Val Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 278
<211> LENGTH: 220
<212> TYPE: PRT
<213> ORGANISM: Artificial Sequence
<220> FEATURE:
<223> OTHER INFORMATION: Synthetic construct

<400> SEQUENCE: 278

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45
```

```
Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Phe Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 279
<211> LENGTH: 220
<212> TYPE: PRT
<213> ORGANISM: Artificial Sequence
<220> FEATURE:
<223> OTHER INFORMATION: Synthetic construct

<400> SEQUENCE: 279

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190
```

```
Gly Phe Val Phe Ser Cys Ser Val Met His Glu Ala Leu His Asn His
        195                 200                 205

Tyr Thr Gln Lys Ser Leu Ser Leu Ser Pro Gly Lys
        210                 215                 220
```

<210> SEQ ID NO 280
<211> LENGTH: 220
<212> TYPE: PRT
<213> ORGANISM: Artificial Sequence
<220> FEATURE:
<223> OTHER INFORMATION: Synthetic construct

<400> SEQUENCE: 280

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
        210                 215                 220
```

<210> SEQ ID NO 281
<211> LENGTH: 220
<212> TYPE: PRT
<213> ORGANISM: Artificial Sequence
<220> FEATURE:
<223> OTHER INFORMATION: Synthetic construct

<400> SEQUENCE: 281

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
```

```
                    50                    55                    60
Arg Glu Glu Gln Tyr Asn Ser Thr Tyr Arg Val Val Ser Val Leu Thr
 65                    70                    75                    80

Val Leu His Gln Asp Trp Leu Asn Gly Lys Glu Tyr Lys Cys Lys Val
                    85                    90                    95

Ser Asn Lys Ala Leu Pro Ala Pro Ile Glu Lys Thr Ile Ser Lys Ala
                    100                   105                   110

Lys Gly Gln Pro Arg Glu Pro Gln Val Tyr Thr Leu Pro Pro Ser Arg
                    115                   120                   125

Asp Glu Leu Thr Lys Asn Gln Val Ser Leu Thr Cys Leu Val Lys Gly
                    130                   135                   140

Phe Tyr Pro Ser Asp Ile Ala Val Glu Trp Glu Ser Tyr Gly Thr Glu
145                   150                   155                   160

Trp Ser Asn Tyr Lys Thr Thr Pro Pro Val Leu Asp Ser Asp Gly Ser
                    165                   170                   175

Phe Phe Leu Tyr Ser Lys Leu Thr Val Ser Lys Glu Glu Trp Gln Gln
                    180                   185                   190

Gly Phe Val Phe Ser Cys Ser Val Met His Glu Ala Leu His Asn His
                    195                   200                   205

Tyr Thr Gln Lys Ser Leu Ser Leu Ser Pro Gly Lys
                    210                   215                   220
```

<210> SEQ ID NO 282
<211> LENGTH: 220
<212> TYPE: PRT
<213> ORGANISM: Artificial Sequence
<220> FEATURE:
<223> OTHER INFORMATION: Synthetic construct

<400> SEQUENCE: 282

```
Pro Cys Pro Ala Pro Glu Leu Leu Gly Gly Pro Ser Val Phe Leu Phe
 1                   5                    10                   15

Pro Pro Lys Pro Lys Asp Thr Leu Met Ile Ser Arg Thr Pro Glu Val
                    20                    25                    30

Thr Cys Val Val Val Asp Val Ser His Glu Asp Pro Glu Val Lys Phe
                    35                    40                    45

Asn Trp Tyr Val Asp Gly Val Glu Val His Asn Ala Lys Thr Lys Pro
 50                    55                    60

Arg Glu Glu Gln Tyr Asn Ser Thr Tyr Arg Val Val Ser Val Leu Thr
 65                    70                    75                    80

Val Leu His Gln Asp Trp Leu Asn Gly Lys Glu Tyr Lys Cys Lys Val
                    85                    90                    95

Ser Asn Lys Ala Leu Pro Ala Pro Ile Glu Lys Thr Ile Ser Lys Ala
                    100                   105                   110

Lys Gly Gln Pro Arg Glu Pro Gln Val Tyr Thr Leu Pro Pro Ser Arg
                    115                   120                   125

Asp Glu Leu Thr Lys Asn Gln Val Ser Leu Thr Cys Leu Val Lys Gly
                    130                   135                   140

Phe Tyr Pro Ser Asp Ile Ala Val Glu Trp Glu Ser Phe Gly Thr Glu
145                   150                   155                   160

Trp Ala Asn Tyr Lys Thr Thr Pro Pro Val Leu Asp Ser Asp Gly Ser
                    165                   170                   175

Phe Phe Leu Tyr Ser Lys Leu Thr Val Thr Lys Glu Glu Trp Gln Gln
                    180                   185                   190

Gly Phe Val Phe Ser Cys Ser Val Met His Glu Ala Leu His Asn His
```

195                 200                 205
Tyr Thr Gln Lys Ser Leu Ser Leu Ser Pro Gly Lys
    210                 215                 220

<210> SEQ ID NO 283
<211> LENGTH: 220
<212> TYPE: PRT
<213> ORGANISM: Artificial Sequence
<220> FEATURE:
<223> OTHER INFORMATION: Synthetic construct

<400> SEQUENCE: 283

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Phe Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 284
<211> LENGTH: 220
<212> TYPE: PRT
<213> ORGANISM: Artificial Sequence
<220> FEATURE:
<223> OTHER INFORMATION: Synthetic construct

<400> SEQUENCE: 284

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Phe Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 285
<211> LENGTH: 220
<212> TYPE: PRT
<213> ORGANISM: Artificial Sequence
<220> FEATURE:
<223> OTHER INFORMATION: Synthetic construct

<400> SEQUENCE: 285

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
            210                 215                 220

<210> SEQ ID NO 286
<211> LENGTH: 220
<212> TYPE: PRT
<213> ORGANISM: Artificial Sequence
<220> FEATURE:
<223> OTHER INFORMATION: Synthetic construct

<400> SEQUENCE: 286

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
            210                 215                 220

<210> SEQ ID NO 287
<211> LENGTH: 220
<212> TYPE: PRT
<213> ORGANISM: Artificial Sequence
<220> FEATURE:
<223> OTHER INFORMATION: Synthetic construct

<400> SEQUENCE: 287

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 288
<211> LENGTH: 220
<212> TYPE: PRT
<213> ORGANISM: Artificial Sequence
<220> FEATURE:
<223> OTHER INFORMATION: Synthetic construct

<400> SEQUENCE: 288

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Phe Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 289
<211> LENGTH: 220
<212> TYPE: PRT
<213> ORGANISM: Artificial Sequence
<220> FEATURE:
<223> OTHER INFORMATION: Synthetic construct

<400> SEQUENCE: 289

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Phe Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 290
<211> LENGTH: 220
<212> TYPE: PRT
<213> ORGANISM: Artificial Sequence
<220> FEATURE:
<223> OTHER INFORMATION: Synthetic construct

<400> SEQUENCE: 290

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
```

```
                85                   90                   95
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Leu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
            210                 215                 220

<210> SEQ ID NO 291
<211> LENGTH: 220
<212> TYPE: PRT
<213> ORGANISM: Artificial Sequence
<220> FEATURE:
<223> OTHER INFORMATION: Synthetic construct

<400> SEQUENCE: 291

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
            210                 215                 220
```

<210> SEQ ID NO 292
<211> LENGTH: 220
<212> TYPE: PRT
<213> ORGANISM: Artificial Sequence
<220> FEATURE:
<223> OTHER INFORMATION: Synthetic construct

<400> SEQUENCE: 292

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Val Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 293
<211> LENGTH: 220
<212> TYPE: PRT
<213> ORGANISM: Artificial Sequence
<220> FEATURE:
<223> OTHER INFORMATION: Synthetic construct

<400> SEQUENCE: 293

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 294
<211> LENGTH: 220
<212> TYPE: PRT
<213> ORGANISM: Artificial Sequence
<220> FEATURE:
<223> OTHER INFORMATION: Synthetic construct

<400> SEQUENCE: 294

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Phe Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 295
<211> LENGTH: 220
```

```
<212> TYPE: PRT
<213> ORGANISM: Artificial Sequence
<220> FEATURE:
<223> OTHER INFORMATION: Synthetic construct

<400> SEQUENCE: 295

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Leu Trp Glu Ser Phe Gly Thr Glu
145                 150                 155                 160

Trp Val Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 296
<211> LENGTH: 220
<212> TYPE: PRT
<213> ORGANISM: Artificial Sequence
<220> FEATURE:
<223> OTHER INFORMATION: Synthetic construct

<400> SEQUENCE: 296

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

```
Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Val Leu Asp Ser Asp Gly Ser
                165                 170                 175

Phe Phe Leu Tyr Ser Lys Leu Thr Val Thr Lys Ser Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 297
<211> LENGTH: 220
<212> TYPE: PRT
<213> ORGANISM: Artificial Sequence
<220> FEATURE:
<223> OTHER INFORMATION: Synthetic construct

<400> SEQUENCE: 297

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Trp Trp Glu Ser Leu Gly His Val
145                 150                 155                 160

Trp Val Asn Gln Lys Thr Thr Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 298
<211> LENGTH: 220
<212> TYPE: PRT
<213> ORGANISM: Artificial Sequence
```

<220> FEATURE:
<223> OTHER INFORMATION: Synthetic construct

<400> SEQUENCE: 298

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Leu Gly His Val
145                 150                 155                 160

Trp Val Asn Gln Gln Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 299
<211> LENGTH: 220
<212> TYPE: PRT
<213> ORGANISM: Artificial Sequence
<220> FEATURE:
<223> OTHER INFORMATION: Synthetic construct

<400> SEQUENCE: 299

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg

```
            115                 120                 125
Asp Glu Leu Thr Lys Asn Gln Val Ser Leu Thr Cys Leu Val Lys Gly
    130                 135                 140

Phe Tyr Pro Ser Asp Ile Ala Val Trp Trp Glu Ser Leu Gly His Val
145                 150                 155                 160

Trp Val Asn Gln Gln Thr Thr Pro Pro Val Leu Asp Ser Asp Gly Ser
                165                 170                 175

Phe Phe Leu Tyr Ser Lys Leu Thr Val Pro Lys Ser Thr Trp Gln Gln
            180                 185                 190

Gly Trp Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 300
<211> LENGTH: 760
<212> TYPE: PRT
<213> ORGANISM: Macaca fascicularis

<400> SEQUENCE: 300

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Gly Val Asp Glu Glu Asn Thr
        35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
            85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
            115                 120                 125

Arg Lys Leu Ser Glu Lys Leu Asp Thr Thr Asp Phe Thr Ser Thr Ile
    130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270
```

```
Ser Leu Asn Ala Ile Gly Val Leu Ile Tyr Met Asp Gln Thr Lys Phe
            275                 280                 285

Pro Ile Val Lys Ala Asp Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335

Ile Ser Arg Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
            355                 360                 365

Glu Asn Lys Ser Val Lys Leu Thr Val Ser Asn Val Leu Lys Glu Thr
        370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Ser Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
            500                 505                 510

Val Lys His Pro Val Thr Gly Arg Ser Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Ala Arg Ala Ala Ala Glu
            580                 585                 590

Val Ala Gly Gln Phe Val Ile Lys Leu Thr His Asp Thr Glu Leu Asn
        595                 600                 605

Leu Asp Tyr Glu Arg Tyr Asn Ser Gln Leu Leu Leu Phe Leu Arg Asp
    610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
        675                 680                 685

Tyr Val Ser Pro Lys Glu Ser Pro Phe Arg His Val Phe Trp Gly Ser
```

-continued

```
                690                 695                 700
Gly Ser His Thr Leu Ser Ala Leu Leu Glu Ser Leu Lys Leu Arg Arg
705                     710                 715                 720

Gln Asn Asn Ser Ala Phe Asn Glu Thr Leu Phe Arg Asn Gln Leu Ala
                    725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 301
<211> LENGTH: 186
<212> TYPE: PRT
<213> ORGANISM: Artificial Sequence
<220> FEATURE:
<223> OTHER INFORMATION: Synthetic construct

<400> SEQUENCE: 301

Met Gly Trp Ser Cys Ile Ile Leu Phe Leu Val Ala Thr Ala Thr Gly
1               5                   10                  15

Ala Tyr Ala Gly Thr Ser Ser Gly Leu Pro Asn Ile Pro Val Gln Thr
            20                  25                  30

Ile Ser Arg Ala Ala Ala Glu Lys Leu Phe Gly Asn Met Glu Gly Asp
        35                  40                  45

Cys Pro Ser Asp Trp Lys Thr Asp Ser Thr Cys Arg Met Val Thr Ser
    50                  55                  60
Glu Ser Lys Asn Val Lys Leu Thr Val Ser Asn Asp Ser Ala Gln Asn
65                  70                  75                  80

Ser Val Ile Ile Val Asp Lys Asn Gly Arg Leu Val Tyr Leu Val Glu
                85                  90                  95

Asn Pro Gly Gly Tyr Val Ala Tyr Ser Lys Ala Ala Thr Val Thr Gly
            100                 105                 110

Lys Leu Val His Ala Asn Phe Gly Thr Lys Lys Asp Phe Glu Asp Leu
        115                 120                 125

Tyr Thr Pro Val Asn Gly Ser Ile Val Ile Val Arg Ala Gly Lys Ile
    130                 135                 140
Thr Phe Ala Glu Lys Val Ala Asn Ala Glu Ser Leu Asn Ala Ile Gly
145                 150                 155                 160

Val Leu Ile Tyr Met Asp Gln Thr Lys Phe Pro Ile Val Asn Ala Glu
                165                 170                 175

Leu Ser Ala Ser His His His His His His
            180                 185

<210> SEQ ID NO 302
<211> LENGTH: 247
<212> TYPE: PRT
<213> ORGANISM: Artificial Sequence
<220> FEATURE:
<223> OTHER INFORMATION: Synthetic construct

<400> SEQUENCE: 302

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45
```

Asp Thr Leu Tyr Ile Thr Arg Glu Pro Glu Val Thr Cys Val Val Val
                50                  55                  60

Asp Val Ser His Glu Asp Pro Gln Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Gly Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Leu Gly His Val Trp Ala Val Tyr Lys
            180                 185                 190

Thr Thr Pro Pro Val Leu Asp Ser Asp Gly Ser Phe Phe Leu Tyr Ser
        195                 200                 205

Lys Leu Thr Val Pro Lys Ser Thr Trp Gln Gln Gly Trp Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 303
<211> LENGTH: 11
<212> TYPE: PRT
<213> ORGANISM: Artificial Sequence
<220> FEATURE:
<223> OTHER INFORMATION: Synthetic construct

<400> SEQUENCE: 303

Glu Trp Glu Ser Phe Gly Thr Glu Trp Ser Ser
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Synthetic construct

<400> SEQUENCE: 304

Glu Trp Glu Ser Tyr Gly Thr Glu Trp Ala Ser
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Synthetic construct

<400> SEQUENCE: 305

Glu Trp Glu Ser Tyr Gly Thr Glu Trp Val Ser
1               5                   10

```
<210> SEQ ID NO 306
<211> LENGTH: 11
<212> TYPE: PRT
<213> ORGANISM: Artificial Sequence
<220> FEATURE:
<223> OTHER INFORMATION: Synthetic construct

<400> SEQUENCE: 306

Glu Trp Glu Ser Tyr Gly Thr Glu Trp Ser Ser
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Synthetic construct

<400> SEQUENCE: 307

Glu Trp Glu Ser Phe Gly Thr Glu Trp Ala Ser
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Synthetic construct

<400> SEQUENCE: 308

Glu Trp Glu Ser Phe Gly Thr Glu Trp Val Ser
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthetic construct

<400> SEQUENCE: 309

Trp Trp Glu Ser Phe Gly Thr Glu Trp Ser Ser
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic construct

<400> SEQUENCE: 310

Trp Trp Glu Ser Tyr Gly Thr Glu Trp Ala Ser
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Synthetic construct

<400> SEQUENCE: 311

Trp Trp Glu Ser Tyr Gly Thr Glu Trp Val Ser
1               5                   10

<210> SEQ ID NO 312
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 312

Trp Trp Glu Ser Tyr Gly Thr Glu Trp Ser Ser
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic construct

<400> SEQUENCE: 313

Trp Trp Glu Ser Phe Gly Thr Glu Trp Ala Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic construct

<400> SEQUENCE: 314

Trp Trp Glu Ser Phe Gly Thr Glu Trp Val Ser
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Synthetic construct

<400> SEQUENCE: 315

Glu Trp Glu Ser Phe Gly Thr Glu Trp Ser Asn
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Synthetic construct

<400> SEQUENCE: 316

Glu Trp Glu Ser Tyr Gly Thr Glu Trp Ala Asn
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Synthetic construct

<400> SEQUENCE: 317

Glu Trp Glu Ser Tyr Gly Thr Glu Trp Val Asn
1               5                   10

<210> SEQ ID NO 318
<211> LENGTH: 11
```

```
<212> TYPE: PRT
<213> ORGANISM: Artificial Sequence
<220> FEATURE:
<223> OTHER INFORMATION: Synthetic construct

<400> SEQUENCE: 318

Glu Trp Glu Ser Tyr Gly Thr Glu Trp Ser Asn
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Synthetic construct

<400> SEQUENCE: 319

Glu Trp Glu Ser Phe Gly Thr Glu Trp Ala Asn
1               5                   10

<210> SEQ ID NO 320
<211> LENGTH: 11
<212> TYPE: PRT
<213> ORGANISM: Artificial Sequence
<220> FEATURE:
<223> OTHER INFORMATION: Synthetic construct

<400> SEQUENCE: 320

Glu Trp Glu Ser Phe Gly Thr Glu Trp Val Asn
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Synthetic construct

<400> SEQUENCE: 321

Trp Trp Glu Ser Phe Gly Thr Glu Trp Ser Asn
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthetic construct

<400> SEQUENCE: 322

Trp Trp Glu Ser Tyr Gly Thr Glu Trp Ala Asn
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Synthetic construct

<400> SEQUENCE: 323

Trp Trp Glu Ser Tyr Gly Thr Glu Trp Val Asn
1               5                   10

<210> SEQ ID NO 324
<211> LENGTH: 11
<212> TYPE: PRT
```

<213> ORGANISM: Artificial Sequence
<220> FEATURE:
<223> OTHER INFORMATION: Synthetic construct

<400> SEQUENCE: 324

Trp Trp Glu Ser Tyr Gly Thr Glu Trp Ser Asn
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic construct

<400> SEQUENCE: 325

Trp Trp Glu Ser Phe Gly Thr Glu Trp Ala Asn
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Synthetic construct

<400> SEQUENCE: 326

Trp Trp Glu Ser Phe Gly Thr Glu Trp Val Asn
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Synthetic construct

<400> SEQUENCE: 327

Leu Trp Glu Ser Phe Gly Thr Glu Trp Ser Ser
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Synthetic construct

<400> SEQUENCE: 328

Leu Trp Glu Ser Tyr Gly Thr Glu Trp Ala Ser
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Synthetic construct

<400> SEQUENCE: 329

Leu Trp Glu Ser Tyr Gly Thr Glu Trp Val Ser
1               5                   10

<210> SEQ ID NO 330
<211> LENGTH: 11
<212> TYPE: PRT
<213> ORGANISM: Artificial Sequence

```
<220> FEATURE:
<223> OTHER INFORMATION: Synthetic construct

<400> SEQUENCE: 330

Leu Trp Glu Ser Tyr Gly Thr Glu Trp Ser Ser
1               5                   10

<210> SEQ ID NO 331
<211> LENGTH: 11
<212> TYPE: PRT
<213> ORGANISM: Artificial Sequence
<220> FEATURE:
<223> OTHER INFORMATION: Synthetic construct

<400> SEQUENCE: 331

Leu Trp Glu Ser Phe Gly Thr Glu Trp Ala Ser
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Synthetic construct

<400> SEQUENCE: 332

Leu Trp Glu Ser Phe Gly Thr Glu Trp Val Ser
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Synthetic construct

<400> SEQUENCE: 333

Trp Trp Glu Ser Leu Gly His Val Trp Ala Val
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Synthetic construct

<400> SEQUENCE: 334

Glu Trp Glu Ser Leu Gly His Val Trp Ala Val
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Synthetic construct

<400> SEQUENCE: 335

Leu Trp Glu Ser Leu Gly His Val Trp Ala Val
1               5                   10

<210> SEQ ID NO 336
<211> LENGTH: 11
<212> TYPE: PRT
<213> ORGANISM: Artificial Sequence
<220> FEATURE:
```

<223> OTHER INFORMATION: Synthetic construct

<400> SEQUENCE: 336

Tyr Trp Glu Ser Leu Gly His Val Trp Ala Val
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Synthetic construct

<400> SEQUENCE: 337

Glu Trp Glu Ser Leu Gly Leu Val Trp Val Phe
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Synthetic construct

<400> SEQUENCE: 338

Trp Trp Glu Ser Leu Gly His Val Trp Val Asn
1               5                   10

<210> SEQ ID NO 339
<211> LENGTH: 11
<212> TYPE: PRT
<213> ORGANISM: Artificial Sequence
<220> FEATURE:
<223> OTHER INFORMATION: Synthetic construct

<400> SEQUENCE: 339

Glu Trp Glu Ser Leu Gly His Val Trp Val Asn
1               5                   10

<210> SEQ ID NO 340
<211> LENGTH: 9
<212> TYPE: PRT
<213> ORGANISM: Artificial Sequence
<220> FEATURE:
<223> OTHER INFORMATION: Synthetic construct

<400> SEQUENCE: 340

Thr Lys Glu Glu Trp Gln Gln Gly Phe
1               5

<210> SEQ ID NO 341
<211> LENGTH: 9
<212> TYPE: PRT
<213> ORGANISM: Artificial Sequence
<220> FEATURE:
<223> OTHER INFORMATION: Synthetic construct

<400> SEQUENCE: 341

Ser Lys Glu Glu Trp Gln Gln Gly Phe
1               5

<210> SEQ ID NO 342
<211> LENGTH: 9
<212> TYPE: PRT
<213> ORGANISM: Artificial Sequence
<220> FEATURE:
<223> OTHER INFORMATION: Synthetic construct -continued

<400> SEQUENCE: 342

Pro Lys Thr Ser Trp Gln Gln Gly Trp
1               5

<210> SEQ ID NO 343
<211> LENGTH: 9
<212> TYPE: PRT
<213> ORGANISM: Artificial Sequence
<220> FEATURE:
<223> OTHER INFORMATION: Synthetic construct

<400> SEQUENCE: 343

Thr Arg Glu Glu Trp Gln Gln Gly Phe
1               5

<210> SEQ ID NO 344
<211> LENGTH: 9
<212> TYPE: PRT
<213> ORGANISM: Artificial Sequence
<220> FEATURE:
<223> OTHER INFORMATION: Synthetic construct

<400> SEQUENCE: 344

Thr Pro Glu Glu Trp Gln Gln Gly Phe
1               5

<210> SEQ ID NO 345
<211> LENGTH: 9
<212> TYPE: PRT
<213> ORGANISM: Artificial Sequence
<220> FEATURE:
<223> OTHER INFORMATION: Synthetic construct

<400> SEQUENCE: 345

Thr Gly Glu Glu Trp Gln Gln Gly Phe
1               5

<210> SEQ ID NO 346
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 346

Thr Val Xaa Lys Xaa Xaa Trp Gln Gln Gly Xaa Val
1               5                   10

<210> SEQ ID NO 347
<211> LENGTH: 220
<212> TYPE: PRT
<213> ORGANISM: Artificial Sequence
<220> FEATURE:
<223> OTHER INFORMATION: Synthetic construct

<400> SEQUENCE: 347

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 348
<211> LENGTH: 220
<212> TYPE: PRT
<213> ORGANISM: Artificial Sequence
<220> FEATURE:
<223> OTHER INFORMATION: Synthetic construct

<400> SEQUENCE: 348

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140
```

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 349
<211> LENGTH: 220
<212> TYPE: PRT
<213> ORGANISM: Artificial Sequence
<220> FEATURE:
<223> OTHER INFORMATION: Synthetic construct

<400> SEQUENCE: 349

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 350
<211> LENGTH: 220
<212> TYPE: PRT
<213> ORGANISM: Artificial Sequence
<220> FEATURE:
<223> OTHER INFORMATION: Synthetic construct

<400> SEQUENCE: 350

Pro Cys Pro Ala Pro Glu Ala Ala Gly Gly Pro Ser Val Phe Leu Phe

```
               1               5                  10                 15
            Pro Pro Lys Pro Lys Asp Thr Leu Met Ile Ser Arg Thr Pro Glu Val
                            20                  25                  30

Thr Cys Val Val Val Asp Val Ser His Glu Asp Pro Glu Val Lys Phe
                        35                  40                  45

Asn Trp Tyr Val Asp Gly Val Glu Val His Asn Ala Lys Thr Lys Pro
                    50                  55                  60

Arg Glu Glu Gln Tyr Asn Ser Thr Tyr Arg Val Val Ser Val Leu Thr
            65                  70                  75                  80

Val Leu His Gln Asp Trp Leu Asn Gly Lys Glu Tyr Lys Cys Lys Val
                            85                  90                  95

Ser Asn Lys Ala Leu Pro Ala Pro Ile Glu Lys Thr Ile Ser Lys Ala
                            100                 105                 110

Lys Gly Gln Pro Arg Glu Pro Gln Val Tyr Thr Leu Pro Pro Ser Arg
                        115                 120                 125

Asp Glu Leu Thr Lys Asn Gln Val Ser Leu Trp Cys Leu Val Lys Gly
                    130                 135                 140

Phe Tyr Pro Ser Asp Ile Ala Val Glu Trp Glu Ser Phe Gly Thr Glu
            145                 150                 155                 160

Trp Ser Ser Tyr Lys Thr Thr Pro Pro Val Leu Asp Ser Asp Gly Ser
                            165                 170                 175

Phe Phe Leu Tyr Ser Lys Leu Thr Val Thr Lys Glu Glu Trp Gln Gln
                            180                 185                 190

Gly Phe Val Phe Ser Cys Ser Val Met His Glu Ala Leu His Asn His
                        195                 200                 205

Tyr Thr Gln Lys Ser Leu Ser Leu Ser Pro Gly Lys
                    210                 215                 220

<210> SEQ ID NO 351
<211> LENGTH: 220
<212> TYPE: PRT
<213> ORGANISM: Artificial Sequence
<220> FEATURE:
<223> OTHER INFORMATION: Synthetic construct

<400> SEQUENCE: 351

Pro Cys Pro Ala Pro Glu Ala Ala Gly Gly Pro Ser Val Phe Leu Phe
            1               5                   10                  15

Pro Pro Lys Pro Lys Asp Thr Leu Met Ile Ser Arg Thr Pro Glu Val
                            20                  25                  30

Thr Cys Val Val Val Asp Val Ser His Glu Asp Pro Glu Val Lys Phe
                        35                  40                  45

Asn Trp Tyr Val Asp Gly Val Glu Val His Asn Ala Lys Thr Lys Pro
                    50                  55                  60

Arg Glu Glu Gln Tyr Asn Ser Thr Tyr Arg Val Val Ser Val Leu Thr
            65                  70                  75                  80

Val Leu His Gln Asp Trp Leu Asn Gly Lys Glu Tyr Lys Cys Lys Val
                            85                  90                  95

Ser Asn Lys Ala Leu Gly Ala Pro Ile Glu Lys Thr Ile Ser Lys Ala
                            100                 105                 110

Lys Gly Gln Pro Arg Glu Pro Gln Val Tyr Thr Leu Pro Pro Ser Arg
                        115                 120                 125

Asp Glu Leu Thr Lys Asn Gln Val Ser Leu Trp Cys Leu Val Lys Gly
                    130                 135                 140

Phe Tyr Pro Ser Asp Ile Ala Val Glu Trp Glu Ser Phe Gly Thr Glu
```

```
                        145                 150                 155                 160
Trp Ser Ser Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
            180                 185                 190
Gly Phe Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 352
<211> LENGTH: 220
<212> TYPE: PRT
<213> ORGANISM: Artificial Sequence
<220> FEATURE:
<223> OTHER INFORMATION: Synthetic construct

<400> SEQUENCE: 352

Pro Cys Pro Ala Pro Glu Leu Leu Gly Gly Pro Ser Val Phe Leu Phe
1               5                   10                  15
Pro Pro Lys Pro Lys Asp Thr Leu Tyr Ile Thr Arg Glu Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
        115                 120                 125
Asp Glu Leu Thr Lys Asn Gln Val Ser Leu Trp Cys Leu Val Lys Gly
    130                 135                 140
Phe Tyr Pro Ser Asp Ile Ala Val Glu Trp Glu Ser Phe Gly Thr Glu
145                 150                 155                 160
Trp Ser Ser Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
            180                 185                 190
Gly Phe Val Phe Ser Cys Ser Val Met His Glu Ala Leu His Asn His
        195                 200                 205
Tyr Thr Gln Lys Ser Leu Ser Leu Ser Pro Gly Lys
    210                 215                 220

<210> SEQ ID NO 353
<211> LENGTH: 220
<212> TYPE: PRT
<213> ORGANISM: Artificial Sequence
<220> FEATURE:
<223> OTHER INFORMATION: Synthetic construct

<400> SEQUENCE: 353

Pro Cys Pro Ala Pro Glu Ala Ala Gly Gly Pro Ser Val Phe Leu Phe
1               5                   10                  15
```

```
Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
            130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 354
<211> LENGTH: 220
<212> TYPE: PRT
<213> ORGANISM: Artificial Sequence
<220> FEATURE:
<223> OTHER INFORMATION: Synthetic construct

<400> SEQUENCE: 354

Pro Cys Pro Ala Pro Glu Ala Ala Gly Gly Pro Ser Val Phe Leu Phe
 1               5                  10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
            130                 135                 140

Phe Tyr Pro Ser Asp Ile Ala Val Glu Trp Glu Ser Phe Gly Thr Glu
145                 150                 155                 160
```

Trp Ser Ser Tyr Lys Thr Thr Pro Pro Val Leu Asp Ser Asp Gly Ser
            165                 170                 175

Phe Phe Leu Tyr Ser Lys Leu Thr Val Thr Lys Glu Glu Trp Gln Gln
        180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 355
<211> LENGTH: 220
<212> TYPE: PRT
<213> ORGANISM: Artificial Sequence
<220> FEATURE:
<223> OTHER INFORMATION: Synthetic construct

<400> SEQUENCE: 355

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
            165                 170                 175

Phe Phe Leu Val Ser Lys Leu Thr Val Thr Lys Glu Glu Trp Gln Gln
        180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 356
<211> LENGTH: 220
<212> TYPE: PRT
<213> ORGANISM: Artificial Sequence
<220> FEATURE:
<223> OTHER INFORMATION: Synthetic construct

<400> SEQUENCE: 356

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

```
Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
            130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 357
<211> LENGTH: 220
<212> TYPE: PRT
<213> ORGANISM: Artificial Sequence
<220> FEATURE:
<223> OTHER INFORMATION: Synthetic construct

<400> SEQUENCE: 357

Pro Cys Pro Ala Pro Glu Ala Ala Gly Gly Pro Ser Val Phe Leu Phe
1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Gly Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
            130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175
```

```
Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 358
<211> LENGTH: 220
<212> TYPE: PRT
<213> ORGANISM: Artificial Sequence
<220> FEATURE:
<223> OTHER INFORMATION: Synthetic construct

<400> SEQUENCE: 358

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Phe Gly Thr Glu
145                 150                 155                 160

Trp Ser Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 359
<211> LENGTH: 220
<212> TYPE: PRT
<213> ORGANISM: Artificial Sequence
<220> FEATURE:
<223> OTHER INFORMATION: Synthetic construct

<400> SEQUENCE: 359

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
```

```
                35                  40                  45
Asn Trp Tyr Val Asp Gly Val Glu Val His Asn Ala Lys Thr Lys Pro
 50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Pro Ala Pro Ile Glu Lys Thr Ile Ser Lys Ala
                100                 105                 110
Lys Gly Gln Pro Arg Glu Pro Gln Val Tyr Thr Leu Pro Pro Ser Arg
                115                 120                 125
Asp Glu Leu Thr Lys Asn Gln Val Ser Leu Ser Cys Ala Val Lys Gly
                130                 135                 140
Phe Tyr Pro Ser Asp Ile Ala Val Glu Trp Ser Phe Gly Thr Glu
145                 150                 155                 160
Trp Ser Ser Tyr Lys Thr Thr Pro Pro Val Leu Asp Ser Asp Gly Ser
                165                 170                 175
Phe Phe Leu Val Ser Lys Leu Thr Val Thr Lys Glu Glu Trp Gln Gln
                180                 185                 190
Gly Phe Val Phe Ser Cys Ser Val Met His Glu Ala Leu His Asn His
                195                 200                 205
Tyr Thr Gln Lys Ser Leu Ser Leu Ser Pro Gly Lys
                210                 215                 220

<210> SEQ ID NO 360
<211> LENGTH: 220
<212> TYPE: PRT
<213> ORGANISM: Artificial Sequence
<220> FEATURE:
<223> OTHER INFORMATION: Synthetic construct

<400> SEQUENCE: 360

Pro Cys Pro Ala Pro Glu Ala Ala Gly Gly Pro Ser Val Phe Leu Phe
  1                   5                  10                  15
Pro Pro Lys Pro Lys Asp Thr Leu Tyr Ile Thr Arg Glu Pro Glu Val
                 20                  25                  30
Thr Cys Val Val Val Asp Val Ser His Glu Asp Pro Glu Val Lys Phe
                 35                  40                  45
Asn Trp Tyr Val Asp Gly Val Glu Val His Asn Ala Lys Thr Lys Pro
 50                  55                  60
Arg Glu Glu Gln Tyr Asn Ser Thr Tyr Arg Val Val Ser Val Leu Thr
 65                  70                  75                  80
Val Leu His Gln Asp Trp Leu Asn Gly Lys Glu Tyr Lys Cys Lys Val
                 85                  90                  95
Ser Asn Lys Ala Leu Gly Ala Pro Ile Glu Lys Thr Ile Ser Lys Ala
                100                 105                 110
Lys Gly Gln Pro Arg Glu Pro Gln Val Tyr Thr Leu Pro Pro Ser Arg
                115                 120                 125
Asp Glu Leu Thr Lys Asn Gln Val Ser Leu Ser Cys Ala Val Lys Gly
                130                 135                 140
Phe Tyr Pro Ser Asp Ile Ala Val Glu Trp Ser Phe Gly Thr Glu
145                 150                 155                 160
Trp Ser Ser Tyr Lys Thr Thr Pro Pro Val Leu Asp Ser Asp Gly Ser
                165                 170                 175
Phe Phe Leu Val Ser Lys Leu Thr Val Thr Lys Glu Glu Trp Gln Gln
```

```
                    180                 185                 190
Gly Phe Val Phe Ser Cys Ser Val Met His Glu Ala Leu His Asn His
                195                 200                 205

Tyr Thr Gln Lys Ser Leu Ser Leu Ser Pro Gly Lys
            210                 215                 220

<210> SEQ ID NO 361
<211> LENGTH: 220
<212> TYPE: PRT
<213> ORGANISM: Artificial Sequence
<220> FEATURE:
<223> OTHER INFORMATION: Synthetic construct

<400> SEQUENCE: 361

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 362
<211> LENGTH: 220
<212> TYPE: PRT
<213> ORGANISM: Artificial Sequence
<220> FEATURE:
<223> OTHER INFORMATION: Synthetic construct

<400> SEQUENCE: 362

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45
```

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
             100                 105                 110

Lys Gly Gln Pro Arg Glu Pro Gln Val Tyr Thr Leu Pro Pro Ser Arg
             115                 120                 125

Asp Glu Leu Thr Lys Asn Gln Val Ser Leu Trp Cys Leu Val Lys Gly
130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
210                 215                 220

<210> SEQ ID NO 363
<211> LENGTH: 220
<212> TYPE: PRT
<213> ORGANISM: Artificial Sequence
<220> FEATURE:
<223> OTHER INFORMATION: Synthetic construct

<400> SEQUENCE: 363

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Gly Ala Pro Ile Glu Lys Thr Ile Ser Lys Ala
             100                 105                 110

Lys Gly Gln Pro Arg Glu Pro Gln Val Tyr Thr Leu Pro Pro Ser Arg
             115                 120                 125

Asp Glu Leu Thr Lys Asn Gln Val Ser Leu Trp Cys Leu Val Lys Gly
130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 364
<211> LENGTH: 220
<212> TYPE: PRT
<213> ORGANISM: Artificial Sequence
<220> FEATURE:
<223> OTHER INFORMATION: Synthetic construct

<400> SEQUENCE: 364

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 365
<211> LENGTH: 220
<212> TYPE: PRT
<213> ORGANISM: Artificial Sequence
<220> FEATURE:
<223> OTHER INFORMATION: Synthetic construct

<400> SEQUENCE: 365

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 366
<211> LENGTH: 220
<212> TYPE: PRT
<213> ORGANISM: Artificial Sequence
<220> FEATURE:
<223> OTHER INFORMATION: Synthetic construct

<400> SEQUENCE: 366

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 367
<211> LENGTH: 220
<212> TYPE: PRT
<213> ORGANISM: Artificial Sequence
<220> FEATURE:
<223> OTHER INFORMATION: Synthetic construct

<400> SEQUENCE: 367

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 368
<211> LENGTH: 220
<212> TYPE: PRT
<213> ORGANISM: Artificial Sequence
<220> FEATURE:
<223> OTHER INFORMATION: Synthetic construct

<400> SEQUENCE: 368

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr

```
                65                  70                  75                  80
Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
                130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 369
<211> LENGTH: 220
<212> TYPE: PRT
<213> ORGANISM: Artificial Sequence
<220> FEATURE:
<223> OTHER INFORMATION: Synthetic construct

<400> SEQUENCE: 369

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
                130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
```

<210> SEQ ID NO 370
<211> LENGTH: 220
<212> TYPE: PRT
<213> ORGANISM: Artificial Sequence
<220> FEATURE:
<223> OTHER INFORMATION: Synthetic construct

<400> SEQUENCE: 370

```
Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 371
<211> LENGTH: 220
<212> TYPE: PRT
<213> ORGANISM: Artificial Sequence
<220> FEATURE:
<223> OTHER INFORMATION: Synthetic construct

<400> SEQUENCE: 371

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 372
<211> LENGTH: 220
<212> TYPE: PRT
<213> ORGANISM: Artificial Sequence
<220> FEATURE:
<223> OTHER INFORMATION: Synthetic construct

<400> SEQUENCE: 372

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Ser Tyr Gly Thr Glu
145                 150                 155                 160

Trp Ala Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 373
<211> LENGTH: 220
<212> TYPE: PRT
<213> ORGANISM: Artificial Sequence
<220> FEATURE:
<223> OTHER INFORMATION: Synthetic construct

<400> SEQUENCE: 373

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 374
<211> LENGTH: 220
<212> TYPE: PRT
<213> ORGANISM: Artificial Sequence
<220> FEATURE:
<223> OTHER INFORMATION: Synthetic construct

<400> SEQUENCE: 374

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 375
<211> LENGTH: 220
<212> TYPE: PRT
<213> ORGANISM: Artificial Sequence
<220> FEATURE:
<223> OTHER INFORMATION: Synthetic construct

<400> SEQUENCE: 375

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 376
```

<211> LENGTH: 220
<212> TYPE: PRT
<213> ORGANISM: Artificial Sequence
<220> FEATURE:
<223> OTHER INFORMATION: Synthetic construct

<400> SEQUENCE: 376

```
Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 377
<211> LENGTH: 220
<212> TYPE: PRT
<213> ORGANISM: Artificial Sequence
<220> FEATURE:
<223> OTHER INFORMATION: Synthetic construct

<400> SEQUENCE: 377

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
```

```
                     100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
            130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 378
<211> LENGTH: 220
<212> TYPE: PRT
<213> ORGANISM: Artificial Sequence
<220> FEATURE:
<223> OTHER INFORMATION: Synthetic construct

<400> SEQUENCE: 378

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
            130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 379
<211> LENGTH: 220
<212> TYPE: PRT
```

<213> ORGANISM: Artificial Sequence
<220> FEATURE:
<223> OTHER INFORMATION: Synthetic construct

<400> SEQUENCE: 379

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 380
<211> LENGTH: 220
<212> TYPE: PRT
<213> ORGANISM: Artificial Sequence
<220> FEATURE:
<223> OTHER INFORMATION: Synthetic construct

<400> SEQUENCE: 380

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

Lys Gly Gln Pro Arg Glu Pro Gln Val Tyr Thr Leu Pro Ser Arg
            115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 381
<211> LENGTH: 220
<212> TYPE: PRT
<213> ORGANISM: Artificial Sequence
<220> FEATURE:
<223> OTHER INFORMATION: Synthetic construct

<400> SEQUENCE: 381

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 382
<211> LENGTH: 220
<212> TYPE: PRT
<213> ORGANISM: Artificial Sequence
<220> FEATURE:

<223> OTHER INFORMATION: Synthetic construct

<400> SEQUENCE: 382

```
Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 383
<211> LENGTH: 220
<212> TYPE: PRT
<213> ORGANISM: Artificial Sequence
<220> FEATURE:
<223> OTHER INFORMATION: Synthetic construct

<400> SEQUENCE: 383

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125
```

```
Asp Glu Leu Thr Lys Asn Gln Val Ser Leu Ser Cys Ala Val Lys Gly
            130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 384
<211> LENGTH: 220
<212> TYPE: PRT
<213> ORGANISM: Artificial Sequence
<220> FEATURE:
<223> OTHER INFORMATION: Synthetic construct

<400> SEQUENCE: 384

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
            130                 135                 140

Phe Tyr Pro Ser Asp Ile Ala Val Glu Trp Glu Ser Tyr Gly Thr Glu
145                 150                 155                 160

Trp Val Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 385
<211> LENGTH: 220
<212> TYPE: PRT
<213> ORGANISM: Artificial Sequence
<220> FEATURE:
<223> OTHER INFORMATION: Synthetic construct
```

<400> SEQUENCE: 385

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 386
<211> LENGTH: 220
<212> TYPE: PRT
<213> ORGANISM: Artificial Sequence
<220> FEATURE:
<223> OTHER INFORMATION: Synthetic construct

<400> SEQUENCE: 386

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly

```
              130                 135                 140
Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
210                 215                 220

<210> SEQ ID NO 387
<211> LENGTH: 220
<212> TYPE: PRT
<213> ORGANISM: Artificial Sequence
<220> FEATURE:
<223> OTHER INFORMATION: Synthetic construct

<400> SEQUENCE: 387

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
210                 215                 220

<210> SEQ ID NO 388
<211> LENGTH: 220
<212> TYPE: PRT
<213> ORGANISM: Artificial Sequence
<220> FEATURE:
<223> OTHER INFORMATION: Synthetic construct

<400> SEQUENCE: 388
```

```
Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
                130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
210                 215                 220

<210> SEQ ID NO 389
<211> LENGTH: 220
<212> TYPE: PRT
<213> ORGANISM: Artificial Sequence
<220> FEATURE:
<223> OTHER INFORMATION: Synthetic construct

<400> SEQUENCE: 389

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
                130                 135                 140
```

```
Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
        210                 215                 220
```

<210> SEQ ID NO 390
<211> LENGTH: 220
<212> TYPE: PRT
<213> ORGANISM: Artificial Sequence
<220> FEATURE:
<223> OTHER INFORMATION: Synthetic construct

<400> SEQUENCE: 390

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
        210                 215                 220
```

<210> SEQ ID NO 391
<211> LENGTH: 220
<212> TYPE: PRT
<213> ORGANISM: Artificial Sequence
<220> FEATURE:
<223> OTHER INFORMATION: Synthetic construct

<400> SEQUENCE: 391

```
Pro Cys Pro Ala Pro Glu Leu Leu Gly Gly Pro Ser Val Phe Leu Phe
1               5                   10                  15
```

```
Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Ser Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
    210                 215                 220

<210> SEQ ID NO 392
<211> LENGTH: 220
<212> TYPE: PRT
<213> ORGANISM: Artificial Sequence
<220> FEATURE:
<223> OTHER INFORMATION: Synthetic construct

<400> SEQUENCE: 392

Pro Cys Pro Ala Pro Glu Ala Ala Gly Gly Pro Ser Val Phe Leu Phe
1                5                  10                  15

Pro Pro Lys Pro Lys Asp Thr Leu Met Ile Ser Arg Thr Pro Glu Val
            20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160
```

Trp Ser Asn Tyr Lys Thr Thr Pro Val Leu Asp Ser Asp Gly Ser
            165                 170                 175

Phe Phe Leu Val Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 393
<211> LENGTH: 220
<212> TYPE: PRT
<213> ORGANISM: Artificial Sequence
<220> FEATURE:
<223> OTHER INFORMATION: Synthetic construct

<400> SEQUENCE: 393

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Val Leu Asp Ser Asp Gly Ser
            165                 170                 175

Phe Phe Leu Val Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 394
<211> LENGTH: 220
<212> TYPE: PRT
<213> ORGANISM: Artificial Sequence
<220> FEATURE:
<223> OTHER INFORMATION: Synthetic construct

<400> SEQUENCE: 394

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val

```
                20              25              30
Thr Cys Val Val Asp Val Ser His Glu Asp Pro Glu Val Lys Phe
        35              40              45
Asn Trp Tyr Val Asp Gly Val Glu Val His Asn Ala Lys Thr Lys Pro
 50              55              60
Arg Glu Glu Gln Tyr Asn Ser Thr Tyr Arg Val Val Ser Val Leu Thr
 65              70              75              80
Val Leu His Gln Asp Trp Leu Asn Gly Lys Glu Tyr Lys Cys Lys Val
                85              90              95
Ser Asn Lys Ala Leu Pro Ala Pro Ile Glu Lys Thr Ile Ser Lys Ala
            100             105             110
Lys Gly Gln Pro Arg Glu Pro Gln Val Tyr Thr Leu Pro Pro Ser Arg
            115             120             125
Asp Glu Leu Thr Lys Asn Gln Val Ser Leu Ser Cys Ala Val Lys Gly
            130             135             140
Phe Tyr Pro Ser Asp Ile Ala Val Glu Trp Glu Ser Tyr Gly Thr Glu
145             150             155             160
Trp Ser Asn Tyr Lys Thr Thr Pro Pro Val Leu Asp Ser Asp Gly Ser
                165             170             175
Phe Phe Leu Val Ser Lys Leu Thr Val Ser Lys Glu Trp Gln Gln
                180             185             190
Gly Phe Val Phe Ser Cys Ser Val Met His Glu Ala Leu His Asn His
                195             200             205
Tyr Thr Gln Lys Ser Leu Ser Leu Ser Pro Gly Lys
            210             215             220
```

<210> SEQ ID NO 395
<211> LENGTH: 220
<212> TYPE: PRT
<213> ORGANISM: Artificial Sequence
<220> FEATURE:
<223> OTHER INFORMATION: Synthetic construct

<400> SEQUENCE: 395

```
Pro Cys Pro Ala Pro Glu Ala Ala Gly Gly Pro Ser Val Phe Leu Phe
 1               5              10              15
Pro Pro Lys Pro Lys Asp Thr Leu Tyr Ile Thr Arg Glu Pro Glu Val
            20              25              30
Thr Cys Val Val Val Asp Val Ser His Glu Asp Pro Glu Val Lys Phe
        35              40              45
Asn Trp Tyr Val Asp Gly Val Glu Val His Asn Ala Lys Thr Lys Pro
 50              55              60
Arg Glu Glu Gln Tyr Asn Ser Thr Tyr Arg Val Val Ser Val Leu Thr
 65              70              75              80
Val Leu His Gln Asp Trp Leu Asn Gly Lys Glu Tyr Lys Cys Lys Val
                85              90              95
Ser Asn Lys Ala Leu Pro Ala Pro Ile Glu Lys Thr Ile Ser Lys Ala
            100             105             110
Lys Gly Gln Pro Arg Glu Pro Gln Val Tyr Thr Leu Pro Pro Ser Arg
            115             120             125
Asp Glu Leu Thr Lys Asn Gln Val Ser Leu Ser Cys Ala Val Lys Gly
            130             135             140
Phe Tyr Pro Ser Asp Ile Ala Val Glu Trp Glu Ser Tyr Gly Thr Glu
145             150             155             160
Trp Ser Asn Tyr Lys Thr Thr Pro Pro Val Leu Asp Ser Asp Gly Ser
```

```
                165                 170                 175
Phe Phe Leu Val Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 396
<211> LENGTH: 220
<212> TYPE: PRT
<213> ORGANISM: Artificial Sequence
<220> FEATURE:
<223> OTHER INFORMATION: Synthetic construct

<400> SEQUENCE: 396

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Ser Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 397
<211> LENGTH: 220
<212> TYPE: PRT
<213> ORGANISM: Artificial Sequence
<220> FEATURE:
<223> OTHER INFORMATION: Synthetic construct

<400> SEQUENCE: 397

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
        210                 215                 220

<210> SEQ ID NO 398
<211> LENGTH: 220
<212> TYPE: PRT
<213> ORGANISM: Artificial Sequence
<220> FEATURE:
<223> OTHER INFORMATION: Synthetic construct

<400> SEQUENCE: 398

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Trp Cys Leu Val Lys Gly
        130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

```
Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 399
<211> LENGTH: 220
<212> TYPE: PRT
<213> ORGANISM: Artificial Sequence
<220> FEATURE:
<223> OTHER INFORMATION: Synthetic construct

<400> SEQUENCE: 399

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 400
<211> LENGTH: 220
<212> TYPE: PRT
<213> ORGANISM: Artificial Sequence
<220> FEATURE:
<223> OTHER INFORMATION: Synthetic construct

<400> SEQUENCE: 400

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45
```

```
Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
            130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 401
<211> LENGTH: 220
<212> TYPE: PRT
<213> ORGANISM: Artificial Sequence
<220> FEATURE:
<223> OTHER INFORMATION: Synthetic construct

<400> SEQUENCE: 401

Pro Cys Pro Ala Pro Glu Ala Ala Gly Gly Pro Ser Val Phe Leu Phe
 1               5                  10                  15

Pro Pro Lys Pro Lys Asp Thr Leu Tyr Ile Thr Arg Glu Pro Glu Val
             20                  25                  30

Thr Cys Val Val Val Asp Val Ser His Glu Asp Pro Glu Val Lys Phe
             35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
             85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
            130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190
```

```
Gly Phe Val Phe Ser Cys Ser Val Met His Glu Ala Leu His Asn His
            195                 200                 205

Tyr Thr Gln Lys Ser Leu Ser Leu Ser Pro Gly Lys
        210                 215                 220

<210> SEQ ID NO 402
<211> LENGTH: 220
<212> TYPE: PRT
<213> ORGANISM: Artificial Sequence
<220> FEATURE:
<223> OTHER INFORMATION: Synthetic construct

<400> SEQUENCE: 402

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 403
<211> LENGTH: 220
<212> TYPE: PRT
<213> ORGANISM: Artificial Sequence
<220> FEATURE:
<223> OTHER INFORMATION: Synthetic construct

<400> SEQUENCE: 403

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
```

```
            50                  55                  60
Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
                130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
                210                 215                 220

<210> SEQ ID NO 404
<211> LENGTH: 220
<212> TYPE: PRT
<213> ORGANISM: Artificial Sequence
<220> FEATURE:
<223> OTHER INFORMATION: Synthetic construct

<400> SEQUENCE: 404

Pro Cys Pro Ala Pro Glu Ala Ala Gly Gly Pro Ser Val Phe Leu Phe
  1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
                 35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Ser Cys Ala Val Lys Gly
                130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                180                 185                 190

Gly Phe Val Phe Ser Cys Ser Val Met His Glu Ala Leu His Asn His
```

```
                 195                 200                 205
Tyr Thr Gln Lys Ser Leu Ser Leu Ser Pro Gly Lys
    210                 215                 220

<210> SEQ ID NO 405
<211> LENGTH: 220
<212> TYPE: PRT
<213> ORGANISM: Artificial Sequence
<220> FEATURE:
<223> OTHER INFORMATION: Synthetic construct

<400> SEQUENCE: 405

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 406
<211> LENGTH: 220
<212> TYPE: PRT
<213> ORGANISM: Artificial Sequence
<220> FEATURE:
<223> OTHER INFORMATION: Synthetic construct

<400> SEQUENCE: 406

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60
```

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Ser Cys Ala Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 407
<211> LENGTH: 220
<212> TYPE: PRT
<213> ORGANISM: Artificial Sequence
<220> FEATURE:
<223> OTHER INFORMATION: Synthetic construct

<400> SEQUENCE: 407

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Ser Cys Ala Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 408
<211> LENGTH: 220
<212> TYPE: PRT
<213> ORGANISM: Artificial Sequence
<220> FEATURE:
<223> OTHER INFORMATION: Synthetic construct

<400> SEQUENCE: 408

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Leu Trp Glu Ser Tyr Gly Thr Glu
145                 150                 155                 160

Trp Ala Ser Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 409
<211> LENGTH: 220
<212> TYPE: PRT
<213> ORGANISM: Artificial Sequence
<220> FEATURE:
<223> OTHER INFORMATION: Synthetic construct

<400> SEQUENCE: 409

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

```
Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220

<210> SEQ ID NO 410
<211> LENGTH: 220
<212> TYPE: PRT
<213> ORGANISM: Artificial Sequence
<220> FEATURE:
<223> OTHER INFORMATION: Synthetic construct

<400> SEQUENCE: 410

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Trp Cys Leu Val Lys Gly
130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
            165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
            195                 200                 205

Tyr Thr Gln Lys Ser Leu Ser Leu Ser Pro Gly Lys
            210                 215                 220
```

<210> SEQ ID NO 411
<211> LENGTH: 220
<212> TYPE: PRT
<213> ORGANISM: Artificial Sequence
<220> FEATURE:
<223> OTHER INFORMATION: Synthetic construct

<400> SEQUENCE: 411

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 412
<211> LENGTH: 220
<212> TYPE: PRT
<213> ORGANISM: Artificial Sequence
<220> FEATURE:
<223> OTHER INFORMATION: Synthetic construct

<400> SEQUENCE: 412

```
Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
```

```
                    85                  90                  95
Ser Asn Lys Ala Leu Pro Ala Pro Ile Glu Lys Thr Ile Ser Lys Ala
                100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Trp Cys Leu Val Lys Gly
        130                 135                 140
Phe Tyr Pro Ser Asp Ile Ala Val Glu Trp Glu Ser Tyr Gly Thr Glu
145                 150                 155                 160
Trp Ser Asn Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
                180                 185                 190
Gly Phe Val Phe Ser Cys Ser Val Met His Glu Ala Leu His Asn His
                195                 200                 205
Tyr Thr Gln Lys Ser Leu Ser Leu Ser Pro Gly Lys
        210                 215                 220

<210> SEQ ID NO 413
<211> LENGTH: 220
<212> TYPE: PRT
<213> ORGANISM: Artificial Sequence
<220> FEATURE:
<223> OTHER INFORMATION: Synthetic construct

<400> SEQUENCE: 413

Pro Cys Pro Ala Pro Glu Ala Ala Gly Gly Pro Ser Val Phe Leu Phe
1               5                   10                  15
Pro Pro Lys Pro Lys Asp Thr Leu Tyr Ile Thr Arg Glu Pro Glu Val
                20                  25                  30
Thr Cys Val Val Val Asp Val Ser His Glu Asp Pro Glu Val Lys Phe
            35                  40                  45
Asn Trp Tyr Val Asp Gly Val Glu Val His Asn Ala Lys Thr Lys Pro
    50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
                100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Trp Cys Leu Val Lys Gly
        130                 135                 140
Phe Tyr Pro Ser Asp Ile Ala Val Glu Trp Glu Ser Tyr Gly Thr Glu
145                 150                 155                 160
Trp Ser Asn Tyr Lys Thr Thr Pro Pro Val Leu Asp Ser Asp Gly Ser
                165                 170                 175
Phe Phe Leu Tyr Ser Lys Leu Thr Val Thr Lys Glu Glu Trp Gln Gln
                180                 185                 190
Gly Phe Val Phe Ser Cys Ser Val Met His Glu Ala Leu His Asn His
                195                 200                 205
Tyr Thr Gln Lys Ser Leu Ser Leu Ser Pro Gly Lys
        210                 215                 220
```

<210> SEQ ID NO 414
<211> LENGTH: 220
<212> TYPE: PRT
<213> ORGANISM: Artificial Sequence
<220> FEATURE:
<223> OTHER INFORMATION: Synthetic construct

<400> SEQUENCE: 414

```
Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Trp Cys Leu Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Tyr Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

<210> SEQ ID NO 415
<211> LENGTH: 220
<212> TYPE: PRT
<213> ORGANISM: Artificial Sequence
<220> FEATURE:
<223> OTHER INFORMATION: Synthetic construct

<400> SEQUENCE: 415

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

Ser Asn Lys Ala Leu Pro Ala Pro Ile Glu Lys Thr Ile Ser Lys Ala
         100                 105                 110

Lys Gly Gln Pro Arg Glu Pro Gln Val Tyr Thr Leu Pro Pro Ser Arg
         115                 120                 125

Asp Glu Leu Thr Lys Asn Gln Val Ser Leu Ser Cys Ala Val Lys Gly
         130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                 165                 170                 175

Phe Phe Leu Val Ser Lys Leu Thr Val Thr Lys Glu Glu Trp Gln Gln
         180                 185                 190

Gly Phe Val Phe Ser Cys Ser Val Met His Glu Ala Leu His Asn His
         195                 200                 205

Tyr Thr Gln Lys Ser Leu Ser Leu Ser Pro Gly Lys
         210                 215                 220

<210> SEQ ID NO 416
<211> LENGTH: 220
<212> TYPE: PRT
<213> ORGANISM: Artificial Sequence
<220> FEATURE:
<223> OTHER INFORMATION: Synthetic construct

<400> SEQUENCE: 416

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
         100                 105                 110

Lys Gly Gln Pro Arg Glu Pro Gln Val Tyr Thr Leu Pro Pro Ser Arg
         115                 120                 125

Asp Glu Leu Thr Lys Asn Gln Val Ser Leu Ser Cys Ala Val Lys Gly
         130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                 165                 170                 175

Phe Phe Leu Val Ser Lys Leu Thr Val Thr Lys Glu Glu Trp Gln Gln
         180                 185                 190

Gly Phe Val Phe Ser Cys Ser Val Met His Glu Ala Leu His Asn His
         195                 200                 205

Tyr Thr Gln Lys Ser Leu Ser Leu Ser Pro Gly Lys
         210                 215                 220

<210> SEQ ID NO 417
<211> LENGTH: 220

```
<212> TYPE: PRT
<213> ORGANISM: Artificial Sequence
<220> FEATURE:
<223> OTHER INFORMATION: Synthetic construct

<400> SEQUENCE: 417

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 418
<211> LENGTH: 220
<212> TYPE: PRT
<213> ORGANISM: Artificial Sequence
<220> FEATURE:
<223> OTHER INFORMATION: Synthetic construct

<400> SEQUENCE: 418

Pro Cys Pro Ala Pro Glu Leu Leu Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

```
Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
        130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                    180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
        210                 215                 220

<210> SEQ ID NO 419
<211> LENGTH: 220
<212> TYPE: PRT
<213> ORGANISM: Artificial Sequence
<220> FEATURE:
<223> OTHER INFORMATION: Synthetic construct

<400> SEQUENCE: 419

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                    85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
        130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
                    180                 185                 190

Gly Phe Val Phe Ser Cys Ser Val Met His Glu Ala Leu His Asn His
                195                 200                 205

Tyr Thr Gln Lys Ser Leu Ser Leu Ser Pro Gly Lys
        210                 215                 220

<210> SEQ ID NO 420
<211> LENGTH: 220
<212> TYPE: PRT
<213> ORGANISM: Artificial Sequence
```

```
<220> FEATURE:
<223> OTHER INFORMATION: Synthetic construct

<400> SEQUENCE: 420

Pro Cys Pro Ala Pro Glu Ala Ala Gly Gly Pro Ser Val Phe Leu Phe
1               5                   10                  15

Pro Pro Lys Pro Lys Asp Thr Leu Tyr Ile Thr Arg Glu Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Ser Cys Ala Val Lys Gly
    130                 135                 140

Phe Tyr Pro Ser Asp Ile Ala Val Glu Trp Glu Ser Tyr Gly Thr Glu
145                 150                 155                 160

Trp Ser Asn Tyr Lys Thr Thr Pro Pro Val Leu Asp Ser Asp Gly Ser
                165                 170                 175

Phe Phe Leu Val Ser Lys Leu Thr Val Thr Lys Glu Glu Trp Gln Gln
            180                 185                 190

Gly Phe Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 421
<211> LENGTH: 247
<212> TYPE: PRT
<213> ORGANISM: Artificial Sequence
<220> FEATURE:
<223> OTHER INFORMATION: Synthetic construct

<400> SEQUENCE: 421

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Tyr Ile Thr Arg Glu Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
```

```
                115                 120                 125
Gly Ala Pro Ile Glu Lys Thr Ile Ser Lys Ala Lys Gly Gln Pro Arg
            130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Tyr Gly Thr Glu Trp Ser Ser Tyr Lys
            180                 185                 190

Thr Thr Pro Pro Val Leu Asp Ser Asp Gly Ser Phe Phe Leu Tyr Ser
                195                 200                 205

Lys Leu Thr Val Thr Lys Ser Glu Trp Gln Gln Gly Phe Val Phe Ser
210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 422
<211> LENGTH: 181
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (97)..(97)
<223> OTHER INFORMATION: Xaa = Asp or Glu

<400> SEQUENCE: 422

Asn Ser Val Ile Ile Val Asp Lys Asn Gly Arg Leu Val Tyr Leu Val
1               5                   10                  15

Glu Asn Pro Gly Gly Tyr Val Ala Tyr Ser Lys Ala Ala Thr Val Thr
                20                  25                  30

Gly Lys Leu Val His Ala Asn Phe Gly Thr Lys Lys Asp Phe Glu Asp
            35                  40                  45

Leu Asp Ser Pro Val Asn Gly Ser Ile Val Ile Val Arg Ala Gly Lys
        50                  55                  60

Ile Thr Phe Ala Glu Lys Val Ala Asn Ala Glu Ser Leu Asn Ala Ile
65                  70                  75                  80

Gly Val Leu Ile Tyr Met Asp Gln Thr Lys Phe Pro Ile Val Asn Ala
                85                  90                  95

Xaa Leu Ser Phe Phe Gly His Ala His Leu Gly Thr Gly Asp Pro Tyr
                100                 105                 110

Thr Pro Gly Phe Pro Ser Phe Asn His Thr Gln Phe Pro Pro Ser Arg
            115                 120                 125

Ser Ser Gly Leu Pro Asn Ile Pro Val Gln Thr Ile Ser Arg Ala Ala
        130                 135                 140

Ala Glu Lys Leu Phe Gly Asn Met Glu Gly Asp Cys Pro Ser Asp Trp
145                 150                 155                 160

Lys Thr Asp Ser Thr Cys Arg Met Val Thr Ser Glu Asn Lys Asn Val
                165                 170                 175

Lys Leu Thr Val Ser
            180

<210> SEQ ID NO 423
<211> LENGTH: 330
```

```
<212> TYPE: PRT
<213> ORGANISM: Artificial Sequence
<220> FEATURE:
<223> OTHER INFORMATION: Synthetic construct

<400> SEQUENCE: 423
```

| | | | | | | | | | | | | | | | |
|---|---|---|---|---|---|---|---|---|---|---|---|---|---|---|---|
|Ala|Ser|Thr|Lys|Gly|Pro|Ser|Val|Phe|Pro|Leu|Ala|Pro|Ser|Ser|Lys|
|1| | | |5| | | |10| | | |15| | | |
|Ser|Thr|Ser|Gly|Gly|Thr|Ala|Ala|Leu|Gly|Cys|Leu|Val|Lys|Asp|Tyr|
| | | |20| | | |25| | | |30| | | | |
|Phe|Pro|Glu|Pro|Val|Thr|Val|Ser|Trp|Asn|Ser|Gly|Ala|Leu|Thr|Ser|
| | |35| | | |40| | | |45| | | | | |
|Gly|Val|His|Thr|Phe|Pro|Ala|Val|Leu|Gln|Ser|Ser|Gly|Leu|Tyr|Ser|
| |50| | | |55| | | |60| | | | | | |
|Leu|Ser|Ser|Val|Val|Thr|Val|Pro|Ser|Ser|Leu|Gly|Thr|Gln|Thr| |
|65| | | |70| | | |75| | | |80| | | |
|Tyr|Ile|Cys|Asn|Val|Asn|His|Lys|Pro|Ser|Asn|Thr|Lys|Val|Asp|Lys|
| | | |85| | | |90| | | |95| | | | |
|Lys|Val|Glu|Pro|Lys|Ser|Cys|Asp|Lys|Thr|His|Thr|Cys|Pro|Pro|Cys|
| | |100| | | |105| | | |110| | | | | |
|Pro|Ala|Pro|Glu|Leu|Leu|Gly|Gly|Pro|Ser|Val|Phe|Leu|Phe|Pro|Pro|
| | |115| | | |120| | | |125| | | | | |
|Lys|Pro|Lys|Asp|Thr|Leu|Met|Ile|Ser|Arg|Thr|Pro|Glu|Val|Thr|Cys|
|130| | | |135| | | |140| | | | | | | |
|Val|Val|Val|Asp|Val|Ser|His|Glu|Asp|Pro|Glu|Val|Lys|Phe|Asn|Trp|
|145| | | |150| | | |155| | | |160| | | |
|Tyr|Val|Asp|Gly|Val|Glu|Val|His|Asn|Ala|Lys|Thr|Lys|Pro|Arg|Glu|
| | | |165| | | |170| | | |175| | | | |
|Glu|Gln|Tyr|Asn|Ser|Thr|Tyr|Arg|Val|Val|Ser|Val|Leu|Thr|Val|Leu|
| | |180| | | |185| | | |190| | | | | |
|His|Gln|Asp|Trp|Leu|Asn|Gly|Lys|Glu|Tyr|Lys|Cys|Lys|Val|Ser|Asn|
| |195| | | |200| | | |205| | | | | | |
|Lys|Ala|Leu|Pro|Ala|Pro|Ile|Glu|Lys|Thr|Ile|Ser|Lys|Ala|Lys|Gly|
| |210| | | |215| | | |220| | | | | | |
|Gln|Pro|Arg|Glu|Pro|Gln|Val|Tyr|Thr|Leu|Pro|Pro|Ser|Arg|Asp|Glu|
|225| | | |230| | | |235| | | |240| | | |
|Leu|Thr|Lys|Asn|Gln|Val|Ser|Leu|Thr|Cys|Leu|Val|Lys|Gly|Phe|Tyr|
| | | |245| | | |250| | | |255| | | | |
|Pro|Ser|Asp|Ile|Ala|Val|Glu|Trp|Glu|Ser|Asn|Gly|Gln|Pro|Glu|Asn|
| | |260| | | |265| | | |270| | | | | |
|Asn|Tyr|Lys|Thr|Thr|Pro|Pro|Val|Leu|Asp|Ser|Asp|Gly|Ser|Phe|Phe|
| |275| | | |280| | | |285| | | | | | |
|Leu|Tyr|Ser|Lys|Leu|Thr|Val|Asp|Lys|Ser|Arg|Trp|Gln|Gln|Gly|Asn|
| |290| | | |295| | | |300| | | | | | |
|Val|Phe|Ser|Cys|Ser|Val|Met|His|Glu|Ala|Leu|His|Asn|His|Tyr|Thr|
|305| | | |310| | | |315| | | |320| | | |
|Gln|Lys|Ser|Leu|Ser|Leu|Ser|Pro|Gly|Lys| | | | | | |
| | | |325| | | |330| | | | | | | | |

```
<210> SEQ ID NO 424
<211> LENGTH: 326
<212> TYPE: PRT
<213> ORGANISM: Artificial Sequence
<220> FEATURE:
<223> OTHER INFORMATION: Synthetic construct

<400> SEQUENCE: 424
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 425
<211> LENGTH: 377
<212> TYPE: PRT
<213> ORGANISM: Artificial Sequence
<220> FEATURE:
<223> OTHER INFORMATION: Synthetic construct

<400> SEQUENCE: 425

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 426
<211> LENGTH: 327
<212> TYPE: PRT
<213> ORGANISM: Artificial Sequence
<220> FEATURE:
<223> OTHER INFORMATION: Synthetic construct

<400> SEQUENCE: 426

Ala Ser Thr Lys Gly Pro Ser Val Phe Pro Leu Ala Pro Cys Ser Arg
1               5                   10                  15
```

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 427
<211> LENGTH: 34
<212> TYPE: PRT
<213> ORGANISM: Artificial Sequence
<220> FEATURE:
<223> OTHER INFORMATION: Synthetic construct

<400> SEQUENCE: 427

Thr Ile Ser Arg Ala Ala Ala Glu Lys Leu Phe Gly Asn Met Glu Gly
1               5                   10                  15

Asp Cys Pro Ser Asp Trp Lys Thr Asp Ser Thr Cys Arg Met Val Thr
            20                  25                  30

Ser Glu
```

<210> SEQ ID NO 428
<211> LENGTH: 83
<212> TYPE: PRT
<213> ORGANISM: Artificial Sequence
<220> FEATURE:
<223> OTHER INFORMATION: Synthetic construct

<400> SEQUENCE: 428

Asp Lys Asn Gly Arg Leu Val Tyr Leu Val Glu Asn Pro Gly Gly Tyr
1               5                   10                  15

Val Ala Tyr Ser Lys Ala Ala Thr Val Thr Gly Lys Leu Val His Ala
                20                  25                  30

Asn Phe Gly Thr Lys Lys Asp Phe Glu Asp Leu Tyr Thr Pro Val Asn
            35                  40                  45

Gly Ser Ile Val Ile Val Arg Ala Gly Lys Ile Thr Phe Ala Glu Lys
        50                  55                  60

Val Ala Asn Ala Glu Ser Leu Asn Ala Ile Gly Val Leu Ile Tyr Met
65                  70                  75                  80

Asp Gln Thr

<210> SEQ ID NO 429
<211> LENGTH: 25
<212> TYPE: PRT
<213> ORGANISM: Artificial Sequence
<220> FEATURE:
<223> OTHER INFORMATION: Synthetic construct

<400> SEQUENCE: 429

Ser Lys Asn Val Lys Leu Thr Val Ser Asn Val Leu Lys Glu Ile Lys
1               5                   10                  15

Ile Leu Asn Ile Phe Gly Val Ile Lys
            20                  25

<210> SEQ ID NO 430
<211> LENGTH: 5
<212> TYPE: PRT
<213> ORGANISM: Artificial Sequence
<220> FEATURE:
<223> OTHER INFORMATION: Synthetic construct

<400> SEQUENCE: 430

Ser Lys Asn Val Lys
1               5

<210> SEQ ID NO 431
<211> LENGTH: 10
<212> TYPE: PRT
<213> ORGANISM: Artificial Sequence
<220> FEATURE:
<223> OTHER INFORMATION: Synthetic construct

<400> SEQUENCE: 431

Ser Lys Asn Val Lys Leu Thr Val Ser Asn
1               5                   10

<210> SEQ ID NO 432
<211> LENGTH: 15
<212> TYPE: PRT
<213> ORGANISM: Artificial Sequence
<220> FEATURE:
<223> OTHER INFORMATION: Synthetic construct

<400> SEQUENCE: 432

Ser Lys Asn Val Lys Leu Thr Val Ser Asn Val Leu Lys Glu Ile
1               5                   10                  15

<210> SEQ ID NO 433
<211> LENGTH: 20
<212> TYPE: PRT
<213> ORGANISM: Artificial Sequence
<220> FEATURE:
<223> OTHER INFORMATION: Synthetic construct

<400> SEQUENCE: 433

Ser Lys Asn Val Lys Leu Thr Val Ser Asn Val Leu Lys Glu Ile Lys
1               5                   10                  15

Ile Leu Asn Ile
            20

<210> SEQ ID NO 434
<211> LENGTH: 25
<212> TYPE: PRT
<213> ORGANISM: Artificial Sequence
<220> FEATURE:
<223> OTHER INFORMATION: Synthetic construct

<400> SEQUENCE: 434

Lys Phe Pro Ile Val Asn Ala Glu Leu Ser Phe Phe Gly His Ala His
1               5                   10                  15

Leu Gly Thr Gly Asp Pro Tyr Thr Pro
            20                  25

<210> SEQ ID NO 435
<211> LENGTH: 5
<212> TYPE: PRT
<213> ORGANISM: Artificial Sequence
<220> FEATURE:
<223> OTHER INFORMATION: Synthetic construct

<400> SEQUENCE: 435

Lys Phe Pro Ile Val
1               5

<210> SEQ ID NO 436
<211> LENGTH: 10
<212> TYPE: PRT
<213> ORGANISM: Artificial Sequence
<220> FEATURE:
<223> OTHER INFORMATION: Synthetic construct

<400> SEQUENCE: 436

Lys Phe Pro Ile Val Asn Ala Glu Leu Ser
1               5                   10

<210> SEQ ID NO 437
<211> LENGTH: 15
<212> TYPE: PRT
<213> ORGANISM: Artificial Sequence
<220> FEATURE:
<223> OTHER INFORMATION: Synthetic construct

<400> SEQUENCE: 437

Lys Phe Pro Ile Val Asn Ala Glu Leu Ser Phe Phe Gly His Ala
1               5                   10                  15

<210> SEQ ID NO 438
<211> LENGTH: 20
<212> TYPE: PRT
<213> ORGANISM: Artificial Sequence
<220> FEATURE:
<223> OTHER INFORMATION: Synthetic construct

<400> SEQUENCE: 438

Lys Phe Pro Ile Val Asn Ala Glu Leu Ser Phe Phe Gly His Ala His
1               5                   10                  15

Leu Gly Thr Gly
            20

<210> SEQ ID NO 439
<211> LENGTH: 24
<212> TYPE: PRT
<213> ORGANISM: Artificial Sequence
<220> FEATURE:
<223> OTHER INFORMATION: Synthetic construct

<400> SEQUENCE: 439

Gly Phe Pro Ser Phe Asn His Thr Gln Phe Pro Pro Ser Arg Ser Ser
1               5                   10                  15

Gly Leu Pro Asn Ile Pro Val Gln
            20

<210> SEQ ID NO 440
<211> LENGTH: 5
<212> TYPE: PRT
<213> ORGANISM: Artificial Sequence
<220> FEATURE:
<223> OTHER INFORMATION: Synthetic construct

<400> SEQUENCE: 440

Asn Ile Pro Val Gln
1               5

<210> SEQ ID NO 441
<211> LENGTH: 10
<212> TYPE: PRT
<213> ORGANISM: Artificial Sequence
<220> FEATURE:
<223> OTHER INFORMATION: Synthetic construct

<400> SEQUENCE: 441

Ser Ser Gly Leu Pro Asn Ile Pro Val Gln
1               5                   10

<210> SEQ ID NO 442
<211> LENGTH: 15
<212> TYPE: PRT
<213> ORGANISM: Artificial Sequence
<220> FEATURE:
<223> OTHER INFORMATION: Synthetic construct

<400> SEQUENCE: 442

Phe Pro Pro Ser Arg Ser Ser Gly Leu Pro Asn Ile Pro Val Gln
1               5                   10                  15

<210> SEQ ID NO 443
<211> LENGTH: 20
<212> TYPE: PRT
<213> ORGANISM: Artificial Sequence
<220> FEATURE:
<223> OTHER INFORMATION: Synthetic construct

<400> SEQUENCE: 443

Phe Asn His Thr Gln Phe Pro Pro Ser Arg Ser Ser Gly Leu Pro Asn
1               5                   10                  15

Ile Pro Val Gln
        20

<210> SEQ ID NO 444
<211> LENGTH: 25
<212> TYPE: PRT
<213> ORGANISM: Artificial Sequence
<220> FEATURE:
<223> OTHER INFORMATION: Synthetic construct

<400> SEQUENCE: 444

Ser Lys Val Trp Arg Asp Gln His Phe Val Lys Ile Gln Val Lys Asp
1               5                   10                  15

Ser Ala Gln Asn Ser Val Ile Ile Val
            20                  25

<210> SEQ ID NO 445
<211> LENGTH: 5
<212> TYPE: PRT
<213> ORGANISM: Artificial Sequence
<220> FEATURE:
<223> OTHER INFORMATION: Synthetic construct

<400> SEQUENCE: 445

Ser Val Ile Ile Val
1               5

<210> SEQ ID NO 446
<211> LENGTH: 10
<212> TYPE: PRT
<213> ORGANISM: Artificial Sequence
<220> FEATURE:
<223> OTHER INFORMATION: Synthetic construct

<400> SEQUENCE: 446

Asp Ser Ala Gln Asn Ser Val Ile Ile Val
1               5                   10

<210> SEQ ID NO 447
<211> LENGTH: 15
<212> TYPE: PRT
<213> ORGANISM: Artificial Sequence
<220> FEATURE:
<223> OTHER INFORMATION: Synthetic construct

<400> SEQUENCE: 447

Lys Ile Gln Val Lys Asp Ser Ala Gln Asn Ser Val Ile Ile Val
1               5                   10                  15

<210> SEQ ID NO 448
<211> LENGTH: 20
<212> TYPE: PRT
<213> ORGANISM: Artificial Sequence
<220> FEATURE:
<223> OTHER INFORMATION: Synthetic construct

<400> SEQUENCE: 448

Asp Gln His Phe Val Lys Ile Gln Val Lys Asp Ser Ala Gln Asn Ser
1               5                   10                  15

Val Ile Ile Val
        20

<210> SEQ ID NO 449
<211> LENGTH: 54
<212> TYPE: PRT
<213> ORGANISM: Artificial Sequence
<220> FEATURE:
<223> OTHER INFORMATION: Synthetic construct

<400> SEQUENCE: 449

Ser Ser Gly Leu Pro Asn Ile Pro Val Gln Thr Ile Ser Arg Ala Ala
1               5                   10                  15

Ala Glu Lys Leu Phe Gly Asn Met Glu Gly Asp Cys Pro Ser Asp Trp
            20                  25                  30

Lys Thr Asp Ser Thr Cys Arg Met Val Thr Ser Glu Ser Lys Asn Val
        35                  40                  45

Lys Leu Thr Val Ser Asn
    50

<210> SEQ ID NO 450
<211> LENGTH: 103
<212> TYPE: PRT
<213> ORGANISM: Artificial Sequence
<220> FEATURE:
<223> OTHER INFORMATION: Synthetic construct

<400> SEQUENCE: 450

Asp Ser Ala Gln Asn Ser Val Ile Ile Val Asp Lys Asn Gly Arg Leu
1               5                   10                  15

Val Tyr Leu Val Glu Asn Pro Gly Gly Tyr Val Ala Tyr Ser Lys Ala
            20                  25                  30

Ala Thr Val Thr Gly Lys Leu Val His Ala Asn Phe Gly Thr Lys Lys
        35                  40                  45

Asp Phe Glu Asp Leu Tyr Thr Pro Val Asn Gly Ser Ile Val Ile Val
    50                  55                  60

Arg Ala Gly Lys Ile Thr Phe Ala Glu Lys Val Ala Asn Ala Glu Ser
65                  70                  75                  80

Leu Asn Ala Ile Gly Val Leu Ile Tyr Met Asp Gln Thr Lys Phe Pro
                85                  90                  95

Ile Val Asn Ala Glu Leu Ser
            100

<210> SEQ ID NO 451
<211> LENGTH: 54
<212> TYPE: PRT
<213> ORGANISM: Artificial Sequence
<220> FEATURE:
<223> OTHER INFORMATION: Synthetic construct

<400> SEQUENCE: 451

Ser Ser Gly Leu Pro Asn Ile Pro Val Gln Thr Ile Ser Arg Ala Ala
1               5                   10                  15

Ala Glu Lys Leu Phe Gly Asn Met Glu Gly Asp Cys Pro Ser Asp Trp
            20                  25                  30

Lys Thr Asp Ser Thr Cys Lys Met Val Thr Ser Glu Asn Lys Ser Val
        35                  40                  45

Lys Leu Thr Val Ser Asn
    50

<210> SEQ ID NO 452
<211> LENGTH: 103
<212> TYPE: PRT
<213> ORGANISM: Artificial Sequence
<220> FEATURE:
<223> OTHER INFORMATION: Synthetic construct

<400> SEQUENCE: 452

```
Asp Ser Ala Gln Asn Ser Val Ile Ile Val Asp Lys Asn Gly Gly Leu
1               5                   10                  15

Val Tyr Leu Val Glu Asn Pro Gly Gly Tyr Val Ala Tyr Ser Lys Ala
            20                  25                  30

Ala Thr Val Thr Gly Lys Leu Val His Ala Asn Phe Gly Thr Lys Lys
        35                  40                  45

Asp Phe Glu Asp Leu Asp Ser Pro Val Asn Gly Ser Ile Val Ile Val
    50                  55                  60

Arg Ala Gly Lys Ile Thr Phe Ala Glu Lys Val Ala Asn Ala Glu Ser
65                  70                  75                  80

Leu Asn Ala Ile Gly Val Leu Ile Tyr Met Asp Gln Thr Lys Phe Pro
                85                  90                  95

Ile Val Lys Ala Asp Leu Ser
            100
```

<210> SEQ ID NO 453
<211> LENGTH: 4
<212> TYPE: PRT
<213> ORGANISM: Artificial Sequence
<220> FEATURE:
<223> OTHER INFORMATION: Synthetic construct

<400> SEQUENCE: 453

```
Gly Gly Gly Gly
1
```

<210> SEQ ID NO 454
<211> LENGTH: 4
<212> TYPE: PRT
<213> ORGANISM: Artificial Sequence
<220> FEATURE:
<223> OTHER INFORMATION: Synthetic construct

<400> SEQUENCE: 454

```
Gly Ser Gly Ser
1
```

<210> SEQ ID NO 455
<211> LENGTH: 4
<212> TYPE: PRT
<213> ORGANISM: Artificial Sequence
<220> FEATURE:
<223> OTHER INFORMATION: Synthetic construct

<400> SEQUENCE: 455

```
Ser Gly Gly Gly
1
```

<210> SEQ ID NO 456
<211> LENGTH: 4
<212> TYPE: PRT
<213> ORGANISM: Artificial Sequence
<220> FEATURE:
<223> OTHER INFORMATION: Synthetic construct

<400> SEQUENCE: 456

```
Gly Ser Gly Gly
1
```

<210> SEQ ID NO 457
<211> LENGTH: 4
<212> TYPE: PRT
<213> ORGANISM: Artificial Sequence

```
<220> FEATURE:
<223> OTHER INFORMATION: Synthetic construct

<400> SEQUENCE: 457

Gly Gly Ser Gly
1

<210> SEQ ID NO 458
<211> LENGTH: 4
<212> TYPE: PRT
<213> ORGANISM: Artificial Sequence
<220> FEATURE:
<223> OTHER INFORMATION: Synthetic construct

<400> SEQUENCE: 458

Gly Gly Gly Ser
1

<210> SEQ ID NO 459
<211> LENGTH: 6
<212> TYPE: PRT
<213> ORGANISM: Artificial Sequence
<220> FEATURE:
<223> OTHER INFORMATION: Synthetic construct

<400> SEQUENCE: 459

His His His His His His
1               5

<210> SEQ ID NO 460
<211> LENGTH: 10
<212> TYPE: PRT
<213> ORGANISM: Artificial Sequence
<220> FEATURE:
<223> OTHER INFORMATION: Synthetic construct

<400> SEQUENCE: 460

His His His His His His His His His His
1               5                   10

<210> SEQ ID NO 461
<211> LENGTH: 15
<212> TYPE: PRT
<213> ORGANISM: Artificial Sequence
<220> FEATURE:
<223> OTHER INFORMATION: Synthetic construct

<400> SEQUENCE: 461

Gly Leu Asn Asp Ile Phe Glu Ala Gln Lys Ile Glu Trp His Glu
1               5                   10                  15

<210> SEQ ID NO 462
<211> LENGTH: 8
<212> TYPE: PRT
<213> ORGANISM: Artificial Sequence
<220> FEATURE:
<223> OTHER INFORMATION: Synthetic construct

<400> SEQUENCE: 462

Asp Tyr Lys Asp Asp Asp Asp Lys
1               5

<210> SEQ ID NO 463
<211> LENGTH: 10
<212> TYPE: PRT
<213> ORGANISM: Artificial Sequence
<220> FEATURE:
```

<223> OTHER INFORMATION: Synthetic construct

<400> SEQUENCE: 463

Glu Gln Lys Leu Ile Ser Glu Glu Asp Leu
1               5                   10

<210> SEQ ID NO 464
<211> LENGTH: 9
<212> TYPE: PRT
<213> ORGANISM: Artificial Sequence
<220> FEATURE:
<223> OTHER INFORMATION: Synthetic construct

<400> SEQUENCE: 464

Tyr Pro Tyr Asp Val Pro Asp Tyr Ala
1               5

<210> SEQ ID NO 465
<211> LENGTH: 99
<212> TYPE: PRT
<213> ORGANISM: Artificial Sequence
<220> FEATURE:
<223> OTHER INFORMATION: Synthetic construct

<400> SEQUENCE: 465

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly Ser

<210> SEQ ID NO 466
<211> LENGTH: 7
<212> TYPE: PRT
<213> ORGANISM: Artificial Sequence
<220> FEATURE:
<223> OTHER INFORMATION: Synthetic construct

<400> SEQUENCE: 466

Glu Asn Leu Tyr Phe Gln Ser
1               5

<210> SEQ ID NO 467
<211> LENGTH: 8
<212> TYPE: PRT
<213> ORGANISM: Artificial Sequence
<220> FEATURE:
<223> OTHER INFORMATION: Synthetic construct

<400> SEQUENCE: 467

Asp Glu Met Glu Glu Cys Ser Gln
1               5

<210> SEQ ID NO 468
<211> LENGTH: 303

```
<212> TYPE: PRT
<213> ORGANISM: Homo sapiens

<400> SEQUENCE: 468

Met Gly His His His His His His His His Ser Ser Gly His
1               5                   10                  15

Ile Glu Gly Arg His Met Ala Ser Met Ser Asp Ser Glu Val Asn Gln
            20                  25                  30

Glu Ala Lys Pro Glu Val Lys Pro Glu Val Lys Pro Glu Thr His Ile
        35                  40                  45

Asn Leu Lys Val Ser Asp Gly Ser Ser Glu Ile Phe Phe Lys Ile Lys
    50                  55                  60

Lys Thr Thr Pro Leu Arg Arg Leu Met Glu Ala Phe Ala Lys Arg Gln
65                  70                  75                  80

Gly Lys Glu Met Asp Ser Leu Arg Phe Leu Tyr Asp Gly Ile Arg Ile
                85                  90                  95

Gln Ala Asp Gln Thr Pro Glu Asp Leu Asp Met Glu Asp Asn Asp Ile
            100                 105                 110

Ile Glu Ala His Arg Glu Gln Ile Gly Gly Ser Gly Leu Asn Asp Ile
        115                 120                 125

Phe Glu Ala Gln Lys Ile Glu Trp His Glu Leu Glu Val Leu Phe Gln
    130                 135                 140

Gly Pro Ser Ser Gly Leu Pro Asn Ile Pro Val Gln Thr Ile Ser Arg
145                 150                 155                 160

Ala Ala Ala Glu Lys Leu Phe Gly Asn Met Glu Gly Asp Cys Pro Ser
                165                 170                 175

Asp Trp Lys Thr Asp Ser Thr Cys Arg Met Val Thr Ser Glu Ser Lys
            180                 185                 190

Asn Val Lys Leu Thr Val Ser Asn Asp Ser Ala Gln Asn Ser Val Ile
        195                 200                 205

Ile Val Asp Lys Asn Gly Arg Leu Val Tyr Leu Val Glu Asn Pro Gly
    210                 215                 220

Gly Tyr Val Ala Tyr Ser Lys Ala Ala Thr Val Thr Gly Lys Leu Val
225                 230                 235                 240

His Ala Asn Phe Gly Thr Lys Lys Asp Phe Glu Asp Leu Tyr Thr Pro
                245                 250                 255

Val Asn Gly Ser Ile Val Ile Val Arg Ala Gly Lys Ile Thr Phe Ala
            260                 265                 270

Glu Lys Val Ala Asn Ala Glu Ser Leu Asn Ala Ile Gly Val Leu Ile
        275                 280                 285

Tyr Met Asp Gln Thr Lys Phe Pro Ile Val Asn Ala Glu Leu Ser
    290                 295                 300

<210> SEQ ID NO 469
<211> LENGTH: 303
<212> TYPE: PRT
<213> ORGANISM: Macacafascicularis

<400> SEQUENCE: 469

Met Gly His His His His His His His His Ser Ser Gly His
1               5                   10                  15

Ile Glu Gly Arg His Met Ala Ser Met Ser Asp Ser Glu Val Asn Gln
            20                  25                  30

Glu Ala Lys Pro Glu Val Lys Pro Glu Val Lys Pro Glu Thr His Ile
        35                  40                  45
```

```
Asn Leu Lys Val Ser Asp Gly Ser Ser Glu Ile Phe Lys Ile Lys
 50                  55                  60
Lys Thr Thr Pro Leu Arg Arg Leu Met Glu Ala Phe Ala Lys Arg Gln
 65                  70                  75                  80
Gly Lys Glu Met Asp Ser Leu Arg Phe Leu Tyr Asp Gly Ile Arg Ile
                 85                  90                  95
Gln Ala Asp Gln Thr Pro Glu Asp Leu Asp Met Glu Asp Asn Asp Ile
                100                 105                 110
Ile Glu Ala His Arg Glu Gln Ile Gly Gly Ser Gly Leu Asn Asp Ile
                115                 120                 125
Phe Glu Ala Gln Lys Ile Glu Trp His Glu Leu Glu Val Leu Phe Gln
130                 135                 140
Gly Pro Ser Ser Gly Leu Pro Asn Ile Pro Val Gln Thr Ile Ser Arg
145                 150                 155                 160
Ala Ala Ala Glu Lys Leu Phe Gly Asn Met Glu Gly Asp Cys Pro Ser
                165                 170                 175
Asp Trp Lys Thr Asp Ser Thr Cys Lys Met Val Thr Ser Glu Asn Lys
                180                 185                 190
Ser Val Lys Leu Thr Val Ser Asn Asp Ser Ala Gln Asn Ser Val Ile
                195                 200                 205
Ile Val Asp Lys Asn Gly Gly Leu Val Tyr Leu Val Glu Asn Pro Gly
210                 215                 220
Gly Tyr Val Ala Tyr Ser Lys Ala Ala Thr Val Thr Gly Lys Leu Val
225                 230                 235                 240
His Ala Asn Phe Gly Thr Lys Lys Asp Phe Glu Asp Leu Asp Ser Pro
                245                 250                 255
Val Asn Gly Ser Ile Val Ile Val Arg Ala Gly Lys Ile Thr Phe Ala
                260                 265                 270
Glu Lys Val Ala Asn Ala Glu Ser Leu Asn Ala Ile Gly Val Leu Ile
                275                 280                 285
Tyr Met Asp Gln Thr Lys Phe Pro Ile Val Lys Ala Asp Leu Ser
290                 295                 300

<210> SEQ ID NO 470
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 470

Thr Xaa Trp Ser Xaa
 1               5

<210> SEQ ID NO 471
<211> LENGTH: 7
<212> TYPE: PRT
<213> ORGANISM: Artificial Sequence
<220> FEATURE:
<223> OTHER INFORMATION: Synthetic construct

<400> SEQUENCE: 471
```

```
Lys Asp Ser Ala Gln Asn Ser
1               5

<210> SEQ ID NO 472
<211> LENGTH: 5
<212> TYPE: PRT
<213> ORGANISM: Artificial Sequence
<220> FEATURE:
<223> OTHER INFORMATION: Synthetic construct

<400> SEQUENCE: 472

Asp Ser Ala Gln Asn
1               5

<210> SEQ ID NO 473
<211> LENGTH: 5
<212> TYPE: PRT
<213> ORGANISM: Artificial Sequence
<220> FEATURE:
<223> OTHER INFORMATION: Synthetic construct

<400> SEQUENCE: 473

Leu Thr Val Ser Asn
1               5

<210> SEQ ID NO 474
<211> LENGTH: 20
<212> TYPE: PRT
<213> ORGANISM: Artificial Sequence
<220> FEATURE:
<223> OTHER INFORMATION: Synthetic construct

<400> SEQUENCE: 474

Met Gly Trp Ser Cys Ile Ile Leu Phe Leu Val Ala Thr Ala Thr Gly
1               5                   10                  15

Ala Tyr Ala Gly
            20
```

ENGINEERED POLYPEPTIDES

CROSS-REFERENCE TO RELATED APPLICATIONS

The present application is a continuation of International Patent Application Serial No. PCT/US2018/018445, filed Feb. 15, 2018, which application claims the benefit of U.S. Patent Application Ser. No. 62/460,692, filed Feb. 17, 2017, U.S. Patent Application Ser. No. 62/543,658, filed Aug. 10, 2017, U.S. Patent Application Ser. No. 62/543,819, filed Aug. 10, 2017, U.S. Patent Application Ser. No. 62/583,314, filed Nov. 8, 2017, and U.S. Patent Application Ser. No. 62/583,426, filed Nov. 8, 2017, the contents of which are incorporated herein by reference for all purposes.

BACKGROUND

The blood-brain barrier (BBB) blocks the passage of most macromolecules from the periphery into the brain and thus limits the therapeutic uses of these macromolecules. Receptors expressed on endothelia, including the endothelium of the blood-brain barrier, can mediate delivery of ligands that bind to the receptors across the blood brain barrier.

BRIEF SUMMARY

In one aspect, the disclosure provides an isolated, recombinant transferrin receptor (TfR) construct, comprising monomeric TfR apical domain, wherein the construct does not include a protease-like domain or helical domain of the TfR. In one embodiment, the construct displays a conserved epitope or antigen and/or retains the approximate three-dimensional structure of the apical domain of the native human TfR, or has a root mean square deviation (RMSD) of less than about 2. In one embodiment, the three-dimensional structure is measured by X-ray crystallography. In one embodiment, the construct comprises human TfR apical domain. In an embodiment, the RMSD between a TfR apical domain construct described herein and the apical domain of native, full-length TfR is about less than 4, about less than 3, or about less than 2, or is between the range of about 1 to about 2. In an embodiment, the RMSD between any one of TfR apical domain constructs having the sequence of any one of SEQ ID NOS: 109, 110, 301, 468, and 469 (e.g., 109, 110, and 301), and the apical domain of native, full-length TfR is about 1.2.

In another aspect, the disclosure features a TfR construct comprising: (a) a first polypeptide comprising a sequence of a first portion of a TfR apical domain; (b) an optional linker; and (c) a second polypeptide comprising a sequence of a second portion of the TfR apical domain, wherein the sequence of the first portion of the TfR apical domain is C-terminal to the sequence of the second portion of the TfR apical domain relative to the full-length TfR sequence, and wherein the first polypeptide, the optional linker, and the second polypeptide are fused in a tandem series.

In some embodiments, last amino acid of the second portion is fused to the first amino acid of the first portion. In some embodiments, the first amino acid of the second polypeptide is fused to the last amino acid of the first polypeptide. In some embodiments, the first polypeptide comprises a C-terminal fragment of a full-length TfR apical domain, and the second polypeptide comprises an N-terminal fragment of the full-length TfR apical domain.

In some embodiments, the first portion of the TfR apical domain comprises 25 to 55 amino acids (e.g., 30 to 55, 35 to 55, 40 to 55, 45 to 55, 50 to 55, 25 to 50, 25 to 45, 25 to 40, 25 to 35, or 25 to 30 amino acids). In some embodiments, the second portion of the TfR apical domain comprises 75 to 120 amino acids (e.g., 80 to 120, 85 to 120, 90 to 120, 95 to 120, 100 to 120, 105 and 110, 115 to 120, 75 to 115, 75 to 110, 75 to 105, 75 to 100, 75 to 95, 75 to 90, 75 to 85, or 75 to 80 amino acids).

In some embodiments, the first polypeptide comprises a sequence having at least 90% sequence identity (e.g., at least 91%, 92%, 93%, 94%, 95%, 96%, 97%, 98%, 99%, or 100% sequence identity) to the sequence of TISRAAAEKLFGNMEGDCPSDWKTDSTCRMVTSE (SEQ ID NO:427). In some embodiments, the first polypeptide comprises a sequence having up to seven amino acid changes (e.g., one, two, three, four, five, six or seven amino acid insertions, deletions, and/or substitutions) relative to the sequence of SEQ ID NO:427. In some embodiments, the second polypeptide comprises a sequence having at least 90% sequence identity (e.g., at least 91%, 92%, 93%, 94%, 95%, 96%, 97%, 98%, 99%, or 100% sequence identity) to the sequence of DKNGRLVYLVENPGGYVAYSKAATVTGKLVHANFGTKKDFEDLYTPVNGSIVIVRAGK ITFAEKVANAESLNAIGVLIYMDQT (SEQ ID NO:428). In some embodiments, the first polypeptide comprises a sequence having up to sixteen amino acid changes (e.g., one, two, three, four, five, six, seven, eight, nine, ten, eleven, twelve, thirteen, fourteen, fifteen, or sixteen amino acid insertions, deletions, and/or substitutions) relative to the sequence of SEQ ID NO:428.

In some embodiments, the TfR apical domain comprises the sequence of SEQ ID NO: 107 or 108.

In some embodiments, the TfR construct binds to an arenavirus (e.g., a Machupo virus).

In some embodiments, the TfR construct comprises: (a) the first polypeptide comprising a sequence having at least 90% sequence identity (e.g., at least 91%, 92%, 93%, 94%, 95%, 96%, 97%, 98%, 99%, or 100% sequence identity) to the sequence of SEQ ID NO:427; (b) the optional linker; and (c) the second polypeptide comprising a sequence having at least 90% sequence identity (e.g., at least 91%, 92%, 93%, 94%, 95%, 96%, 97%, 98%, 99%, or 100% sequence identity) to the sequence of SEQ ID NO:428.

In some embodiments, the TfR construct comprises: (a) the first polypeptide comprising a sequence having up to seven amino acid changes (e.g., one, two, three, four, five, six or seven amino acid insertions, deletions, and/or substitutions) relative to the sequence of SEQ ID NO:427; (b) the optional linker; and (c) the second polypeptide comprising a sequence having up to sixteen amino acid changes (e.g., one, two, three, four, five, six, seven, eight, nine, ten, eleven, twelve, thirteen, fourteen, fifteen, or sixteen amino acid insertions, deletions, and/or substitutions) relative to the sequence of SEQ ID NO:428.

In some embodiments, the first polypeptide at the C-terminus further comprises a sequence having at least 90% sequence identity (e.g., at least 91%, 92%, 93%, 94%, 95%, 96%, 97%, 98%, 99%, or 100% sequence identity) or up to five amino acid changes (e.g., one, two, three, four, or five amino acid insertions, deletions, and/or substitutions) relative to the sequence SKNVKLTVSNVLKEIKILNIFGVIK (SEQ ID NO:429), or a fragment thereof. In some embodiments, the second polypeptide at the C-terminus further comprises a sequence having at least 90% sequence identity (e.g., at least 91%, 92%, 93%, 94%, 95%, 96%, 97%, 98%, 99%, or 100% sequence identity) or up to five amino acid changes (e.g., one, two, three, four, or five amino acid insertions, deletions, and/or substitutions) relative to the sequence KFPIVNAELSFFGHAHLGTGDPYTP (SEQ ID NO:434), or a fragment thereof. In some embodiments, the first polypeptide at the N-terminus further comprises a sequence having at least 90% sequence identity (e.g., at least 91%, 92%, 93%, 94%, 95%, 96%, 97%, 98%, 99%, or 100% sequence identity) or up to five amino acid changes (e.g., one, two, three, four, or five amino acid insertions, deletions, and/or substitutions) relative to the sequence GFPSF-NHTQFPPSRSSGLPNIPVQ (SEQ ID NO:439), or a fragment thereof. In some embodiments, the second polypeptide at the N-terminus further comprises a sequence having at least 90% sequence identity (e.g., at least 91%, 92%, 93%, 94%, 95%, 96%, 97%, 98%, 99%, or 100% sequence identity) or up to five amino acid changes (e.g., one, two, three, four, or five amino acid insertions, deletions, and/or substitutions) relative to the sequence SKVWRDQH-FVKIQVKDSAQNSVIIV (SEQ ID NO:444), or a fragment thereof.

In particular embodiments, the first polypeptide comprises a sequence having at least 90% sequence identity (e.g., at least 91%, 92%, 93%, 94%, 95%, 96%, 97%, 98%, 99%, or 100% sequence identity) or up to ten amino acid changes (e.g., one, two, three, four, five, six, seven, eight, nine, or ten amino acid insertions, deletions, and/or substitutions) relative to the sequence S SGLPNIPVQTIS-RAAAEKLFGNMEGDCPSDWKTDSTCRMVTSESKN-VKLTVSN (SEQ ID NO:449). In particular embodiments, the second polypeptide comprises a sequence having at least 90% sequence identity (e.g., at least 91%, 92%, 93%, 94%, 95%, 96%, 97%, 98%, 99%, or 100% sequence identity) or up to twenty amino acid changes (e.g., one, two, three, four, five, six, seven, eight, nine, ten, eleven, twelve, thirteen, fourteen, fifteen, sixteen, seventeen, eighteen, nineteen, or twenty amino acid insertions, deletions, and/or substitutions) relative to the sequence D SAQNSVIIVDKNGR-LVYLVENPGGYVAYSKAATVTGKLVHANFGTKKD-FEDLYTPVN GSIVIVRAGKITFAEKVANAESLNAIGVLIYMDQTKF-PIVNAELS (SEQ ID NO:450).

In some embodiments, the first polypeptide is directly fused to the second polypeptide in a tandem series. In certain embodiments, the TfR construct comprises the first polypeptide having the sequence of SEQ ID NO:449 and the second polypeptide having the sequence of SEQ ID NO:450, wherein the C-terminus of the first polypeptide is fused to the N-terminus of the second polypeptide. In certain embodiments, the TfR construct comprises the first polypeptide having the sequence of SSGLPNIPVQTIS-RAAAEKLFGNMEGDCPSDWKTDSTCKMVTSENKS-VKLTVSN (SEQ ID NO:451) and the second polypeptide having the sequence of D SAQNSVIIVDKNGGLVYLV-ENPGGYVAYSKAATVTGKLVHANFGTKKDFEDLD SPVN GSIVIVRAGKITFAEKVANAESLNAIGVLIYM-DQTKFPIVKADLS (SEQ ID NO:452), wherein the C-terminus of the first polypeptide is fused to the N-terminus of the second polypeptide.

In some embodiments, the linker comprises or consists of 1 to 10 amino acids (e.g., 1 to 8, 1 to 6, 1 to 4, or 1 or 2 amino acids; e.g., 1, 2, 3, 4, 5, 6, 7, 8, 9, or 10 amino acids). In particular embodiments, the linker is G, GG, GGG, or GGGG (SEQ ID NO:453). In particular embodiments, the linker comprises a protein loop domain. In some embodiments, the N- and C-termini of the protein loop domain are less than 5 Å apart.

In some embodiments, the TfR construct further comprises a purification peptide. For example, the purification peptide may be fused to the N-terminus or C-terminus of the TfR construct.

In some embodiments, the TfR construct further comprises a cleavage peptide. For example, the cleavage peptide may be fused to the N-terminus or C-terminus of the TfR construct.

In another aspect, the disclosure features an isolated polynucleotide comprising a nucleotide sequence encoding a TfR construct described herein. In another aspect, the disclosure also features a vector comprising the polynucleotide described above. In a further aspect, the disclosure also features a host cell comprising the polynucleotide described above or the vector described above.

In another aspect, the disclosure features a method of identifying an agent that binds the apical domain of a TfR. The method comprises: (a) contacting a TfR construct described herein with the agent; and (b) determining whether the agent binds to the TfR construct.

In some embodiments, the agent is a polypeptide or a protein. In some embodiments, the agent is a modified Fc polypeptide or modified Fc polypeptide dimer. In yet other embodiments, the agent is an antibody.

In some embodiments, the determining step (b) is performed by ELISA or by surface plasmon resonance.

In yet another aspect, the disclosure features a method of manufacturing a recombinant TfR apical domain construct, comprising expressing a gene comprising a first polynucleotide and a second polynucleotide fused in a tandem series, wherein the first polynucleotide encodes a C-terminal fragment of a full-length TfR apical domain, and the second polynucleotide encodes an N-terminal fragment of the full-length TfR apical domain.

In some embodiments, the first and second polynucleotides are fused in the tandem series such that, when expressed, the first amino acid of the N-terminal fragment of the domain is linked in primary sequence to the last amino acid of the C-terminal fragment of the domain.

In some embodiments, the gene further comprises an optional linker polynucleotide that encodes an optional protein linker, wherein when expressed, the first amino acid of the N-terminal fragment of the domain is linked in primary sequence to the last amino acid of the linker, and the first amino acid of the linker is linked in primary sequence to the last amino acid of the C-terminal fragment of the domain.

In some embodiments, the gene encodes the first polynucleotide, the optional linker polynucleotide, and the second polynucleotide in the tandem series such that, when expressed, the expressed protein is in a cyclic structure form. In some embodiments, the method further comprises purifying the expressed protein to obtain the isolated recombinant TfR apical domain construct.

An aspect of the disclosure also includes an isolated, recombinant human TfR apical domain construct made according to the above method.

Another aspect includes an isolated, recombinant TfR apical domain construct comprising the amino acid sequence of any one of SEQ ID NOS: 109, 110, 301, 468, and 469 (e.g., 109, 110, and 301).

Another aspect includes an isolated, recombinant TfR apical domain construct comprising an amino acid sequence having at least about 90% sequence identity (e.g., at least 91%, 92%, 93%, 94%, 95%, 96%, 97%, 98%, 99%, or 100% sequence identity) to any one of SEQ ID NOS:109, 110, 301, 468, and 469 (e.g., 109, 110, and 301).

In another aspect, provided herein is a polypeptide that is capable of being actively transported across the blood brain barrier (BBB) comprising: (a) a modified Fc polypeptide, or fragment thereof, (b) a first site within the modified Fc polypeptide or fragment that specifically binds to a BBB receptor; and (c) a second site that binds to a neonatal Fc receptor (FcRn). In some embodiments, the second site is a native FcRn binding site. In some embodiments, the FcRn binding site is within the modified Fc polypeptide. In some embodiments, the FcRn binding site comprises amino acid changes relative to the native Fc sequence that extend serum half-life. In certain embodiments, the amino acid changes comprise substitutions of Tyr at position 25, Thr at position 27, and Glu at position 29, wherein the positions of the residues are determined with reference to SEQ ID NO: 1. Alternatively, in other embodiments, the amino acid changes comprise substitutions of Leu at position 201 and Ser at position 207, wherein the positions of the residues are determined with reference to SEQ ID NO: 1. Alternatively, in further embodiments, the amino acid changes comprise a substitution of Ser or Ala at position 207, wherein the position of the residue is determined with reference to SEQ ID NO: 1.

In some embodiments, the modified Fc polypeptide or fragment comprises at least 50 amino acids (e.g., at least 60, 75, 90, or 95 amino acids) that correspond to a native Fc polypeptide amino acid sequence, e.g., at least 50 contiguous amino acids. In certain embodiments, the modified Fc polypeptide or fragment comprises at least 100 amino acids (e.g., at least 125, 140, 150, 160, 175, or 180 amino acids) that correspond to a native Fc polypeptide amino acid sequence.

In some embodiments, the first site within the modified Fc polypeptide or fragment comprises at least one modified amino acid in a β-sheet of the Fc polypeptide. In certain embodiments, the β-sheet is in the CH2 domain. In certain embodiments, the β-sheet is in the CH3 domain. In some embodiments, the first site includes a substitution of at least one solvent-exposed amino acid. In some embodiments, the first site includes substitutions in at least two solvent-exposed amino acids, wherein the two solvent-exposed residues in a loop region or in a β-sheet are not in the same loop region or the same β-sheet.

In some embodiments, the modified Fc polypeptide or fragment sequence comprises a modified CH2 domain sequence, which can be derived from a human IgG1, IgG2, IgG3, or IgG4 CH2 domain sequence. In some embodiments, the modifications to the CH2 domain comprise at least two substitutions of amino acids in a set of amino acids selected from the group consisting of: (a) residues 47, 49, 56, 58, 59, 60, 61, 62, and 63; (b) residues 39, 40, 41, 42, 43, 44, 68, 70, 71, and 72; (c) residues 41, 42, 43, 44, 45, 65, 66, 67, 69, and 73; and (d) residues 45, 47, 49, 95, 97, 99, 102, 103, and 104; wherein positions of the residues are determined with reference to SEQ ID NO: 1.

In some embodiments, the modified Fc polypeptide or fragment sequence comprises a modified CH3 domain sequence, which can be is derived from a human IgG1, IgG2, IgG3, or IgG4 CH3 domain sequence. In some embodiments, the modifications to the CH3 domain comprise at least two substitutions of amino acids in a set of amino acids selected from the group consisting of: (a) residues 157, 159, 160, 161, 162, 163, 186, 189, and 194; and (b) residues 118, 119, 120, 122, 210, 211, 212, and 213; wherein positions of the residues are determined with reference to SEQ ID NO:1.

In some embodiments, the modified Fc polypeptide or fragment has an amino acid sequence identity of at least 75% as compared to the corresponding wild-type Fc polypeptide or fragment. In further embodiments, the identity is at least 80%, 90%, 92%, or 95%.

The modified Fc polypeptide or fragment can have effector function or in alternative embodiments, does not have effector function. In certain embodiments, the modified Fc polypeptide or fragment includes a modification that reduces effector function. In some embodiments, the modification that reduces effector function comprises substitutions of Leu at position 7 and Leu at position 8, wherein the positions of the residues are determined with reference to SEQ ID NO: 1. In some embodiments, the modification that reduces effector function further comprises a substitution of Pro at position 102, wherein the position of the residue is determined with reference to SEQ ID NO: 1.

In a further aspect, provided herein is a dimeric protein comprising the polypeptide or fragment as described in the preceding paragraphs. In some embodiments, the dimeric protein is a heterodimer comprising a first and a second polypeptide chain, wherein the first polypeptide chain comprises the first site that specifically binds to a BBB receptor. In certain embodiments, the second the second polypeptide chain does not comprise a site that specifically binds to a BBB receptor. In some embodiments, the dimeric protein is a homodimer comprising a first and a second polypeptide chain, wherein the first and second polypeptide chains each comprise a site that specifically binds to a BBB receptor.

In some embodiments, the BBB receptor is selected from the group consisting of transferrin receptor (TfR), insulin receptor, insulin-like growth factor receptor (IGF-R), low density lipoprotein receptor (LDLR), low density lipoprotein receptor-related protein 1 (LRP1), low density lipoprotein receptor-related protein 2 (LRP2), low density lipoprotein receptor-related protein 8 (LRP8), GLUT1, basigin, diphtheria toxin receptor, membrane-bound precursor of heparin binding epidermal growth factor-like growth factor (HB-EGF), melanotransferrin, and vasopressin receptor. In certain embodiments, the BBB receptor is TfR. In still other embodiments, the BBB receptor is IGF-R.

In some embodiments the polypeptide specifically binds to the BBB receptor without competing for binding with an endogenous ligand of the receptor. In certain embodiments, the BBB receptor is transferrin receptor and the endogenous ligand is transferrin.

In some embodiments, the polypeptide as described in the preceding paragraphs further comprises a biologically active polypeptide. In certain embodiments, the biologically active polypeptide is a therapeutically active polypeptide. In some embodiments, uptake into brain of the biologically active polypeptide is at least ten-fold greater as compared to uptake of the biologically active polypeptide when the modified Fc polypeptide or fragment is not present. In some embodiments, uptake into brain of the biologically active polypeptide is at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, as compared to uptake of the biologically active polypeptide when the modified Fc polypeptide or fragment is not present.

In a further aspect, provided herein is a protein that is capable of being actively transported across the BBB, the protein comprising: (a) an antibody variable region sequence that is capable of binding an antigen, or antigen-binding fragment thereof, and (b) a polypeptide comprising a modified Fc polypeptide, or a fragment thereof, wherein the modified Fc polypeptide or fragment contains a first binding site that specifically binds to a BBB receptor; and a second binding site that binds to a neonatal Fc receptor (FcRn). In some embodiments, the antibody variable region sequence comprises a Fab domain. In some embodiments, the Fab domain binds to a Tau protein (e.g., a human Tau protein) or a fragment thereof. The Tau protein may be a phosphorylated Tau protein, an unphosphorylated Tau protein, a splice isoform of Tau protein, an N-terminal truncated Tau protein, a C-terminal truncated Tau protein, and/or a fragment thereof. In some embodiments, the Fab domain binds to a beta-secretase 1 (BACE1) protein (e.g., a human BACE1 protein) or a fragment thereof. The BACE1 protein may be a splice isoform of BACE1 protein or a fragment thereof. In some embodiments, the Fab domain binds to a triggering receptor expressed on myeloid cells 2 (TREM2) protein (e.g., a human TREM2 protein) or a fragment thereof. In other embodiments, the Fab domain binds to an alpha-synuclein protein (e.g., a human alpha-synuclein protein) or a fragment thereof. The alpha-synuclein protein may be a monomeric alpha-synuclein, an oligomeric alpha-synuclein, an alpha-synuclein fibril, a soluble alpha-synuclein, and/or a fragment thereof. In some embodiments, the antibody variable region sequence comprises two antibody variable region heavy chains and two antibody variable region light chains, or respective fragments thereof.

In some embodiments, the variable region may bind to a Tau protein (e.g., a human Tau protein) or a fragment thereof. In some embodiments, the variable region may bind to a phosphorylated Tau protein, an unphosphorylated Tau protein, a splice isoform of Tau protein, an N-terminal truncated Tau protein, and/or a C-terminal truncated Tau protein, or a fragment thereof. In some embodiments, the variable region may bind to a beta-secretase 1 (BACE1) protein (e.g., a human BACE1 protein) or a fragment thereof. In some embodiments, the variable region may bind to one or more splice isoforms of BACE1 protein or a fragment thereof. In some embodiments, the variable region may bind to a human triggering receptor expressed on myeloid cells 2 (TREM2) protein or a fragment thereof. In some embodiments, the variable region may bind to a human alpha-synuclein protein or a fragment thereof. In some embodiments, the variable domain may bind to a monomeric human alpha-synuclein, oligomeric human alpha-synuclein, human alpha-synuclein fibrils, and/or soluble human alpha-synuclein, or a fragment thereof.

In some embodiments, the protein comprises a single modified Fc polypeptide or fragment that binds to the BBB receptor. In other embodiments, the protein comprises two modified Fc polypeptides or fragments that binds to the BBB receptor.

In some embodiments, the uptake of the protein into the brain is at least 10-fold greater as compared either to (a) the same protein without the polypeptide comprising a modified Fc polypeptide or fragment or (b) the same protein with the polypeptide comprising an Fc polypeptide or Fc polypeptide fragment that does not contain the modifications that result in BBB receptor binding.

In a further aspect, provided herein is a conjugate comprising (a) a polypeptide as described in the preceding paragraphs; and (b) therapeutic or diagnostic agent; wherein the conjugate is capable of being transported across the blood-brain barrier. In some embodiments, uptake of the therapeutic or diagnostic agent to the brain is increased by at least 10-, 20-, 30-, 40-, or 50-fold relative to the uptake of the therapeutic or diagnostic agent absent the polypeptide.

BRIEF DESCRIPTION OF THE DRAWINGS

FIG. 1A shows ELISA results for clone CH2A2.5. FIG. 1B shows ELISA results for clone CH2A2.1. FIG. 1C shows ELISA results for clone CH2A2.4. FIG. 1D shows ELISA results for CH2A2.16.

FIG. 2A shows results for the experiments where soluble holo-Tf was added. FIG. 2B shows results for the experiments where soluble TfR was added.

FIG. 3A shows the results of a phage ELISA where TfR was coated on an ELISA plate and clone CH2C.23, displayed on phage, was added in the presence or absence of a large excess of holo-Tf (5 μM). FIG. 3B shows CH2C clones, in Fc-Fab fusion format, binding to human or cyno TfR-coated ELISA plates. FIG. 3C shows the results of phage ELISAs where human TfR, cyno TfR, holo-Tf, anti-Myc, or streptavidin was coated on an ELISA plate and phage-displayed clones CH2C.17 and CH2C.22 were added at various dilutions, in the absence or presence of holo-Tf. These data show that these clones did not compete with holo-Tf for binding to TfR. FIG. 3D shows an Octet® (i.e., biolayer interferometry) kinetics trace for clone CH2C.7 binding to TfR-biotin coated on an anti-streptavidin sensor, in the presence of 5 μM holo-Tf and background subtracted for binding of holo-Tf alone, indicating no competition for binding with Tf.

FIGS. 4A and 4B show binding of CH3B clones to TfR in the presence or absence of holo-Tf. FIG. 4A shows the results of a phage ELISA where human TfR, cyno TfR, holo-Tf, anti-Myc, or streptavidin was coated on an ELISA plate and phage-displayed clones CH3B.11 and CH3B.12 were added at various dilutions, in the absence or presence of holo-Tf. These data show that these clones did not compete with holo-Tf for binding to TfR. FIG. 4B shows CH3B clones binding to human or cyno TfR-coated ELISA plates. Fc regions comprising the CH3B clone sequences were fused to Fab fragments and were assayed in a dimer format.

FIG. 7A shows binding of CH3C variants to human TfR coated on ELISA plates. FIG. 7B shows binding of CH3C variants to human TfR coated on ELISA plates in the presence of 5 µM holo-Tf. FIG. 7C shows binding of CH3C variants to cyno TfR coated on ELISA plates.

FIG. 9A shows microscopy data. FIG. 9B shows a graph of the number of puncta per well.

FIG. 11A shows binding to human TfR. FIG. 11B shows binding to cyno TfR.

FIG. 12A shows binding of CH3C variants to human TfR coated on ELISA plates. FIG. 12B shows binding of CH3C variants to human TfR coated on ELISA plates in the presence of 5 µM holo-Tf.

FIGS. 14A-14C show binding of CH3C clones identified from the first soft randomization library to CHO-K1 cells. Cells were distributed in 96-well V bottom plates, and varying concentrations of the CH3C clones, formatted as Fc-Fab fusions, were added. After 1 hour incubation at 4° C., the plates were spun and washed, and then incubated with goat-anti-human-IgG-Alexa Fluor® 647 secondary antibody at 4° C. for 30 minutes. After additional washing of the cells, the plates were read on a FACSCanto™ II flow cytometer, and median fluorescence values in the APC (647 nm) channel were determined using FlowJo® software. FIG. 14A shows CHO-K1 cells that overexpressed human TfR. FIG. 14B shows CHO-K1 cells that overexpressed cyno TfR. FIG. 14C shows CHO-K1 parental cells that did not express human TfR.

FIG. 15A shows the location of the apical domain on the human TfR protein. The inset shows a close-up view of the seven residues that differ between human and cyno TfR. FIG. 15B shows a sequence alignment containing the seven residues that differ between human (SEQ ID NO:107) and cyno (SEQ ID NO:108) TfR. The consensus sequence is SEQ ID NO:422.

FIG. 16A shows Myc expression of various TfR apical domain mutants, showing that the expression level of the mutants was similar and normalized. FIG. 16B shows CH3C.18 binding to wild-type and mutant human TfR apical domains, showing reduced binding to the R208G mutant. FIG. 16C shows CH3C.35 binding to wild-type and mutant human TfR apical domains, showing reduced binding to the R208G mutant. FIG. 16D shows CH3C.18 binding to wild-type human and cyno TfR apical domains and the G208R mutant cyno apical domain, showing recovery of binding to the mutant. FIG. 16E shows CH3C.35 binding to wild-type human and cyno TfR apical domains and the G208R mutant cyno apical domain, showing recovery of binding to the mutant.

FIG. 17A shows paratope mapping of CH3C.35 by ELISA binding to human TfR for reversion mutants. FIG. 17B shows paratope mapping of CH3C.35 by ELISA binding to cyno TfR for reversion mutants. FIG. 17C shows paratope mapping of CH3C.18 by ELISA binding to human TfR for reversion mutants. FIG. 17D shows paratope mapping of CH3C.18 by ELISA binding to cyno TfR for reversion mutants.

FIGS. 18A-18D show the design of CH3C consensus maturation libraries. FIG. 18A shows the consensus library based on the CH3C.35-like sequences. FIG. 18B shows the consensus library based on the CH3C. 18-like sequences. FIG. 18C shows the gap libraries based on CH3C. 18 and CH3C.35. FIG. 18D shows the aromatics library based on CH3C.18.

FIG. 19A shows data for CH3C.3.2-1. FIG. 19B shows data for CH3C.3.2-19. FIG. 19C shows data for CH3C.3.2-5. FIG. 19D shows data for CH3C.18. FIG. 19E shows data for CH3C.35.

37A depicts hydrogen bonds and non-bonded contacts between residues in clone CH3C.18 (Chain A) and the apical domain of the transferrin receptor (Chain D).

FIG. 38 shows an alignment of human IgG1, IgG2, IgG3, and IgG4 amino acid sequences (SEQ ID NOS:423-426).

FIG. 39A depicts the structural architecture (top) of the TfR apical domain and the CH3C.35 Fc, and the binding surfaces (within 5 Å) (bottom) of the TfR apical domain and the CH3C.35 Fc. The co-complex structure was solved at 3.4 Å resolution. The structure reveals the epitope on the TfR apical domain bound to CH3C.35. The CH3C.35 library side chains are all contacting the TfR (within 5 Å). CH3C.35 library residues: Y157, T159, E160, W161, S162, T186, E189, and W194. Non-library residues: F196, S156, Q192. FIGS. 39B and 39C show enlarged views of the binding interface between clone CH3C.35 and the apical domain of the transferrin receptor depicted in FIG. 39A.

FIGS. 41A and 41B depict binding between polypeptides of the present invention and the transferrin receptor. FIG. 41A depicts hydrogen bonds and non-bonded contacts between residues in clone CH3C.35 (Chain A) and the apical domain of the transferrin receptor (Chain D).

FIG. 41B depicts hydrogen bonds and non-bonded contacts between residues in clone CH3C.35 (Chain B) and the apical domain of the transferrin receptor (Chain C).

FIG. 42A shows that Ab210 and CH3C.35.9:Ab153 exhibited faster clearance due to TfR-mediated clearance compared to control IgG (Ab122) and Ab153. FIG. 42B shows that Ab153, Ab210, and CH3C.35.9:Ab153, which all bind to and inhibit BACE1, exhibited significant Aβ340 reduction in plasma.

FIG. 43A shows that animals dosed with Ab210 and CH3C.35.9:Ab153 showed about 70% reduction in CSF Aβ340 compared to Ab153 and control IgG (Ab122). FIG. 43B shows that animals dosed with Ab210 and CH3C.35.9:Ab153 showed about 75% reduction in sAPPβ/sAPPα ratio compared to Ab153 and control IgG (Ab122). n=4/group. Line graphs represent mean±SEM.

FIGS. 46A and 46B depict serum huIgG1 in serum and plasma Aβ concentration in plasma, showing peripheral exposure of dosed compounds and resulting effects on plasma Aβ levels over time. FIGS. 46C and 46D depict Aβ and sAPPβ/sAPPα in CSF of cynomolgus monkeys following dosing (mean±SEM, n=4-5 per group).

DETAILED DESCRIPTION

I. Introduction

Figure 1A:
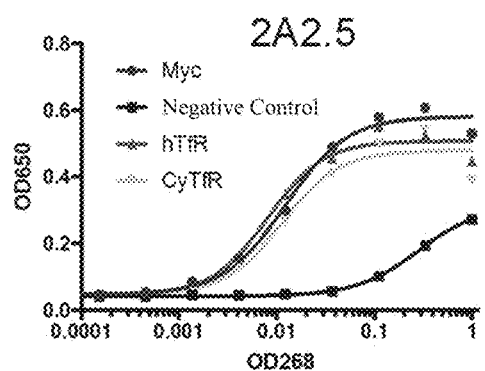
FIGS. 1A-1D show phage ELISA results for four CH2A2 clones. CH2A2 Fc variants were expressed on the surface of phage and tested for binding to anti-c-Myc antibody 9E10 (expression control), a negative control, human transferrin receptor (TfR), and cynomolgus (cyno) TfR coated on a plate. The x-axis shows $OD_{268}$ of phage solution, which is a measure of phage concentration.
Figure 1B:
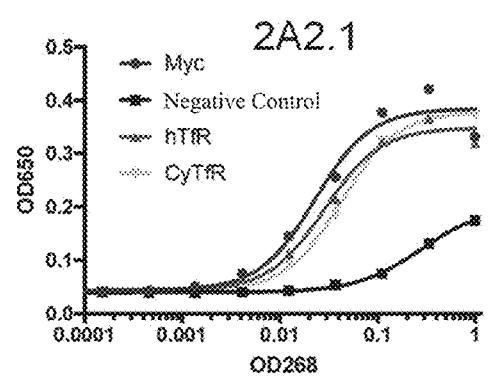
Figure 1C:
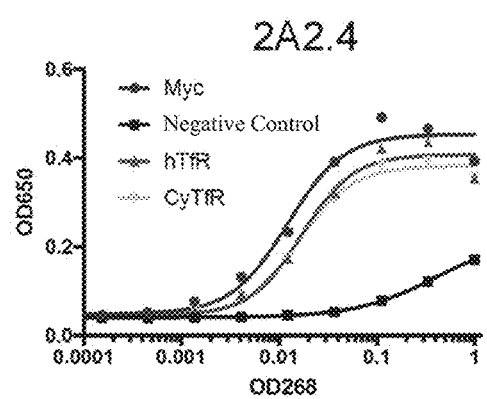
Figure 1D:
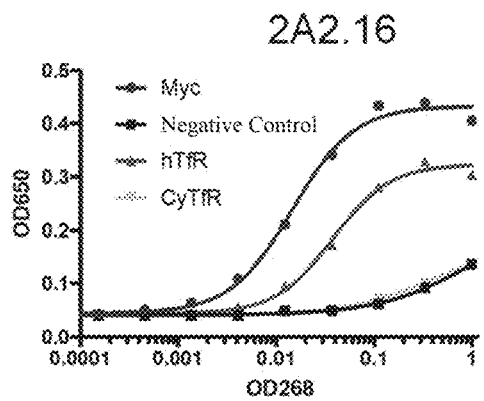

Described herein are polypeptides that can be actively transported across the blood-brain barrier (BBB). In one aspect, the invention is based, in part, on the discovery that certain sets of amino acids in an Fc region can be modified to generate an Fc polypeptide capable of binding to a blood-brain barrier receptor. Fc polypeptides as described herein additionally bind to the neonatal Fc receptor (FcRn). These polypeptides can be used to transport therapeutic agents (e.g., therapeutic polypeptides, antibody variable regions, and small molecules) in order to treat disorders and diseases where brain delivery is advantageous. Also described herein are transferrin receptor (TfR) constructs that comprise a monomeric TfR apical domain or one or more portions of the TfR apical domain which have been circularly permuted relative to the full-length TfR sequence. A TfR construct may comprise two distinct portions of the TfR apical domain fused to each other in a tandem series with an optional linker. A TfR construct as described herein may bind to an arenavirus (e.g., a Machupo virus).

In some embodiments, a CH3 or CH2 domain polypeptide can be substituted to generate a polypeptide that binds a BBB receptor, e.g., a transferrin receptor. Thus, in one aspect, provided herein are BBB binding polypeptides that have multiple substitutions at a set of amino acids (i) 157, 159, 160, 161, 162, 163, 186, 189, and 194; or (ii) 118, 119, 120, 122, 210, 211, 212, and 213 as numbered with reference to SEQ ID NO: 1. In some embodiments, a BBB binding polypeptide of the present invention has multiple substitutions at a set of amino acids (iii) 47, 49, 56, 58, 59, 60, 61, 62, and 63; (iv) 39, 40, 41, 42, 43, 44, 68, 70, 71, and 72; (v) 41, 42, 43, 44, 45, 65, 66, 67, 69, and 73; or (vi) 45, 47, 49, 95, 97, 99, 102, 103, and 104 as numbered with reference to SEQ ID NO: 1. Anywhere from four to all of the amino acid positions of a set may be substituted. For purposes of this disclosure, a substitution is determined with reference to SEQ ID NO: 1. Thus, an amino acid is considered to be a substitution if it differs from the corresponding amino acid in position SEQ ID NO: 1 even if the amino acid is present at that position in a naturally occurring Fc polypeptide.

Also provided herein are methods of generating a BBB receptor-binding polypeptide by generating variant polypeptides having substitutions at multiple positions of set (i), (ii), (iii), (iv), (v), or (vi). Such variants can be analyzed for BBB receptor-binding and further mutated to enhance binding as described herein.

In a further aspect, provided herein are treatment methods and methods of using a BBB receptor-binding polypeptide to target a composition to BBB receptor-expressing cells, e.g., to deliver the composition to that cell, or to deliver a composition across an endothelium such as the blood-brain barrier.

II. Definitions

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

A "transferrin receptor" or "TfR" as used in the context of this invention refers to transferrin receptor protein 1. The human transferrin receptor 1 polypeptide sequence is set forth in SEQ ID NO:235. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO: 107.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region. In general, an Fc polypeptide contains constant region sequences including at least the CH2 domain and/or the CH3 domain and may contain at least part of the hinge region, but does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

The term "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a 32-microglobulin of about 15 kDa in size.

As used herein, an "FcRn binding site" refers to the region of an Fc polypeptide that binds to FcRn. In human IgG, the FcRn binding site, as numbered using the EU numbering scheme, includes L251, M252, 1253, S254, R255, T256, M428, H433, N434, H435, and Y436. These positions correspond to positions 24 to 29, 201, and 206 to 209 of SEQ ID NO:1.

As used herein, a "native FcRn binding site" refers to a region of an Fc polypeptide that binds to FcRn and that has the same amino acid sequence as the region of a naturally occurring Fc polypeptide that binds to FcRn.

The terms "CH3 domain" and "CH2 domain" as used herein refer to immunoglobulin constant region domain polypeptides. In the context of IgG antibodies, a CH3 domain polypeptide refers to the segment of amino acids from about position 341 to about position 447 as numbered according to the EU numbering scheme, and a CH2 domain polypeptide refers to the segment of amino acids from about position 231 to about position 340 as numbered according to the EU numbering scheme. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. In the context of IgG antibodies, an Fc region refers to the segment of amino acids from about position 231 to about position 447 as numbered according to the EU numbering scheme. As used herein, the term "Fc region" may also include at least a part of a hinge region of an antibody. An illustrative hinge region sequence is set forth in SEQ ID NO:234.

The term "variable region" refers to a domain in an antibody heavy chain or light chain that derived from a germline Variable (V) gene, Diversity (D) gene, or Joining (J) gene (and not derived from a Constant (C and C6) gene segment), and that gives an antibody its specificity for binding to an antigen. Typically, an antibody variable region comprises four conserved "framework" regions interspersed with three hypervariable "complementarity determining regions."

As used herein, the term "linker" refers to a peptide or protein linkage between two elements, e.g., between two polypeptides in a TfR construct. In some embodiments, a linker may contain 1 to 10 amino acids (e.g., 1 to 8, 1 to 6, 1 to 4, or 1 or 2 amino acids; e.g., 1, 2, 3, 4, 5, 6, 7, 8, 9, or 10 amino acids). In other embodiments, a linker may be a protein loop domain, in which the N- and C-termini of the protein loop domain are less than 5 Å apart (e.g., less than 4 Å, 3 Å, 2 Å, or 1 Å apart). In some embodiments, the protein loop domain may be a globular protein having 800 or less amino acids (e.g., 800, 780, 760, 740, 720, 700, 680, 660, 640, 620, 600, 580, 560, 540, 520, 500, 480, 460, 440, 420, 400, 380, 360, 340, 320, 300, 280, 260, 240, 220, 200, 180, 160, 140, 120, or 100 amino acids).

As used herein, the term "purification peptide" refers a peptide of any length that can be used for purification, isolation, or identification of a polypeptide. A purification peptide may be fused to a polypeptide for use in purifying the polypeptide and/or isolating the polypeptide from, e.g., a cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be used to purify a TfR construct are described in detail further herein.

As used herein, the term "cleavage peptide" refers to an amino acid sequence that is recognized and cleaved, i.e., through hydrolysis of the peptide backbone, by a specific protease. The specificity of a protease relies largely on the protease recognition of the cleavage sequence.

As used herein, the term "tandem series" refers to the arrangement of polypeptides in which the amino acids of one polypeptide are placed after those of another polypeptide in a single polypeptide. For example, a TfR construct may comprise a first polypeptide, an optional linker, and a second polypeptide fused to each other in a tandem series, i.e., the C-terminus of the first polypeptide is fused to the N-terminus of the optional linker, and the C-terminus of the optional linker is fused to the N-terminus of the second polypeptide.

The terms "wild-type," "native," and "naturally occurring" with respect to a CH3 or CH2 domain are used herein to refer to a domain that has a sequence that occurs in nature.

In the context of this invention, the term "mutant" with respect to a mutant polypeptide or mutant polynucleotide is used interchangeably with "variant." A variant with respect to a given wild-type CH3 or CH2 domain reference sequence can include naturally occurring allelic variants. A "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, or at least 95% or greater, that are identical over a specified region when compared and aligned for maximum correspondence over a comparison window, or designated region as measured using one a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence.

Thus, for example, an amino acid residue in a polypeptide "corresponds to" an amino acid in the region of SEQ ID NO: 1 from amino acids 114-220 when the residue aligns with the amino acid in SEQ ID NO:1 when optimally aligned to SEQ ID NO:1. The polypeptide that is aligned to the reference sequence need not be the same length as the reference sequence.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

The phrase "specifically binds" or "selectively binds" to a target, e.g., transferrin receptor, when referring to a polypeptide comprising a modified CH3 and/or modified CH2 domain as described herein, refers to a binding reaction whereby the polypeptide binds to the target with greater affinity, greater avidity, and/or greater duration than it binds to a structurally different target, e.g., a target not in the transferrin receptor family. In typical embodiments, the polypeptide has at least 5-fold, 6-fold, 7-fold, 8-fold, 9-fold, 10-fold, 20-fold, 25-fold, 50-fold, or 100-fold, or greater affinity for a transferrin receptor compared to an unrelated target when assayed under the same affinity assay conditions. In some embodiments, a modified CH3 and/or modified CH2 domain polypeptide specifically binds to an epitope on a transferrin receptor that is conserved among species, e.g., conserved between non-human primate and human species. In some embodiments, a polypeptide may bind exclusively to a human transferrin receptor.

The term "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human.

The terms "treatment," "treating," and the like are used herein to generally mean obtaining a desired pharmacologic and/or physiologic effect. "Treating" or "treatment" may refer to any indicia of success in the treatment or amelioration of an injury, disease, or condition, including any objective or subjective parameter such as abatement, remission, improvement in patient survival, increase in survival time or rate, diminishing of symptoms or making the injury, disease, or condition more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutically acceptable excipient" refers to a non-active pharmaceutical ingredient that is biologically or pharmacologically compatible for use in humans or animals, such as but not limited to a buffer, carrier, or preservative.

As used herein, a "therapeutic amount" or "therapeutically effective amount" of an agent is an amount of the agent that treats, alleviates, abates, or reduces the severity of symptoms of a disease in a subject. A "therapeutic amount" or "therapeutically effective amount" of an agent may improve patient survival, increase survival time or rate, diminish symptoms, make an injury, disease, or condition more tolerable, slow the rate of degeneration or decline, or improve a patient's physical or mental well-being.

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, the polypeptides described herein are administered intravenously.

III. Modified Polypeptides that can be Transported Across the BBB

In one aspect, provided herein are modified polypeptides that bind to a blood-brain barrier (BBB) receptor and are capable of being transported across the BBB. BBB receptors are expressed on BBB endothelia, as well as other cell and tissue types. Binding of a modified polypeptide to the BBB receptor can initiate internalization of the polypeptide and transport across the BBB. Such receptors include, but are not limited to, transferrin receptor (TfR), insulin receptor, insulin-like growth factor receptor (IGF-R), low density lipoprotein receptor (LDLR), low density lipoprotein receptor-related protein 1 (LRP1), low density lipoprotein receptor-related protein 2 (LRP2), low density lipoprotein receptor-related protein 8 (LRP8), GLUT1, basigin, diphtheria toxin receptor, membrane-bound precursor of heparin binding epidermal growth factor-like growth factor (HB-EGF), melanotransferrin, and vasopressin receptor. In some embodiments, the BBB receptor is TfR or IGF-R.

Modified Fc Polypeptides

In certain aspects, a polypeptide as provided herein that is capable of being transported across the BBB comprises a Fc polypeptide that has been modified (e.g., by one or more amino acid substitutions relative to the native Fc polypeptide) to have a BBB receptor-binding site. In certain embodiments, the substitution is of a solvent-exposed amino acid. A solvent-exposed amino acid refers to an amino acid at or near the surface of a polypeptide that is accessible to an aqueous, physiological liquid milieu in which the polypeptide functions in vivo. A solvent-exposed residue typically has more than 50% of the side chains in contact with solvent, although in some cases, less than 50%, e.g., from 25% to 49%, of the side chains are exposed. Solvent-exposed amino acids include those that are present in β-sheets, α-helices, and/or loops.

Solvent-exposed amino acids that are modified in accordance with the present invention are typically present in a set of amino acids (also referred to herein as a register) that can comprise a contiguous surface in a defined three-dimensional area. Solvent-exposed amino acids can be identified based on a model of an IgG, e.g., anti-HIV IgG B12 (pdb: 1 HZH). The solvent accessible surface area (Å2) for the residue at each position can be calculated using the program PDBePISA, available from the European Bioinformatics Institute (EMBL-EBI). This value can be normalized to the maximal potential accessible surface area for each corresponding amino acid to yield a "percent exposed" value for each residue. Highly solvent exposed residues can then be mapped back to the structure of the IgG and visually grouped into sets, e.g., sets of approximately 5-15 residues, 6-12 residues, 7-12 residues, or 8-10 residues, that present a surface area patch. In some embodiments, such as surface area patch totals 600 to 1500 Å$^2$ of solvent exposed surface. In alternative embodiments, the surface area of a patch can total 750-1000 Å$^2$. In some instances, amino acid residues that have side chains that are less than 50% exposed may also be included to ensure that the surface area patches are contiguous or semi-contiguous.

The secondary structure, e.g., β-sheets, loops, and helices in immunoglobulins can be determined from crystal structures using software, such as PyMol or SwissPDB Viewer, that allow viewing of polypeptide backbone secondary structures. For example, an analysis of a crystal structure of an Fc polypeptide bound to FcgammaRI (PDB ID number 4W4O) can be used to determine which amino acids fall within the various structural regions and to help determine which amino acid side chains may be solvent-exposed. Illustrative sets of amino acid residues at positions that correspond to a surface area patch include the following six sets, as numbered with reference to SEQ ID NO:1: (i) 157, 159, 160, 161, 162, 163, 186, 189, and 194; (ii) 118, 119, 120, 122, 210, 211, 212, and 213; (iii) 47, 49, 56, 58, 59, 60, 61, 62, and 63; (iv) 39, 40, 41, 42, 43, 44, 68, 70, 71, and 72; (v) 41, 42, 43, 44, 45, 65, 66, 67, 69, and 73; and (vi) 45, 47, 49, 95, 97, 99, 102, 103, and 104. Modifications to such patches and additional examples of amino acids that can be modified (e.g., substituted) to generate BBB receptor-binding polypeptides are described in detail herein.

Figure 38:
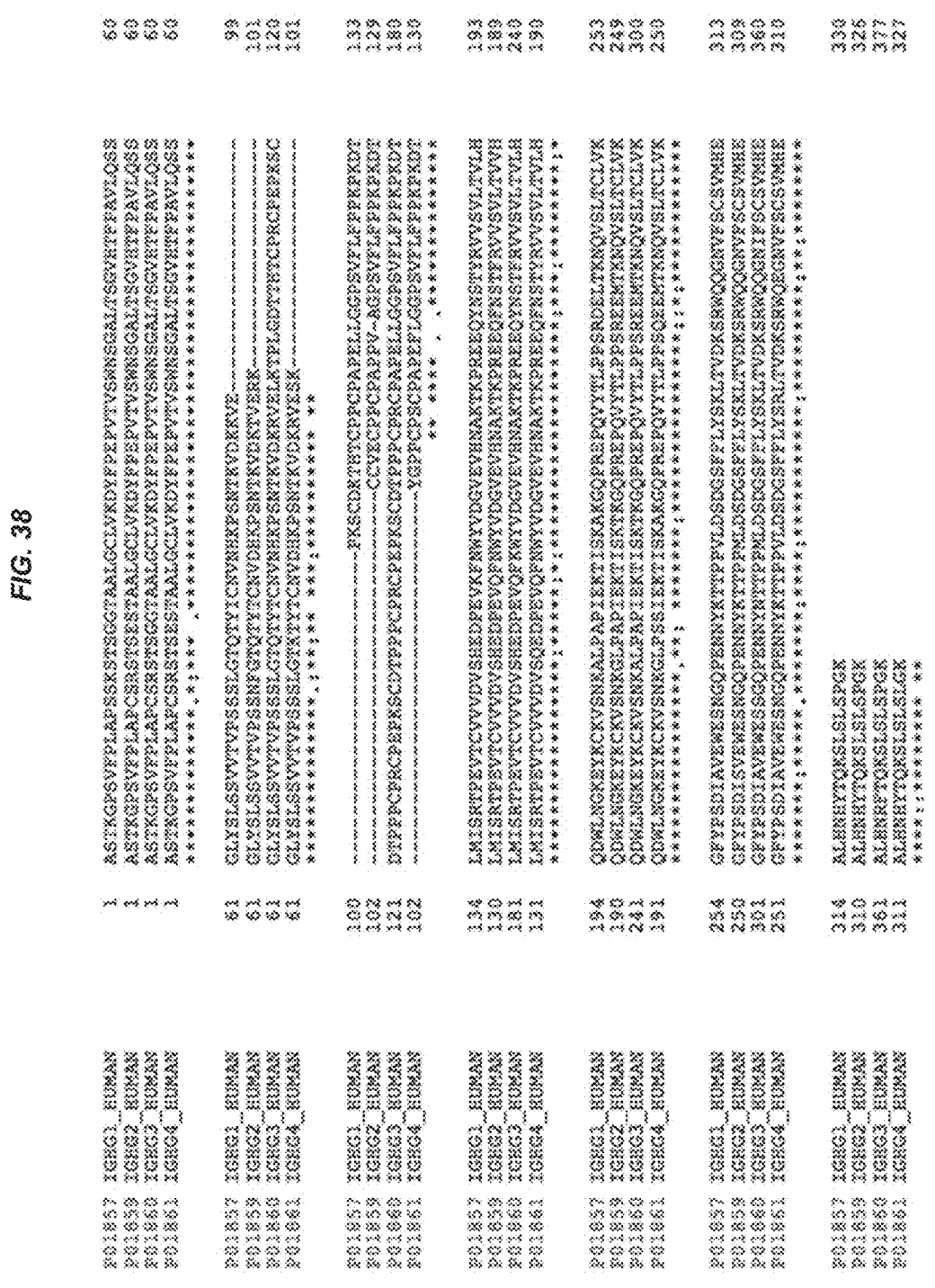

Amino acid residues, e.g., solvent-exposed surface residues, of an Fc polypeptide that can be modified in accordance with the invention are numbered herein with reference to SEQ ID NO:1. Any Fc polypeptide, e.g., an IgG1, IgG2, IgG3, or IgG4 Fc polypeptide, may have modifications, e.g., amino acid substitutions, in one or more sets of residues (e.g., solvent-exposed residues) that correspond to residues at the noted positions in SEQ ID NO:1. An alignment of the human IgG1 amino acid sequence of SEQ ID NO:1 with human IgG2, IgG3, and IgG4 is shown in FIG. 38. The positions of each of the IgG2, IgG3, and IgG4 sequences that correspond to any given position of SEQ ID NO:1 can be readily determined.

A modified polypeptide of the invention that binds to a BBB receptor and can be transported across the BBB can have at least 70% identity, at least 75% identity, at least 80% identity, at least 85% identity, at least 90% identity, or at least 95% identity to a native Fc region sequence or a fragment thereof, e.g., a fragment of at least 50 amino acids or at least 100 amino acids, or greater in length. In some embodiments, the native Fc amino acid sequence is the Fc region sequence of SEQ ID NO:1, i.e., amino acids 4-220 of SEQ ID NO:1. In some embodiments, the modified polypeptide has at least 70% identity, at least 75% identity, at least 80% identity, at least 85% identity, at least 90% identity, or at least 95% identity to amino acids 4-220 of SEQ ID NO:1, or a fragment thereof, e.g., a fragment of at least 50 amino acids or at least 100 amino acids, or greater in length.

In some embodiments, a modified Fc polypeptide of the present invention comprises at least 50 amino acids, or at least 60, 65, 70, 75, 80, 85, 90, or 95 or more, or at least 100 amino acids, or more, that correspond to a native Fc region amino acid sequence. In some embodiments, the invention comprises at least 25 contiguous amino acids, or at least 30, 35, 40, or 45 contiguous amino acids, or 50 contiguous amino acids, or at least 60, 65, 70, 75, 80 85, 90, or 95 or more contiguous amino acids, or 100 or more contiguous amino acids, that correspond to a native Fc region amino acid sequence, such as SEQ ID NO:1

In some embodiments, a modified Fc polypeptide in accordance with the invention comprises at least one substitution, and typically two, three, four five, six, seven, eight, nine, or ten substitutions in a set of amino acid positions comprising 39, 40, 41, 42, 43, 44, 68, 70, 71, and 72, wherein the positions are determined with reference to SEQ ID NO:1 and the substitution(s) are relative to the amino acid residues that occur at the respective positions in SEQ ID NO: 1.

In some embodiments, a modified Fc polypeptide in accordance with the invention comprises at least one substitution, and typically two, three, four, five, six, seven, eight, or nine substitutions in a set of amino acid positions comprising 47, 49, 56, 58, 59, 60, 61, 62, and 63, wherein the positions are determined with reference to SEQ ID NO:1 and the substitution(s) are relative to the amino acid residues that occur at the respective positions in SEQ ID NO: 1.

In some embodiments, a modified Fc polypeptide in accordance with the invention comprises at least one substitution, and typically two, three, four, five, six, seven, eight, nine, or ten substitutions in a set of amino acid positions comprising 41, 42, 43, 44, 45, 65, 66, 67, 69, and 73, wherein the positions are determined with reference to SEQ ID NO:1 and the substitution(s) are relative to the amino acid residues that occur at the respective positions in SEQ ID NO: 1.

In some embodiments, a modified Fc polypeptide in accordance with the invention comprises at least one substitution, and typically two, three, four, five, six, seven, eight, or nine substitutions in a set of amino acid positions comprising 45, 47, 49, 95, 97, 99, 102, 103, and 104, wherein the positions are determined with reference to SEQ ID NO:1 and the substitution(s) are relative to the amino acid residues that occur at the respective positions in SEQ ID NO: 1.

In some embodiments, a modified Fc polypeptide in accordance with the invention comprises at least one substitution, and typically two, three, four, five, six, or seven substitutions in a set of amino acid positions comprising 118, 119, 120, 122, 210, 211, 212, and 213, wherein the positions are determined with reference to SEQ ID NO: 1 and the substitution(s) are relative to the amino acid residues that occur at the respective positions in SEQ ID NO: 1.

In some embodiments, a modified Fc polypeptide in accordance with the invention comprises at least one substitution, and typically two, three, four, five, six, seven, eight, or nine substitutions in a set of amino acid positions comprising 157, 159, 160, 161, 162, 163, 186, 189, and 194, wherein the positions are determined with reference to SEQ ID NO:1 and the substitution(s) are relative to the amino acid residues that occur at the respective positions in SEQ ID NO:1.

FcRn Binding Sites

A polypeptide of the present invention that can be transported across the BBB additionally comprises an FcRn binding site. In some embodiments, the FcRn binding site is within the modified Fc polypeptide or a fragment thereof.

In some embodiments, the FcRn binding site comprises a native FcRn binding site. In some embodiments, the FcRn binding site does not comprise amino acid changes relative to the amino acid sequence of a native FcRn binding site. In some embodiments, the native FcRn binding site is an IgG binding site, e.g., a human IgG binding site. In some embodiments, the FcRn binding site comprises a modification that alters FcRn binding.

In some embodiments, an FcRn binding site has one or more amino acid residues that are mutated, e.g., substituted, wherein the mutation(s) increase serum half-life or do not substantially reduce serum half-life (i.e., reduce serum half-life by no more than 25% compared to a counterpart BBB receptor-binding protein having the wild type residues at the mutated positions when assayed under the same conditions). In some embodiments, an FcRn binding site has one or more amino acid residues that are substituted at positions 24 to 29, 201, and 206 to 209, wherein the positions are determined with reference to SEQ ID NO:1.

In some embodiments, the FcRn binding site comprises one or more mutations, relative to a native human IgG sequence, that extend serum half-life of the modified polypeptide. In some embodiments, a mutation, e.g., a substitution, is introduced at one or more of positions 17-30, 52-57, 80-90, 156-163, and 201-208 as determined with reference to SEQ ID NO:1 (which positions correspond to positions 244-257, 279-284, 307-317, 383-390, and 428-435 using EU numbering). In some embodiments, one or more mutations are introduced at positions 24, 25, 27, 28, 29, 80, 81, 82, 84, 85, 87, 158, 159, 160, 162, 201, 206, 207, or 209 as determined with reference to SEQ ID NO:1 (which positions correspond to positions 251, 252, 254, 255, 256, 307, 308, 309, 311, 312, 314, 385, 386, 387, 389, 428, 433, 434, or 436 using EU numbering). In some embodiments, mutations are introduced into one, two, or three of positions 25, 27, and 29 as determined with reference to SEQ ID NO: 1 (which correspond to positions 252, 254, and 256 using EU numbering). In some embodiments, the mutations are M25Y, S27T, and T29E as numbered with reference to SEQ ID NO:1. In some embodiments, a modified Fc polypeptide of the present invention further comprises mutations M25Y, S27T, and T29E. In some embodiments, a modified Fc polypeptide comprises a substitution at one, two or all three of positions T307, E380, and N434 according to EU numbering (which correspond to T80, E153, and N207 as numbered with reference to SEQ ID NO:1). In some embodiments, the mutations are T307Q and N434A (SEQ ID NO:1, T80Q and N207A). In some embodiments, a modified Fc polypeptide comprises mutations T307A, E380A, and N434A (SEQ ID NO:1, T80A, E153A, and N207A). In some embodiments, a modified Fc polypeptide comprises substitutions at positions T250 and M428 (which correspond to T23 and M201 as numbered with reference to SEQ ID NO: 1). In some embodiments, the Fc polypeptide comprises mutations T250Q and/or M428L (SEQ ID NO:1, T23Q and M201L). In some embodiments, a modified Fc polypeptide comprises substitutions at positions M428 and N434 (which correspond to M201 and N207 as numbered with reference to SEQ ID NO: 1). In some embodiments, a modified Fc polypeptide comprises substitutions M428L and N434S (which correspond to M201L and N207S as numbered with reference to SEQ ID NO:1). In some embodiments, a modified Fc polypeptide comprises an N434S or N434A substitution (which corresponds to N207S or N207A as numbered with reference to SEQ ID NO: 1).

IV. Transferrin Receptor-Binding Polypeptides

This section describes generation of modified Fc polypeptides in accordance with the invention that bind to a blood-brain barrier (BBB) receptor and are capable of being transported across the BBB using transferrin receptor as an illustrative BBB receptor.

CH3 Transferrin Receptor-Binding Polypeptides

In some embodiments, the domain that is modified is a human Ig CH3 domain, such as an IgG CH3 domain. The CH3 domain can be of any IgG subtype, i.e., from IgG1, IgG2, IgG3, or IgG4. In the context of IgG antibodies, a CH3 domain refers to the segment of amino acids from about position 341 to about position 447 as numbered according to the EU numbering scheme. The positions in the CH3 domain for purposes of identifying the corresponding set of amino acid positions for transferrin receptor binding are determined with reference to SEQ ID NO:3 or determined with reference to amino acids 114-220 of SEQ ID NO:1 unless otherwise specified. Substitutions are also determined with reference to SEQ ID NO:1, i.e., an amino acid is considered to be a substitution relative to the amino acid at the corresponding position in SEQ ID NO:1. SEQ ID NO:1 includes a partial hinge region sequence, PCP, as amino acids 1-3. The numbering of the positions in the CH3 domain with reference to SEQ ID NO: 1 includes the first three amino acids.

As indicated above, sets of residues of a CH3 domain that can be modified in accordance with the invention are numbered herein with reference to SEQ ID NO: 1. Any CH3 domain, e.g., an IgG1, IgG2, IgG3, or IgG4 CH3 domain, may have modifications, e.g., amino acid substitutions, in one or more sets of residues that correspond to residues at the noted positions in SEQ ID NO: 1. An alignment of the human IgG1 amino acid sequence of SEQ ID NO:1 with human IgG2, IgG3, and IgG4 is shown in FIG. 38. The positions of each of the IgG2, IgG3, and IgG4 sequences that correspond to any given position of SEQ ID NO: 1 can be readily determined.

One of skill understands that CH2 and CH3 domains of other immunoglobulin isotypes, e.g., IgM, IgA, IgE, IgD, etc. may be similarly modified by identifying the amino acids in those domains that correspond to sets (i)-(vi) described herein. Modifications may also be made to corresponding domains from immunoglobulins from other species, e.g., non-human primates, monkey, mouse, rat, rabbit, dog, pig, chicken, and the like.

In one embodiment, a modified CH3 domain polypeptide that specifically binds transferrin receptor binds to the apical domain of the transferrin receptor at an epitope that comprises position 208 of the full length human transferrin receptor sequence (SEQ ID NO:235), which corresponds to position 11 of the human transferrin receptor apical domain sequence set forth in SEQ ID NO:107. SEQ ID NO:107 corresponds to amino acids 198-378 of the human transferrin receptor-1 uniprotein sequence P02786 (SEQ ID NO:235). In some embodiments, the modified CH3 domain polypeptide binds to the apical domain of the transferrin receptor at an epitope that comprises positions 158, 188, 199, 207, 208, 209, 210, 211, 212, 213, 214, 215, and/or 294 of the full length human transferrin receptor sequence (SEQ ID NO:235). The modified CH3 domain polypeptide may bind to the transferrin receptor without blocking or otherwise inhibiting binding of transferrin to the receptor. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 19%, 18%, 17%, 16%, 15%, 14%, 13%, 12%, 11%, 10%, 9%, 8%, 7%, 6%, 5%, 4%, 3%, 2%, or 1%). Illustrative CH3 domain polypeptides that exhibit this binding specificity include polypeptides having amino acid substitutions at positions 157, 159, 160, 161, 162, 163, 186, 189, and 194 as determined with reference to amino acids 114-220 of SEQ ID NO:1.

CH3 Transferrin Receptor Binding Set (i): 157, 159, 160, 161, 162, 163, 186, 189, and 194

In some embodiments, a modified CH3 domain polypeptide in accordance with the invention comprises at least three or at least four, and typically five, six, seven, eight, or nine substitutions in a set of amino acid positions comprising 157, 159, 160, 161, 162, 163, 186, 189, and 194 (set i). Illustrative substitutions that may be introduced at these positions are shown in Table 6. In some embodiments, the amino acid at position 161 and/or 194 is an aromatic amino acid, e.g., Trp, Phe, or Tyr. In some embodiments, the amino acid at position 161 is Trp. In some embodiments, the amino acid at position 161 is Gly. In some embodiments, the aromatic amino acid at position 194 is Trp or Phe.

In some embodiments, a modified CH3 domain polypeptide that specifically binds a transferrin receptor comprises at least one position having a substitution, relative to SEQ ID NO: 1, as follows: Leu, Tyr, Met, or Val at position 157; Leu, Thr, His, or Pro at position 159; Val, Pro, or an acidic amino acid at position 160; an aromatic amino acid, e.g., Trp or Gly (e.g., Trp) at position 161; Val, Ser, or Ala at position 162; an acidic amino acid, Ala, Ser, Leu, Thr, or Pro at position 186; Thr or an acidic amino acid at position 189; or Trp, Tyr, His, or Phe at position 194. In some embodiments, a modified CH3 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set. Thus, for example, Ile may be present at position 157, 159, and/or position 186. In some embodiments, the acidic amino acid at position one, two, or each of positions 160, 186, and 189 is Glu. In other embodiments, the acidic amino acid at one, two or each of positions 160, 186, and 189 is Asp. In some embodiments, two, three, four five, six, seven, or all eight of positions 157, 159, 160, 161, 162, 186, 189, and 194 have an amino acid substitution as specified in this paragraph.

In some embodiments, a CH3 domain polypeptide having modifications in set (i) comprises a native Asn at position 163. In some embodiments, the modified CH3 domain polypeptide comprises Gly, His, Gln, Leu, Lys, Val, Phe, Ser, Ala, or Asp at position 163. In some embodiments, the modified CH3 domain polypeptide further comprises one, two, three, or four substitutions at positions comprising 153, 164, 165, and 188. In some embodiments, Trp, Tyr, Leu, or Gln may be present at position 153. In some embodiments, Ser, Thr, Gln, or Phe may be present at position 164. In some embodiments, Gln, Phe, or His may be present at position 165. In some embodiments, Glu may be present at position 188.

In certain embodiments, the modified CH3 domain polypeptide comprises two, three, four, five, six, seven, eight nine, or ten positions selected from the following: Trp, Leu, or Glu at position 153; Tyr or Phe at position 157; Thr at position 159; Glu at position 160; Trp at position 161; Ser, Ala, Val, or Asn at position 162; Ser or Asn at position 163; Thr or Ser at position 186; Glu or Ser at position 188; Glu at position 189; and/or Phe at position 194. In some embodiments, the modified CH3 domain polypeptide comprises all eleven positions as follows: Trp, Leu, or Glu at position 153; Tyr or Phe at position 157; Thr at position 159; Glu at position 160; Trp at position 161; Ser, Ala, Val, or Asn at position 162; Ser or Asn at position 163; Thr or Ser at position 186; Glu or Ser at position 188; Glu at position 189; and/or Phe at position 194.

In certain embodiments, the modified CH3 domain polypeptide comprises Leu or Met at position 157; Leu, His, or Pro at position 159; Val at position 160; Trp at position 161; Val or Ala at position 162; Pro at position 186; Thr at position 189; and/or Trp at position 194. In some embodiments, the modified CH3 domain polypeptide further comprises Ser, Thr, Gln, or Phe at position 164. In some embodiments, a modified CH3 domain polypeptide further comprises Trp, Tyr, Leu, or Gln at position 153 and/or Gln, Phe, or His at position 165. In some embodiments, Trp is present at position 153 and/or Gln is present at position 165. In some embodiments, a modified CH3 domain polypeptide does not have a Trp at position 153.

In other embodiments, a modified CH3 domain polypeptide comprises Tyr at position 157; Thr at position 159; Glu or Val and position 160; Trp at position 161; Ser at position 162; Ser or Thr at position 186; Glu at position 189; and/or Phe at position 194. In some embodiments, the modified CH3 domain polypeptide comprises a native Asn at position 163. In certain embodiments, the modified CH3 domain polypeptide further comprises Trp, Tyr, Leu, or Gln at position 153; and/or Glu at position 188. In some embodiments, the modified CH3 domain polypeptide further comprises Trp at position 153 and/or Glu at position 188.

In additional embodiments, the modified CH3 domain further comprises one, two, or three positions selected from the following: position 187 is Lys, Arg, Gly, or Pro; position 197 is Ser, Thr, Glu, or Lys; and position 199 is Ser, Trp, or Gly.

In some embodiments, the modified CH3 domain comprises one or more of the following substitutions: Trp at position 153; Thr at position 159; Trp at position 161; Val at position 162; Ser or Thr at position 186; Glu at position 188; and/or Phe at position 194.

In some embodiments, a modified CH3 domain polypeptide that specifically binds transferrin receptor has at least 70% identity, at least 75% identity, at least 80% identity, at least 85% identity, at least 90% identity, or at least 95% identity to amino acids 114-220 of any one of SEQ ID NOS:4-29 and 236-299. In some embodiments, such a modified CH3 domain polypeptide comprises amino acids 157-163 and/or 186-194 of any one of SEQ ID NOS:4-29 and 236-299. In some embodiments, such a modified CH3 domain polypeptide comprises amino acids 153-163 and/or 186-194 of any one of SEQ ID NOS:4-29 and 236-299. In some embodiments, a modified CH3 domain polypeptide comprises amino acids 153-163 and/or 186-199 of any one of SEQ ID NOS:4-29 and 236-299.

In some embodiments, a modified CH3 domain polypeptide has at least 70% identity, at least 75% identity, at least 80% identity, at least 85% identity, at least 90% identity, or at least 95% identity to amino acids 114-220 of SEQ ID NO: 1, with the proviso that the percent identity does not include the set of positions 157, 159, 160, 161, 162, 163, 186, 189, and 194. In some embodiments, the modified CH3 domain polypeptide comprises amino acids 157-163 and/or amino acids 186-194 as set forth in any one of SEQ ID NOS:4-29 and 236-299.

In some embodiments, a modified CH3 domain polypeptide has at least 70% identity, at least 75% identity, at least 80% identity, at least 85% identity, at least 90% identity, or at least 95% identity to any one of SEQ ID NOS:4-29 and 236-299, with the proviso that at least five, six, seven, eight, nine, ten, eleven, twelve, thirteen, fourteen, fifteen or sixteen of the positions that correspond to positions 153, 157, 159, 160, 161, 162, 163, 164, 165, 186, 187, 188, 189, 194, 197, and 199 of any one of SEQ ID NOS:4-29 and 236-299 are not deleted or substituted.

In some embodiments, the modified CH3 domain polypeptide has at least 75% identity, at least 80% identity, at least 85% identity, at least 90% identity, or at least 95% identity to any one of SEQ ID NOS:4-29 and 236-299 and also comprises at least five, six, seven, eight, nine, ten, eleven, twelve, thirteen, fourteen, fifteen or sixteen of the positions as follows: Trp, Tyr, Leu, Gln, or Glu at position 153; Leu, Tyr, Met, or Val at position 157; Leu, Thr, His, or Pro at position 159; Val, Pro, or an acidic amino acid at position 160; an aromatic amino acid, e.g., Trp, at position 161; Val, Ser, or Ala at position 162; Ser or Asn at position 163; Ser, Thr, Gln, or Phe at position 164; Gln, Phe, or His at position 165; an acidic amino acid, Ala, Ser, Leu, Thr, or Pro at position 186; Lys, Arg, Gly or Pro at position 187; Glu or Ser at position 188; Thr or an acidic amino acid at position 189; Trp, Tyr, His or Phe at position 194; Ser, Thr, Glu or Lys at position 197; and Ser, Trp, or Gly at position 199.

In some embodiments, a transferrin receptor-binding polypeptide comprises the amino acid sequence of any one of SEQ ID NOS: 116-130. In other embodiments, a transferrin receptor-binding polypeptide comprises the amino acid sequence of any one of SEQ ID NOS: 116-130, but in which one or two amino acids are substituted. In some embodiments, the polypeptide comprises the amino acid sequence of any one of SEQ ID NOS: 116-130, but in which three amino acids are substituted.

In some embodiments, a transferrin receptor-binding polypeptide comprises the amino acid sequence of any one of SEQ ID NOS: 131-139. In other embodiments, a transferrin receptor-binding polypeptide comprises the amino acid sequence of any one of SEQ ID NOS:131-139, but in which one or two amino acids are substituted. In some embodiments, the polypeptide comprises the amino acid sequence of any one of SEQ ID NOS: 131-139, but in which three or four amino acids are substituted.

In some embodiments, a transferrin receptor-binding polypeptide comprises the amino acid sequence of any one of SEQ ID NOS:303-339. In other embodiments, a transferrin receptor-binding polypeptide comprises the amino acid sequence of any one of SEQ ID NOS:303-339, but in which one or two amino acids are substituted. In some embodiments, the polypeptide comprises the amino acid sequence of any one of SEQ ID NOS:303-339, but in which three amino acids are substituted.

In some embodiments, a transferrin receptor-binding polypeptide comprises the amino acid sequence of any one of SEQ ID NOS:136, 138, and 340-345. In other embodiments, a transferrin receptor-binding polypeptide comprises the amino acid sequence of any one of SEQ ID NOS:136, 138, and 340-345, but in which one or two amino acids are substituted. In some embodiments, the polypeptide comprises the amino acid sequence of any one of SEQ ID NOS: 136, 138, and 340-345, but in which three or four amino acids are substituted.

In additional embodiments, a transferrin receptor-binding polypeptide comprises amino acids 157-194, amino acids 153-194, or amino acids 153-199, of any one of SEQ ID NOS:4-29 and 236-299. In further embodiments, the polypeptide comprises an amino acid sequence having at least 75% identity, at least 80% identity, at least 85% identity, at least 90% identity, or at least 95% identity to amino acids 157-194 of any one of SEQ ID NOS:4-29 and 236-299, or to amino acids 153-194, or to amino acids 153-199, of any one of SEQ ID NOS:4-29 and 236-299.

In some embodiments, the polypeptide comprises any one of SEQ ID NOS:4-29 and 236-299. In further embodiments, the polypeptide comprises any one of SEQ ID NOS:4-29 and 236-299 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:4-29 and 236-299 as determined without the first three amino acids "PCP" at the amino-terminal end.

CH3 Transferrin Receptor Binding Set (ii): 118, 119, 120, 122, 210, 211, 212, and 213

In some embodiments, a modified CH3 domain polypeptide in accordance with the invention comprises at least three or at least four, and typically five, six, seven, or eight substitutions in a set of amino acid positions comprising 118, 119, 120, 122, 210, 211, 212, and 213 (set ii). Illustrative substitutions that may be introduced at these positions are shown in Table 5. In some embodiments, the modified CH3 domain polypeptide comprises Gly at position 210; Phe at position 211; and/or Asp at position 213. In some embodiments, Glu is present at position 213. In certain embodiments, a modified CH3 domain polypeptide comprises at least one substitution at a position as follows: Phe or Ile at position 118; Asp, Glu, Gly, Ala, or Lys at position 119; Tyr, Met, Leu, Ile, or Asp at position 120; Thr or Ala at position 122; Gly at position 210; Phe at position 211; His Tyr, Ser, or Phe at position 212; or Asp at position 213. In some embodiments, two, three, four, five, six, seven, or all eight of positions 118, 119, 120, 122, 210, 211, 212, and 213 have a substitution as specified in this paragraph. In some embodiments, a modified CH3 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, a modified CH3 domain polypeptide that specifically binds transferrin receptor has at least 70% identity, at least 75% identity, at least 80% identity, at least 85% identity, at least 90% identity, or at least 95% identity to amino acids 114-220 of any one of SEQ ID NOS:30-46. In some embodiments, such a modified CH3 domain polypeptide comprises amino acids 118-122 and/or amino acids 210-213 of any one of SEQ ID NOS:30-46.

In some embodiments, a modified CH3 domain polypeptide of the has at least 70% identity, at least 75% identity, at least 80% identity, at least 85% identity, at least 90% identity, or at least 95% identity to amino acids 114-220 of SEQ ID NO: 1, with the proviso that the percent identity does not include the set of positions 118, 119, 120, 122, 210, 211, 212, and 213. In some embodiments, the modified CH3 domain polypeptide comprises amino acids 118-122 and/or amino acids 210-213 as set forth in any one of SEQ ID NOS:30-46.

In some embodiments, a transferrin receptor-binding polypeptide comprises the amino acid sequence of any one of SEQ ID NOS:140-153. In other embodiments, a transferrin receptor-binding polypeptide comprises the amino acid sequence of any one of SEQ ID NOS:140-153, but in which one or two amino acids are substituted.

In some embodiments, a transferrin receptor-binding polypeptide comprises the amino acid sequence of any one of SEQ ID NOS:154-157. In other embodiments, a transferrin receptor-binding polypeptide comprises the amino acid sequence of any one of SEQ ID NOS:154-157, but in which one amino acid is substituted or in which two amino acids are substituted.

In additional embodiments, a transferrin receptor-binding polypeptide comprises amino acids 118-213 of any one of SEQ ID NOS:30-46. In further embodiments, the polypeptide may comprise an amino acid sequence having at least 75% identity, at least 80% identity, at least 85% identity, at least 90% identity, or at least 95% identity to amino acids 118-213 of any one of SEQ ID NOS:30-46.

In some embodiments, the polypeptide comprises any one of SEQ ID NOS:30-46. In further embodiments, the polypeptide comprises any one of SEQ ID NOS:30-46 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:30-46 or to any one of SEQ ID NOS:30-46 as determined without the first three amino acids "PCP" at the amino-terminal end.

CH2 Transferrin Receptor-Binding Polypeptides

In some embodiments, the domain that is modified is a human Ig CH2 domain, such as an IgG CH2 domain. The CH2 domain can be of any IgG subtype, i.e., from IgG1, IgG2, IgG3, or IgG4. In the context of IgG antibodies, a CH2 domain refers to the segment of amino acids from about position 231 to about position 340 as numbered according to the EU numbering scheme. The positions in the CH2 domain for purposes of identifying the corresponding set of amino acid positions for transferrin receptor binding are determined with reference to SEQ ID NO:2 or determined with reference to amino acids 4-113 of SEQ ID NO: 1. Substitutions are also determined with reference to SEQ ID NO: 1, i.e., an amino acid is considered to be a substitution relative to the amino acid at the corresponding position in SEQ ID NO: 1. SEQ ID NO: 1 includes a partial hinge region sequence, PCP, as amino acids 1-3. The three residues are not part of the Fc region; however, the numbering of the positions in the CH2 domain with reference to SEQ ID NO:1 includes the first three amino acids.

As indicated above, sets of residues of a CH2 domain that can be modified in accordance with the invention are numbered herein with reference to SEQ ID NO: 1. Any CH2 domain, e.g., an IgG1, IgG2, IgG3, or IgG4 CH2 domain, may have modifications, e.g., amino acid substitutions, in one or more sets of residues that correspond to residues at the noted positions in SEQ ID NO: 1. An alignment of the human IgG1 amino acid sequence of SEQ ID NO:1 with human IgG2, IgG3, and IgG4 is shown in FIG. 38. The positions of each of the IgG2, IgG3, and IgG4 sequences that correspond to any given position of SEQ ID NO: 1 can be readily determined.

In one embodiment, a modified CH2 domain polypeptide that specifically binds transferrin receptor binds to an epitope in the apical domain of the transferrin receptor. The human transferrin receptor apical domain sequence is set forth in SEQ ID NO: 107, which corresponds to amino acids 198-378 of the human transferrin receptor-1 uniprotein sequence P02786. The modified CH2 domain polypeptide may bind to the transferrin receptor without blocking or otherwise inhibiting binding of transferrin to the receptor. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 19%, 18%, 17%, 16%, 15%, 14%, 13%, 12%, 11%, 10%, 9%, 8%, 7%, 6%, 5%, 4%, 3%, 2%, or 1%).

CH2 Transferrin Receptor Binding Set (iii): 47, 49, 56, 58, 59, 60, 61, 62, and 63

In some embodiments, a modified CH2 domain polypeptide in accordance with the invention comprises at least three or at least four, and typically five, six, seven, eight, or nine substitutions in a set of amino acid positions comprising 47, 49, 56, 58, 59, 60, 61, 62, and 63 (set iii). Illustrative substitutions that may be introduced at these positions are shown in Table 1. In some embodiments, the modified CH2 domain polypeptide comprises Glu at position 60 and/or Trp at position 61. In some embodiments, the modified CH2 domain polypeptide comprises at least one substitution at a position as follows: Glu, Gly, Gln, Ser, Ala, Asn, Tyr, or Trp at position 47; Ile, Val, Asp, Glu, Thr, Ala, or Tyr at position 49; Asp, Pro, Met, Leu, Ala, Asn, or Phe at position 56; Arg, Ser, Ala, or Gly at position 58; Tyr, Trp, Arg, or Val at position 59; Glu at position 60; Trp or Tyr at position 61; Gln, Tyr, His, Ile, Phe, Val, or Asp at position 62; or Leu, Trp, Arg, Asn, Tyr, or Val at position 63. In some embodiments, two, three, four, five, six, seven, eight, or all nine of positions 47, 49, 56, 58, 59, 60, 61, 62, and 63 have a substitution as specified in this paragraph. In some embodiments, a modified CH2 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, a modified CH2 domain polypeptide comprises Glu, Gly, Gln, Ser, Ala, Asn, or Tyr at position 47; Ile, Val, Asp, Glu, Thr, Ala, or Tyr at position 49; Asp, Pro, Met, Leu, Ala, or Asn at position 56; Arg, Ser, or Ala at position 58; Tyr, Trp, Arg, or Val at position 59; Glu at position 60; Trp at position 61; Gln, Tyr, His, Ile, Phe, or Val at position 62; and/or Leu, Trp, Arg, Asn, or Tyr at position 63. In some embodiments, the modified CH2 domain polypeptide comprises Arg at position 58; Tyr or Trp at position 59; Glu at position 60; Trp at position 61; and/or Arg or Trp at position 63.

In some embodiments, a modified CH2 domain polypeptide that specifically binds transferrin receptor has at least 70% identity, at least 75% identity, at least 80% identity, at least 85% identity, at least 90% identity, or at least 95% identity to amino acids 4-113 of any one of SEQ ID NOS:47-62. In some embodiments, such a modified CH2 domain polypeptide comprises amino acids 47-49 and/or amino acids 56-63 of any one of SEQ ID NOS:47-62.

In some embodiments, a modified CH2 domain polypeptide of the present invention has at least 70% identity, at least 75% identity, at least 80% identity, at least 85% identity, at least 90% identity, or at least 95% identity to amino acids 4-113 of SEQ ID NO: 1, with the proviso that the percent identity does not include the set of positions 47, 49, 56, 58, 59, 60, 61, 62, and 63. In some embodiments, the modified CH2 domain polypeptide comprises amino acids 47-49 and/or amino acids 56-63 as set forth in any one of SEQ ID NOS:47-62.

In some embodiments, a transferrin receptor-binding polypeptide comprises the amino acid sequence of any one of SEQ ID NOS:158-171. In other embodiments, a transferrin receptor-binding polypeptide comprises the amino acid sequence of any one of SEQ ID NOS:158-171, but in which one amino acid is substituted.

In some embodiments, a transferrin receptor-binding polypeptide comprises the amino acid sequence of any one of SEQ ID NOS:172-186. In other embodiments, a transferrin receptor-binding polypeptide comprises the amino acid sequence of any one of SEQ ID NOS:172-186, but in which one amino acid is substituted or in which two amino acids are substituted. In other embodiments, a transferrin receptor-binding polypeptide comprises the amino acid sequence of any one of SEQ ID NOS:172-186, but in which three or four amino acids are substituted.

In additional embodiments, a transferrin receptor-binding polypeptide comprises amino acids 47-63 of any one of SEQ ID NOS:47-62. In further embodiments, the polypeptide may comprise an amino acid sequence having at least 75% identity, at least 80% identity, at least 85% identity, at least 90% identity, or at least 95% identity to amino acids 47-63 of any one of SEQ ID NOS:47-62.

In some embodiments, the polypeptide comprises any one of SEQ ID NOS:47-62. In further embodiments, the polypeptide comprises any one of SEQ ID NOS:47-62 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:47-62 or to any one of SEQ ID NOS:47-62 as determined without the first three amino acids "PCP" at the amino-terminal end.

CH2 Transferrin Receptor Binding Set (iv): 39, 40, 41, 42, 43, 44, 68, 70, 71, and 72

In some embodiments, a modified CH2 domain polypeptide in accordance with the invention comprises at least three or at least four, and typically five, six, seven, eight, nine, or ten substitutions in a set of amino acid positions comprising 39, 40, 41, 42, 43, 44, 68, 70, 71, and 72 (set iv). Illustrative substitutions that may be introduced at these positions are shown in Table 2. In some embodiments, the modified CH2 domain polypeptide comprises Pro at position 43, Glu at position 68, and/or Tyr at position 70. In some embodiments, the modified CH2 domain polypeptide comprises at least one substitution at a position as follows: Pro, Phe, Ala, Met, or Asp at position 39; Gln, Pro, Arg, Lys, Ala, Ile, Leu, Glu, Asp, or Tyr at position 40; Thr, Ser, Gly, Met, Val, Phe, Trp, or Leu at position 41; Pro, Val, Ala, Thr, or Asp at position 42; Pro, Val, or Phe at position 43; Trp, Gln, Thr, or Glu at position 44; Glu, Val, Thr, Leu, or Trp at position 68; Tyr, His, Val, or Asp at position 70; Thr, His, Gln, Arg, Asn, or Val at position 71; or Tyr, Asn, Asp, Ser, or Pro at position 72. In some embodiments, two, three, four, five, six, seven, eight, nine, or all ten of positions 39, 40, 41, 42, 43, 44, 68, 70, 71, and 72 have a substitution as specified in this paragraph. In some embodiments, a modified CH2 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, a modified CH2 domain polypeptide comprises Pro, Phe, or Ala at position 39; Gln, Pro, Arg, Lys, Ala, or Ile at position 40; Thr, Ser, Gly, Met, Val, Phe, or Trp at position 41; Pro, Val, or Ala at position 42; Pro at position 43; Trp or Gln at position 44; Glu at position 68; Tyr at position 70; Thr, His, or Gln at position 71; and/or Tyr, Asn, Asp, or Ser at position 72.

In some embodiments, a modified CH2 domain polypeptide comprises Met at position 39; Leu or Glu at position 40; Trp at position 41; Pro at position 42; Val at position 43; Thr at position 44; Val or Thr at position 68; His at position 70; His, Arg, or Asn at position 71; and/or Pro at position 72.

In some embodiments, a modified CH2 domain polypeptide comprises Asp at position 39; Asp at position 40; Leu at position 41; Thr at position 42; Phe at position 43; Gln at position 44; Val or Leu at position 68; Val at position 70; Thr at position 71; and/or Pro at position 72.

In some embodiments, a modified CH2 domain polypeptide that specifically binds transferrin receptor has at least 70% identity, at least 75% identity, at least 80% identity, at least 85% identity, at least 90% identity, or at least 95% identity to amino acids 4-113 of any one of SEQ ID NOS:63-85. In some embodiments, such a modified CH2 domain polypeptide comprises amino acids 39-44 and/or amino acids 68-72 of any one of SEQ ID NOS:63-85.

In some embodiments, a modified CH2 domain polypeptide of the present invention has at least 70% identity, at least 75% identity, at least 80% identity, at least 85% identity, at least 90% identity, or at least 95% identity to amino acids 4-113 of SEQ ID NO: 1, with the proviso that the percent identity does not include the set of positions 39, 40, 41, 42, 43, 44, 68, 70, 71, and 72. In some embodiments, the modified CH2 domain polypeptide comprises amino acids 39-44 and/or amino acids 68-72 as set forth in any one of SEQ ID NOS:63-85.

In some embodiments, a transferrin receptor-binding polypeptide comprises the amino acid sequence of any one of SEQ ID NOS:187-204. In other embodiments, a transferrin receptor-binding polypeptide comprises the amino acid sequence of any one of SEQ ID NOS:187-204, but in which one or two amino acids are substituted. In other embodiments, a transferrin receptor-binding polypeptide comprises the amino acid sequence of any one of SEQ ID NOS:187-204, but in which three amino acids are substituted.

In some embodiments, a transferrin receptor-binding polypeptide comprises the amino acid sequence of any one of SEQ ID NOS:205-215. In other embodiments, a transferrin receptor-binding polypeptide comprises the amino acid sequence of any one of SEQ ID NOS:205-215, but in which one amino acid is substituted or in which two amino acids are substituted.

In additional embodiments, a transferrin receptor-binding polypeptide comprises amino acids 39-72 of any one of SEQ ID NOS:63-85. In further embodiments, the polypeptide comprises an amino acid sequence having at least 75% identity, at least 80% identity, at least 85% identity, at least 90% identity, or at least 95% identity to amino acids 39-72 of any one of SEQ ID NOS:63-85.

In some embodiments, the polypeptide comprises any one of SEQ ID NOS:63-85. In further embodiments, the polypeptide comprises any one of SEQ ID NOS:63-85 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:63-85 or to any one of SEQ ID NOS:63-85 as determined without the first three amino acids "PCP" at the amino-terminal end.

CH2 Transferrin Receptor Binding Set (v): 41, 42, 43, 44, 45, 65, 66, 67, 69, and 73

In some embodiments, a modified CH2 domain polypeptide in accordance with the invention comprises at least three or at least four, and typically five, six, seven, eight, nine, or ten substitutions in a set of amino acid positions comprising 41, 42, 43, 44, 45, 65, 66, 67, 69, and 73 (set v). Illustrative substitutions that may be introduced at these positions are shown in Table 3. In some embodiments, the modified CH2 domain polypeptide comprises at least one substitution at a position as follows: Val or Asp at position 41; Pro, Met, or Asp at position 42; Pro or Trp at position 43; Arg, Trp, Glu, or Thr at position 44; Met, Tyr, or Trp at position 45; Leu or Trp at position 65; Thr, Val, Ile, or Lys at position 66; Ser, Lys, Ala, or Leu at position 67; His, Leu, or Pro at position 69; or Val or Trp at position 73. In some embodiments, two, three, four, five, six, seven, eight, nine, or all ten of positions 41, 42, 43, 44, 45, 65, 66, 67, 69, and 73 have a substitution as specified in this paragraph. In some embodiments, a modified CH2 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified CH2 domain polypeptide comprises Val at position 41; Pro at position 42; Pro at position 43; Arg or Trp at position 44; Met at position 45; Leu at position 65; Thr at position 66; Ser at position 67; His at position 69; and/or Val at position 73.

In some embodiments, the modified CH2 domain polypeptide comprises Asp at position 41; Met or Asp at position 42; Trp at position 43; Glu or Thr at position 44; Tyr or Trp at position 45; Trp at position 65; Val, Ile, or Lys at position 66; Lys, Ala, or Leu at position 67; Leu or Pro at position 69; and/or Trp at position 73.

In some embodiments, a modified CH2 domain polypeptide that specifically binds transferrin receptor has at least 70% identity, at least 75% identity, at least 80% identity, at least 85% identity, at least 90% identity, or at least 95% identity to amino acids 4-113 of any one of SEQ ID NOS:86-90. In some embodiments, such a modified CH3 domain polypeptide comprises amino acids 41-45 and/or amino acids 65-73 of any one of SEQ ID NOS:86-90.

In some embodiments, a modified CH2 domain polypeptide of the present invention has at least 70% identity, at least 75% identity, at least 80% identity, at least 85% identity, at least 90% identity, or at least 95% identity to amino acids 4-113 of SEQ ID NO: 1, with the proviso that the percent identity does not include the set of positions 41, 42, 43, 44, 45, 65, 66, 67, 69, and 73. In some embodiments, the modified CH2 domain polypeptide comprises amino acids 41-45 and/or amino acids 65-73 as set forth in any one of SEQ ID NOS:86-90.

In some embodiments, a transferrin receptor-binding polypeptide comprises the amino acid sequence of any one of SEQ ID NOS:216-220. In other embodiments, a transferrin receptor-binding polypeptide comprises the amino acid sequence of any one of SEQ ID NOS:216-220, but in which one or two amino acids are substituted.

In some embodiments, a transferrin receptor-binding polypeptide comprises the amino acid sequence of any one of SEQ ID NOS:221-224. In other embodiments, a transferrin receptor-binding polypeptide comprises the amino acid sequence of any one of SEQ ID NOS:221-224, but in which one amino acid is substituted or in which two amino acids are substituted. In other embodiments, a transferrin receptor-binding polypeptide comprises the amino acid sequence of any one of SEQ ID NOS:221-224, but in which three or four amino acids are substituted.

In additional embodiments, a transferrin receptor-binding polypeptide comprises amino acids 41-73 of any one of SEQ ID NOS:86-90. In further embodiments, the polypeptide may comprise a sequence having at least 75% identity, at least 80% identity, at least 85% identity, at least 90% identity, or at least 95% identity to amino acids 41-73 of any one of SEQ ID NOS:86-90.

In some embodiments, the polypeptide comprises any one of SEQ ID NOS:86-90. In further embodiments, the polypeptide comprises any one of SEQ ID NOS:86-90 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:86-90 or to any one of SEQ ID NOS:86-90 as determined without the first three amino acids "PCP" at the amino-terminal end.

CH2 Transferrin Receptor Binding Set (vi): 45, 47, 49, 95, 97, 99, 102, 103, and 104

In some embodiments, a modified CH2 domain polypeptide in accordance with the invention comprises at least three or at least four, and typically five, six, seven, eight, or nine substitutions in a set of amino acid positions comprising 45, 47, 49, 95, 97, 99, 102, 103, and 104 (set vi). Illustrative substitutions that may be introduced at these positions are shown in Table 4. In some embodiments, the modified CH2 domain polypeptide comprises Trp at position 103. In some embodiments, the modified CH2 domain polypeptide comprises at least one substitution at a position as follows: Trp, Val, Ile, or Ala at position 45; Trp or Gly at position 47; Tyr, Arg, or Glu at position 49; Ser, Arg, or Gln at position 95; Val, Ser, or Phe at position 97; Ile, Ser, or Trp at position 99; Trp, Thr, Ser, Arg, or Asp at position 102; Trp at position 103; or Ser, Lys, Arg, or Val at position 104. In some embodiments, two, three, four, five, six, seven, eight, or all nine of positions 45, 47, 49, 95, 97, 99, 102, 103, and 104 have a substitution as specified in this paragraph. In some embodiments, a modified CH2 domain polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified CH2 domain polypeptide comprises two, three, four, five, six, seven, eight, or nine positions selected from the following: position 45 is Trp, Val, Ile, or Ala; position 47 is Trp or Gly; position 49 is Tyr, Arg, or Glu; position 95 is Ser, Arg, or Gln; position 97 is Val, Ser, or Phe; position 99 is Ile, Ser, or Trp; position 102 is Trp, Thr, Ser, Arg, or Asp; position 103 is Trp; and position 104 is Ser, Lys, Arg, or Val.

In some embodiments, the modified CH2 domain polypeptide comprises Val or Ile at position 45; Gly at position 47; Arg at position 49; Arg at position 95; Ser at position 97; Ser at position 99; Thr, Ser, or Arg at position 102; Trp at position 103; and/or Lys or Arg at position 104.

In some embodiments, a modified CH2 domain polypeptide that specifically binds transferrin receptor has at least 70% identity, at least 75% identity, at least 80% identity, at least 85% identity, at least 90% identity, or at least 95% identity to amino acids 4-113 of any one of SEQ ID NOS:91-95. In some embodiments, such a modified CH3 domain polypeptide comprises amino acids 45-49 and/or amino acids 95-104 of any one of SEQ ID NOS:91-95.

In some embodiments, a modified CH2 domain polypeptide of the present invention has at least 70% identity, at least 75% identity, at least 80% identity, at least 85% identity, at least 90% identity, or at least 95% identity to amino acids 4-113 of SEQ ID NO: 1, with the proviso that the percent identity does not include the set of positions 45, 47, 49, 95, 97, 99, 102, 103, and 104. In some embodiments, the modified CH2 domain polypeptide comprises amino acids 45-49 and/or amino acids 95-104 as set forth in any one of SEQ ID NOS:91-95.

In some embodiments, a transferrin receptor-binding polypeptide comprises the amino acid sequence of any one of SEQ ID NOS:225-228. In other embodiments, a transferrin receptor-binding polypeptide comprises the amino acid sequence of any one of SEQ ID NOS:225-228, but in which one or two amino acids are substituted.

In some embodiments, a transferrin receptor-binding polypeptide comprises the amino acid sequence of any one of SEQ ID NOS:229-233. In other embodiments, a transferrin receptor-binding polypeptide comprises the amino acid sequence of any one of SEQ ID NOS:229-223, but in which one amino acid is substituted or in which two amino acids are substituted. In other embodiments, a transferrin receptor-binding polypeptide comprises the amino acid sequence of any one of SEQ ID NOS:229-233, but in which three, four, or five amino acids are substituted.

In additional embodiments, a transferrin receptor-binding polypeptide comprises amino acids 45-104 of any one of SEQ ID NOS:91-95. In further embodiments, the polypeptide may have at least 75% identity, at least 80% identity, at least 85% identity, at least 90% identity, or at least 95% identity to amino acids 45-104 of any one of SEQ ID NOS:91-95.

In some embodiments, the polypeptide comprises any one of SEQ ID NOS:91-95. In further embodiments, the polypeptide comprises any one of SEQ ID NOS:91-95 without the first three amino acids "PCP" at the amino-terminal end. In further embodiments, the polypeptide may have at least 75% identity, at least 80% identity, at least 85% identity, at least 90% identity, or at least 95% identity to any one of SEQ ID NOS:91-95 or to any one of SEQ ID NOS:91-95 as determined without the first three amino acids "PCP" at the amino-terminal end.

V. Additional Mutations in an Fc Region that Comprises a Modified CH3 or CH2 Domain Polypeptide An Fc polypeptide as provided herein that is modified to bind a BBB receptor and initiate transport across the BBB may also comprise additional mutations, e.g., to increase serum stability, to modulate effector function, to influence glyscosylation, to reduce immunogenicity in humans, and/or to provide for knob and hole heterodimerization of Fc polypeptides.

In some embodiments, a modified Fc polypeptide in accordance with the invention has an amino acid sequence identity of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to a corresponding wild-type Fc polypeptide (e.g., a human IgG1, IgG2, IgG3, or IgG4 Fc polypeptide).

A modified Fc polypeptide in accordance with the invention may also have other mutations introduced outside of the specified sets of amino acids, e.g., to influence glyscosylation, to increase serum half-life or, for CH3 domains, to provide for knob and hole heterodimerization of polypeptides that comprise the modified CH3 domain. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). Such additional mutations are at a position in the polypeptide that does not have a negative effect on binding of the modified CH3 or CH2 domain to the transferrin receptor.

In one illustrative embodiment of a knob and hole approach for dimerization, a position corresponding to position 139 of SEQ ID NO:1 of a first Fc polypeptide subunit to be dimerized has a tryptophan in place of a native threonine and a second Fc polypeptide subunit of the dimer has a valine at a position corresponding to position 180 of SEQ ID NO:1 in place of the native tyrosine. The second subunit of the Fc polypeptide may further comprise a substitution in which the native threonine at the position corresponding to position 139 of SEQ ID NO:1 is substituted with a serine and a native leucine at the position corresponding to position 141 of SEQ ID NO:1 is substituted with an alanine.

A modified Fc polypeptide as described herein may also be engineered to contain other modifications for heterodimerization, e.g., electrostatic engineering of contact residues within a CH3-CH3 interface that are naturally charged or hydrophobic patch modifications.

In some embodiments, modifications to enhance serum half-life may be introduced. For example, in some embodiments, a modified Fc polypeptide as described herein comprises a CH2 domain comprising a Tyr at a position corresponding to position 25 of SEQ ID NO:1, Thr at a position corresponding to 27 of SEQ ID NO: 1, and Glu at a position corresponding to position 29 of SEQ ID NO: 1. Alternatively, a modified Fc polypeptide as described herein may comprise M201L and N207S substitutions as numbered with reference to SEQ ID NO:1. Alternatively, a modified Fc polypeptide as described herein may comprise an N207S or N207A substitution as numbered with reference to SEQ ID NO: 1.

Fc Effector Functions

In some embodiments, a modified Fc polypeptide as described herein has an effector function, i.e., they have the ability to induce certain biological functions upon binding to an Fc receptor expressed on an effector cell that mediates the effector function. Effector cells include, but are not limited to, monocytes, macrophages, neutrophils, dendritic cells, eosinophils, mast cells, platelets, B cells, large granular lymphocytes, Langerhans' cells, natural killer (NK) cells, and cytotoxic T cells.

Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, a modified Fc polypeptide as described herein may include additional modifications that reduce effector function. Alternatively, in some embodiments, a modified Fc region comprising a modified CH2 or CH3 domain of the invention may include additional modifications that enhance effector function.

Illustrative Fc polypeptide mutations that modulate an effector function include, but are not limited to, substitutions in a CH2 domain, e.g., at positions corresponding to positions 7 and 8 of SEQ ID NO:1. In some embodiments, the substitution a modified CH2 domain comprise Ala at positions 7 and 8 of SEQ ID NO: 1. In some embodiments, the substitutions in a modified CH2 domain comprise Ala at positions 7 and 8 and Gly at position 102 of SEQ ID NO: 1.

Additional Fc polypeptide mutations that modulate an effector function include, but are not limited to, one or more substitutions at positions 238, 265, 269, 270, 297, 327 and 329 (EU numbering scheme, which correspond to positions 11, 38, 42, 43, 70, 100, and 102 as numbered with reference to SEQ ID NO:1). Illustrative substitutions (as numbered with EU numbering scheme), include the following: Position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, and P331S. Multiple substitutions may also be present, e.g., L234A and L235A of a human IgG1 Fc region; L234A, L235A, and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region. In some embodiments, a modified Fc polypeptide of the invention may have one or more amino acid substitutions that modulate ADCC, e.g., substitutions at positions 298, 333, and/or 334 of the Fc region, according to the EU numbering scheme.

In some embodiments, a modified Fc polypeptide as described herein may have one or more amino acid substitutions that increase or decrease ADCC or may have mutations that alter C1q binding and/or CDC.

Illustrative Fc Polypeptides Comprising Additional Mutations

A modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may comprise additional mutations including a knob mutation (e.g., T139W as numbered with reference to SEQ ID NO:1), hole mutations (e.g., T139S, L141A, and Y180V as numbered with reference to SEQ ID NO: 1), mutations that modulate effector function (e.g., L7A, L8A, and/or P102G (e.g., L7A and L8A) as numbered with reference to SEQ ID NO: 1), and/or mutations that increase serum stability (e.g., (i) M25Y, S27T, and T29E as numbered with reference to SEQ ID NO:1, or (ii) N207S with or without M201L as numbered with reference to SEQ ID NO:1 as numbered with reference to SEQ ID NO: 1).

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have a knob mutation (e.g., T139W as numbered with reference to SEQ ID NO: 1) and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have a knob mutation.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have a knob mutation and mutations that modulate effector function.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have a knob mutation and mutations that increase serum stability.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have a knob mutation, mutations that modulate effector function, and mutations that increase serum stability.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have hole mutations (e.g., T139S, L141A, and Y180V as numbered with reference to SEQ ID NO: 1) and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have hole mutations.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have hole mutations (e.g., T139S, L141A, and Y180V as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have hole mutations and mutations that modulate effector function.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have hole mutations (e.g., T139S, L141A, and Y180V as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have hole mutations and mutations that increase serum stability.

In some embodiments, a modified Fc polypeptide as described herein (e.g., any one of clones CH3C.35.20.1, CH3C.35.23.2, CH3C.35.23.3, CH3C.35.23.4, CH3C.35.21.17.2, and CH3C.35.23) may have hole mutations (e.g., T139S, L141A, and Y180V as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of any one of SEQ ID NOS:4-95 and 236-299. In some embodiments, a modified Fc polypeptide having the sequence of any one of SEQ ID NOS:4-95 and 236-299 may be modified to have hole mutations, mutations that modulate effector function, and mutations that increase serum stability.

Clone CH3C.35.20.1

In some embodiments, clone CH3C.35.20.1 may have a knob mutation (e.g., T139W as numbered with reference to SEQ ID NO:1) and at least 85% identity, at least 90% identity, or at least 95% identity to the sequence of SEQ ID NO:349. In some embodiments, clone CH3C.35.20.1 with the knob mutation has the sequence of SEQ ID NO:349.

In some embodiments, clone CH3C.35.20.1 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:350 or 351. In some embodiments, clone CH3C.35.20.1 with the knob mutation and the mutations that modulate effector function has the sequence of SEQ ID NO:350 or 351.

In some embodiments, clone CH3C.35.20.1 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:352. In some embodiments, clone CH3C.35.20.1 with the knob mutation and the mutations that increase serum stability has the sequence of SEQ ID NO:352.

In some embodiments, clone CH3C.35.20.1 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:353 or 354. In some embodiments, clone CH3C.35.20.1 with the knob mutation, the mutations that modulate effector function, and the mutations that increase serum stability has the sequence of SEQ ID NO:353 or 354.

In some embodiments, clone CH3C.35.20.1 may have hole mutations (e.g., T139S, L141A, and Y180V as numbered with reference to SEQ ID NO:1) and at least 85% identity, at least 90% identity, or at least 95% identity to the sequence of SEQ ID NO:355. In some embodiments, clone CH3C.35.20.1 with the hole mutations has the sequence of SEQ ID NO:355.

In some embodiments, clone CH3C.35.20.1 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:356 or 357. In some embodiments, clone CH3C.35.20.1 with the hole mutations and the mutations that modulate effector function has the sequence of SEQ ID NO:356 or 357.

In some embodiments, clone CH3C.35.20.1 may have hole mutations (e.g., T139S, L141A, and Y180V as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:358. In some embodiments, clone CH3C.35.20.1 with the hole mutations and the mutations that increase serum stability has the sequence of SEQ ID NO:358.

In some embodiments, clone CH3C.35.20.1 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:359 or 360. In some embodiments, clone CH3C.35.20.1 with the hole mutations, the mutations that modulate effector function, and the mutations that increase serum stability has the sequence of SEQ ID NO:359 or 360.

Clone CH3C.35.23.2

In some embodiments, clone CH3C.35.23.2 may have a knob mutation (e.g., T139W as numbered with reference to SEQ ID NO:1) and at least 85% identity, at least 90% identity, or at least 95% identity to the sequence of SEQ ID NO:361. In some embodiments, clone CH3C.35.23.2 with the knob mutation has the sequence of SEQ ID NO:361.

In some embodiments, clone CH3C.35.23.2 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:362 or 363. In some embodiments, clone CH3C.35.23.2 with the knob mutation and the mutations that modulate effector function has the sequence of SEQ ID NO:362 or 363.

In some embodiments, clone CH3C.35.23.2 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:364. In some embodiments, clone CH3C.35.23.2 with the knob mutation and the mutations that increase serum stability has the sequence of SEQ ID NO:364.

In some embodiments, clone CH3C.35.23.2 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:365 or 366. In some embodiments, clone CH3C.35.23.2 with the knob mutation, the mutations that modulate effector function, and the mutations that increase serum stability has the sequence of SEQ ID NO:365 or 366.

In some embodiments, clone CH3C.35.23.2 may have hole mutations (e.g., T139S, L141A, and Y180V as numbered with reference to SEQ ID NO:1) and at least 85% identity, at least 90% identity, or at least 95% identity to the sequence of SEQ ID NO:367. In some embodiments, clone CH3C.35.23.2 with the hole mutations has the sequence of SEQ ID NO:367.

In some embodiments, clone CH3C.35.23.2 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:368 or 369. In some embodiments, clone CH3C.35.23.2 with the hole mutations and the mutations that modulate effector function has the sequence of SEQ ID NO:368 or 369.

In some embodiments, clone CH3C.35.23.2 may have hole mutations (e.g., T139S, L141A, and Y180V as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:370. In some embodiments, clone CH3C.35.23.2 with the hole mutations and the mutations that increase serum stability has the sequence of SEQ ID NO:370.

In some embodiments, clone CH3C.35.23.2 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:371 or 372. In some embodiments, clone CH3C.35.23.2 with the hole mutations, the mutations that modulate effector function, and the mutations that increase serum stability has the sequence of SEQ ID NO:371 or 372.

Clone CH3C.35.23.3

In some embodiments, clone CH3C.35.23.3 may have a knob mutation (e.g., T139W as numbered with reference to SEQ ID NO:1) and at least 85% identity, at least 90% identity, or at least 95% identity to the sequence of SEQ ID NO:373. In some embodiments, clone CH3C.35.23.3 with the knob mutation has the sequence of SEQ ID NO:373.

In some embodiments, clone CH3C.35.23.3 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:374 or 375. In some embodiments, clone CH3C.35.23.3 with the knob mutation and the mutations that modulate effector function has the sequence of SEQ ID NO:374 or 375.

In some embodiments, clone CH3C.35.23.3 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:376. In some embodiments, clone CH3C.35.23.3 with the knob mutation and the mutations that increase serum stability has the sequence of SEQ ID NO:376.

In some embodiments, clone CH3C.35.23.3 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:377 or 378. In some embodiments, clone CH3C.35.23.3 with the knob mutation, the mutations that modulate effector function, and the mutations that increase serum stability has the sequence of SEQ ID NO:377 or 378.

In some embodiments, clone CH3C.35.23.3 may have hole mutations (e.g., T139S, L141A, and Y180V as numbered with reference to SEQ ID NO:1) and at least 85% identity, at least 90% identity, or at least 95% identity to the sequence of SEQ ID NO:379. In some embodiments, clone CH3C.35.23.3 with the hole mutations and the sequence of SEQ ID NO:379.

In some embodiments, clone CH3C.35.23.3 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:380 or 381. In some embodiments, clone CH3C.35.23.3 with the hole mutations and the mutations that modulate effector function has the sequence of SEQ ID NO:380 or 381.

In some embodiments, clone CH3C.35.23.3 may have hole mutations (e.g., T139S, L141A, and Y180V as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:382. In some embodiments, clone CH3C.35.23.3 with the hole mutations and the mutations that increase serum stability has the sequence of SEQ ID NO:382.

In some embodiments, clone CH3C.35.23.3 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:383 or 384. In some embodiments, clone CH3C.35.23.3 with the hole mutations, the mutations that modulate effector function, and the mutations that increase serum stability has the sequence of SEQ ID NO:383 or 384.

Clone CH3C.35.23.4

In some embodiments, clone CH3C.35.23.4 may have a knob mutation (e.g., T139W as numbered with reference to SEQ ID NO:1) and at least 85% identity, at least 90% identity, or at least 95% identity to the sequence of SEQ ID NO:385. In some embodiments, clone CH3C.35.23.4 with the knob mutation has the sequence of SEQ ID NO:385.

In some embodiments, clone CH3C.35.23.4 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:386 or 387. In some embodiments, clone CH3C.35.23.4 with the knob mutation and the mutations that modulate effector function has the sequence of SEQ ID NO:386 or 387.

In some embodiments, clone CH3C.35.23.4 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:388. In some embodiments, clone CH3C.35.23.4 with the knob mutation and the mutations that increase serum stability has the sequence of SEQ ID NO:388.

In some embodiments, clone CH3C.35.23.4 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:389 or 390. In some embodiments, clone CH3C.35.23.4 with the knob mutation, the mutations that modulate effector function, and the mutations that increase serum stability has the sequence of SEQ ID NO:389 or 390.

In some embodiments, clone CH3C.35.23.4 may have hole mutations (e.g., T139S, L141A, and Y180V as numbered with reference to SEQ ID NO:1) and at least 85% identity, at least 90% identity, or at least 95% identity to the sequence of SEQ ID NO:391. In some embodiments, clone CH3C.35.23.4 with the hole mutations has the sequence of SEQ ID NO:391.

In some embodiments, clone CH3C.35.23.4 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:392 or 393. In some embodiments, clone CH3C.35.23.4 with the hole mutations and the mutations that modulate effector function has the sequence of SEQ ID NO:392 or 393.

In some embodiments, clone CH3C.35.23.4 may have hole mutations (e.g., T139S, L141A, and Y180V as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:394. In some embodiments, clone CH3C.35.23.4 with the hole mutations and the mutations that increase serum stability has the sequence of SEQ ID NO:394.

In some embodiments, clone CH3C.35.23.4 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:395 or 396. In some embodiments, clone CH3C.35.23.4 with the hole mutations, the mutations that modulate effector function, and the mutations that increase serum stability has the sequence of SEQ ID NO:395 or 396.

Clone CH3C.35.21.17.2

In some embodiments, clone CH3C.35.21.17.2 may have a knob mutation (e.g., T139W as numbered with reference to SEQ ID NO: 1) and at least 85% identity, at least 90% identity, or at least 95% identity to the sequence of SEQ ID NO:397. In some embodiments, clone CH3C.35.21.17.2 with the knob mutation has the sequence of SEQ ID NO:397.

In some embodiments, clone CH3C.35.21.17.2 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), and at least 85% identity, at least 90% identity, or at least 95% identity to the sequence of SEQ ID NO:398 or 399. In some embodiments, clone CH3C.35.21.17.2 with the knob mutation and the mutations that modulate effector function has the sequence of SEQ ID NO:398 or 399.

In some embodiments, clone CH3C.35.21.17.2 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:400. In some embodiments, clone CH3C.35.21.17.2 with the knob mutation and the mutations that increase serum stability has the sequence of SEQ ID NO:400.

In some embodiments, clone CH3C.35.21.17.2 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO:1), and at least 85% identity, at least 90% identity, or at least 95% identity to the sequence of SEQ ID NO:401 or 402. In some embodiments, clone CH3C.35.21.17.2 with the knob mutation, the mutations that modulate effector function, and the mutations that increase serum stability has the sequence of SEQ ID NO:401 or 402.

In some embodiments, clone CH3C.35.21.17.2 may have hole mutations (e.g., T139S, L141A, and Y180V as numbered with reference to SEQ ID NO:1) and at least 85% identity, at least 90% identity, or at least 95% identity to the sequence of SEQ ID NO:403. In some embodiments, clone CH3C.35.21.17.2 with the hole mutations has the sequence of SEQ ID NO:403.

In some embodiments, clone CH3C.35.21.17.2 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:404 or 405. In some embodiments, clone CH3C.35.21.17.2 with the hole mutations and the mutations that modulate effector function has the sequence of SEQ ID NO:404 or 405.

In some embodiments, clone CH3C.35.21.17.2 may have hole mutations (e.g., T139S, L141A, and Y180V as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:406. In some embodiments, clone CH3C.35.21.17.2 with the hole mutations and the mutations that increase serum stability has the sequence of SEQ ID NO:406.

In some embodiments, clone CH3C.35.21.17.2 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO:1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:407 or 408. In some embodiments, clone CH3C.35.21.17.2 with the hole mutations, the mutations that modulate effector function, and the mutations that increase serum stability has the sequence of SEQ ID NO:407 or 408.

Clone CH3C.35.23

In some embodiments, clone CH3C.35.23 may have a knob mutation (e.g., T139W as numbered with reference to SEQ ID NO:1) and at least 85% identity, at least 90% identity, or at least 95% identity to the sequence of SEQ ID NO:409. In some embodiments, clone CH3C.35.23 with the knob mutation has the sequence of SEQ ID NO:409.

In some embodiments, clone CH3C.35.23 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO:1), and at least 85% identity, at least 90% identity, or at least 95% identity to the sequence of SEQ ID NO:410 or 411. In some embodiments, clone CH3C.35.23 with the knob mutation and the mutations that modulate effector function has the sequence of SEQ ID NO:410 or 411.

In some embodiments, clone CH3C.35.23 may have a knob mutation (e.g., T139W as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:412. In some embodiments, clone CH3C.35.23 with the knob mutation and the mutations that increase serum stability has the sequence of SEQ ID NO:412.

In some embodiments, clone CH3C.35.23 may have a knob mutation (e.g., T139W as numbered with reference to SEQ ID NO: 1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:413 or 414. In some embodiments, clone CH3C.35.23 with the knob mutation, the mutations that modulate effector function, and the mutations that increase serum stability has the sequence of SEQ ID NO:413 or 414.

In some embodiments, clone CH3C.35.23 may have hole mutations (e.g., T139S, L141A, and Y180V as numbered with reference to SEQ ID NO:1) and at least 85% identity, at least 90% identity, or at least 95% identity to the sequence of SEQ ID NO:415. In some embodiments, clone CH3C.35.23 with the hole mutations has the sequence of SEQ ID NO:415.

In some embodiments, clone CH3C.35.23 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO: 1), and at least 85% identity, at least 90% identity, or at least 95% identity to the sequence of SEQ ID NO:416 or 417. In some embodiments, clone CH3C.35.23 with the hole mutations and the mutations that modulate effector function has the sequence of SEQ ID NO:416 or 417.

In some embodiments, clone CH3C.35.23 may have hole mutations (e.g., T139S, L141A, and Y180V as numbered with reference to SEQ ID NO: 1), mutations that increase serum stability (e.g., M25Y, S27T, and T29E as numbered with reference to SEQ ID NO:1), and at least 85% identity, at least 90% identity, or at least 95% identity to the sequence of SEQ ID NO:418. In some embodiments, clone CH3C.35.23 with the hole mutations and the mutations that increase serum stability has the sequence of SEQ ID NO:418.

In some embodiments, clone CH3C.35.23 may have hole mutations (e.g., T139S, L141A, and Y180V as numbered with reference to SEQ ID NO:1), mutations that modulate effector function (e.g., L7A, L8A, and/or P102G (e.g., L7A and L8A) as numbered with reference to SEQ ID NO: 1), mutations that increase serum stability (e.g., M25Y, S27T, and T29E as numbered with reference to SEQ ID NO: 1), and at least 85% identity, at least 90% identity, or at least 95% identity to the sequence of SEQ ID NO:419 or 420. In some embodiments, clone CH3C.35.23 with the hole mutations, the mutations that modulate effector function, and the mutations that increase serum stability has the sequence of SEQ ID NO:419 or 420.

VI. Formats for BBB Receptor Binding Proteins

In some embodiments, a modified BBB receptor-binding polypeptide of the present invention comprising a modified Fc polypeptide and FcRn binding site as described herein is a subunit of a protein dimer. In some embodiments, the dimer is a heterodimer. In some embodiments, the dimer is a homodimer. In some embodiments, the dimer comprises a single Fc polypeptide that binds to the BBB receptor, i.e., is monovalent for BBB receptor binding. In some embodiments, the dimer comprises a second polypeptide that binds to the BBB receptor. The second polypeptide may comprise the same modified Fc polypeptide to provide a bivalent homodimer protein, or a second modified Fc polypeptide of the present invention may provide a second BBB receptor-binding site.

BBB receptor-binding polypeptides of the present invention and dimeric or multimeric proteins comprising polypeptides may have a broad range of binding affinities, e.g., based on the format of the polypeptide. For example, in some embodiments, a polypeptide comprising a modified Fc polypeptide as described herein has an affinity for the BBB receptor ranging anywhere from 1 pM to 10 μM. In some embodiments, affinity may be measured in a monovalent format. In other embodiments, affinity may be measured in a bivalent format, e.g., as a protein dimer comprising a modified Fc polypeptide.

Methods for analyzing binding affinity, binding kinetics, and cross-reactivity to analyze binding to a BBB receptor are known in the art. These methods include, but are not limited to, solid-phase binding assays (e.g., ELISA assay), immunoprecipitation, surface plasmon resonance (e.g., Biacore™ (GE Healthcare, Piscataway, N.J.)), kinetic exclusion assays (e.g., KinExA®), flow cytometry, fluorescence-activated cell sorting (FACS), BioLayer interferometry (e.g., Octet® (FortéBio, Inc., Menlo Park, Calif.)), and Western blot analysis. In some embodiments, ELISA is used to determine binding affinity and/or cross-reactivity. Methods for performing ELISA assays are known in the art and are also described in the Example section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity. FcRn binding of a BBB receptor-binding polypeptide may also be evaluated using these types of assays. FcRn binding is typically assayed under acidic conditions, e.g., at a pH of about 5 to about 6.

VII. BBB Receptor-Binding Protein Conjugates

In some embodiments, a modified polypeptide that binds a BBB receptor and initiates transport across the BBB comprises a modified Fc polypeptide as described herein and further comprises a partial or full hinge region. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:234). In further embodiments, the polypeptide, which may comprise a hinge or partial hinge region, is further joined to another moiety, for example, an immunoglobulin variable region, thus generating a BBB receptor-binding polypeptide-variable region fusion polypeptide. The variable region may bind to any antigen of interest, e.g., a therapeutic neurological target, or a diagnostic neurological target.

In some embodiments, the BBB receptor-binding polypeptide (e.g., modified Fc polypeptide) is joined to a variable region via a linker. As indicated in the preceding paragraph, the BBB receptor-binding polypeptide (e.g., modified Fc polypeptide) may be joined to the variable region by a hinge region. In some embodiments, the BBB receptor-binding polypeptide (e.g., modified Fc polypeptide) may be joined to the variable region by a peptide linker. The peptide linker may be configured such that it allows for the rotation of the variable region and the BBB receptor-binding polypeptide relative to each other; and/or is resistant to digestion by proteases. In some embodiments, the linker may be a flexible linker, e.g., containing amino acids such as Gly, Asn, Ser, Thr, Ala, and the like. Such linkers are designed using known parameters. For example, the linker may have repeats, such as Gly-Ser repeats.

The variable region may be in any antibody format, e.g., a Fab or scFv format. In some embodiments, an antibody variable region sequence comprises two antibody variable region heavy chains and two antibody variable region light chains, or respective fragments thereof.

In some embodiments, the variable region joined to a BBB receptor-binding polypeptide (e.g., modified Fc polypeptide) may bind to a Tau protein (e.g., a human Tau protein) or a fragment thereof. In some embodiments, the variable region may bind to a phosphorylated Tau protein, an unphosphorylated Tau protein, a splice isoform of Tau protein, an N-terminal truncated Tau protein, a C-terminal truncated Tau protein, and/or a fragment thereof.

In some embodiments, the variable region joined to a BBB receptor-binding polypeptide (e.g., modified Fc polypeptide) may bind to a beta-secretase 1 (BACE1) protein (e.g., a human BACE1 protein) or a fragment thereof. In some embodiments, the variable region may bind to one or more splice isoforms of BACE1 protein or a fragment thereof.

In some embodiments, the variable region joined to a BBB receptor-binding polypeptide (e.g., modified Fc polypeptide) may bind to a triggering receptor expressed on myeloid cells 2 (TREM2) protein (e.g., a human TREM2 protein) or a fragment thereof.

In some embodiments, the variable region joined to a BBB receptor-binding polypeptide (e.g., modified Fc polypeptide) may bind to an alpha-synuclein protein (e.g., a human alpha-synuclein protein) or a fragment thereof. In some embodiments, the variable domain may bind to a monomeric alpha-synuclein, oligomeric alpha-synuclein, alpha-synuclein fibrils, soluble alpha-synuclein, and/or a fragment thereof.

A BBB receptor-binding polypeptide (e.g., modified Fc polypeptide) may also be joined to a polypeptide other than an immunoglobulin variable region that targets an antigen of interest. In some embodiments, such a polypeptide is joined to the BBB receptor-binding polypeptide using a peptide linker, e.g., a flexible linker, as described above.

In some embodiments, a BBB receptor-binding polypeptide may be joined to a polypeptide, e.g., a therapeutic polypeptide, that is desirable to target to a cell expressing the BBB receptor-binding polypeptide. In some embodiments, the BBB receptor polypeptide is joined to a biologically active polypeptide for transport across the BBB, e.g., a soluble protein, e.g., an extracellular domain of a receptor or a growth factor, a cytokine, or an enzyme.

In still other embodiments, the BBB receptor-binding polypeptide may be joined to a peptide or protein useful in protein purification, e.g., polyhistidine, epitope tags, e.g., FLAG, c-Myc, hemagglutinin tags and the like, glutathione S transferase (GST), thioredoxin, protein A, protein G, or maltose binding protein (MBP). In some cases, the peptide or protein to which the BBB binding polypeptide is fused may comprise a protease cleavage site, such as a cleavage site for Factor Xa or Thrombin. In certain embodiments, the linkage is cleavable by an enzyme present in the central nervous system.

Non-polypeptide agents may also be joined to a BBB receptor-binding polypeptide. Such agents include cytotoxic agents, imaging agents, a DNA or RNA molecule, or a chemical compound. In some embodiments, the agent may be a therapeutic or imaging chemical compound. In some embodiments, the agent is a small molecule, e.g., less than 1000 Da, less than 750 Da, or less than 500 Da.

An agent, either a polypeptide or non-polypeptide, may be joined to the N-terminal or C-terminal region of the BBB receptor-binding polypeptide, or attached to any region of the polypeptide, so long as the agent does not interfere with binding of the BBB-receptor binding polypeptide to the BBB receptor and the FcRn receptor.

In various embodiments, the conjugates can be generated using well-known chemical cross-linking reagents and protocols. For example, there are a large number of chemical cross-linking agents that are known to those skilled in the art and useful for cross-linking the polypeptide with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homoprotein polymers. A wide variety of heterobifunctional cross-linkers are known in the art, including N-hydroxysuccinimide (NHS) or its water soluble analog N-hydroxysulfosuccinimide (sulfo-NHS), succinimidyl 4-(N-maleimidomethyl)cyclohexane-1-carboxylate (SMCC), m-maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio) propionate (SPDP), and succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Disuccinimidyl subcrate (DSS), bismaleimidohexane (BMH) and dimethylpimelimidate.2HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers.

The agent of interest may be a therapeutic agent, including cytotoxic agents and the like, or a chemical moiety. In some embodiments, the agent may be a peptide or small molecule therapeutic or imaging agent.

VIII. Methods of Engineering Fc Polypeptides to Bind a BBB Receptor

Overview of Engineering Methods

In a further aspect, methods of engineering an Fc polypeptide to have a BBB receptor binding specificity are provided. In some embodiments, modification of an Fc polypeptide comprises substituting various amino acids in the sets of solvent-exposed amino acid residues, e.g., set (i) and/or set (ii) as described herein.

In some embodiments, the method comprises modifying a polynucleotide that encodes the Fc polypeptide to incorporate amino acid changes at one, two, three, four, five, six, seven, eight, nine, or ten, or all of the positions of a set solvent-exposed surface amino acids. In some embodiments, the method comprises modifying a polynucleotide that encodes the Fc polypeptide to incorporate amino acid changes at the desired number of positions in two or more sets of amino acids. The amino acids introduced into the desired positions may be generated by randomization or partial randomization to generate a library of Fc polypeptides with amino acid substitutions at the various positions of a set. In some embodiments, the Fc polypeptide may contain part of, or all of, a full hinge region.

Polypeptides comprising the mutated Fc polypeptides may be expressed using any number of systems. For example, in some embodiments, mutant polypeptides are expressed in a display system, e.g., a viral display system, a cell surface display system such as a yeast display system, an mRNA display system, or a polysomal display system. In other illustrative embodiments, mutant polypeptides are expressed as soluble polypeptides that are secreted from the host cell. The library is screened using known methodology to identify a polypeptide that binds the BBB receptor of interest, which may be further characterized to determine binding kinetics. Additional mutations may then be introduced into selected clones, either at positions in the initial set of amino acids or at other positions outside of the set, e.g., at solvent-exposed amino acids near the paratope.

Illustrative Embodiments of Engineering Methods

DNA template sequences can be prepared that have a wild type Fc polypeptide, or a fragment thereof, e.g., a CH2 or CH3 domain. In some embodiments, the template sequence that is mutated further encodes an antibody variable region. In some embodiments, the template sequence encodes an Fc polypeptide that is mutated at desired positions and expressed in the absence of an antibody variable region.

The expression system may be any system that can be used for screening mutated polypeptides for binding to a BBB receptor of interest. In some embodiments, the template sequence is prepared in a phagemid vector. In certain embodiments, the template sequence is genetically fused to the pIII coat protein of a phage.

In some embodiments, mutated Fc polypeptides are prepared in a yeast display vector. For example, the template sequence may be fused to the yeast cell wall protein Aga2p, e.g., at either the N- or C-terminus of Aga2p. The yeast strain may provide for inducible expression of the Aga2p coat protein, for example, the yeast strain may be EBY100.

In some embodiments, mutations are introduced into the desired amino acid positions using random mutagenesis techniques such as error-prone PCR.

Following mutagenesis, mutated nucleic acids are introduced into the display system of interest and expressed for screening for binding to the BBB receptor of interest. Any number of screening techniques can be used. In typical embodiments, expressed proteins are screened using ELISA.

Selected Fc polypeptides that bind the BBB receptor of interest may be subjected to additional rounds of mutation in which further mutations are introduced into a desired set of amino acids or at positions outside of the positions designated for a given set. In some embodiments, "NNK" randomization is used to introduce the further mutations. NNK randomization uses primers that comprise degenerate NNK tricodons, where N refers to "A, C, G, or T" and K refers to "G or T." For example, in NNK randomization, trinucleotides are mixed in a specified ratio in order to achieve a predetermined mix of particular amino acids (for example, 70% wild-type); or mixed so that there is not bias for or against certain amino acids. Libraries are generated by performing PCR amplification of fragments of the Fc region corresponding to regions or randomization and then assembled using end primers for ligation in to a vector, e.g., a phagemid vector. Alternatively, further mutations can be introduced using Kunkel mutagenesis other mutagenesis technique to introduce diversity at desired positions.

Binding properties of mutated Fc polypeptide can be evaluated using numerous assays, for example, binding affinity and/or cross-reactivity can be determined by ELISA, surface plasmon resonance, kinetic exclusion assays, or interferometry assays.

Upon identification of modified BBB receptor-binding polypeptides that have desired binding properties, polypeptides are additionally screened for transport across the BBB and/or alternative pharmacokinetic parameters. Method of screening for transport comprise evaluating uptake of the BBB receptor polypeptide into the brain using an animal model. Uptake can be assessed by numerous assays, e.g., that measure protein levels or an activity of a biologically active protein or other agent linked to the BBB receptor-binding protein. Protein levels can be conveniently determined by immunoassay using an antibody that specifically binds to the BBB receptor-binding polypeptide or an antibody as a secondary reagent that binds to a reagent that is specific for the BBB receptor-binding polypeptide. In some embodiments, transport across the blood brain barrier is assessed by measuring the amount of an agent that is joined to the BBB receptor-binding polypeptide that is taken up by the brain. As detailed above, the agent may be a polypeptide such as an immunoglobulin variable region that binds an antigen, an enzyme, or other polypeptide agent. Additional parameters such as serum half-life of a BBB receptor-binding polypeptide may also be evaluated in the animal model.

In some embodiments, transport of a BBB receptor-binding polypeptide may be assessed by determining the biological activity in the brain of an agent joined to the BBB receptor-binding polypeptide. For example, the activity of an enzyme that is joined to the BBB receptor-binding polypeptide may be assessed by direct assay for enzymatic activity in the brain, or a region of the brain. Alternatively, the activity of an enzyme may be evaluated by measuring the level of a substrate for that enzyme in the brain that remains after transport via the BBB receptor-binding polypeptide. In some embodiments, the activity of an antibody therapeutic joined to a BBB receptor-binding polypeptide may be evaluated by determining the level or activity of a target antigen to which the therapeutic antibody binds. BBB receptor binding mediated by a modified Fc polypeptide of the present invention typically increases uptake of a biologically active agent joined to the BBB receptor-binding polypeptide by at least 5-fold, and often at least 10-fold, or at least 20-fold, or greater, compared to uptake of the agent in the absence of the modified Fc polypeptide.

IX. TfR Constructs

The disclosure also features an isolated, recombinant transferrin receptor (TfR) construct, comprising monomeric TfR apical domain, wherein the construct does not include a protease-like domain or helical domain of the TfR. In one embodiment, the construct displays a conserved epitope or antigen and/or retains the approximate three-dimensional structure of the apical domain of the native human TfR, or has a RMSD of less than about 2. In one embodiment, the three-dimensional structure is measured by X-ray crystallography. In one embodiment, the construct comprises a human TfR apical domain.

Moreover, the disclosure also features TfR constructs that comprise one or more portions of the TfR apical domain which have been circularly permuted relative to the full-length TfR sequence. A TfR construct may comprise two distinct portions of the TfR apical domain fused to each other in a tandem series with an optional linker. A TfR construct may comprise: (a) a first polypeptide comprising a sequence of a first portion of a TfR apical domain; (b) an optional linker; and (c) a second polypeptide comprising a sequence of a second portion of the TfR apical domain, wherein the sequence of the first portion of the TfR apical domain is C-terminal to the sequence of the second portion of the TfR apical domain relative to the full-length TfR sequence, and wherein the first polypeptide, the optional linker, and the second polypeptide are fused in a tandem series (i.e., the C-terminus of the first polypeptide is fused to the N-terminus of the optional linker, and the C-terminus of the optional linker is fused to the N-terminus of the second polypeptide). In certain embodiments, the TfR construct does not include a linker. Accordingly, the first polypeptide in the TfR construct may be fused directly to the second polypeptide. A TfR construct as described herein may bind to an arenavirus (e.g., a Machupo virus).

A TfR construct may comprise a first polypeptide comprising a sequence having at least 90% sequence identity (e.g., at least 91%, 92%, 93%, 94%, 95%, 96%, 97%, 98%, 99%, or 100% sequence identity) to the sequence of TISRAAAEKLFGNMEGDCPSDWKTDSTCRMVTSE (SEQ ID NO:427); an optional linker; and a second polypeptide comprising a sequence having at least 90% sequence identity (e.g., at least 91%, 92%, 93%, 94%, 95%, 96%, 97%, 98%, 99%, or 100% sequence identity) to the sequence of DKNGRLVYLVENPGGYVAYSKAATVTGKLVHANF GTKKDFEDLYTPVNGSIVIVRAGK ITFAEKVAN-AESLNAIGVLIYMDQT (SEQ ID NO:428), in which the first polypeptide, the optional linker, and the second polypeptide are fused in a tandem series.

In some embodiments, the first polypeptide at the C-terminus further comprises a sequence having at least 90% sequence identity (e.g., at least 91%, 92%, 93%, 94%, 95%, 96%, 97%, 98%, 99%, or 100% sequence identity) to the sequence SKNVKLTVSNVLKEIKILNIFGVIK (SEQ ID NO:429), or a fragment thereof. As non-limiting examples, the fragment at the C-terminus of the first polypeptide has the sequence SKNVK (SEQ ID NO:430), SKNVKLTVSN (SEQ ID NO:431), SKNVKLTVSNVLKEI (SEQ ID NO:432), or SKNVKLTVSNVLKEIKILNI (SEQ ID NO:433). In some embodiments, the first polypeptide at the N-terminus further comprises a sequence having at least 90% sequence identity (e.g., at least 91%, 92%, 93%, 94%, 95%, 96%, 97%, 98%, 99%, or 100% sequence identity) to the sequence GFPSFNHTQFPPSRSSGLPNIPVQ (SEQ ID NO:439), or a fragment thereof. As non-limiting examples, the fragment at the N-terminus of the first polypeptide has the sequence NIPVQ (SEQ ID NO:440), SSGLPNIPVQ (SEQ ID NO:441), FPPSRSSGLPNIPVQ (SEQ ID NO:442), or FNHTQFPPSRSSGLPNIPVQ (SEQ ID NO:443).

In some embodiments, the second polypeptide at the C-terminus further comprises a sequence having at least 90% sequence identity (e.g., at least 91%, 92%, 93%, 94%, 95%, 96%, 97%, 98%, 99%, or 100% sequence identity) to the sequence KFPIVNAELSFFGHAHLGTGDPYTP (SEQ ID NO:434), or a fragment thereof. As non-limiting examples, the fragment at the C-terminus of the second polypeptide has the sequence KFPIV (SEQ ID NO:435), KFPIVNAELS (SEQ ID NO:436), KFPIVNAELSFFGHA (SEQ ID NO:437), or KFPIVNAELSFFGHAHLGTG (SEQ ID NO:438). In some embodiments, the second polypeptide at the N-terminus further comprises a sequence having at least 90% sequence identity (e.g., at least 91%, 92%, 93%, 94%, 95%, 96%, 97%, 98%, 99%, or 100% sequence identity) to the sequence SKVWRDQHFVKIQVKD-SAQNSVIIV (SEQ ID NO:444), or a fragment thereof. As non-limiting examples, the fragment at the N-terminus of the second polypeptide has the sequence SVIIV (SEQ ID NO:445), DSAQNSVIIV (SEQ ID NO:446), KIQVKD-SAQNSVIIV (SEQ ID NO:447), or DQHFVKIQVKD-SAQNSVIIV (SEQ ID NO:448).

In some embodiments, the first polypeptide of the TfR construct comprises a sequence having at least 90% sequence identity (e.g., at least 91%, 92%, 93%, 94%, 95%, 96%, 97%, 98%, 99%, or 100% sequence identity) to the sequence SSGLPNIPVQTISRAAAEKLFGNMEGDCPSD-WKTDSTCRMVTSESKNVKLTVSN (SEQ ID NO:449). In some embodiments, the second polypeptide comprises a sequence having at least 90% sequence identity (e.g., at least 91%, 92%, 93%, 94%, 95%, 96%, 97%, 98%, 99%, or 100% sequence identity) to the sequence DSAQNSVIIVDKNGR-LVYLVENPGGYVAYSKAATVTGKLVHANFGTKKD-FEDLYTPVN GSIVIVRAGKITFAEKVANAESLNAIGV-LIYMDQTKFPIVNAELS (SEQ ID NO:450). In certain embodiments, the TfR construct comprises the first polypeptide having the sequence of SEQ ID NO:449 and the second polypeptide having the sequence of SEQ ID NO:450, wherein the C-terminus of the first polypeptide is fused to the N-terminus of the second polypeptide. In certain embodiments, the TfR construct comprises the first polypeptide having the sequence of SSGLPNIPVQTIS-RAAAEKLFGNMEGDCPSDWKTDSTCKMVTSENKS-VKLTVSN (SEQ ID NO:451) and the second polypeptide having the sequence of DSAQNSVIIVDKNGGLVYLVEN-PGGYVAYSKAATVTGKLVHANFGTKKDFEDLDSPVN GSIVIVRAGKITFAEKVANAESLNAIGVLIYMDQTKF-PIVKADLS (SEQ ID NO:452), wherein the C-terminus of the first polypeptide is fused to the N-terminus of the second polypeptide.

In certain embodiments, the TfR constructs described herein have improved three-dimensional structures, such as natural folding, and properties, such as presenting a conserved epitope or antigen as in the natural state. For example, in three-dimensional space, the TfR constructs fold in such a way to better mimic the transferrin receptor apical domain in its natural, folded state, when part of the complete transferrin receptor complex.

In another example, the structural features of the TfR constructs described herein allow them to be displayed, with the natural, three-dimensional folding, on a variety of cells, including phage, yeast, and other cell types, including eukaryotic cells. Displaying the TfR constructs described herein with proper, natural folding leads to improved screening results when using the TfR constructs to identify high-affinity proteins, antibodies, or other binding molecules that bind to the apical domain of transferrin receptors in vivo, under natural conditions found, for example, during the administration of therapeutic molecules to treat various diseases or disorders, as such methods are described herein. For example, when the entire protein transferrin receptor is expressed and displayed on a cell surface, it displays as a dimer, which gives an avidity effect, thus resulting in the identification of binding proteins having lower affinity for the TfR apical domain. The structural features of the TfR constructs described herein, allow the apical domain to be expressed and displayed as a monomer on the cell surface, allowing for the study and identification of monomeric interactions between binding molecules and the apical domain, and allowing for the identification of higher affinity molecules.

Manufacturing Methods

Another aspect of the disclosure relates to an isolated, recombinant transferrin receptor (TfR) construct, comprising a monomeric TfR apical domain, wherein the construct does not include a protease-like domain or helical domain of the TfR. In one embodiment, the construct displays a conserved epitope or antigen and/or retains the approximate three-dimensional structure of the apical domain of the native human TfR (e.g., SEQ ID NO: 107), or has a RMSD of less than about 2. In another embodiment, the three-dimensional structure is measured by X-ray crystallography. One method used to determine the three-dimensional structure includes X-ray crystallography. Crystals may be prepared using flash-cooling by direct immersion in liquid nitrogen using the crystallization mother liquor supplemented with a polar solvent, for example 20% (v/v) ethylene glycol. X-ray intensity data may be collected at an advanced photon source (APS) (SER-CAT beam line of the Advanced Photon Source, Argonne National Laboratory) using a high-speed detector (Rayonix 300). Data collected may be indexed, integrated, and scaled using the program HKL-2000 (HKL Research, Inc.). The crystal structure of the complex may be determined by molecular replacement with PHASER using the TfR apical domain monomer as the initial search model. The model can then be refined by rigid-body refinement followed by restrained refinement using REFMAC. All crystallographic calculations may be performed with the CCP4 suite of programs (Winn et al., *Acta. Cryst. D*67:235-242 (2011)). Model building of the complex into the electron density may be done using the graphics program COOT (Emsley et al., *Acta. Cryst. D*66: 486-501 (2010)).

In another embodiment, the level of conservation of the epitopes, antigens, or approximate three-dimensional structures between the TfR apical domain constructs described herein and the corresponding native, full-length TfR is determined. In one example, human TfR apical domain constructs described herein are compared to the native, full-length human TfR. The determination method may be done by aligning a crystal structure of a TfR apical domain construct described herein (e.g., any of SEQ ID NOS: 109, 110, 301, 468, and 469 (e.g., 109, 110, and 301)) and an apical domain within a native, full length TfR (e.g., human TfR, such as PDB code: 3KAS). Root mean square deviation (RMSD) between the two structures may be then determined as is well-known to one of skill in the art, for example, using MOE v2016.0802 (Chemical Computing Group).

In an embodiment, the RMSD between a TfR apical domain construct described herein and the apical domain of native, full-length TfR is about less than 4, about less than 3, or about less than 2, or is between the range of about 1 to about 2.

In an embodiment, the RMSD between a TfR apical domain construct described herein and the apical domain of native, full-length TfR is between the range of about 1 and about 1.5.

In one embodiment, the RMSD between any one of TfR apical domain constructs having a sequence of any one of SEQ ID NOS:109, 110, 301, 468, and 469 (e.g., 109, 110, and 301), and the apical domain of native, full-length TfR is between the range of about 1 and about 1.5. In one example, the RMSD is about 1.2.

Another aspect relates to a method of producing, purifying, and isolating recombinant TfR apical domain constructs. The method includes expressing a TfR apical domain gene comprising a first polynucleotide, an optional linker polynucleotide, and a second polynucleotide fused in a tandem series, wherein the first polynucleotide encodes a C-terminal fragment of the domain, the optional linker polynucleotide encodes an optional protein linker, and the second polynucleotide encodes an N-terminal fragment of the domain. In one embodiment, the polynucleotides are fused in the tandem series such that, when expressed, the first amino acid of the N-terminal fragment of the domain is linked in primary sequence to the last amino acid of the C-terminal fragment. In another embodiment, the TfR apical domain gene includes an optional linker, such that that, when expressed, the first amino acid of the N-terminal fragment of the domain is linked in primary sequence to the last amino acid of the linker, and the first amino acid of the linker is linked in primary sequence to the last amino acid of the C-terminal fragment. In another embodiment, the gene comprises the first polynucleotide, the optional linker polynucleotide, and the second polynucleotide in the tandem series such that, when expressed, the expressed protein is in a cyclic structure form. The method further includes purifying the expressed protein to obtain the isolated recombinant TfR apical domain construct.

In one example, the first amino acid of the N-terminal fragment of the second polypeptide in a TfR construct and last amino acid of the C-terminal fragment of the first polypeptide in the TfR construct are selected within or near the apical domain of TfR such that when the protein is expressed, it exhibits a conserved, approximate three-dimensional structure and folding of the domain as found in the full-length TfR protein and its dimerized form. In one example, the amino acids are selected based on their near proximity to each other in three-dimensional space, which can be obtained from a known crystal structure of the full-length transferrin receptor (for example PDB code 1SUV (resolution of 7.5 Å); Cheng, Y., et al, *Cell* 116:565-576 (2004) or, for higher resolution of 2.4 Å, PDB code 3KAS; Abraham, J., et al., *Nat. Struct. Mol. Biol.* 17: 438-444 (2010), both of which are incorporated herein by reference in their entirety for all purposes), or from a computer model of the receptor, or as known to one of ordinary skill in the art.

In another embodiment, the amino acids are selected from anti-parallel β-strands between the apical domain and the remainder of the receptor protein. In another example, the amino acids are selected from two polypeptide regions connecting the β-strands, or loops. In another example, the amino acids are selected from two polypeptide regions connecting the β-strands, in which the polypeptide regions include a C-terminal region comprising the sequence VSN, and an N-terminal region comprising the sequence KDSAQNS (SEQ ID NO:471). In one example, the amino acid selected for the N-terminal region of the second polypeptide in a TfR construct is D (from the sequence DSAQN (SEQ ID NO:472)), and this amino acid is linked to the last amino acid in the C-terminal region of the first polypeptide in the TfR construct, N (from the sequence LTVSN (SEQ ID NO:473)). In another embodiment, the amino acids are selected as described further in Example 2, to give the apical domain proteins of SEQ ID NOS:109 and 110 for human and cynomolgus monkey, respectively.

Therefore, in another embodiment, the method of producing, purifying, and isolating recombinant TfR apical domain construct, further comprises (i) identifying an N-terminal fragment and a C-terminal fragment, and their respective amino acids, within or near the apical domain of TfR for permuting, and (ii) designing a gene expression vector comprising polynucleotides encoding the N- and C-terminal fragments and amino acids, wherein the polynucleotides are fused such that when expressed, the first amino acid of the N-terminal fragment of the domain is fused in primary sequence to the last amino acid of the C-terminal fragment, and (iii) expressing the apical domain construct.

In other embodiments, the TfR constructs described herein allow for the precise study of interactions between a binding molecule and the TfR apical domain, using for example, X-ray crystallography and Nuclear Magnetic Resonance Spectroscopy (made possible with the constructs described herein due to the TfR apical domain constructs having relatively low enough molecular weight for these studies, while the full-length TfR complex has relatively high molecular weight).

Linker

A linker between two polypeptides in a TfR construct may contain 1 to 10 amino acids (e.g., 1 to 8, 1 to 6, 1 to 4, or 1 or 2 amino acids; e.g., 1, 2, 3, 4, 5, 6, 7, 8, 9, or 10 amino acids). Suitable linkers include, for example, linkers containing flexible amino acid residues such as glycine and serine. Examples of linkers include, but are not limited to, G, GG, GGG, GGGG (SEQ ID NO:453), GS, GGS, GSGS (SEQ ID NO:454), SGGG (SEQ ID NO:455), GSGG (SEQ ID NO:456), GGSG (SEQ ID NO:457), and GGGS (SEQ ID NO:458).

In other embodiments, a linker between two polypeptides in a TfR construct may be a protein loop domain, in which the N- and C-termini of the protein loop domain are less than 5 Å apart (e.g., less than 4 Å, 3 Å, 2 Å, or 1 Å apart). In some embodiments, the protein loop domain may be a globular protein. In some embodiments, the protein loop domain may have 800 or less amino acids (e.g., 800, 780, 760, 740, 720, 700, 680, 660, 640, 620, 600, 580, 560, 540, 520, 500, 480, 460, 440, 420, 400, 380, 360, 340, 320, 300, 280, 260, 240, 220, 200, 180, 160, 140, 120, or 100 amino acids). In some embodiments, the protein loop domain may be a globular protein having 800 or less amino acids (e.g., 800, 780, 760, 740, 720, 700, 680, 660, 640, 620, 600, 580, 560, 540, 520, 500, 480, 460, 440, 420, 400, 380, 360, 340, 320, 300, 280, 260, 240, 220, 200, 180, 160, 140, 120, or 100 amino acids). A protein loop domain may have a secondary or tertiary structure that has the N- and C-termini of the structure less than 5 Å (e.g., less than 4 Å, 3 Å, 2 Å, or 1 Å apart). In some embodiments, when a protein loop domain is inserted between the first polypeptide and the second polypeptide of a TfR construct, in which the C-terminus of the first polypeptide is fused to the N-terminus of the protein loop domain and the N-terminus of the second polypeptide is fused to the C-terminus of the protein loop domain, the proximity of the N- and C-termini of the protein loop domain brings the first polypeptide and the second polypeptide close to each other such that the amino acids in the first polypeptide may interact with the amino acids in the second polypeptide via, e.g., hydrogen bonding, and the TfR construct may form a secondary structure, e.g., a β-sheet.

Signal Peptide

The TfR construct may further include a signal peptide, for example, one that causes secretion of the construct when expressed in a cell (e.g., a eukaryotic cell such as a mammalian cell). Any signal peptide known in the art may be used in conjunction with the TfR constructs described herein, for example, MGWSCIILFLVATATGAYAG (SEQ ID NO:474). Signal peptides can be attached to the N- or C-terminus of the construct, as appropriate.

Purification Peptide

A TfR construct may also include one or more purification peptides to facilitate purification and isolation of the TfR construct from, e.g., a whole cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be fused to a TfR construct include, but are not limited to, a histidine peptide, an Avi tag, a FLAG peptide, a myc peptide, and a hemagglutinin (HA) peptide. A histidine peptide (HHHHHH (SEQ ID NO:459) or HHHHHHHHHH (SEQ ID NO:460)) binds to nickel-functionalized agarose affinity column with micromolar affinity. An Avi tag (GLNDIFEAQKIEWHE (SEQ ID NO:461)) may be biotinylated by the enzyme BirA.

Biotinylated Avi tag can then bind to streptavidin for purification. In some embodiments, a FLAG peptide includes the sequence DYKDDDDK (SEQ ID NO:462). In some embodiments, a myc peptide includes the sequence EQKLISEEDL (SEQ ID NO:463). In some embodiments, an HA peptide includes the sequence YPYDVPDYA (SEQ ID NO:464).

Cleavage Peptide

A cleavage peptide refers to an amino acid sequence that can be recognized and cleaved by certain proteases. For example, a cleavage peptide may be placed between the purification peptide and the rest of the TfR construct such that once the TfR construct is expressed and purified, the cleavage peptide can be cleaved to remove the purification peptide. Once the protease is in proximity to the cleavage peptide, it recognizes and cleaves, i.e., through hydrolysis of the peptide backbone, the cleavage peptide. Examples of protease and cleavage peptide pairs include, but are not limited to, the Ubiquitin-like-specific protease 1 (Ulpl) and its cleavage sequence Smt3 (MSDSEVNQEAKPEVKPEVKPETHINLKVSDGSSEIFFKIKKTTPLRRLMEAFAKRQGKE MDSLRFLYDGIRIQADQTPEDLDMEDNDIIEAHREQIGGS (SEQ ID NO:465), the tobacco etch virus nuclear inclusion A (TEV) protease and its cleavage sequence ENLYFQS (SEQ ID NO:466), and the nonstructural protein 3 protease domain of the hepatitis C virus (NS3 HCV) and its cleavage sequence DEMEECSQ (SEQ ID NO:467).

X. Nucleic Acids, Vectors, and Host Cells

Modified BBB receptor-binding polypeptides and TfR constructs as described herein are typically prepared using recombinant methods. Accordingly, in some aspects, the invention provides isolated nucleic acids comprising a nucleic acid sequence encoding any of the polypeptides comprising modified Fc polypeptides or any of the TfR constructs as described herein, and host cells into which the nucleic acids are introduced that are used to replicate the polypeptide-encoding nucleic acids and/or to express the polypeptides or the TfR constructs. In some embodiments, the host cell is eukaryotic, e.g., a human cell.

In another aspect, polynucleotides are provided that comprise a nucleotide sequence that encodes the polypeptides or the TfR constructs described herein. The polynucleotides may be single-stranded or double-stranded. In some embodiments, the polynucleotide is DNA. In particular embodiments, the polynucleotide is cDNA. In some embodiments, the polynucleotide is RNA.

In some embodiments, the polynucleotide is included within a nucleic acid construct. In some embodiments, the construct is a replicable vector. In some embodiments, the vector is selected from a plasmid, a viral vector, a phagemid, a yeast chromosomal vector, and a non-episomal mammalian vector.

In some embodiments, the polynucleotide is operably linked to one or more regulatory nucleotide sequences in an expression construct. In one series of embodiments, the nucleic acid expression constructs are adapted for use as a surface expression library. In some embodiments, the library is adapted for surface expression in yeast. In some embodiments, the library is adapted for surface expression in phage. In another series of embodiments, the nucleic acid expression constructs are adapted for expression of the polypeptide or the TfR construct in a system that permits isolation of the polypeptide or the TfR construct in milligram or gram quantities. In some embodiments, the system is a mammalian cell expression system. In some embodiments, the system is a yeast cell expression system.

Expression vehicles for production of a recombinant polypeptide include plasmids and other vectors. For instance, suitable vectors include plasmids of the following types: pBR322-derived plasmids, pEMBL-derived plasmids, pEX-derived plasmids, pBTac-derived plasmids, and pUC-derived plasmids for expression in prokaryotic cells, such as *E. coli*. The pcDNAI/amp, pcDNAI/neo, pRc/CMV, pSV2gpt, pSV2neo, pSV2-dhfr, pTk2, pRSVneo, pMSG, pSVT7, pko-neo, and pHyg-derived vectors are examples of mammalian expression vectors suitable for transfection of eukaryotic cells. Alternatively, derivatives of viruses such as the bovine papilloma virus (BPV-1), or Epstein-Barr virus (pHEBo, pREP-derived, and p205) can be used for transient expression of polypeptides in eukaryotic cells. In some embodiments, it may be desirable to express the recombinant polypeptide by the use of a baculovirus expression system. Examples of such baculovirus expression systems include pVL-derived vectors (such as pVL1392, pVL1393, and pVL941), pAcUW-derived vectors (such as pAcUW1), and pBlueBac-derived vectors. Additional expression systems include adenoviral, adeno-associated virus, and other viral expression systems.

Vectors may be transformed into any suitable host cell. In some embodiments, the host cells, e.g., bacteria or yeast cells, may be adapted for use as a surface expression library. In some cells, the vectors are expressed in host cells to express relatively large quantities of the polypeptide or the TfR construct. Such host cells include mammalian cells, yeast cells, insect cells, and prokaryotic cells. In some embodiments, the cells are mammalian cells, such as Chinese Hamster Ovary (CHO) cell, baby hamster kidney (BHK) cell, NS0 cell, Y0 cell, HEK293 cell, COS cell, Vero cell, or HeLa cell.

A host cell transfected with an expression vector encoding a transferrin receptor-binding polypeptide or the TfR construct can be cultured under appropriate conditions to allow expression of the polypeptide or the TfR construct to occur. The polypeptides or the TfR construct may be secreted and isolated from a mixture of cells and medium containing the polypeptides or the TfR constructs. Alternatively, the polypeptide or the TfR construct may be retained in the cytoplasm or in a membrane fraction and the cells harvested, lysed, and the polypeptide or the TfR construct isolated using a desired method.

XI. Therapeutic Methods

A BBB-receptor binding polypeptide in accordance with the invention may be used therapeutically in many indications. In some embodiments, the BBB receptor-binding polypeptide is used to deliver a therapeutic agent to a target cell type that expresses the BBB receptor. In typical embodiments, a BBB receptor-binding polypeptide may be used to transport a therapeutic moiety across an endothelium, e.g., the blood-brain barrier, to be taken up by the brain.

In some embodiments, a BBB receptor-binding polypeptide of the present invention may be used, e.g., conjugated to a therapeutic agent, to deliver the therapeutic agent to treat a neurological disorder such as a disease of the brain or central nervous system (CNS). Illustrative diseases include Alzheimer's Disease, Parkinson's disease, amyotrophic lateral sclerosis, frontotemporal dementia, vascular dementia, Lewy body dementia, Pick's disease, primary age-related tauopathy, or progressive supranuclear palsy. In some embodiments, the disease may be a tauopathy, a prion disease (such as bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, or a nervous system heterodegenerative disorders (such as Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, Friedreich's ataxia, Spinal muscular atrophy, and Unverricht-Lundborg syndrome). In certain embodiments, the disease is a primary cancer of the CNS. In some embodiments, the disease is metastatic cancer that has metastasized to the brain. In some embodiments, the disease is stroke or multiple sclerosis. In some embodiments, the patient may be asymptomatic, but has a marker that is associated with the disease of the brain or CNS. In some embodiments, the use of a BBB receptor-binding polypeptide of the present invention in the manufacture of a medicament for treating a neurological disorder is provided.

In some embodiments, the method further comprises administering to the subject one or more additional therapeutic agents. For example, in some embodiments for treating a disease of the brain or central nervous system, the method may comprise administering to the subject a neuroprotective agent, e.g., an anticholinergic agent, a dopaminergic agent, a glutamatergic agent, a histone deacetylase (HDAC) inhibitor, a cannabinoid, a caspase inhibitor, melatonin, an anti-inflammatory agent, a hormone (e.g., estrogen or progesterone), or a vitamin. In some embodiments, the method comprises administering to the subject an agent for use in treating a cognitive or behavioral symptom of a neurological disorder (e.g., an antidepressant, a dopamine agonist, or an anti-psychotic).

A BBB receptor-binding polypeptide of the present invention is administered to a subject at a therapeutically effective amount or dose. Illustrative dosages include a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In some embodiments, a patient initially is given a low dose, which is then increased to an efficacious dosage tolerable to the patient. Determination of an effective amount is well within the capability of those skilled in the art.

In various embodiments, a BBB receptor-binding polypeptide of the present invention is administered parenterally. In some embodiments, the polypeptide is administered intravenously. Intravenous administration can be by infusion, e.g., over a period of from about 10 to about 30 minutes, or over a period of at least 1 hour, 2 hours, or 3 hours. In some embodiments, the polypeptide is administered as an intravenous bolus. Combinations of infusion and bolus administration may also be used.

In some parenteral embodiments, a BBB receptor-binding polypeptide is administered intraperitoneally, subcutaneously, intradermally, or intramuscularly. In some embodiments, the polypeptide is administered intradermally or intramuscularly. In some embodiments, the polypeptide is administered intrathecally, such as by epidural administration, or intracerebroventricularly.

In other embodiments, a transferrin receptor-binding polypeptide may be administered orally, by pulmonary administration, intranasal administration, intraocular administration, or by topical administration. Pulmonary administration can also be employed, e.g., by use of an inhaler or nebulizer, and formulation with an aerosolizing agent.

XII. Pharmaceutical Compositions and Kits

In another aspect, pharmaceutical compositions and kits comprising a BBB receptor-binding polypeptide in accordance with the invention are provided.

Pharmaceutical Compositions

Guidance for preparing formulations for use in the present invention can be found in any number of handbooks for pharmaceutical preparation and formulation that are known to those of skill in the art.

In some embodiments, a pharmaceutical composition comprises a transferrin receptor-binding polypeptide as described herein and further comprises one or more pharmaceutically acceptable carriers and/or excipients. A pharmaceutically acceptable carrier includes any solvents, dispersion media, or coatings that are physiologically compatible and that preferably does not interfere with or otherwise inhibit the activity of the active agent. Various pharmaceutically acceptable excipients are well-known.

In some embodiments, the carrier is suitable for intravenous, intrathecal, intracerebroventricular, intramuscular, oral, intraperitoneal, transdermal, topical, or subcutaneous administration. Pharmaceutically acceptable carriers can contain one or more physiologically acceptable compounds that act, for example, to stabilize the composition or to increase or decrease the absorption of the polypeptide. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are also available in the art.

The pharmaceutical compositions described herein can be manufactured in a manner that is known to those of skill in the art, e.g., by means of conventional mixing, dissolving, granulating, dragee-making, emulsifying, encapsulating, entrapping, or lyophilizing processes. The following methods and excipients are merely exemplary and are in no way limiting.

For oral administration, a BBB receptor-binding polypeptide can be formulated by combining it with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the polypeptides with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as a cross-linked polyvinyl pyrrolidone, agar, or alginic acid or a salt thereof such as sodium alginate.

As disclosed above, a BBB receptor-binding polypeptide as described herein can be formulated for parenteral administration by injection, e.g., by bolus injection or continuous infusion. For injection, the polypeptides can be formulated into preparations by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. In some embodiments, polypeptides can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions, or emulsions in oily or aqueous vehicles, and can contain formulatory agents such as suspending, stabilizing, and/or dispersing agents.

In some embodiments, a BBB receptor-binding polypeptide is prepared for delivery in a sustained-release, controlled release, extended-release, timed-release, or delayed-release formulation, for example, in semi-permeable matrices of solid hydrophobic polymers containing the active agent. Various types of sustained-release materials have been established and are well-known by those skilled in the art. Extended-release formulations include film-coated tablets, multiparticulate or pellet systems, matrix technologies using hydrophilic or lipophilic materials and wax-based tablets with pore-forming excipients. Sustained-release delivery systems can, depending on their design, release the compounds over the course of hours or days, for instance, over 4, 6, 8, 10, 12, 16, 20, 24 hours or more. Usually, sustained release formulations can be prepared using naturally occurring or synthetic polymers, for instance, polymeric vinyl pyrrolidones, such as polyvinyl pyrrolidone; carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions of the invention may vary depending on the particular use envisioned. The determination of the appropriate dosage or route of administration is well within the skill of one in the art. Suitable dosages are also described in Section VII above.

Kits

In some embodiments, kits comprising a BBB receptor-binding polypeptide as described herein are provided. In some embodiments, the kits are for use in preventing or treating a neurological disorder such as a disease of the brain or central nervous system (CNS).

In some embodiments, the kit further comprises one or more additional therapeutic agents. For example, in some embodiments, the kit comprises a BBB receptor-binding polypeptide as described herein and further comprises one or more additional therapeutic agents for use in the treatment of a neurological disorder. In some embodiments, the kit further comprises instructional materials containing directions (i.e., protocols) for the practice of the methods described herein (e.g., instructions for using the kit for administering a composition across the blood-brain barrier). While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD-ROM), and the like. Such media may include addresses to internet sites that provide such instructional materials.

XIII. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results. Efforts have been made to ensure accuracy with respect to numbers used (e.g., amounts, temperatures, etc.), but some experimental error and deviation may be present. The practice of the present invention will employ, unless otherwise indicated, conventional methods of protein chemistry, biochemistry, recombinant DNA techniques and pharmacology, within the skill of the art. Such techniques are explained fully in the literature. Additionally, it should be apparent to one of skill in the art that the methods for engineering as applied to certain libraries can also be applied to other libraries described herein.

Generation of a BBB receptor-binding polypeptide is illustrated using TfR as an example. The methods illustrated herein can be performed using alternative BBB receptors as the target.

Example 1. Generation of TfR Target

DNA encoding the transferrin receptor (TfR) ectodomain (ECD) (residues 121-760 of the human (SEQ ID NO:235) or cyno (SEQ ID NO:300) TfR) was cloned into a mammalian expression vector with C-terminal cleavable His- and Avi-tags. The plasmid was transfected and expressed in HEK293 cells. The ectodomain was purified from the harvested supernatant using Ni-NTA chromatography followed by size-exclusion chromatography to remove any aggregated protein. The yield was about 5 mg per liter of culture. The protein was stored in 10 mM $K_3PO_4$ (pH 6.7), 100 mM KCl, 100 mM NaCl, and 20% glycerol and frozen at −20° C.

DNA encoding the permuted TfR apical domain (SEQ ID NO:301) (residues 326-379 and 194-296 of the human or cyno TfR) was cloned into a pET28 vector with an N-terminal His-tag for purification and an Avi-tag for in vivo biotinylation. The plasmid was co-transformed with a BirA expression vector into BL21 (DE3) cells. Cells were grown in LB media at 37° C. until log phase, and then induced with 1 mM isopropyl 1-thio-β-D-galactopyranoside (IPTG) followed by culture overnight at 18° C. The cells were lysed and the soluble fraction was applied to an Ni-NTA column for affinity purification followed by size-exclusion chromatography to remove any aggregated protein. The yield was about 10 mg per liter of culture. The protein was stored in 50 mM HEPES (pH 7.5), 150 mM NaCl, and 1 mM DTT and frozen at −20° C.

The purified TfR ECDs were biotinylated using an EZ-link sulfo-NHS-LC-Biotin kit (obtained from Thermo Scientific). Five-fold molar excess of biotin was used for the reaction. The excess biotin was removed by extensively dialyzing against PBS.

The Avi-tagged TfR ECDs and apical domains was biotinylated using BirA-500 (BirA biotin-protein ligase standard reaction kit from Avidity, LLC). After reaction, the labeled proteins were further purified by size-exclusion chromatography to remove excess BirA enzyme. The final material was stored in 10 mM $K_3PO_4$ (pH 6.7), 100 mM KCl, 100 mM NaCl, and 20% glycerol and frozen at −20° C.

Example 2. Design and Characterization of Engineered Transferrin Receptor-Binding Polypeptides This example describes the design, generation, and characterization of polypeptides of the present invention. For the purposes of this example and comparing the amino acids that are the same in clone sequences, a "conserved" mutation is considered to be one that occurred in all of the identified clones (not a conservative amino acid substitution), while a "semi-conserved" mutation is one that occurs in >50% of clones.

Unless otherwise indicated, the positions of amino acid residues in this section are numbered based on SEQ ID NO: 1, a human IgG1 wild-type Fc region having three residues from the hinge, PCP, at the amino-terminal end.

Design of Polypeptide Fc Region Domain Libraries

New molecular recognition was engineered into polypeptide Fc regions by selecting certain solvent exposed surface patches for modification, constructing surface display libraries in which the amino acid composition of the selected patch was altered by randomization and then screening the surface-displayed sequence variants for desired functionality using standard expression display techniques. As used herein, the term "randomization" includes partial randomization as well as sequence changes with pre-defined nucleotide or amino acid mixing ratios. Typical surface-exposed patches selected for randomization had areas between about 600 to 1500 Å$^2$, and comprised about 7 to 15 amino acids.

Clone Registers

The following registers were designed and generated according to the methods described herein. As used herein, the term "register" refers to a series of surface-exposed amino acid residues that form a contiguous surface that can be altered (e.g., by the introduction of mutations into the peptide coding gene sequences to produce amino acid substitutions, insertions, and/or deletions at the positions listed in the registers).

CH2 Register A2 Set (iii)

The CH2A2 register (Table 1) included amino acid positions 47, 49, 56, 58, 59, 60, 61, 62, and 63 as numbered with reference to the human IgG1 Fc region amino acid sequence set forth in SEQ ID NO: 1. The CH2A2 register was designed to form a surface along a beta sheet, an adjacent turn, and a following loop. It is well removed from both the FcγR and FcRn binding sites.

CH2 Register C Set (iv)

The CH2C register (Table 2) included amino acid positions 39, 40, 41, 42, 43, 44, 68, 70, 71, and 72 as numbered with reference to the human IgG1 Fc region amino acid sequence set forth in SEQ ID NO:1. The CH2C register utilizes solvent-exposed residues along a series of loops near the hinge and very close to the FcγR binding site of the CH2 region.

CH2 Register D Set (v)

The CH2D register (Table 3) included amino acid positions 41, 42, 43, 44, 45, 65, 66, 66, 69, and 73 as numbered with reference to the human IgG1 Fc region amino acid sequence set forth in SEQ ID NO:1. The CH2D register, similar to CH2C, utilizes solvent-exposed residues along a series of loops at the top of the CH2 region, very close to the FcγR binding site. The CH2C and CH2D registers largely share one loop and differ in the second loop utilized for binding.

CH2 Register E3 Set (vi)

The CH2E3 register (Table 4) included amino acid positions 45, 47, 49, 95, 97, 99, 102, 103, and 104 as numbered with reference to the human IgG1 Fc region amino acid sequence set forth in SEQ ID NO: 1. The CH2E3 register positions are also close to the FcγR binding site, but utilize solvent-exposed residues on beta sheets that are adjacent to the loops near the FcγR binding site, in addition to some of the loop residues.

CH3 Register B Set (ii)

The CH3B register (Table 5) included amino acid positions 118, 119, 120, 122, 210, 211, 212, and 213 as numbered with reference to the human IgG1 Fc region amino acid sequence set forth in SEQ ID NO: 1. The CH3B register is largely made up of solvent-exposed residues on two parallel beta sheets along with several less-structured residues near the C-terminus of the CH3 region. It is distant from the FcγR and FcRn binding sites.

CH3 Register C Set (i)

The CH3C register (Table 6) included amino acid positions 157, 159, 160, 161, 162, 163, 186, 189, and 194 as numbered with reference to the human IgG1 Fc region amino acid sequence set forth in SEQ ID NO:1. The CH3C register positions form a contiguous surface by including surface-exposed residues from two loops, both distant from the FcγR and FcRn binding sites.

Generation of Phage-Display Libraries

A DNA template coding for the wild-type human Fc sequence (SEQ ID NO:1) was synthesized and incorporated into a phagemid vector. The phagemid vector contained an ompA or pelB leader sequence, the Fc insert fused to c-Myc and 6×His epitope tags, and an amber stop codon followed by M13 coat protein pIII.

Primers containing "NNK" tricodons at the corresponding positions for randomization were generated, where N is any DNA base (i.e., A, C, G, or T) and K is either G or T. Alternatively, primers for "soft" randomization were used, where a mix of bases corresponding to 70% wild-type base and 10% of each of the other three bases was used for each randomization position. Libraries were generated by performing PCR amplification of fragments of the Fc region corresponding to regions of randomization and then assembled using end primers containing SfiI restriction sites, then digested with SfiI and ligated into the phagemid vectors. Alternatively, the primers were used to conduct Kunkel mutagenesis. Methods of performing Kunkel mutagenesis will be known to one of skill in the art. The ligated products or Kunkel products were transformed into electrocompetent E. coli cells of strain TG1 (obtained from Lucigen®). The E. coli cells were infected with M13K07 helper phage after recovery and grown overnight, after which library phage were precipitated with 5% PEG/NaCl, resuspended in 15% glycerol in PBS, and frozen until use. Typical library sizes ranged from about $10^9$ to about $10^{11}$ transformants. Fc-dimers were displayed on phage via pairing between pIII-fused Fc and soluble Fc not attached to pIII (the latter being generated due to the amber stop codon before pIII).

Generation of Yeast-Display Libraries

A DNA template coding for the wild-type human Fc sequence was synthesized and incorporated into a yeast display vector. For CH2 and CH3 libraries, the Fc polypeptides were displayed on the Aga2p cell wall protein. Both vectors contained prepro leader peptides with a Kex2 cleavage sequence, and a c-Myc epitope tag fused to the terminus of the Fc.

Yeast display libraries were assembled using methods similar to those described for the phage libraries, except that amplification of fragments was performed with primers containing homologous ends for the vector. Freshly prepared electrocompetent yeast (i.e., strain EBY100) were electroporated with linearized vector and assembled library inserts. Electroporation methods will be known to one of skill in the art. After recovery in selective SD-CAA media, the yeast were grown to confluence and split twice, then induced for protein expression by transferring to SG-CAA media. Typical library sizes ranged from about $10^7$ to about $10^9$ transformants. Fc-dimers were formed by pairing of adjacently displayed Fc monomers.

General Methods for Phage Selection

Phage methods were adapted from Phage Display: A Laboratory Manual (Barbas, 2001). Additional protocol details can be obtained from this reference.

Plate Sorting Methods

Human TfR target was coated on MaxiSorp® microtiter plates (typically 200 µL at 1-10 g/mL in PBS) overnight at 4° C. All binding was done at room temperature unless otherwise specified. The phage libraries were added into each well and incubated overnight for binding. Microtiter wells were washed extensively with PBS containing 0.05% Tween® 20 (PBST) and bound phage were eluted by incubating the wells with acid (typically 50 mM HCl with 500 mM KCl, or 100 mM glycine, pH 2.7) for 30 minutes. Eluted phage were neutralized with 1 M Tris (pH 8) and amplified using TG1 cells and M13/KO7 helper phage and grown overnight at 37° C. in 2YT media containing 50 µg/mL carbenacillin and 50 ug/mL Kanamycin. The titers of phage eluted from a target-containing well were compared to titers of phage recovered from a non-target-containing well to assess enrichment. Selection stringency was increased by subsequently decreasing the incubation time during binding and increasing washing time and number of washes.

Bead Sorting Methods

Human TfR target was biotinylated through free amines using NHS-PEG4-Biotin (obtained from Pierce™). For biotinylation reactions, a 3- to 5-fold molar excess of biotin reagent was used in PBS. Reactions were quenched with Tris followed by extensive dialysis in PBS. The biotinylated target was immobilized on streptavidin-coated magnetic beads, (i.e., M280-streptavidin beads obtained Thermo Fisher). The phage display libraries were incubated with the target-coated beads at room temperature for 1 hour. The unbound phage were then removed and beads were washed with PBST. The bound phage were eluted by incubating with 50 mM HCl containing 500 mM KCl (or 0.1 M glycine, pH 2.7) for 30 minutes, and then neutralized and propagated as described above for plate sorting.

After three to five rounds of panning, single clones were screened by either expressing Fc on phage or solubly in the E. coli periplasm. Such expression methods will be known to one of skill in the art. Individual phage supernatants or periplasmic extracts were exposed to blocked ELISA plates coated with target or a negative control and were subsequently detected using HRP-conjugated goat anti-Fc (obtained from Jackson Immunoresearch) for periplasmic extracts or anti-M13 (GE Healthcare) for phage, and then developed with TMB reagent (obtained from Thermo Fisher). Wells with $OD_{450}$ values greater than around 5-fold over background were considered positive clones and sequenced, after which some clones were expressed either as a soluble Fc fragment or fused to Fab fragments General Methods for Yeast Selection Bead Sorting (Magnetic-Assisted Cell Sorting (MACS)) Methods MACS and FACS selections were performed similarly to as described in Ackerman, et al. 2009 Biotechnol. Prog. 25(3), 774. Streptavidin magnetic beads (e.g., M-280 streptavidin beads from ThermoFisher) were labeled with biotinylated target and incubated with yeast (typically 5-10× library diversity). Unbound yeast were removed, the beads were washed, and bound yeast were grown in selective media and induced for subsequent rounds of selection.

Fluorescence-Activated Cell Sorting (FACS) Methods

Yeast were labeled with anti-c-Myc antibody to monitor expression and biotinylated target (concentration varied depending on the sorting round). In some experiments, the target was pre-mixed with streptavidin-Alexa Fluor® 647 in order to enhance the avidity of the interaction. In other experiments, the biotinylated target was detected after binding and washing with streptavidin-Alexa Fluor® 647. Singlet yeast with binding were sorted using a FACS Aria III cell sorter. The sorted yeast were grown in selective media then induced for subsequent selection rounds.

After an enriched yeast population was achieved, yeast were plated on SD-CAA agar plates and single colonies were grown and induced for expression, then labeled as described above to determine their propensity to bind to the target. Positive single clones were subsequently sequenced for binding target, after which some clones were expressed either as a soluble Fc fragment or as fused to Fab fragments.

General Methods for Screening

Screening by ELISA

Clones were selected from panning outputs and grown in individual wells of 96-well deep-well plates. The clones were either induced for periplasmic expression using auto-induction media (obtained from EMD Millipore) or infected with helper phage for phage-display of the individual Fc variants on phage. The cultures were grown overnight and spun to pellet E. coli. For phage ELISA, phage containing supernatant was used directly. For periplasmic expression, pellets were resuspended in 20% sucrose, followed by dilution at 4:1 with water, and shaken at 4° C. for 1 hour. Plates were spun to pellet the solids and supernatant was used in the ELISA.

ELISA plates were coated with target, typically at 0.5 mg/mL overnight, then blocked with 1% BSA before addition of phage or periplasmic extracts. After a 1-hour incubation and washing off unbound protein, HRP-conjugated secondary antibody was added (i.e., anti-Fc or anti-M13 for soluble Fc or phage-displayed Fc, respectively) and incubated for 30 minutes. The plates were washed again, and then developed with TMB reagent and quenched with 2N sulfuric acid. Absorbance at 450 nm was quantified using a plate reader (BioTek®) and binding curves were polotted using Prism software where applicable. Absorbance signal for tested clones was compared to negative control (phage or paraplasmic extract lacking Fc). In some assays, soluble holo-transferrin or other competitor was added during the binding step, typically at significant molar excess (greater than 10-fold excess).

Screening by Flow Cytometry

Fc variant polypeptides (expressed either on phage, in periplasmic extracts, or solubly as fusions to Fab fragments) were added to cells in 96-well V-bottom plates (about 100,000 cells per well in PBS+1% BSA (PBSA)), and incubated at 4° C. for 1 hour. The plates were subsequently spun and the media was removed, and then the cells were washed once with PBSA. The cells were resuspended in PBSA containing secondary antibody (typically goat anti-human-IgG-Alexa Fluor® 647 (obtained from Thermo Fisher)). After 30 minutes, the plates were spun and the media was removed, the cells were washed 1-2 times with PBSA, and then the plates were read on a flow cytometer (i.e., a FACSCanto™ II flow cytometer). Median fluorescence values were calculated for each condition using FlowJo software and binding curves were plotted with Prism software.

CH2A2 Clone Generation and Characterization

Selections with CH2A2 Library Against Transferrin Receptor (TfR)

Phage and yeast libraries against CH2A2 were panned and sorted against TfR as described above. Clones binding human and/or cynomolgous (cyno) TfR were identified in ELISA assays, as described in the section titled "Screening by ELISA" above, after four rounds of phage panning. Sequences of representative clones fell into two groups: group 1 containing 15 unique sequences (i.e., SEQ ID NOS:47-61) and group 2 containing a single unique sequence (i.e., SEQ ID NO:62). Group 1 sequences had a conserved Glu-Trp motif at positions 60-61. No consensus appeared at any other positions, though position 58 favored Arg and position 59 favored Trp or Tyr.

Characterization of CH2A2 Clones

Individual CH2A2 variants were expressed on the surface of phage and assayed for binding to human TfR, cyno TfR, or an irrelevant control by ELISA. Expression of Fc was confirmed by ELSA against anti-Myc antibody 9E10, which bound to the C-terminal c-Myc epitope tag. The data for four representative clones, shown in FIGS. 1A-1D, demonstrated that all were well-expressed and bound to human TfR, while none bound to the irrelevant control. The three clones from group 1 also bound to cyno TfR, whereas the one clone from group 2 (i.e., clone 2A2.16) was specific for human TfR.

Figure 2A:
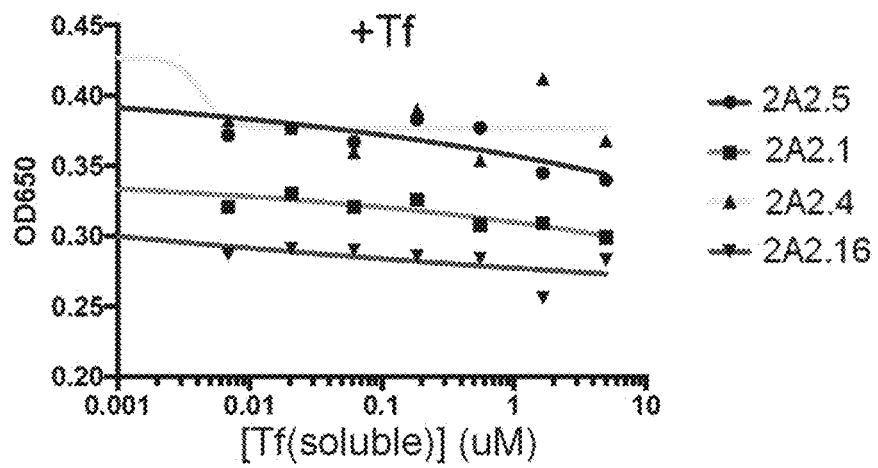
FIGS. 2A and 2B show phage ELISA results for CH2A2 clones binding to human TfR. Phage were added to TfR-coated ELISA plates at the approximate binding $EC_{50}$, and soluble holo-Tf or soluble TfR was added at varying concentrations. The data show that the CH2A2 clones competed with soluble TfR for binding to plate-coated TfR, but did not compete with holo-Tf.
Figure 2B:
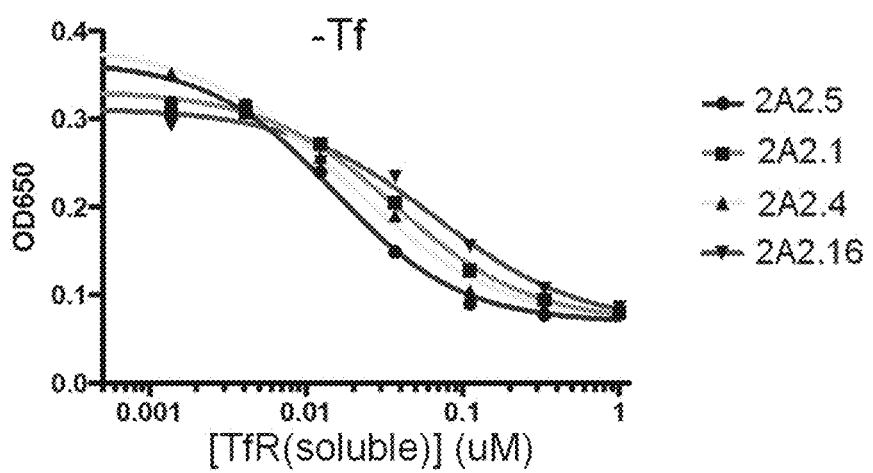

In a second assay, the concentration of phage was kept constant (i.e., at the approximate $EC_{50}$) and a varying concentration of a soluble competitor, either holo-transferrin or human TfR, was added. FIGS. 2A and 2B show that binding was not appreciably impacted by addition of holo-transferrin at concentrations up to 5 μM. Conversely, soluble human TfR could compete for binding to surface-adsorbed human TfR, indicating a specific interaction.

The CH2A2 variants are expressed as Fc fusions to anti-BACE1 Fab fragments by cloning into an expression vector containing an anti-BACE1 variable region sequence. After expression in 293 or CHO cells, the resulting CH2A2-Fab fusions were purified by Protein A and size-exclusion chromatography, and then assayed for binding using ELISAs, surface plasmon resonance (SPR; i.e., using a Biacore™ instrument), biolayer interferometry (i.e., using an Octet® RED system), cell binding (e.g., flow cytometry), and other methods described herein. Additionally, the resulting polypeptide-Fab fusions are characterized for stability by thermal melting, freeze-thaw, and heat-accelerated denaturation.

Additional Engineering of CH2A2 Clones

Two secondary libraries were constructed to enhance the binding affinity of the initial hits against human and cyno TfR. The first library was generated based on the group 1 clones. The conserved EW motif at positions 60 and 61 was held invariant, and the semi-conserved R at position 58 was mutated using soft randomization. The other library positions (i.e., positions 47, 49, 56, 59, 62, and 63) were mutated by saturation mutagenesis. The second library was constructed based on the group 2 clone. This library was generated by soft randomization of the original CH2A2 library positions, but used clone 2A2.16 (SEQ ID NO:62) as the template (rather than wild-type Fc (SEQ ID NO: 1)). Both libraries were constructed for phage and yeast display using methods described above.

The libraries were then screened using methods described above and several clones that bound human TfR by ELISA were identified (Table 1).

CH2C Clone Generation and Characterization

Selections with CH2C Library Against Transferrin Receptor (TR)

Phage and yeast libraries against CH2C were panned and sorted against TfR as described above. Clones binding human and/or cynomolgous (cyno) TfR were identified in ELISA assays, as described in the section titled "Screening by ELISA" above, after four rounds of phage panning (i.e., group 1 and 4 clones), and additional clones were identified after four or five yeast sort rounds (i.e., group 2 and 3 clones), by yeast binding assays as described in the section titled "General Methods for Yeast Selection" above. Sequences of representative clones fell into four groups: group 1 containing 16 unique sequences (i.e., SEQ ID NOS:63-78), group 2 containing 4 unique sequences (i.e., SEQ ID NOS:79-82), group 3 containing 2 unique sequences (i.e., SEQ ID NOS:83-84), and group 4 containing a single sequence (i.e., SEQ ID NO:85). The group 1 sequences had a semi-conserved Pro at position 39, a semi-conserved Pro at position 42, a conserved Pro at position 43, a semi-conserved Trp at position 44, a semi-conserved Glu at position 68, a conserved Tyr at position 70, and little specific preference at other library positions. The group 2 sequences had a conserved Met at position 39, a semi-conserved L at position 40, a conserved Pro at position 42, a conserved Val at position 43, a semi-conserved Pro at position 44, a semi-conserved Thr at position 68, a conserved His at position 70, and a conserved Pro at position 72. The two group 3 sequences only differed at position 68, where either a Val or Leu was present. Group 4 consisted of a single clone (i.e., CH2C.23) with a sequence as indicated in SEQ ID NO:85.

Characterization of CH2C Clones

Figure 3A:
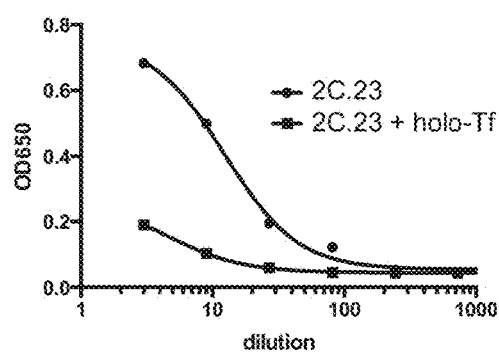
FIGS. 3A-3D show binding of CH2C clones to TfR in the presence or absence of holo-Tf
Figure 3B:
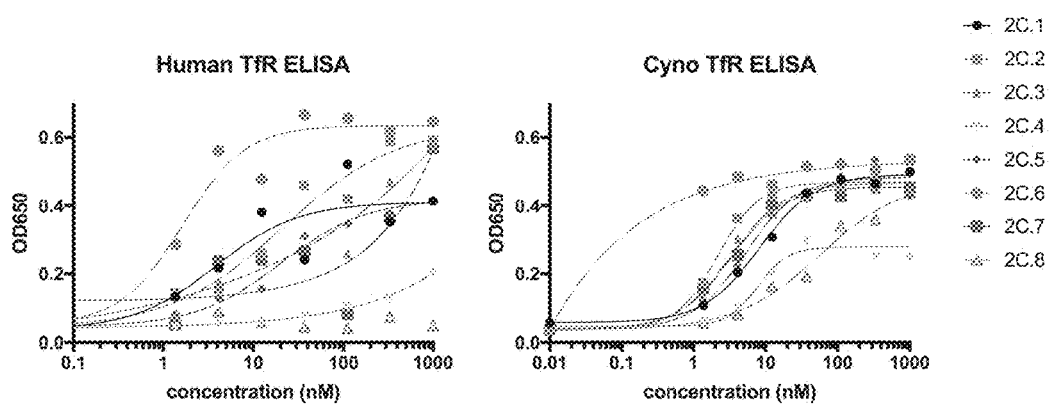
Figure 3C:
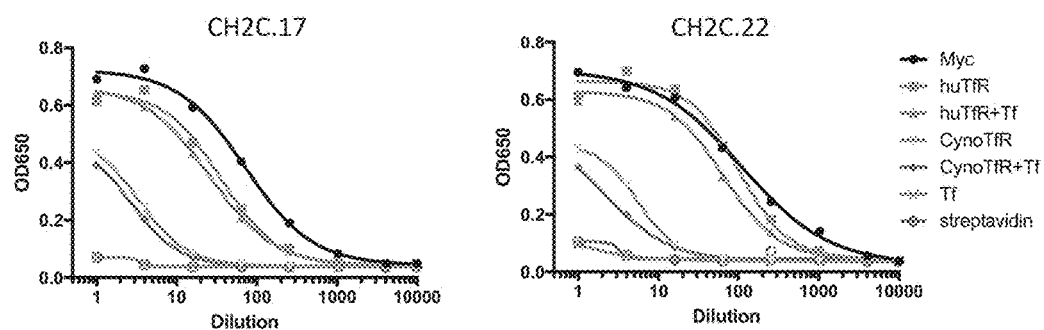
Figure 3D:
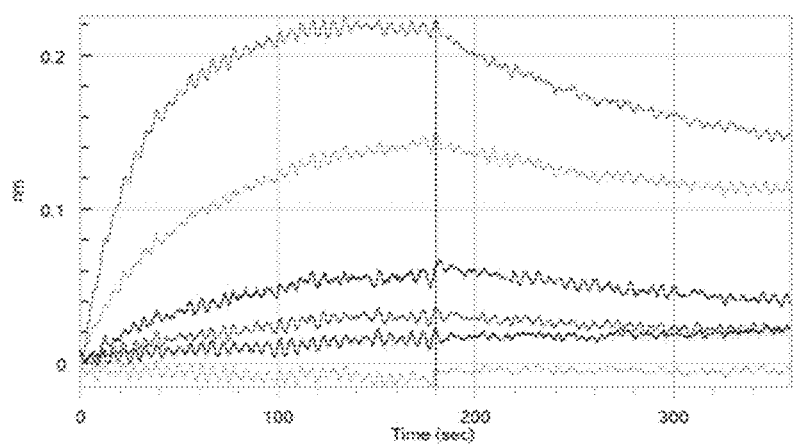

The CH2C variants were expressed as Fc fusions to Fab fragments by cloning into an expression vector containing an anti-BACE1 benchmark variable region sequence. After expression in 293 or CHO cells, the resulting polypeptide-Fab fusions were purified by Protein A and size-exclusion chromatography, then assayed for binding to human or cyno TfR. As shown in FIG. 3A, the group 4 clone CH2C.23 competed with holo-transferrin. Clones belonging to sequence group 1 are shown in binding titrations against human and cyno TfR in FIG. 3B. Representative clones from other sequence groups were tested on phage for binding in the presence or absence of holo-Tf (see, FIG. 3C), and clone CH2C.7 was tested for binding to human TfR in the presence of holo-transferrin by biolayer interferometry (i.e., using an Octet® RED system; see, FIG. 3D). Most clones showed some cross-reactivity to cyno TfR, and except for clone CH2C.23, the clones that were tested did not compete with holo-Tf.

Additional Engineering of CH2C Clones

Additional engineering methods, similar to those described above for CH2A2 for the design and screening of additional libraries, are used to improve the affinity of CH2C clones.

CH3B Clone Generation and Characterization

Selections with CH3B Library Against Transferrin Receptor (TR)

Phage and yeast libraries against CH3B were panned and sorted against TfR as described above. Clones binding human and/or cyno TfR were identified in ELISA assays, as described in the section titled "Screening by ELISA" above, after four rounds of phage panning, and additional clones were identified after four or five yeast sort rounds, by yeast binding assays as described in the section titled "General Methods for Yeast Selection" above. All 17 clones (i.e., SEQ ID NOS:30-46) identified from both phage and yeast had related sequences; the sequences had a semi-conserved Phe at position 118, a semi-conserved negatively charged Asp or Glu at position 119, a semi-conserved Thr at position 122, a conserved G at position 210, a conserved Phe at position 211, a semi-conserved His at position 212, and a conserved Asp at position 213. Several clones had a T123I mutation, which was not a position intentionally mutated in the library design, but presumably was introduced by recombination or PCR error.

Characterization of CH3B Clones

Two representative clones, CH3B.11 (SEQ ID NO:40) and CH3B.12 (SEQ ID NO:41), were expressed on the surface of phage and tested for binding to human and cyno TfR in the presence or absence of holo-Tf. Neither clone was affected by the addition of holo-Tf (FIG. 4A). Additionally, the CH3B variants were expressed as fusions to Fab fragments by cloning into an expression vector containing an anti-BACE1 variable region sequence. After expression in 293 or CHO cells, the resulting polypeptide-Fab fusions were purified by Protein A and size-exclusion chromatography, then assayed for binding to human or cyno TfR (FIG. 4B). All showed specific binding to both orthologs.

Additional Engineering of CH3B Clones

Figure 5:
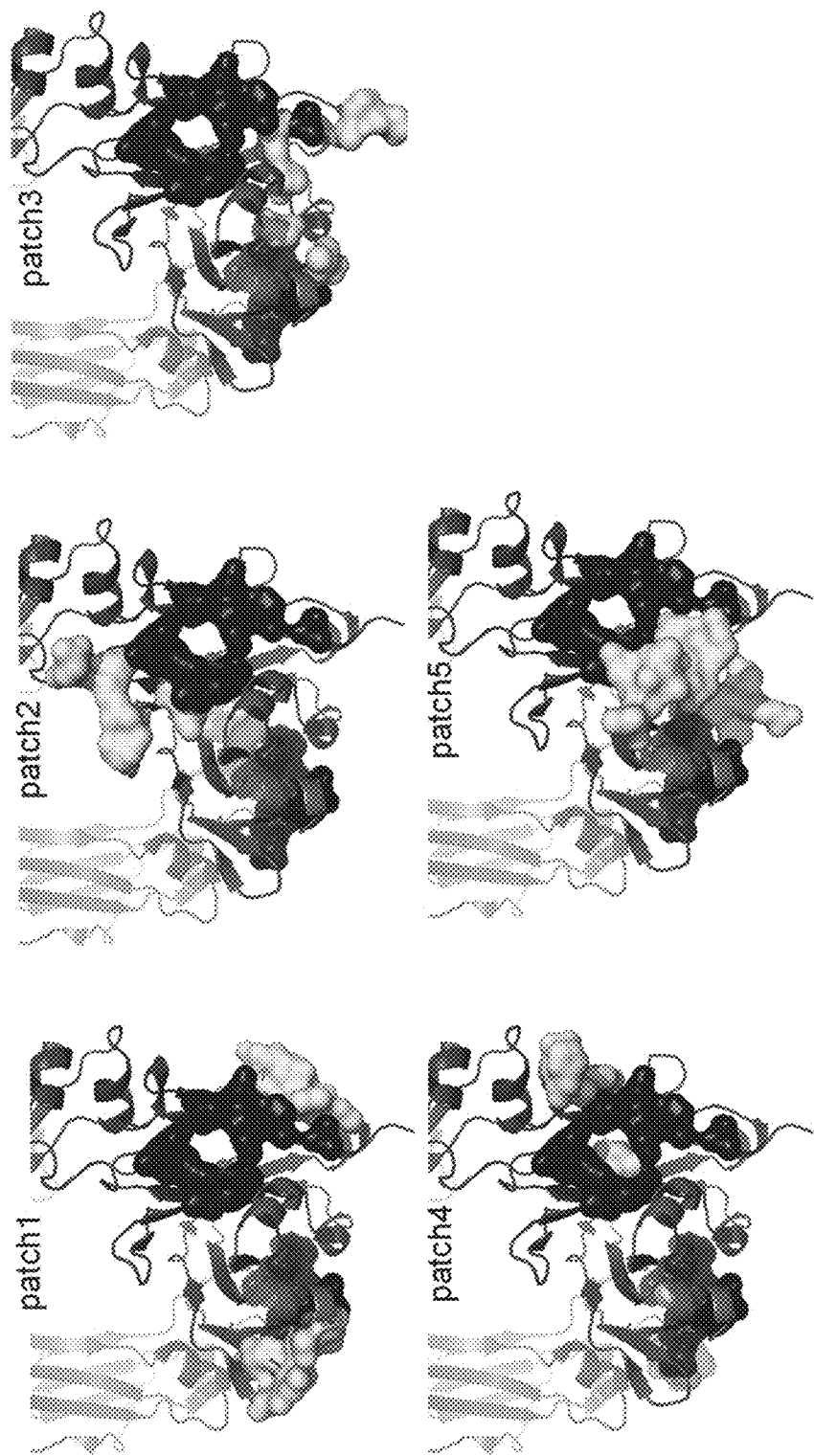
FIG. 5 shows NNK patch libraries for maturation of CH3B clones. Ribbons show the backbone of the CH3 domain, where the dark surfaces represent the original CH3B registers and the light surface patches represent the expanded repertoires.

Additional engineering methods, similar to those described above for CH2A2 for the design and screening of additional libraries, were used to improve the affinity of CH3B clones. In particular, several series of four to seven residue patches near the paratope were selected for additional diversification, as shown in FIG. 5 (the dark surface represents the original library register; the light patch represents the newly mutagenized positions). Clone CH3B.12 (SEQ ID NO:41) was used as a starting point; the residues selected for saturation (i.e., NNK) mutagenesis were as follows:

CH3B-patch1 (SEQ ID NO:101): amino acid positions 127, 128, 129, 131, 132, 133, and 134;

CH3B-patch2 (SEQ ID NO: 102): amino acid positions 121, 206, 207, and 209;

CH3B-patch3 (SEQ ID NO:103): amino acid positions 125, 214, 217, 218, 219, and 220;

CH3B-patch4 (SEQ ID NO:104): amino acid positions 115, 117, 143, 174, and 176; and CH3B-patch5 (SEQ ID NO:105): amino acid positions 155, 157, 158, 193, 194, and 195.

The libraries were generated using PCR mutagenesis and put into yeast and phage as described in the sections titled "Generation of Phage-Display Libraries" and "Generation of Yeast-Display Libraries" above. The libraries were screened using methods described above and several clones that bound human TfR by ELISA were identified (Table 5).

CH2D Clone Generation and Characterization

Selections with CH2D Library Against Transferrin Receptor (TJR)

Phage libraries against CH2D were panned against TfR as described above. Clones binding human and/or cyno TfR were identified in ELISA assays, as described in the section titled "Screening by ELISA" above. Five unique clones were identified which were grouped into two sequence families of 2 and 3 sequences, respectively (Table 3). Sequence group 1 (i.e., clones CH2D.1 (SEQ ID NO:86) and CH2D.2 (SEQ ID NO:87)) had a conserved VPPXM (SEQ ID NO: 111) motif at positions 40-45, an SLTS (SEQ ID NO: 112) motif at positions 64-67, and V at position 73. Mutations at position 40 were not included in the design and were likely due to PCR error or recombination. Sequence group 2 (i.e., clones CH2D.3 (SEQ ID NO:88), CH2D.4 (SEQ ID NO:89), and CH2D.5 (SEQ ID NO:90)) had a conserved D at position 41, a semi-conserved D at position 42, a conserved W at position 43, a semi-conserved E at position 44, a conserved aromatic (W or Y) at position 45, a conserved PW motif at positions 64-65, and a conserved W at position 73.

Characterization and Additional Engineering of CH2D Clones

CH2D variants were expressed as fusions to Fab fragments by cloning into an expression vector containing an anti-BACE1 variable region sequence. After expression in 293 or CHO cells, the resulting polypeptide-Fab fusions were purified by Protein A and size-exclusion chromatography, then assayed for binding to cyno and human TfR in the presence or absence of holo-Tf using methods previously described herein.

CH2E3 Clone Generation and Characterization

Selections with CH2E3 Library Against Transferrin Receptor (TR)

Phage libraries against CH2E3 were panned against TfR as described above. Clones binding human and/or cyno TfR were identified in ELISA assays, as described in the section titled "Screening by ELISA" above. Three sequence groups were identified from 5 sequences, though two of the groups only consisted of one unique sequence each (Table 4). Sequence group 2, which had 3 unique sequences (i.e., clones CH2E3.2 (SEQ ID NO:92), CH2E3.3 (SEQ ID NO:93), and CH2E3.4 (SEQ ID NO:94)), had a semi-conserved Val at position 45, a conserved Gly at position 47, a conserved Arg at position 49, a conserved Arg at position 95, a conserved Ser at positions 97 and 99, a conserved Trp at position 103, and an Arg or Lys at position 104.

Characterization and Additional Engineering of CH2E3 Clones

CH2E3 variants were expressed as fusions to Fab fragments by cloning into an expression vector containing an anti-BACE1 benchmark variable region sequence. After expression in 293 or CHO cells, the resulting polypeptide-Fab fusions were purified by Protein A and size-exclusion chromatography, then assayed for binding to cyno and human TfR in the presence or absence of holo-Tf using methods for binding previously described herein.

CH3C Clone Generation and Characterization

Selections with CH3C Library Against Transferrin Receptor (TfR)

Figure 6:
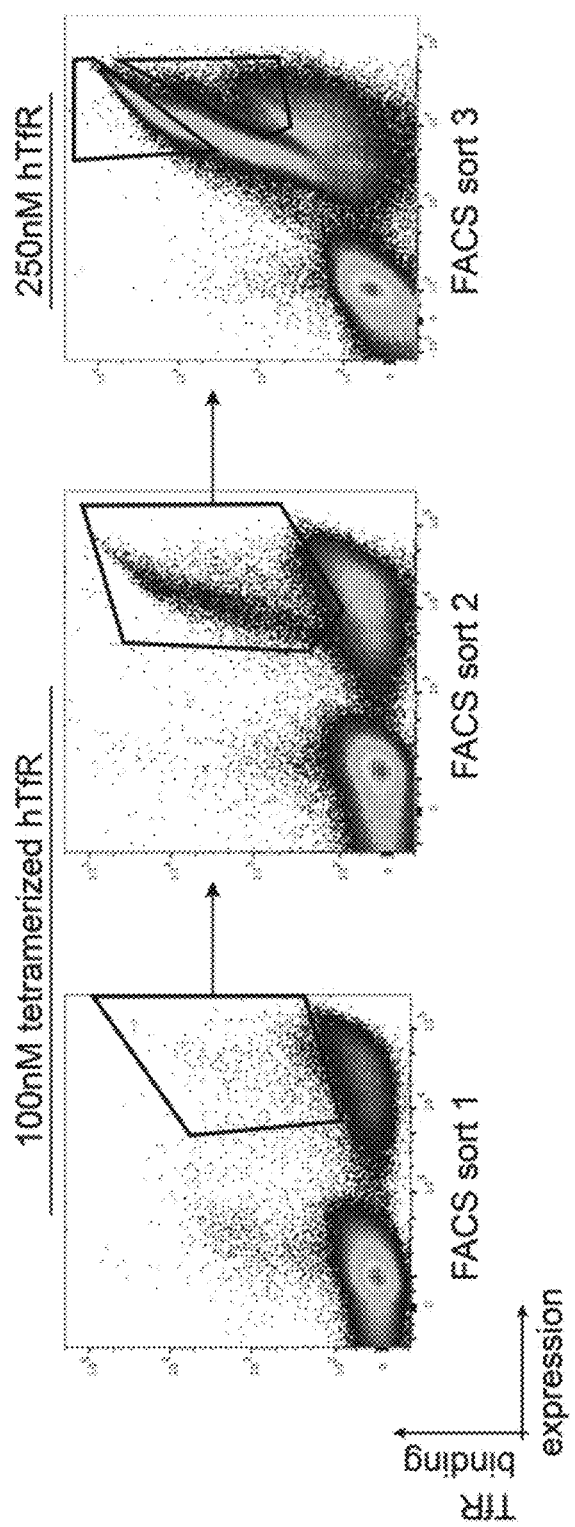
FIG. 6 shows FACS plots for CH3C clone selections on yeast, showing enrichment of binding population after 3 sort rounds. In sort rounds 1 and 2, biotinylated TfR was pre-loaded on streptavidin-Alexa Fluor® 647 prior to incubating with the yeast. In sort round 3, biotinylated TfR was incubated with the yeast first, and streptavidin-Alexa Fluor® 647 was added for secondary detection. In all sort rounds, expression was monitored using a chicken anti-c-Myc antibody (obtained from Thermo Fisher) against the C-terminal Myc tag on the yeast display construct.

Yeast libraries against CH3C were panned and sorted against TfR as described above. Population enrichment FACS plots for the first three sort rounds are shown in FIG. 6. After an additional two rounds of sorting, single clones were sequenced and four unique sequences (i.e., clones CH3C.1 (SEQ ID NO:4), CH3C.2 (SEQ ID NO:5), CH3C.3 (SEQ ID NO:6), and CH3C.4 (SEQ ID NO:7)) were identified. These sequences had a conserved Trp at position 161, and all had an aromatic residue (i.e., Trp, Tyr, or His) at position 194. There was a great deal of diversity at other positions.

Characterization of First Generation CH3C Clones

Figure 7A:
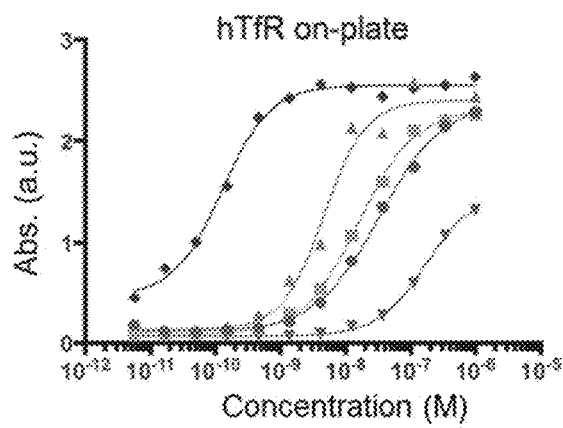
FIGS. 7A-7C show binding of CH3C clones to TfR in the presence or absence of holo-Tf Clones were assayed in a Fc-Fab fusion format. Ab204, a standard antibody with variable regions that bind to TfR, was used as a positive control in this assay.
Figure 7B:
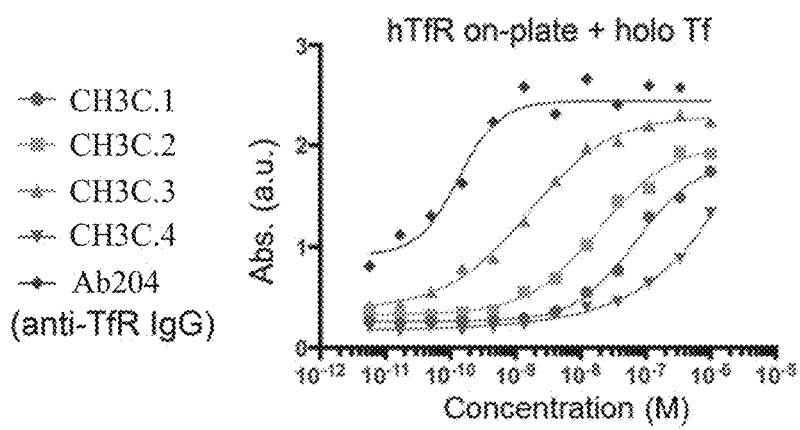
Figure 7C:
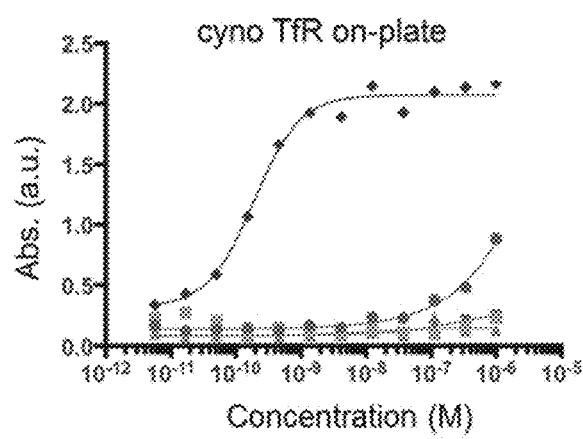
Figure 8:
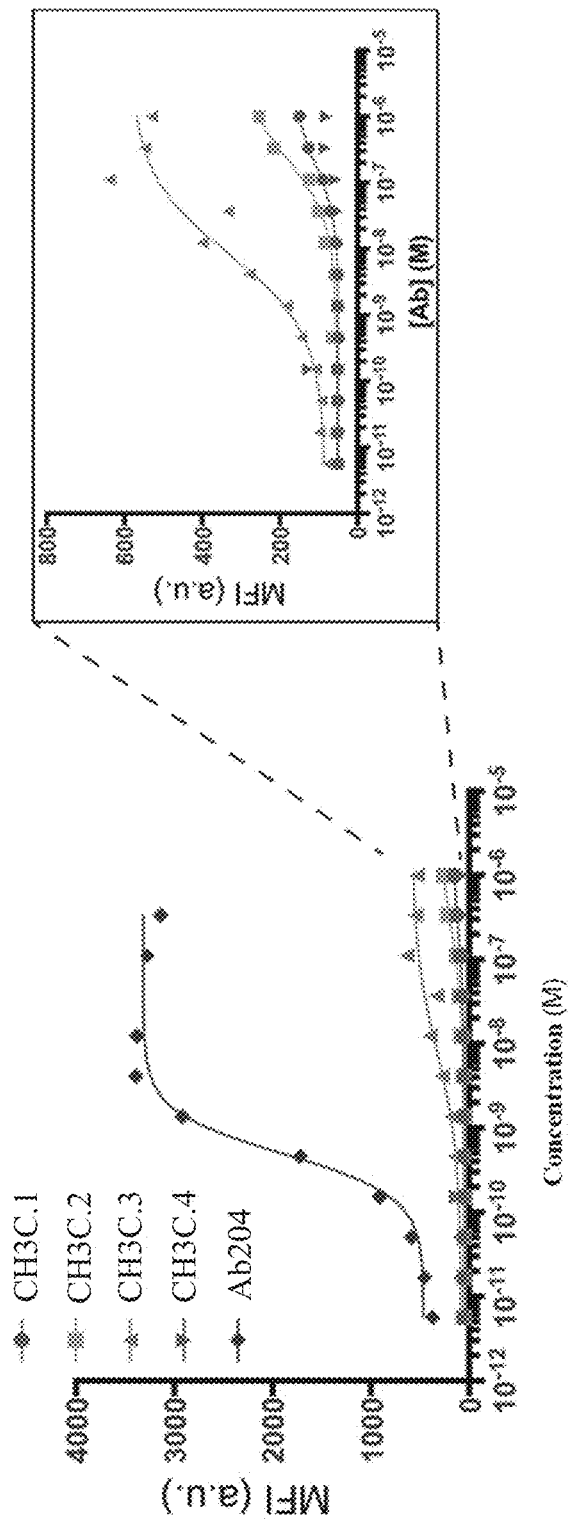
FIG. 8 shows binding of CH3C clones to 293F cells, which endogenously express human TfR. Cells were distributed in 96-well V bottom plates, and varying concentrations of the CH3C clones, formatted as Fc-Fab fusion binding proteins, were added. After 1 hour incubation at 4° C., the plates were spun and washed, and then incubated with goat-anti-human-IgG-Alexa Fluor® 647 secondary antibody at 4° C. for 30 minutes. After additional washing of the cells, the plates were read on a FACSCanto™ II flow cytometer, and median fluorescence values in the APC (647 nm) channel were determined using FlowJo® software.

The four clones selected from the CH3C library were expressed as Fc fusions to Fab fragments in CHO or 293 cells, and purified by Protein A and size-exclusion chromatography, and then screened for binding to cyno and human TfR in the presence or absence of holo-Tf by ELISA. As shown in FIG. 7, the clones all bound to human TfR and the binding was not affected by the addition of excess (5 µM) holo-Tf. However, the clones did not bind appreciably to cyno TfR. Clones were also tested for binding to 293F cells, which endogenously express human TfR. FIG. 8 shows that while the clones bound to 293F cells, the overall binding was substantially weaker than the high-affinity positive control.

Figure 9A:
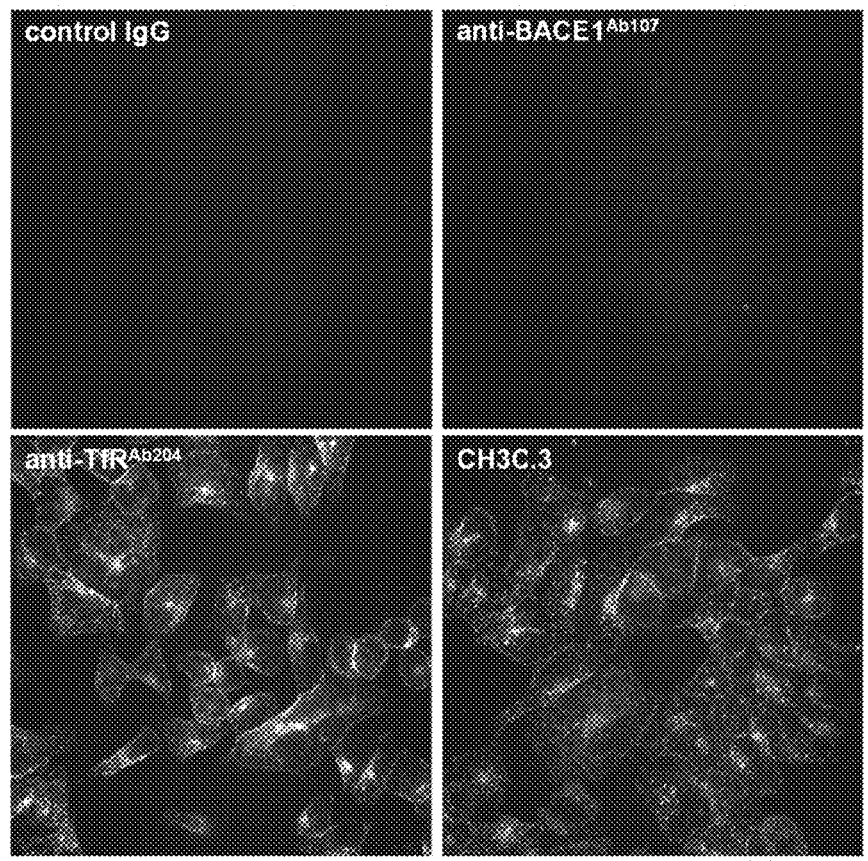
FIGS. 9A and 9B show internalization of CH3C.3 in HEK293 cells, which endogenously express human TfR. CH3C.3 or controls were added at 1 µM concentration at 37° C. and 8% $CO_2$ concentration for 30 minutes, then the cells were washed, permeabilized, and stained with anti-human-IgG-Alexa Fluor® 488 secondary antibody. After additional washing, the cells were imaged by fluorescence microscopy and the number of puncta was quantified.
Figure 9B:
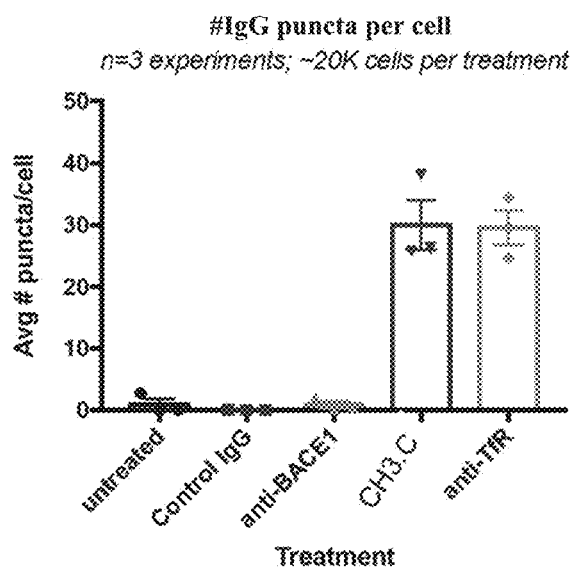

Next it was tested whether clone CH3C.3 could internalize in TfR-expressing cells. Adherent HEK293 cells were grown in 96-well plates to about 80% confluence, media was removed, and samples were added at 1 µM concentrations: CH3C.3 anti-TfR benchmark positive control antibody (Ab204), anti-BACE1 benchmark negative control antibody (Ab107), and human IgG isotype control (obtained from Jackson Immunoresearch). The cells were incubated at 37° C. and 8% $CO_2$ concentration for 30 minutes, then washed, permeabilized with 0.1% Triton™ X-100, and stained with anti-human-IgG-Alexa Fluor® 488 secondary antibody. After additional washing, the cells were imaged under a high content fluorescence microscope (i.e., an Opera Phenix™ system), and the number of puncta per cell was quantified, as shown in FIG. 9. At 1 M, clone CH3C.3 showed a similar propensity for internalization to the positive anti-TfR control, while the negative controls showed no internalization.

Secondary Engineering of CH3C Clones

Additional libraries were generated to improve the affinity of the initial CH3C hits against human TfR, and to attempt to introduce binding to cyno TfR. A soft randomization approach was used, wherein DNA oligos were generated to introduce soft mutagenesis based on each of the original four hits. The first portion of the register (WESXGXXXXXYK; SEQ ID NO: 113) and the second portion of the register (TVXKXXWQQGXV; SEQ ID NO:114) were built via separate fragments, so the soft randomized registers were shuffled during PCR amplification (e.g., the first portion of the register from clone CH3C. 1 was mixed with the second portion of the register from clones CH3C.1, CH3C.2, CH3C.3, and CH3C.4, and so forth). The fragments were all mixed and then introduced into yeast for surface expression and selection.

Figure 10:
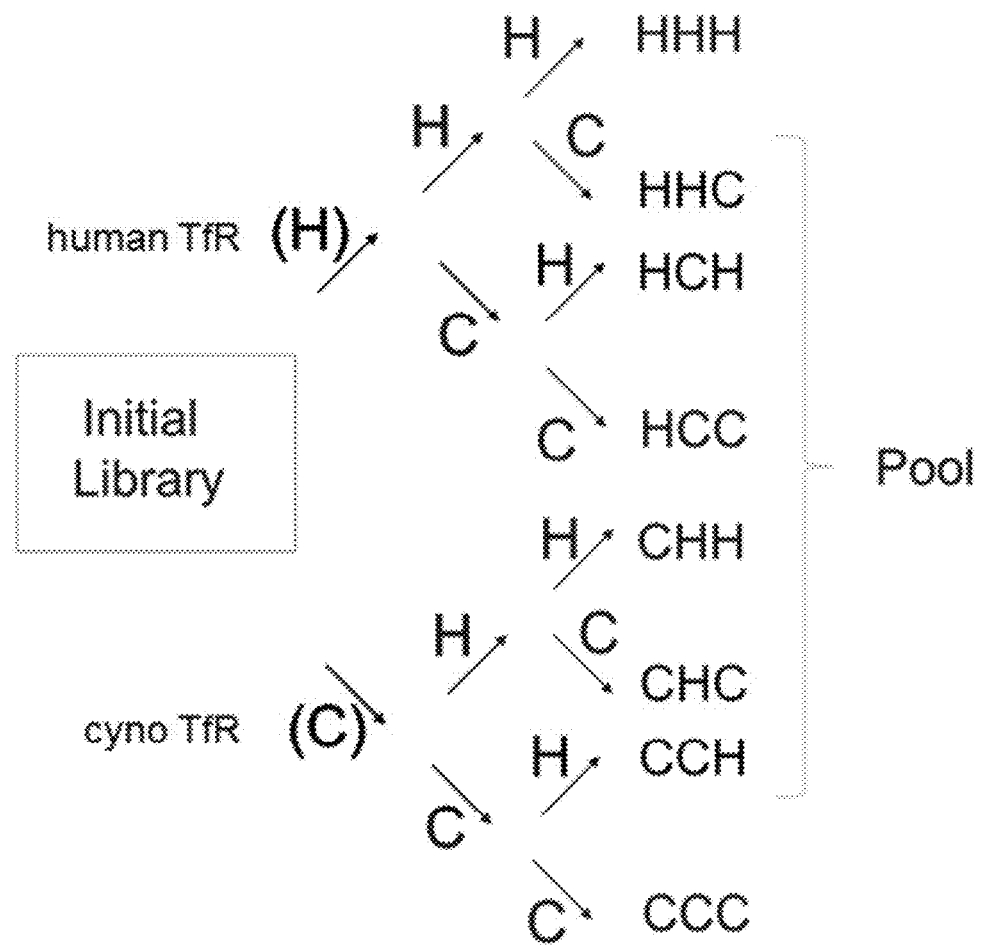
FIG. 10 shows the selection scheme for the CH3C soft library. The initial library was sorted by MACS against either human (H) or cyno (C) TfR. The resulting yeast pools were then split and each sorted against human or cyno TfR as in the first FACS sort round. The resulting pools were split again for another FACS sort round. Finally, the HHH and CCC pools were kept separate and the other pools which had seen both species of target were finally pooled.
Figure 11A:
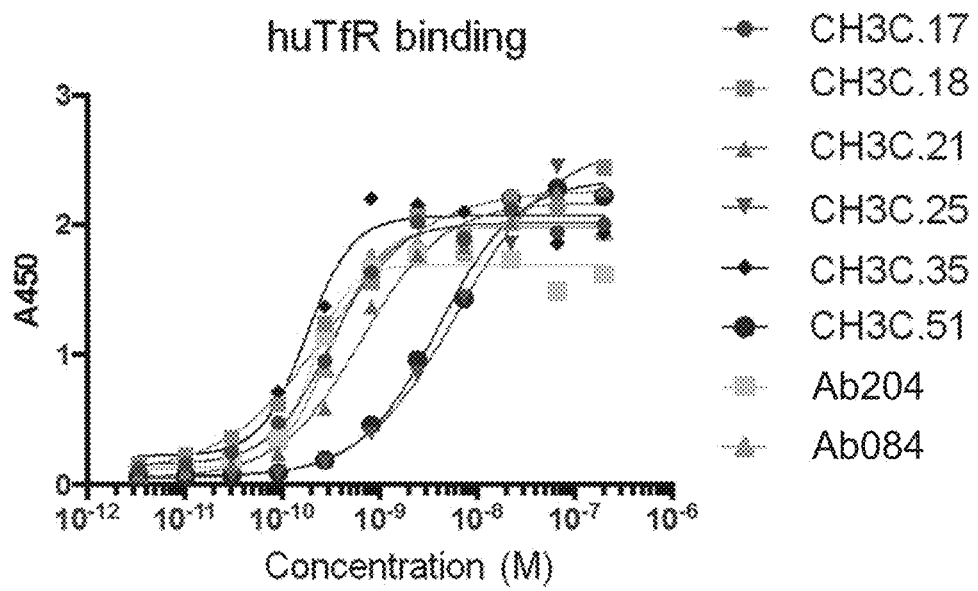
FIGS. 11A and 11B show binding of CH3C clones identified from the first soft randomization library to human and cyno TfR. Positive controls were Ab204, a high affinity anti-TfR antibody, and Ab084, a low-affinity anti-TfR antibody.
Figure 11B:
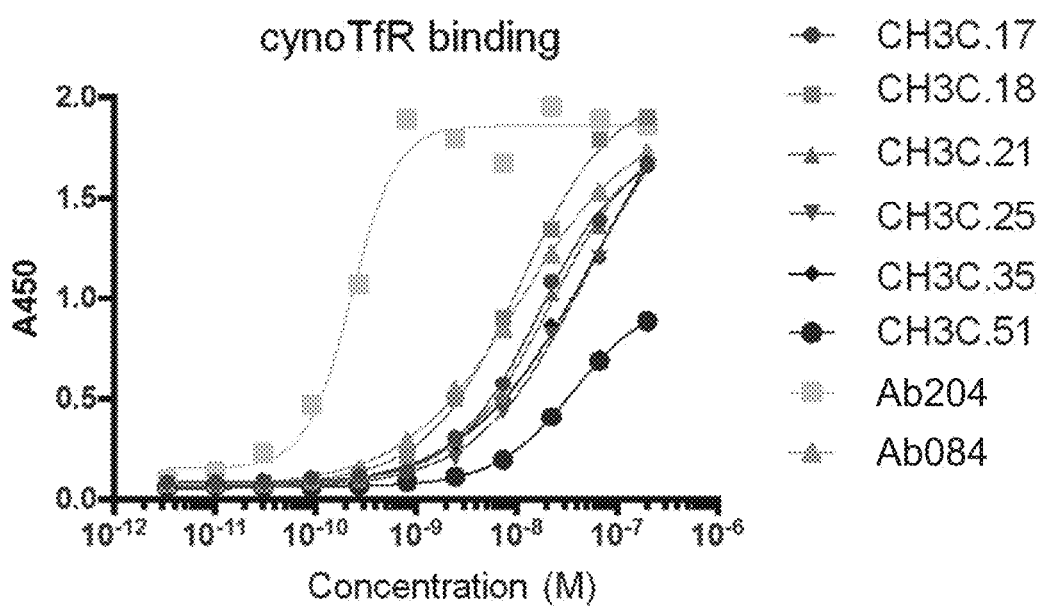

The selection scheme is shown in FIG. 10. After one round of MACS and three rounds of FACS, individual clones were sequenced (clones CH3C.17 (SEQ ID NO:8), CH3C.18 (SEQ ID NO:9), CH3C.21 (SEQ ID NO:10), CH3C.25 (SEQ ID NO:11), CH3C.34 (SEQ ID NO:12), CH3C.35 (SEQ ID NO:13), CH3C.44 (SEQ ID NO:14), and CH3C.51 (SEQ ID NO:15)). The selected clones fell into two general sequence groups. Group 1 clones (i.e., clones CH3C.18, CH3C.21, CH3C.25, and CH3C.34) had a semi-conserved Leu at position 157, a Leu or His at position 159, a conserved and a semi-conserved Val at positions 160 and 162, respectively, and a semi-conserved P-T-W motif at positions 186, 189, and 194, respectively. Group 2 clones had a conserved Tyr at position 157, the motif TXWSX (SEQ ID NO:470) at positions 159-163, and the conserved motif S/T-E-F at positions 186, 189, and 194, respectively. Clones CH3C.18 and CH3.35 were used in additional studies as representative members of each sequence group. It was noted that clone CH3C.51 had the first portion of its register from group 1 and the second portion of its register from group 2.

Binding Characterization of CH3C Clones from the Soft Mutagenesis Library

Figure 12A:
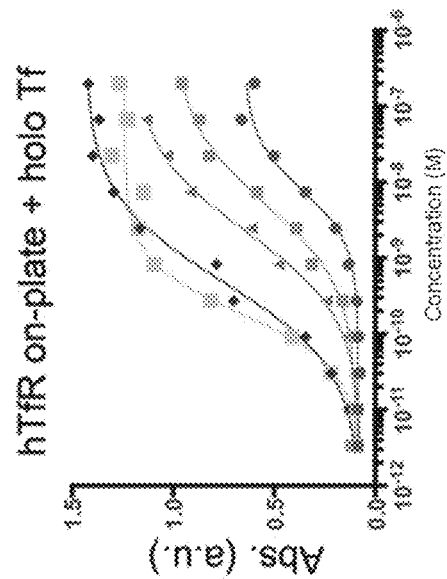
FIGS. 12A and 12B show binding of CH3C clones identified from the first soft randomization library to human TfR in the presence or absence of holo-Tf. Clones were in Fc-Fab fusion format. Ab204, a high affinity anti-TfR antibody, was used as a positive control in this assay.
Figure 12B:
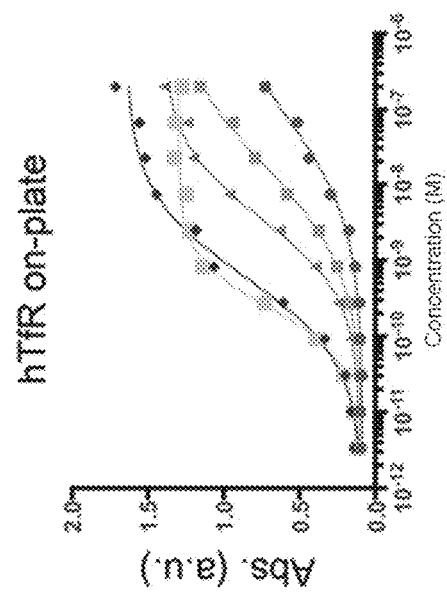

Clones from the soft mutagenesis library were reformatted as Fc-Fab fusion polypeptides and expressed and purified as described above. As shown in FIG. 12, these variants had improved ELISA binding to human TfR as compared to the top clone from the initial library selections (CH3C.3), and also did not compete with holo-Tf. The $EC_{50}$ values, as shown below in Table 7, were not appreciably affected beyond the margin of error of the experiment by the presence or absence of holo-Tf.

TABLE 7

$EC_{50}$ values (nM) for ELISA binding of CH3C variants to TfR in the presence or absence of holo-Tf

| Clone | −Tf | +Tf |
|---|---|---|
| CH3C.3 | 8.1 | 6.3 |
| CH3C.17 | 5.3 | 17 |
| CH3C.18 | 6.9 | 3.5 |
| CH3C.25 | 51 | 48 |
| CH3C.35 | 0.49 | 0.61 |
| CH3C.51 | 160 | 36 |
| Ab204 | 1.6 | 0.24 |

Figure 13:
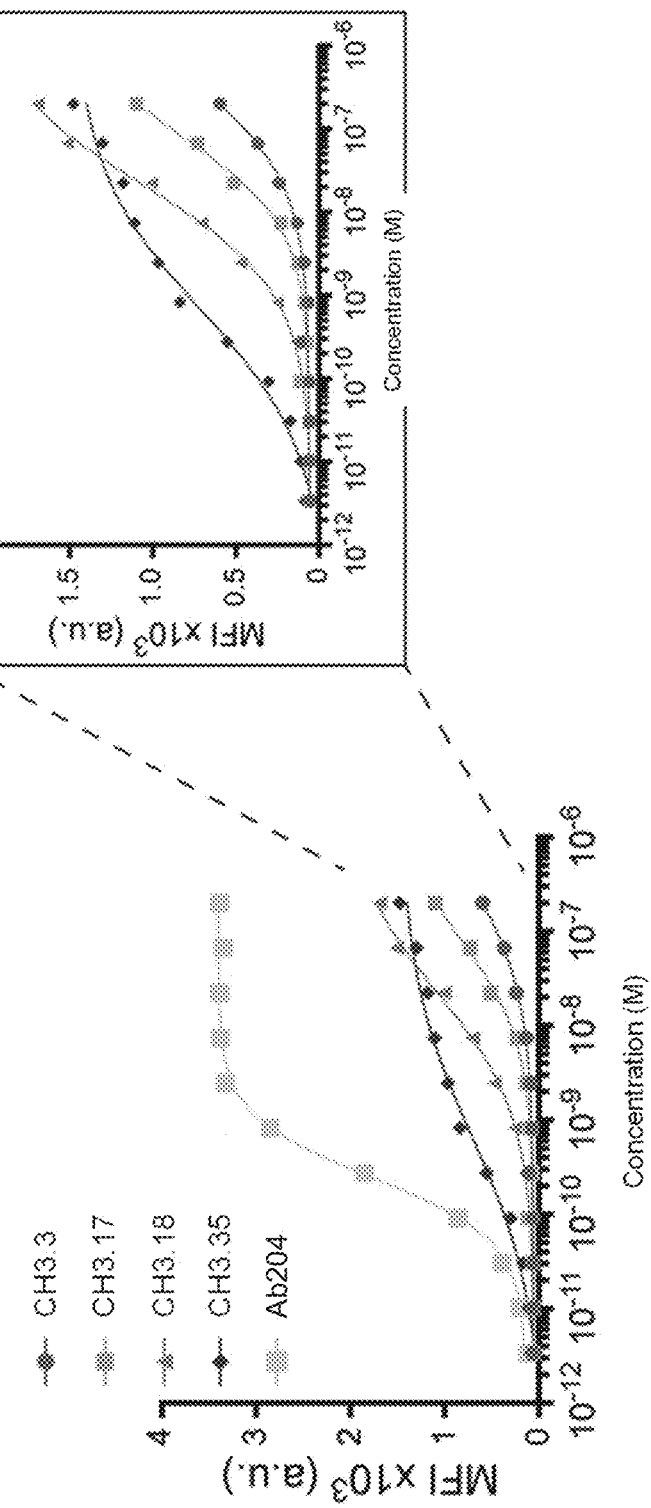
FIG. 13 shows binding of CH3C clones identified from the first soft randomization library to 293F cells. Cells were distributed in 96-well V bottom plates, and varying concentrations of the CH3C clones, formatted as Fc-Fab fusion proteins, were added. After 1 hour incubation at 4° C., the plates were spun and washed, and then incubated with goat-anti-human-IgG-Alexa Fluor®647 secondary antibody at 4° C. for 30 minutes. After additional washing of the cells, the plates were read on a FACSCanto™ II flow cytometer, and median fluorescence values in the APC (647 nm) channel were determined using FlowJo® software.
Figure 15A:
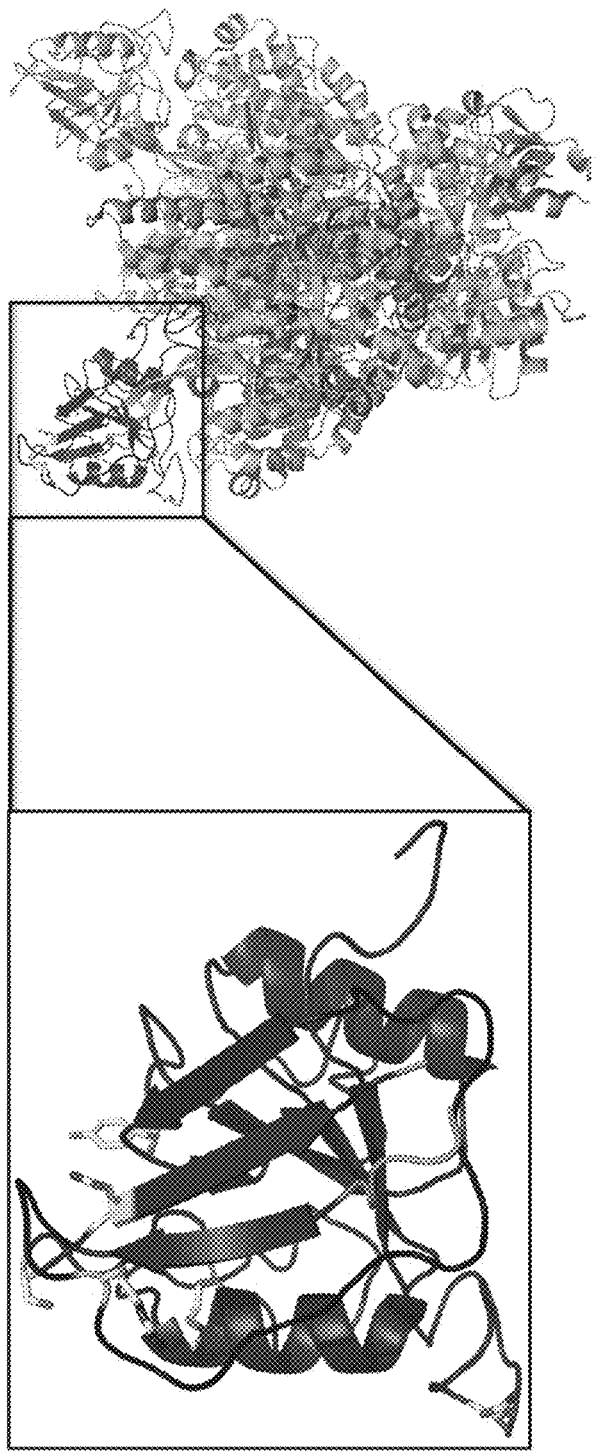
FIGS. 15A and 15B show the TfR apical domain.
Figure 15B:
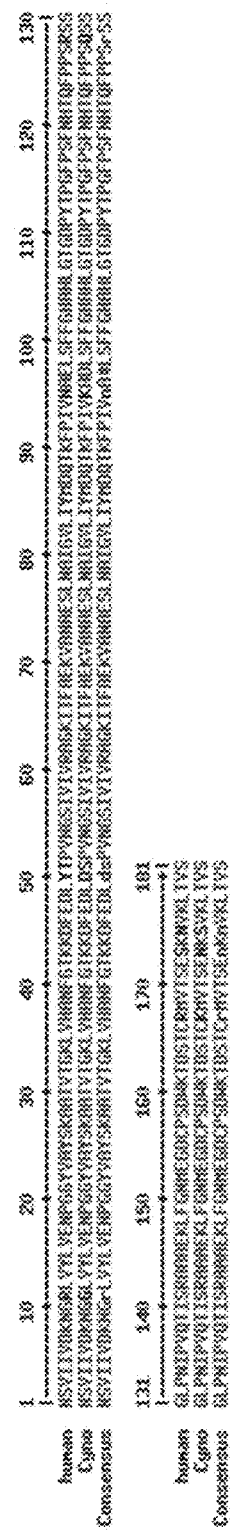

Notably, clone CH3C.35 bound to human TfR about as well as the high affinity anti-Tfr control antibody Ab204. The clones selected from the soft randomization library also had improved cell binding to 293F cells, as shown in FIG. 13. In a similar cell binding assay, these clones were tested for binding to CHO-K1 cells that stably express high levels of human or cyno TfR on their surface. The clones selected from the soft randomization library bound to cells expressing human TfR (FIG. 14A) as well as cyno TfR (FIG. 14B) and did not bind to the parental CHO-K1 cells (FIG. 14C). The magnitude and binding $EC_{50}$ values were substantially lower for cyno TfR as compared to human TfR. Data is summarized in Table 8 below.

TABLE 8

$EC_{50}$ and max. MFI (Median Fluorescence Intensity) values for CH3C clones binding to cells

| Clone | 293F EC50 (nM) | 293F MFI at 200 nM | CHO-huTfR EC$_{50}$ (nM) | CHO-huTf MFI at 200 nM | CHO-cyTfR EC$_{50}$ (nM) | CHO-cyTfR MFI at 200 nM |
|---|---|---|---|---|---|---|
| CH3C.3 | n.d. | 1385 | 6.5 | 10296 | n.d. | 941 |
| CH3C.17 | n.d. | 1556 | 4.2 | 13933 | >50 | 8205 |
| CH3C.18 | 22 | 2100 | 2.3 | 22997 | 6.6 | 9614 |
| CH3C.25 | n.d. | 314 | 17 | 11434 | >50 | 12515 |
| CH3C.35 | 0.67 | 1481 | 2.6 | 22059 | 11 | 8292 |
| CH3C.51 | n.d. | 784 | 27 | 11892 | >50 | 14455 |
| Ab204 | 0.25 | 3404 | 1.8 | 35744 | 2.4 | 41041 |

Epitope Mapping

To determine whether the engineered CH3C Fc regions bound to the apical domain of TfR, TfR apical domain (SEQ ID NOS:107 and 108 for human and cyno, respectively) was expressed on the surface of phage. To properly fold and display the apical domain, one of the loops had to be truncated and the sequence needed to be circularly permuted; the sequences expressed on phage are identified as SEQ ID NOS: 109 and 110 for human and cyno, respectively. Clones CH3C.18 and CH3C.35 were coated on ELISA plates and the previously described phage ELISA protocol was followed. Briefly, after washing and blocking with 1% PBSA, dilutions of phage displaying were added and incubated at room temperature for 1 hour. The plates were subsequently washed and anti-M13-HRP was added, and after additional washing the plates were developed with TMB substrate and quenched with 2N $H_2SO_4$. Both CH3C.18 and CH3C.35 bound to the apical domain in this assay.

Figure 16A:
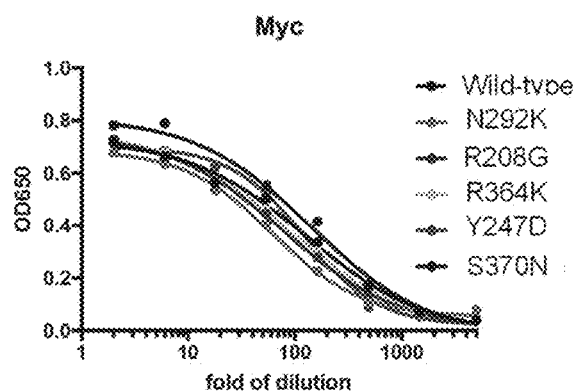
FIGS. 16A-16E show binding of CH3C clones to the apical domain displayed on phage.
Figure 16B:
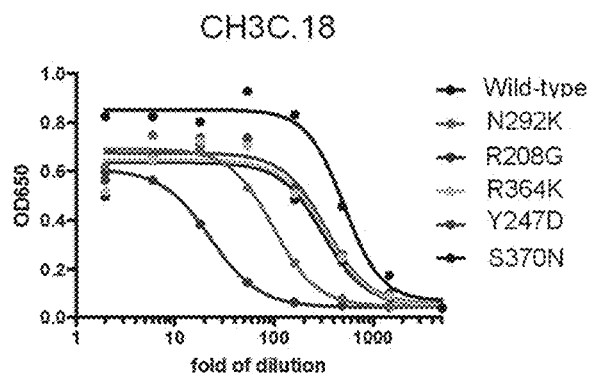
Figure 16C:
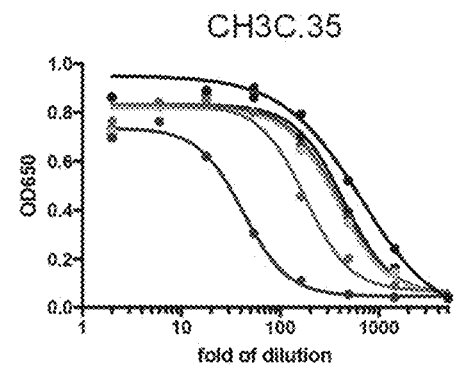
Figure 16D:
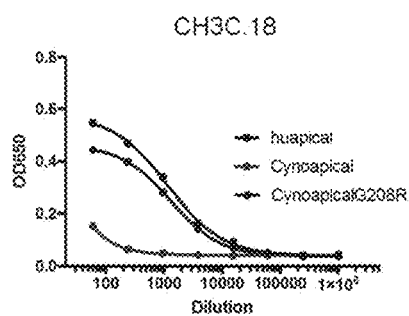
Figure 16E:
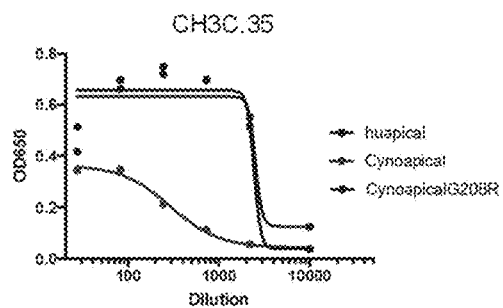
Figure 17A:
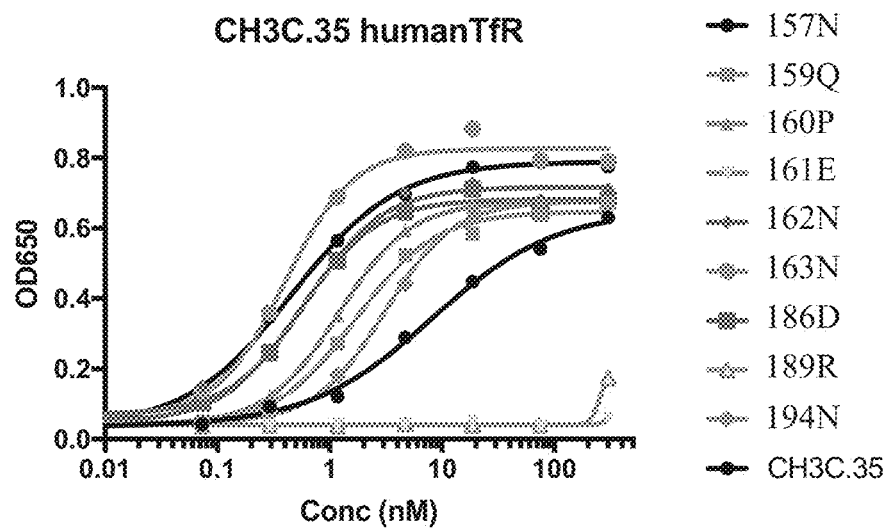
FIGS. 17A-17D show paratope mapping of CH3C variants by reverting mutated positions to wild-type residues.
Figure 17B:
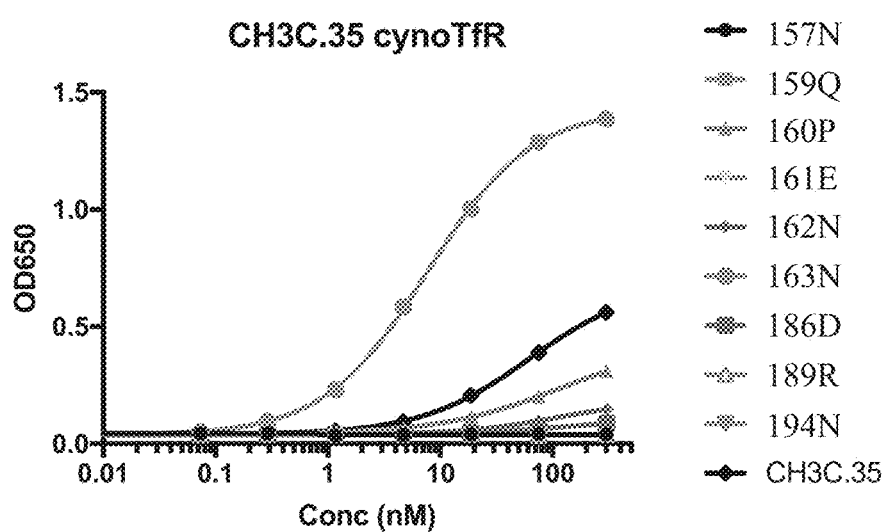
Figure 17C:
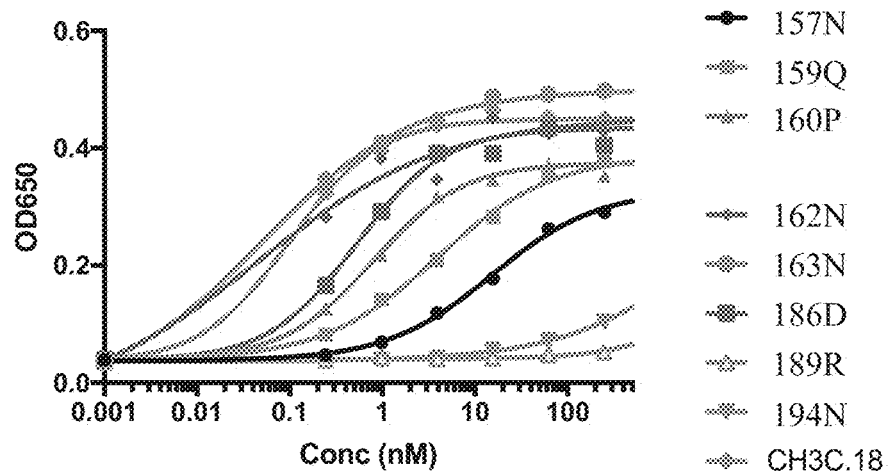
Figure 17D:
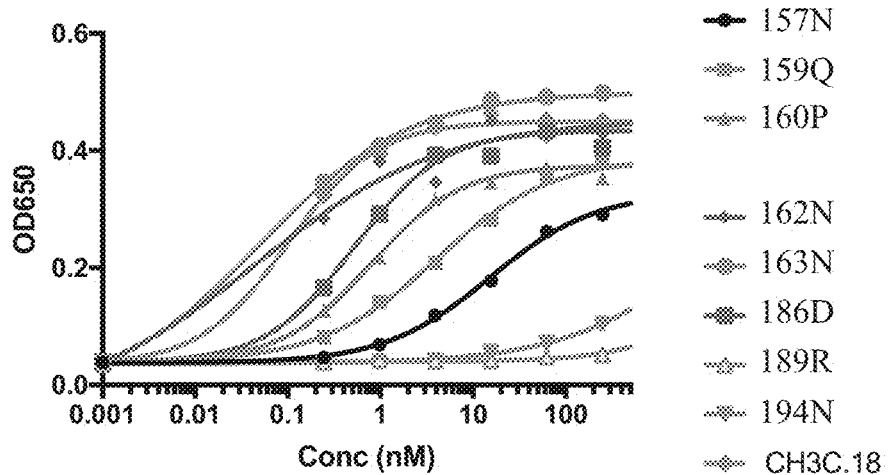
Figure 19A:
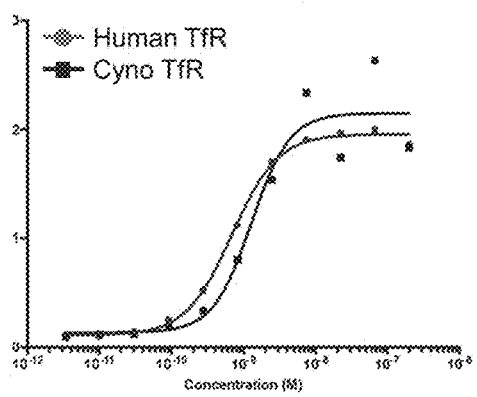
FIGS. 19A-19E show binding ELISAs of CH3C variants from consensus maturation libraries to human or cyno TfR. The new variants (i.e., CH3C.3.2-1, CH3C.3.2-5, and CH3C.3.2-19) had similar binding $EC_{50}$ values to cyno and human TfR, whereas the parental clones CH3C.18 and CH3C.35 had significantly better $EC_{50}$ values for human versus cyno TfR.
Figure 19B:
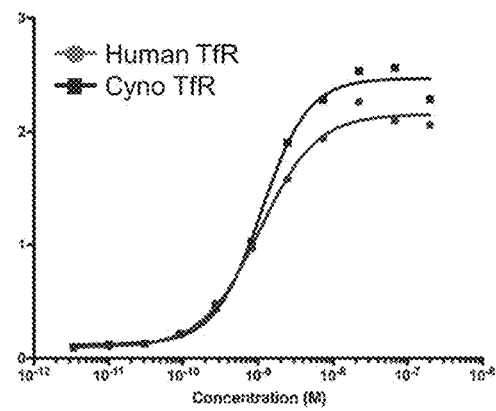
Figure 19C:
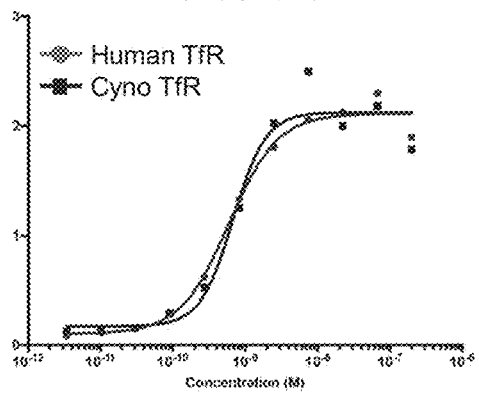
Figure 19D:
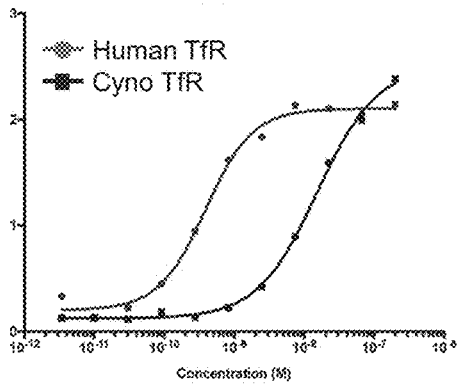
Figure 19E:
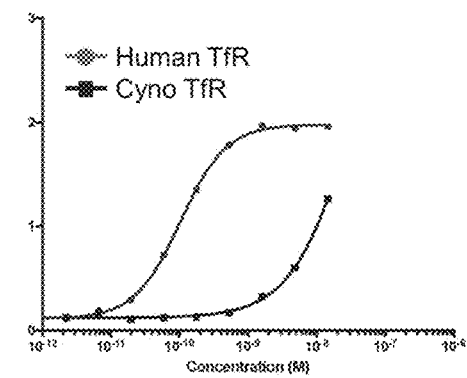

Since binding to cyno TfR was known to be much weaker than binding to human TfR, it was hypothesized that one or more of the amino acid differences between cyno and human apical domains was likely responsible for the binding difference. Therefore, a series of six-point mutations was made in the human TfR apical domain where the human residue was replaced with the corresponding cyno residue. These mutants were displayed on phage and the phage concentrations were normalized by $OD_{268}$ and binding to CH3C.18 and CH3C.35 was tested by phage ELISA titration (FIGS. 16B and 16C). Capture on anti-Myc antibody 9E10 showed that display levels for all mutants were similar (FIG. 16A). Binding to the human TfR mutations clearly showed a strong effect of the R208G mutation, which suggested that this residue is a key part of the epitope and is negatively impacted by the cyno residue at this position. The G208R mutation was made on phage-displayed cyno apical domain and it was shown that this mutation dramatically improved binding to cyno apical domain (FIGS. 16D and 16E). These results show that the CH3C clones bound to the apical domain of TfR and that position 208 was important for binding, while positions 247, 292, 364, 370, and 372 were significantly less important.

Paratope Mapping

To understand which residues in the Fc domain were most critical for TfR binding, a series of mutant CH3C.18 and CH3C.35 clones was created in which each mutant had a single position in the TfR binding register mutated back to wild-type. The resulting variants were expressed recombinantly as CH3C Fc-Fab fusions and tested for binding to human or cyno TfR (FIG. 17). For CH3C.35, positions 161 and 194 were absolutely critical for binding; reversion of either of these to wild-type completely ablated binding to human TfR. Surprisingly, reverting position 163 to wild-type provided a dramatic boost to cyno TfR binding, while having little effect on human binding. Conversely, the reversion of residue 163 to wild-type had little effect in CH3C.18, but in this variant reversion of positions 189 and 194 completely abolished binding to human TfR. In both variants, other single reversions had modest (detrimental) impact on human TfR binding, while in many cases binding to cyno TfR was abolished.

Additional Engineering to Improve Binding to Cyno TfR

Additional libraries were prepared to further increase the affinity of the CH3C variants for cyno TfR. These libraries were designed to be of less than about $10^7$ clones in terms of theoretical diversity, so that the full diversity space could be explored using yeast surface display. The design of these libraries is shown in FIG. 18. Four library designs were used; all libraries were generated using degenerate oligos with NNK or other degenerate codon positions, and amplified by overlap PCR, as described above.

The first library was based on the consensus of CH3C.35-like sequences (FIG. 18A). Here, positions 157-161 were held constant as YGTEW (SEQ ID NO:115), while positions 162, 163, 186, 189, and 194 were mutated using saturation mutagenesis.

The second library was based on the consensus of CH3C.18-like sequences (FIG. 18B). Here, position 157 was restricted to Leu and Met, position 159 was restricted to Leu and His, position 160 was held constant as Val, position 161 was restricted to Trp and Gly, position 162 was restricted to Val and Ala, position 163 was fully randomized, position 164 was added to the register and fully randomized, position 186 was soft randomized, position 189 was fully randomized, and position 194 was restricted to aromatic amino acids and Leu.

The third library added new randomized positions to the library (FIG. 18C). Two versions were generated, one each with CH3C.18 and CH3C.35 as the starting register, and then additional positions were randomized by saturation mutagenesis: E153, E155, Y164, S188, and Q192.

The fourth library held certain positions constant for CH3C.18 but allowed variation at other positions, with less bias than the consensus library (FIG. 18D). Positions 160, 161, and 186 were fixed, and positions 157, 159, 162, 163, and 189 were randomized by saturating mutagenesis; position 194 was mutated but restricted to aromatic residues and Leu.

The libraries were selected in yeast for four to five rounds against cynoTfR and single clones were sequenced and converted to polypeptide-Fab fusions, as described above. The greatest enrichment in cynoTfR binding was observed from the second library (i.e., derivatives of the CH3.18 parent), though there was also some loss in huTfR binding.

Binding Characterization of CH3C Maturation Clones

Binding ELISAs were conducted with purified CH3C Fc-Fab fusion variants with human or cyno TfR coated on the plate, as described above. The variants from the CH3C.18 maturation library, CH3C3.2-1, CH3C.3.2-5, and CH3C.3.2-19, bound human and cyno TfR with approximately equivalent $EC_{50}$ values, whereas the parent clone CH3C.18, and CH3C.35, had greater than 10-fold better binding to human versus cyno TfR (FIG. 19).

Figure 20:
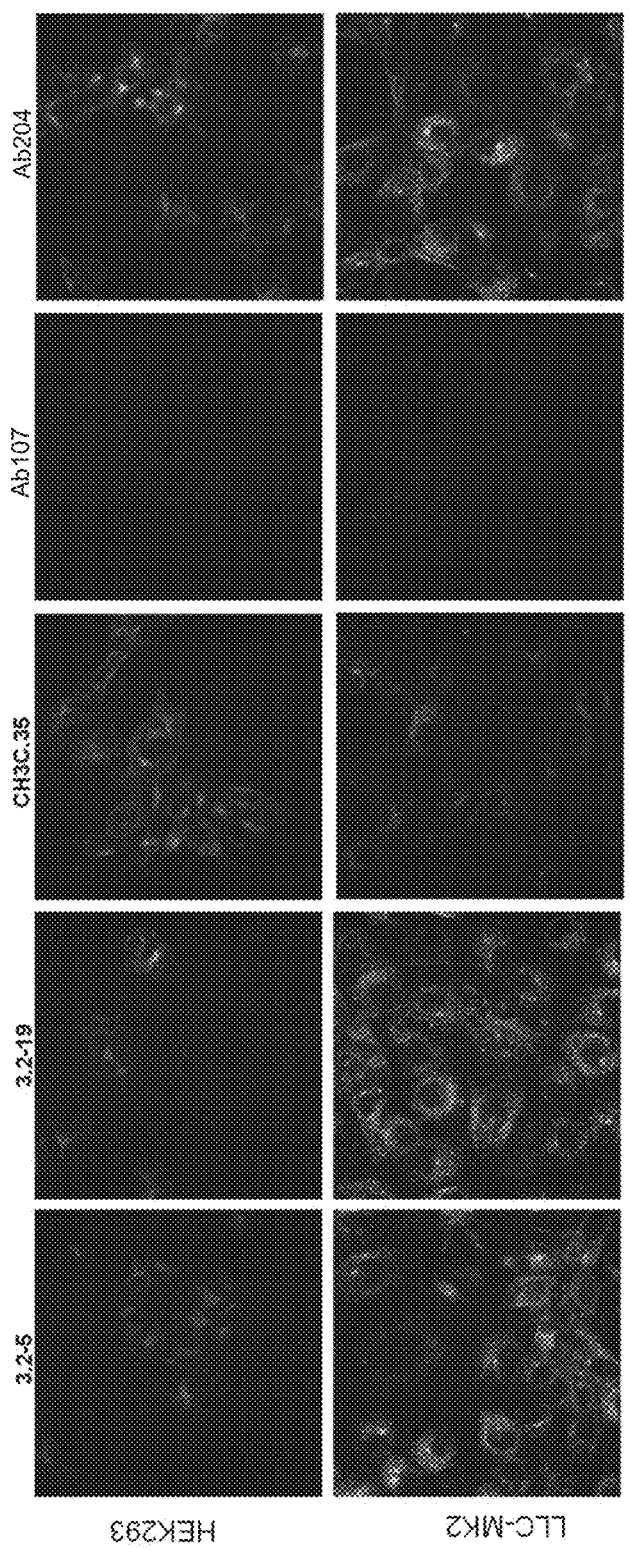
FIG. 20 shows internalization of CH3C variants from consensus maturation libraries in human (HEK293) and monkey (LLC-MK2) cells. Clones CH3C.3.2-5 and CH3C3.2-19, which had similar human and cyno TfR affinities, had significantly improved uptake in monkey cells as compared to clone CH3C.35, which bound better to human TfR. Ab107, an anti-BACE1 antibody, was used as a negative control. (BACE1 is not expressed on HEK293 or MK2 cells). Ab204, an anti-TfR antibody, was used as a positive control.

Next, it was tested whether the new polypeptides internalized in human and monkey cells. Using the protocol previously described above in the section titled "Characterization of first generation CH3C clones," internalization in human HEK293 cells and rhesus LLC-MK2 cells was tested. As shown in FIG. 20, the variants that similarly bound human and cyno TfR, CH3C.3.2-5 and CH3C.3.2-19, had significantly improved internalization in LLC-MK2 cells as compared with CH3C.35.

Additional Engineering of CH3C Clones

Figure 21:
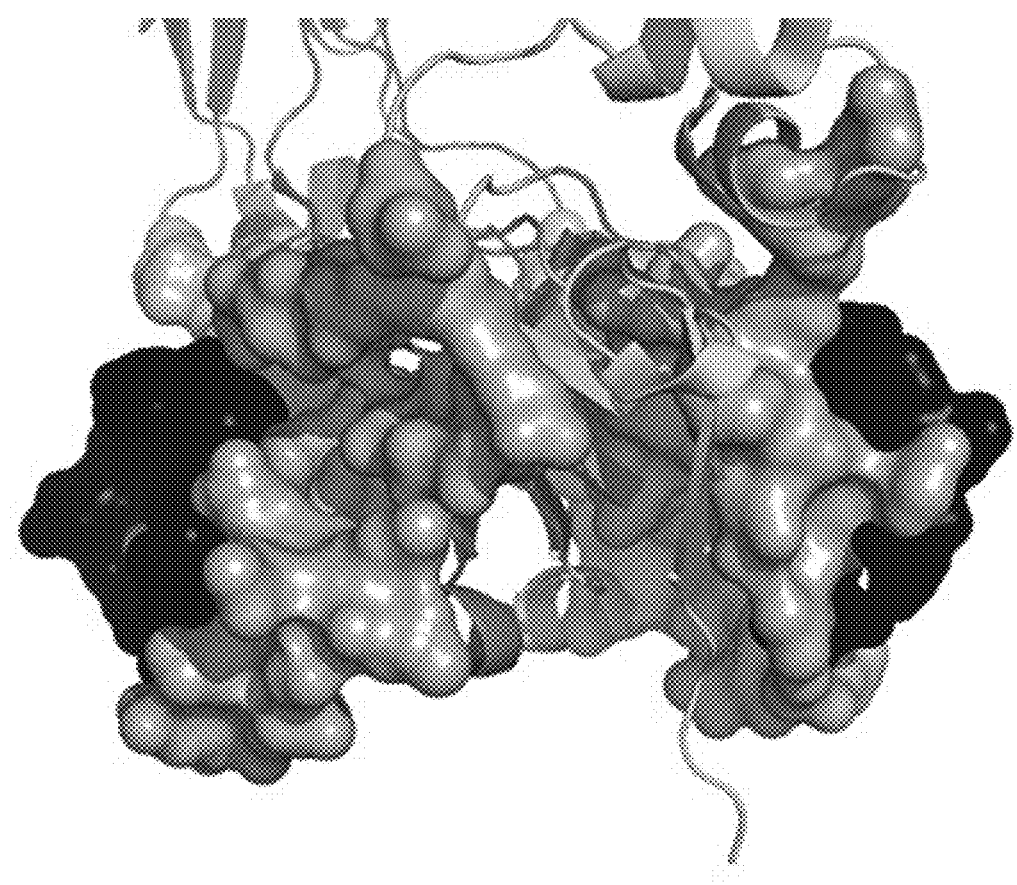
FIG. 21 shows a map of NNK walk residues depicted on the CH3 structure (adapted from PDB 4W40

Additional engineering to further affinity mature clones CH3C.18 and CH3C.35 involved adding additional mutations to the backbone (i.e., non-register) positions that enhanced binding through direct interactions, second-shell interactions, or structure stabilization. This was achieved via generation and selection from an "NNK walk" or "NNK patch" library. The NNK walk library involved making one-by-one NNK mutations of residues that are near to the paratope. By looking at the structure of Fc bound to FcgRI (PDB ID: 4W40), 44 residues near the original library register, as shown in FIG. 21, were identified as candidates for interrogation. Specifically, the following residues were targeted for NNK mutagenesis: K21, R28, Q115, R117, E118, Q120, T132, K133, N134, Q135, S137, K143, E153, E155, S156, G158, Y164, K165, T166, D172, S173, D174, S176, K182, L183, T184, V185, K187, S188, Q191, Q192, G193, V195, F196, S197, S199, Q211, S213, S215, L216, S217, P218, G219, and K220. The 44 single point NNK libraries were generated using Kunkel mutagenesis, and the products were pooled and introduced to yeast via electroporation, as described above for other yeast libraries.

Figure 22:
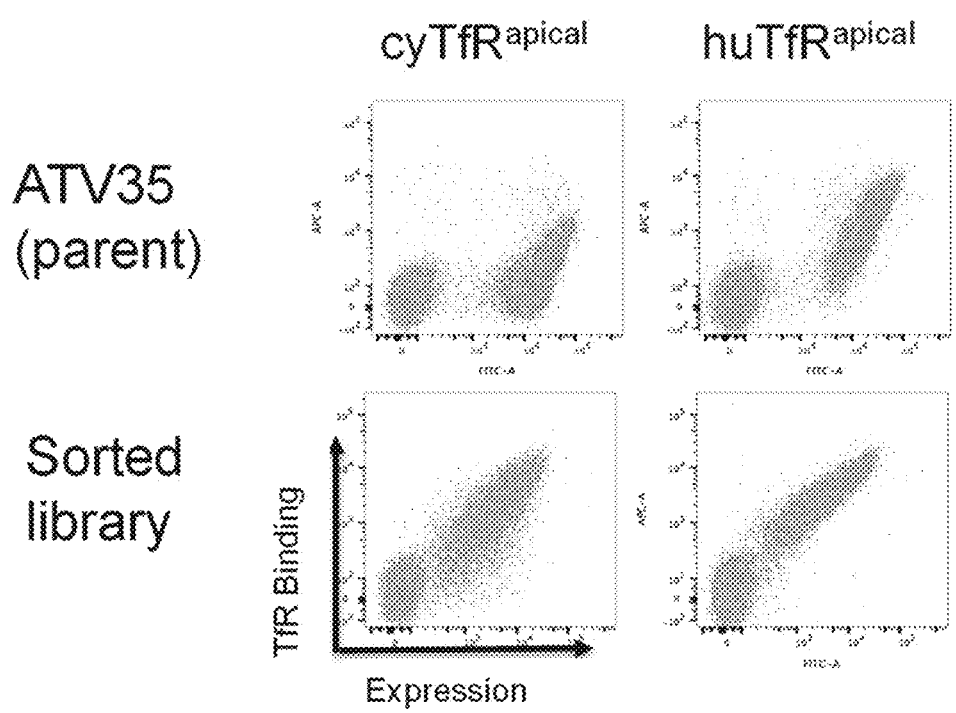

The combination of these mini-libraries (each of which had one position mutated, resulting in 20 variants) generated a small library that was selected using yeast surface display for any positions that lead to higher affinity binding. Selections were performed as described above, using TfR apical domain proteins (FIG. 22). After three rounds of sorting, clones from the enriched yeast library were sequenced, and several "hot-spot" positions were identified where certain point mutations significantly improved the binding to apical domain proteins. For CH3C.35, these mutations included E153 (mutated to Trp, Tyr, Leu, or Gln) and S188 (mutated to Glu). The sequences of the CH3C.35 single and combination mutants are set forth in SEQ ID NOS:21-23, 236-241, and 297-299. For CH3C.18, these mutations included E153 (mutated to Trp, Tyr, or Leu) and K165 (mutated to Gln, Phe, or His). The sequences of the CH3C.18 single mutants are set forth in SEQ ID NOS:242-247.

The "NNK patch" approach was similar to that described above for the CH3B library, but with patches directly adjacent to the CH3C register. Clone CH3C.35 was used as a starting point and the following libraries were generated:

CH3C-patch1: amino acid positions: K21, R28, Y164, K165, and T166;

CH3C-patch2: amino acid positions: Q115, R117, E118, Q120, and K143;

CH3C-patch3: amino acid positions: T132, K133, N134, Q135, and S137;

CH3C-patch4: amino acid positions: E153, E155, S156, and G158;

CH3C-patch5: amino acid positions: D172, S173, D174, S176, and K182;

CH3C-patch6: amino acid positions: L183, T184, V185, K187, and S188;

CH3C-patch7: amino acid positions: Q191, Q192, G193, V195, and F196;

CH3C-patch8: amino acid positions: S197, S199, Q211, S213, and S215; and

CH3C-patch9: amino acid positions: L216, S217, P218, G219, and K220.

Selections were performed as described above, using TfR apical domain proteins. However, no clones with enhanced binding were identified.

Additional Maturation Libraries to Improve CH3C.35 Affinity

An additional library to identify combinations of mutations from the NNK walk library, while adding several additional positions on the periphery of these, was generated as described for previous yeast libraries. In this library, the YxTEWSS and TxxExxxxF motifs were kept constant, and six positions were completely randomized: E153, K165, K187, S188, S197, and S199. Positions E153 and S188 were included because they were "hot spots" in the NNK walk library. Positions K165, S197, and S199 were included because they make up part of the core that may position the binding region, while K187 was selected due to its adjacency to position 188.

This library was sorted, as previously described, with the cyno TfR apical domain only. The enriched pool was sequenced after five rounds, and the sequences of the CH3 regions of the identified unique clones are set forth in SEQ ID NOS:248-265.

Exploration of Acceptable Diversity within the Original Register and Hot Spots for CH3C.35.21

Figure 23A:
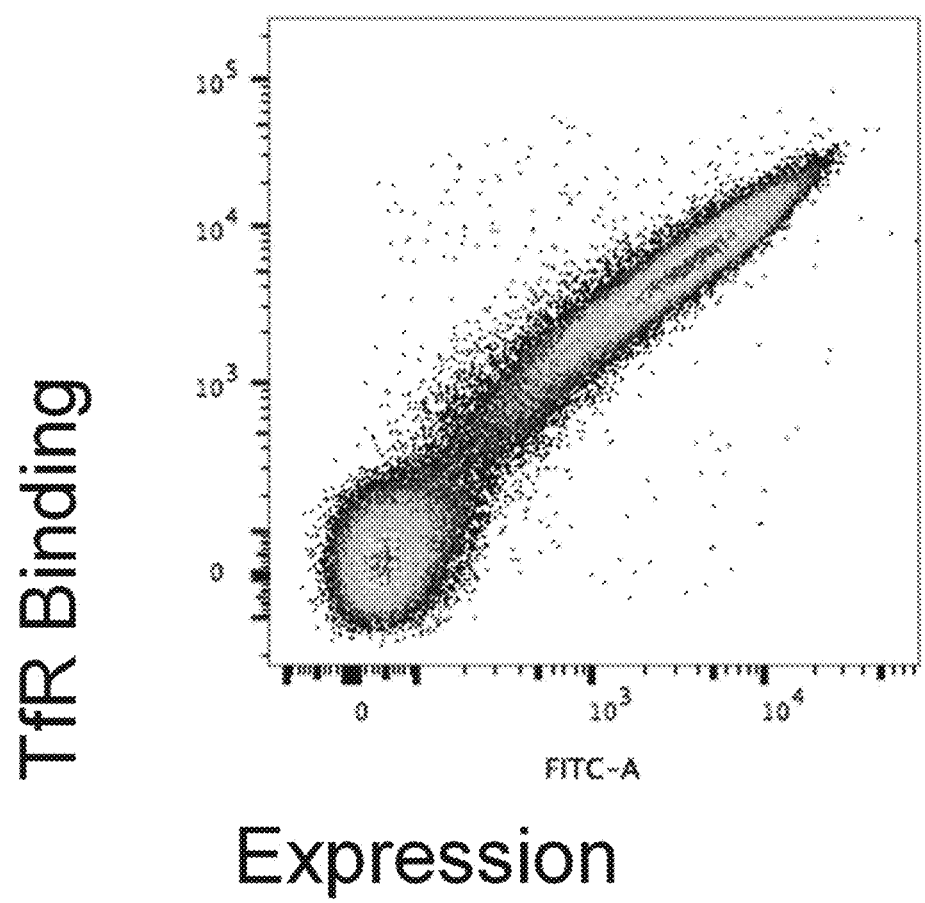
Figure 23B:
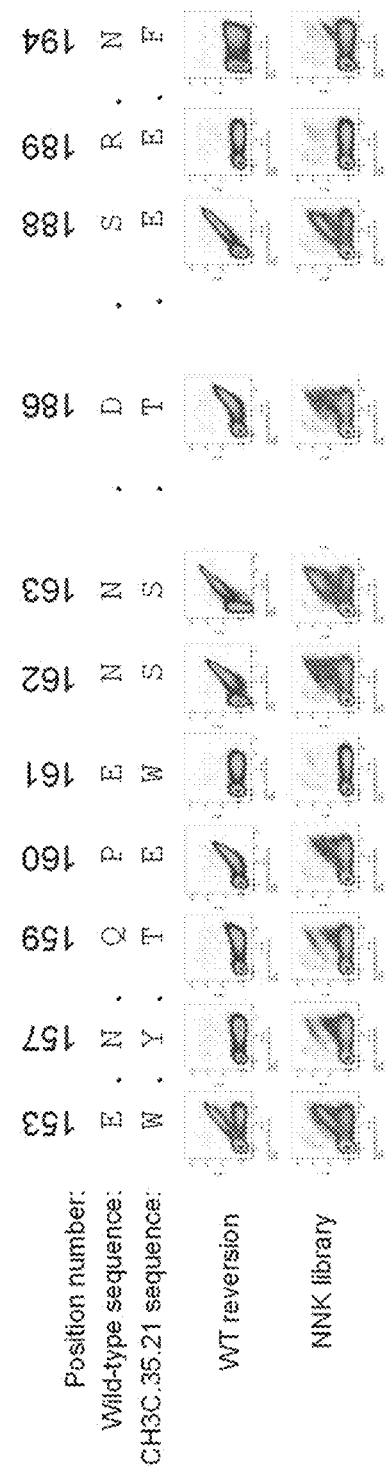
Figure 24A:
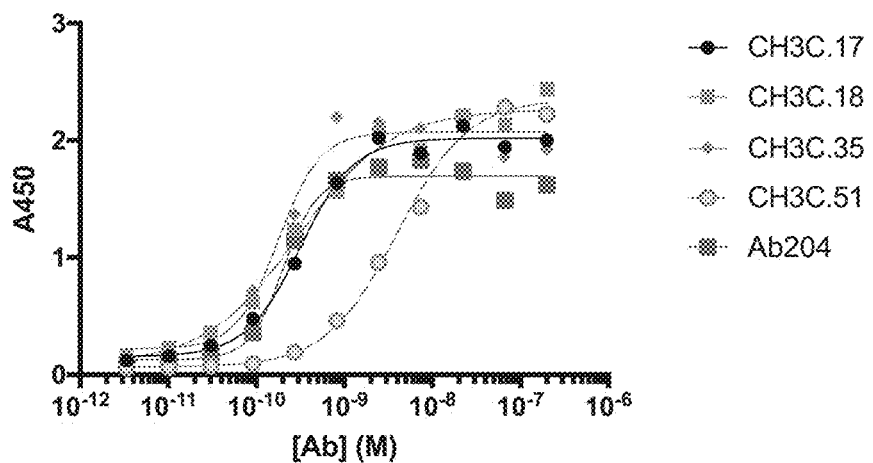
Figure 24B:
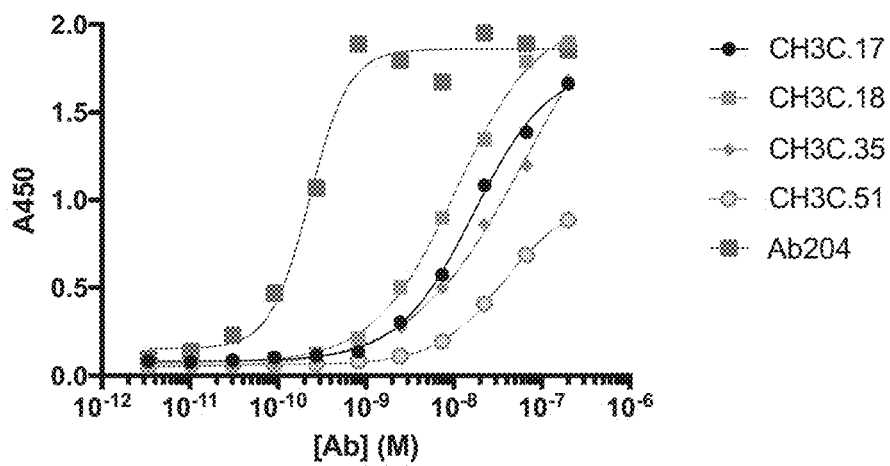
Figure 24C:
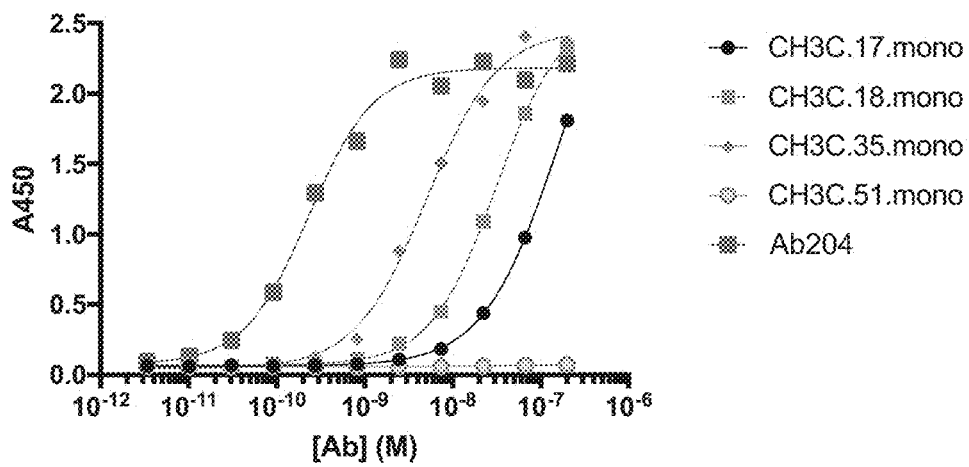
Figure 24D:
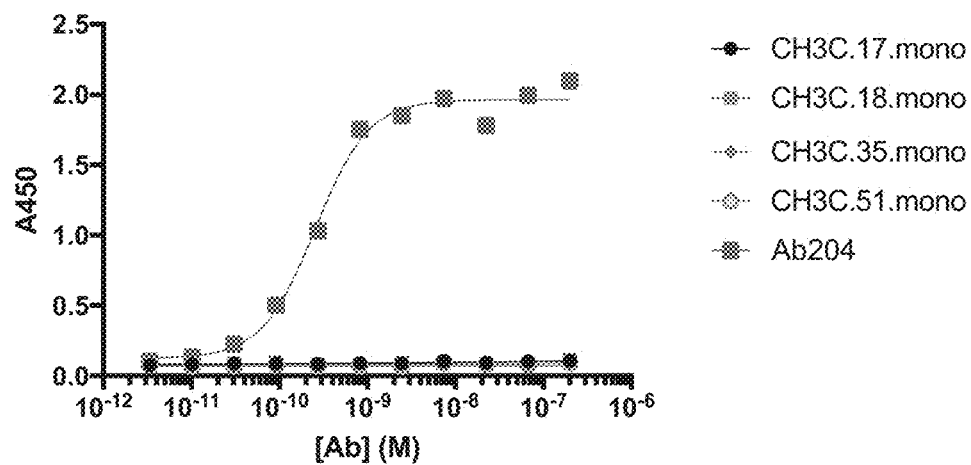
Figure 25A:
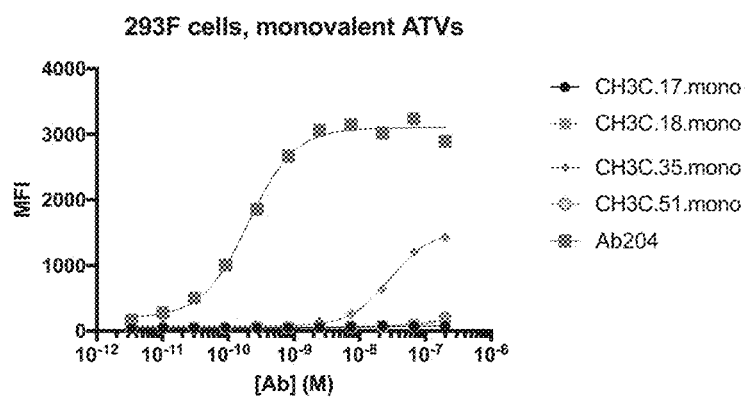
Figure 25B:
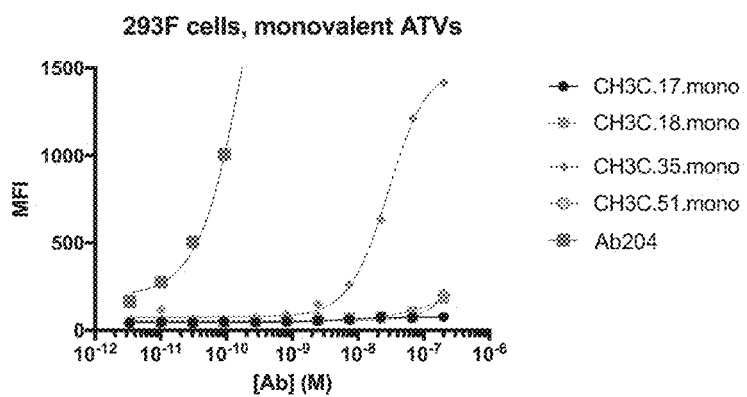
Figure 25C:
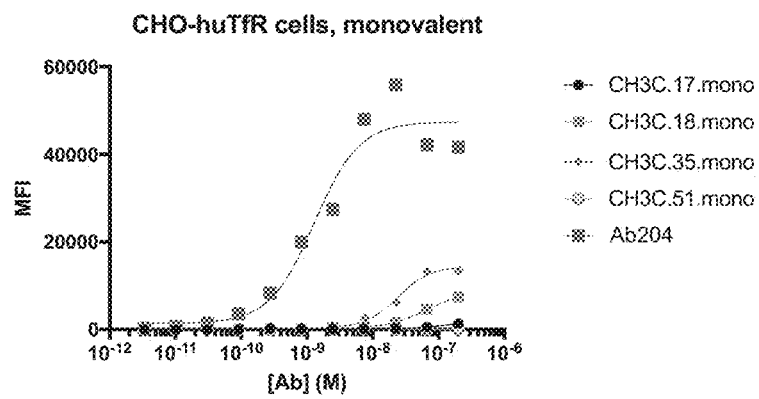
Figure 25D:
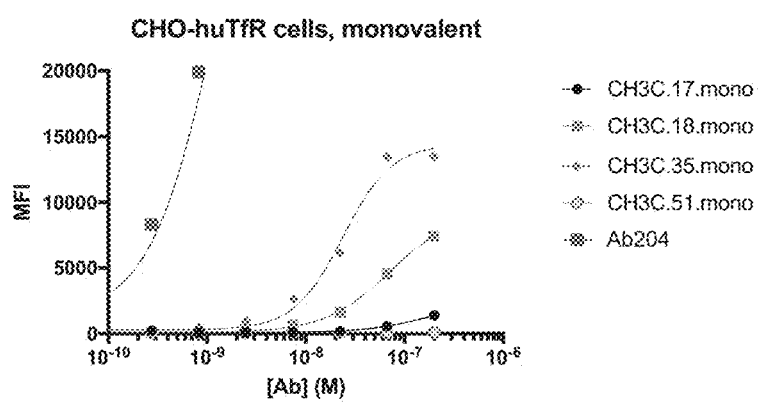
Figure 25E:
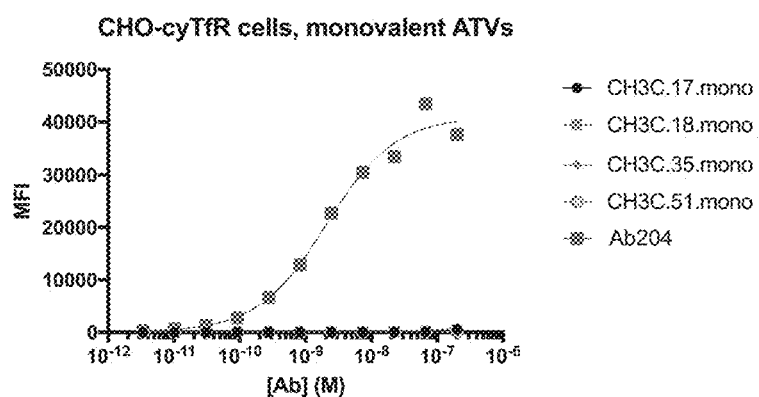
Figure 26:
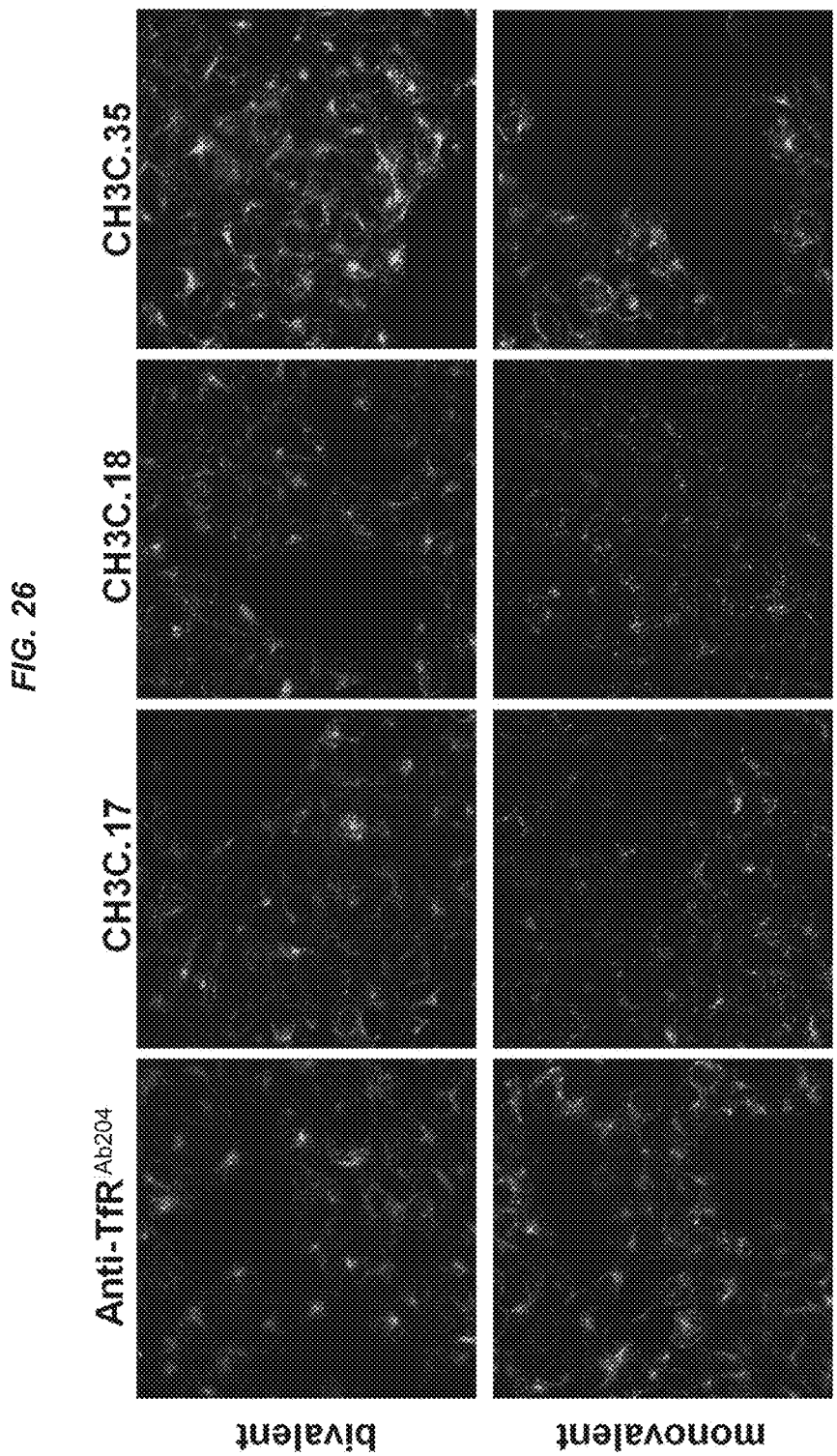
Figure 27E:
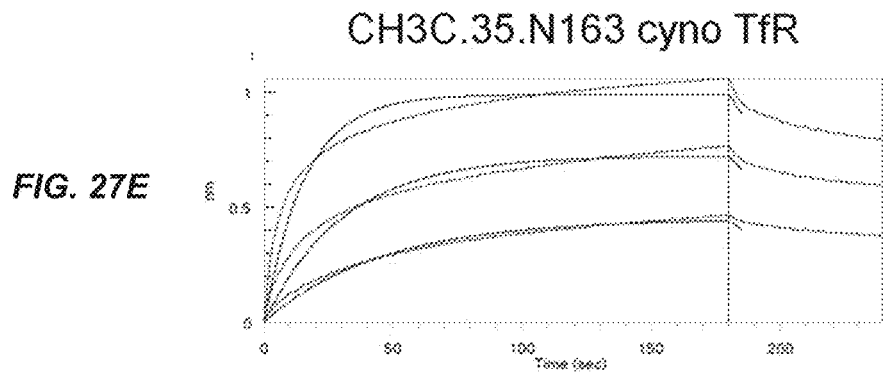
Figure 27F:
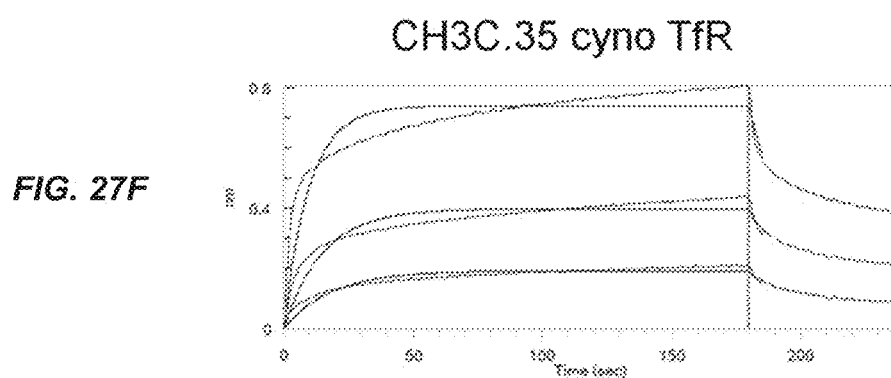
Figure 27G:
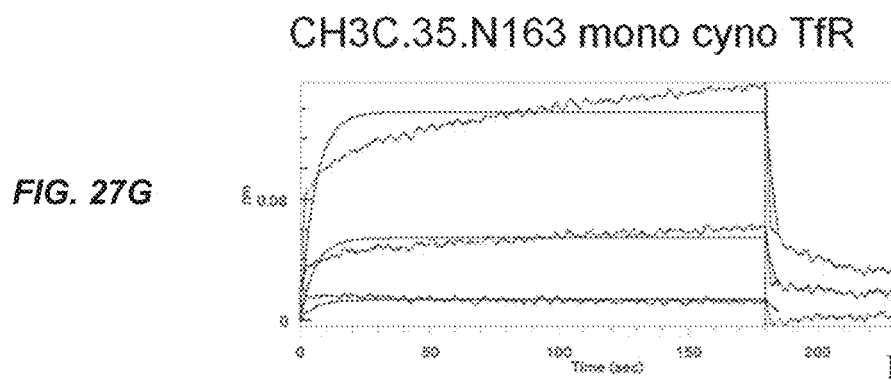
Figure 27H:
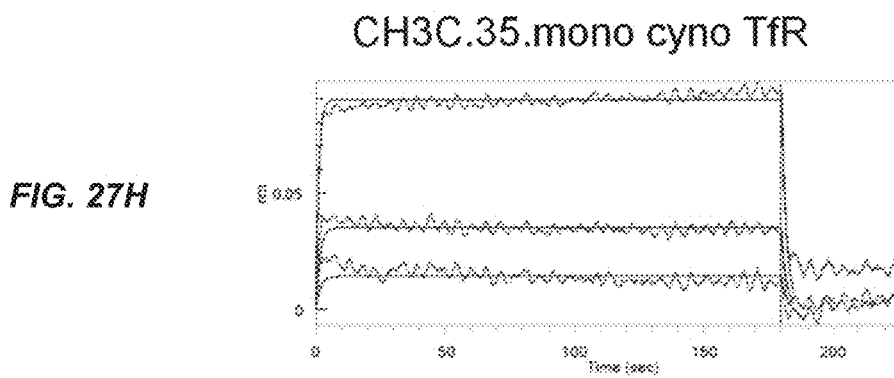
Figure 28A:
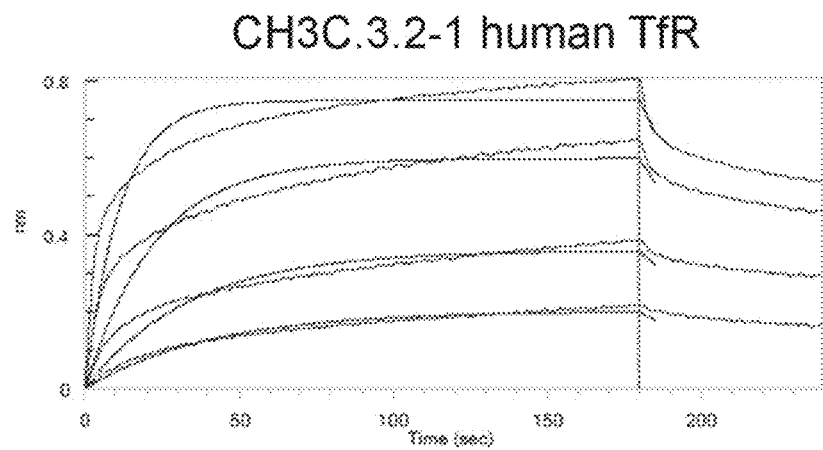
Figure 28B:
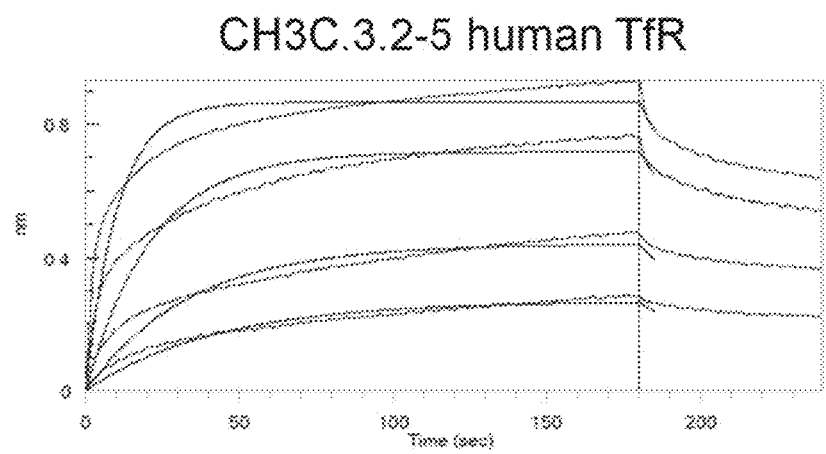
Figure 28C:
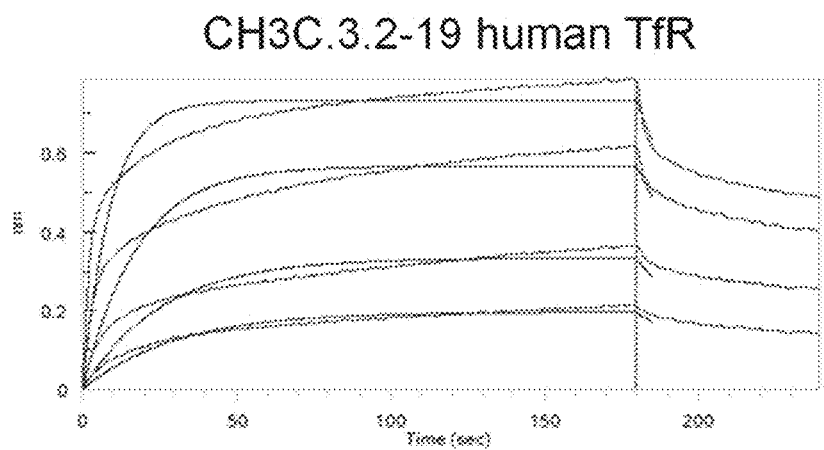
Figure 28D:
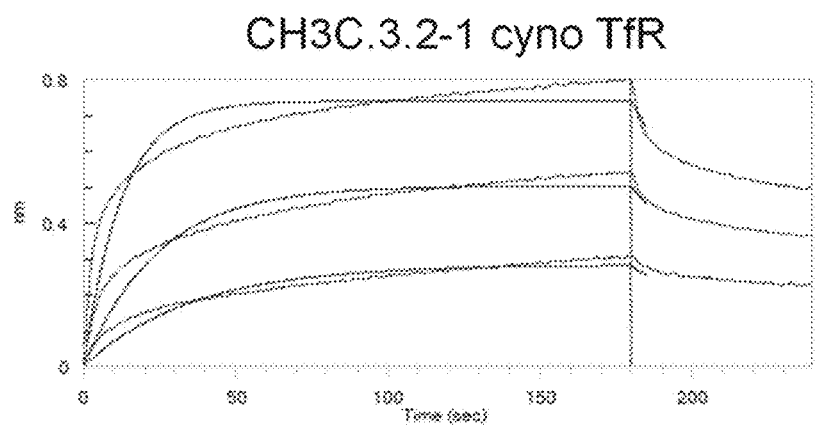
Figure 28E:
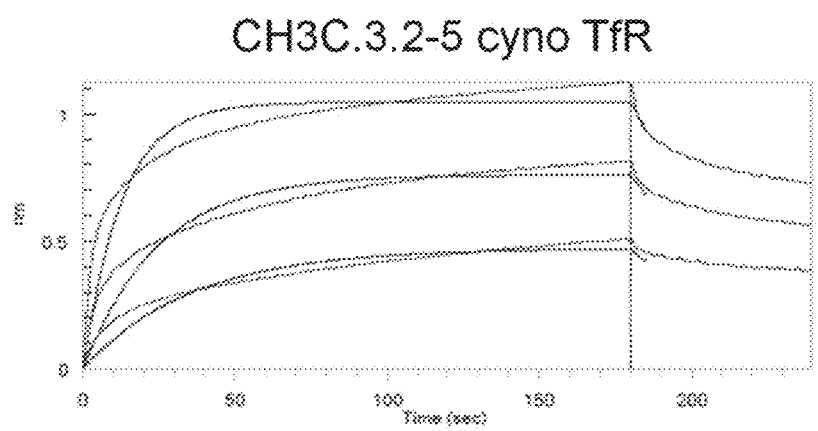
Figure 28F:
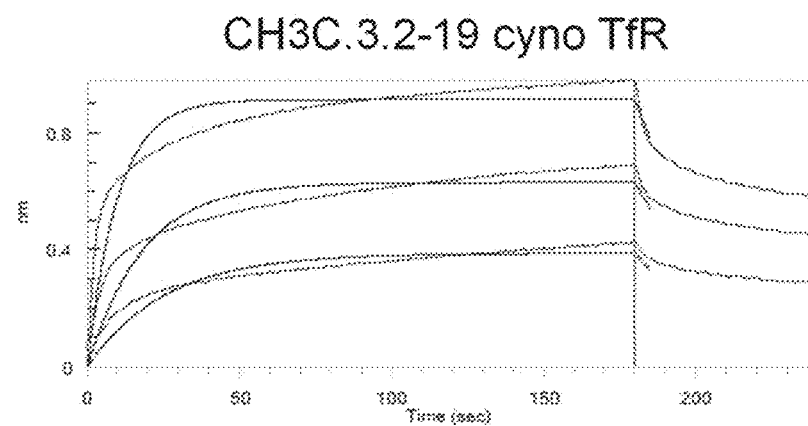

The next libraries were designed to explore the totality of acceptable diversity in the main binding paratope. The approach taken was similar to the NNK walk libraries. Each of the original register positions (157, 159, 160, 161, 162, 163, 186, 189, and 194) plus the two hot spots (153 and 188) were individually randomized with NNK codons to generate a series of single-position saturation mutagenesis libraries on yeast. In addition, each position was individually reverted to the wild-type residue, and these individual clones were displayed on yeast. FIG. 23 shows binding of the parental clone CH3C.35.21 as compared to the wild-type reversions and single-position NNK libraries. It was noted that positions 153, 162, 163, and 188 were the only positions that retained substantial binding to TfR upon reversion to the wild-type residue (some residual but greatly diminished binding was observed for reversion of 186 to wild-type).

The single-position NNK libraries were sorted for three rounds against the human TfR apical domain to collect the top ~5% of binders, and then at least 16 clones were sequenced from each library. The results indicate what amino acids at each position can be tolerated without significantly reducing binding to human TfR, in the context of the CH3C.35 clone. A summary is below:

Position 153: Trp, Leu, or Glu;
Position 157: Tyr or Phe;
Position 159: Thr only;
Position 160: Glu only;
Position 161: Trp only;
Position 162: Ser, Ala, or Val (note that although the wild type Asn residue seems to retain some binding, it did not appear following library sorting);
Position 163: Ser or Asn;
Position 186: Thr or Ser;
Position 188: Glu or Ser;
Position 189: Glu only; and
Position 194: Phe only.

The above residues, when substituted into clone CH3C.35 as single changes or in combinations, represent paratope diversity that retains binding to TfR apical domain. Clones having mutations at these positions are shown in Table 9, and the sequences of the CH3 domains of these clones are set forth in SEQ ID NOS:237-241, 264, and 266-296.

Monovalent Polypeptide-Fab Fusions

Generation of Monovalent TfR-Binding Polypeptide-Fab Fusions

Although Fc domains naturally form homodimers, a series of asymmetric mutations known as “knobs-in-holes” can lead to preferential heterodimerization of two Fc fragments, where one Fc unit has the T139W knob mutation (which corresponds to position 366 using EU numbering scheme) and the other Fc unit has the T139S, L141A, and Y180V hole mutations (positions 366, 368, and 407, respectively using EU numbering scheme). In some embodiments, a modified CH3 domain of the invention comprises a Trp at position 139. In some embodiments, a modified CH3 domain of the invention comprises a Ser at position 139, an Ala at position 141 and a Val at position 180. Heterodimeric TfR-binding polypeptides were expressed in 293 or CHO cells by transient co-transfection of two plasmids (i.e., a knob-Fc and a hole-Fc), while polypeptide-Fab fusions were expressed by transient co-transfection of three plasmids (i.e., a knob-Fc-Fab heavy chain, a hole-Fc-Fab heavy chain, and a common light chain). Purification of secreted heterodimeric polypeptides or polypeptide-Fab fusions was performed identically to that for homodimers (i.e., a two-column purification using Protein A followed by size-exclusion, and then concentration and buffer exchange if required). Mass-spectrometry or hydrophobic interaction chromatography was used to determine the amount of heterodimer versus homodimer (e.g., knob-knob or hole-hole paired Fc's) formed. From typical preps, greater than 95% of polypeptides, and often greater than 98%, were heterodimers. For clarity, all monovalent TfR binders (Fc homodimers) generated in this fashion were named “ZZ.mono” where ZZ was the name of the polypeptide and “.mono” indicated monovalent TfR binding. For heterodimeric polypeptides and polypeptide-Fab fusions, the mutations that conferred TfR binding included the “knob” mutation, whereas a non-TfR-binding Fc region was used with the “hole” region, unless otherwise indicated. In some cases, additional mutations that alter Fc properties were also included in these constructs, such as L7A/L8A, M25Y/S27T/T29E, N207S, or N207S/M201L for modified FcγR or FcRn binding, respectively.

Binding Characterization of CH3C. Mono Fc Polypeptides

Binding of monovalent CH3C polypeptides was measured in an ELISA using a modification of the procedure described above. Streptavidin was coated on 96-well ELISA plates overnight at 1 μg/mL in PBS. After washing, the plates were blocked with 1% BSA in PBS, then biotinylated human or cyno TfR was added at 1 μg/mL and incubated for 30 minutes. After additional washing, polypeptides were added to the plates at serial dilutions, and incubated for 1 hour. The plates were washed and secondary antibody (i.e., anti-kappa-HRP, 1:5,000) was added for 30 minutes and the plates were washed again. The plates were developed with TMB substrate and quenched with 2N $H_2SO_4$ and then absorbance at 450 nm was read on a BioTek® plate reader. Results are shown in FIG. 24, which directly compares standard (i.e., bivalent TfR-binding) and monovalent TfR-binding polypeptides. Ab204 is a high affinity anti-TfR control antibody.

Additional testing was performed for binding to 293F cells, which endogenously express human TfR, as well as CHO-K1 cells that were stably transfected with human TfR or cyno TfR (FIG. 25).

In general, substantially reduced binding to human TfR for monovalent polypeptides was observed as compared to bivalent polypeptides, and cyno binding was too weak to be detected in these assays for the monovalent polypeptides.

Next it was tested whether monovalent versions of CH3C polypeptides could internalize in human-TfR expressing HEK293 cells. Methods described above for internalization assays were used. As shown in FIG. 26, which compares bivalent and monovalent polypeptides, the monovalent peptides could also internalize, but the overall signal was weaker than for the respective bivalent versions, presumably due to the loss of binding affinity/avidity.

Kinetics of Binding for CH3C Polypeptides Measured by Biolayer Interferometry

Binding kinetics were determined for several monovalent and bivalent CH3C polypeptide variants, fused to anti-BACE1 Fabs, and compared to their bivalent equivalents using biolayer interferometry (i.e., using an Octet® RED system). TfR was captured on a streptavidin sensor, then CH3C polypeptides were bound and washed off. Sensograms were fitted to a 1:1 binding model; the $K_D$ (app) value for bivalent polypeptides represented avid binding to the TfR dimer. The results are shown in Table 10 and FIGS. 27 and 28.

TABLE 10

Kinetics for CH3C polypeptides using Octet ® Red

| Polypeptide | $K_D$ (app) (nM) [human TfR] | $K_D$ (app) (nM) [cyno TfR] |
|---|---|---|
| CH3C.35.N163 | 67 | 374 |
| CH3C.35.N163.mono | 251 | n.d. |
| CH3C.35 | 59 | 934 |
| CH3C.35.mono | 483 | n.d. |
| CH3C.3.2-1 | 337 | 367 |
| CH3C.3.2-5 | 270 | 385 |
| CH3C.3.2-19 | 367 | 454 | n.d. = not determined due to too low binding signal

The polypeptides that were converted to monovalent format had significantly weaker $K_D$ (app) values, due to loss of avidity. Clones CH3C.3.2-1, CH3C.3.2-5, and CH3C.3.2-19, which were previously shown to have similar human and cyno TfR binding by ELISA, also had very similar $K_D$ (app) values between human and cyno TfR. An attempt was made to test the monovalent forms of these polypeptides, but the binding in this assay was too weak to calculate kinetic parameters.

Example 3. Binding Characterization of Additional CH3C Variants Using Biacore™

The affinity of clone variants for recombinant TfR apical domain was determined by surface plasmon resonance using a Biacore™ T200 instrument. Biacore™ Series S CM5 sensor chips were immobilized with anti-human Fab (human Fab capture kit from GE Healthcare). 5 g/mL of polypeptide-Fab fusion was captured for 1 minute on each flow cell and serial 3-fold dilutions of human or cyno apical domain were injected at a flow rate of 30 μL/min at room temperature. Each sample was analyzed with a 45-second association and a 3-minute dissociation. After each injection, the chip was regenerated using 10 mM glycine-HCl (pH 2.1). Binding response was corrected by subtracting the RU from a flow cell capturing an irrelevant IgG at similar density. Steady-state affinities were obtained by fitting the response at equilibrium against the concentration using Biacore™ T200 Evaluation Software v3.1.

To determine the affinity of clone variants for recombinant TfR ectodomain (ECD), Biacore™ Series S CM5 sensor chips were immobilized with streptavidin. Biotinylated human or cyno TfR ECD was captured for 1 minute on each flow cell and serial 3-fold dilutions of clone variants were injected at a flow rate of 30 μL/min at room temperature. Each sample was analyzed with a 45-second association and a 3-minute dissociation. The binding response was corrected by subtracting the RU from a flow cell without TfR ECD at a similar density. Steady-state affinities were obtained by fitting the response at equilibrium against the concentration using Biacore™ T200 Evaluation Software v3.1.

The binding affinities are summarized in Table 11. Affinities were obtained by steady-state fitting.

TABLE 11

Binding affinities for additional CH3C variants

| Clone | Human TfR (uM) | Cyno TfR (uM) | Human apical TfR (uM) | Cyno apical TfR (uM) |
|---|---|---|---|---|
| CH3C.35.19.mono | 0.4 | 5.9 | 0.37 | 5.6 |
| CH3C.35.20.mono | 0.25 | 6.7 | 0.17 | 8 |
| CH3C.35.21.mono | 0.1 | 2.1 | 0.12 | 2.2 |
| CH3C.35.24.mono | 0.29 | 3.3 | 0.23 | 3 |
| CH3C.35.21.11.mono | 0.24 | 4 | 0.13 | 2.2 |
| CH3C.35.21.16.mono | 0.18 | 1.8 | 0.12 | 1.9 |
| CH3C.35.21.17.mono | 0.3 | 2.9 | 0.13 | 2.6 |
| CH3C.35.mono | 0.61 | >10 | 0.61 | >10 |
| CH3C.35.N153.mono | 0.42 | >10 | 0.95 | >10 |
| CH3C.35.bi | 0.22 | >2 | not tested | not tested |
| CH3C.35.N153.bi | 0.37 | 3.3 | not tested | not tested |
| CH3C.3.2-19.bi | 5.2 | 5.6 | not tested | not tested |
| CH3C.35.19.bi | 0.074 | 1.5 | not tested | not tested |
| CH3C.35.20.bi | 0.054 | 1.7 | not tested | not tested |
| CH3C.35.21.bi | 0.049 | 0.7 | not tested | not tested |
| CH3C.35.24.bi | 0.061 | 0.65 | not tested | not tested |

Example 4. Binding Characterization of CH3C Variants to FcRn

FcRn binding assays were performed using a FortéBio® Octet® RED384 instrument using FortéBio® Streptavidin biosensors. Biotinylated recombinant BACE1 was diluted to a concentration of 10 μg/mL in kinetic buffer (obtained from FortéBio®) and captured onto individual biosensors for 1 minute. A baseline was then established for 1 minute in kinetic buffer. 10 μg/mL of the polypeptide-Fab fusions (comprising anti-BACE1 Fab arms) were bound to the sensor tips in the presence or absence of 1 uM human TfR ECD. Recombinant human FcRn (pH5.5) binding to immobilized polypeptide-Fab fusion was analyzed with a 3-minute association and a 3-minute dissociation.

The sensograms obtained from these experiments (FIG. 29), indicate that polypeptide-Fab fusion variants bound to FcRn at acidic pH (pH 5.5) and that TfR binding did not appreciably interfere with FcRn binding.

Example 5. Pharmacokinetic/Pharmacodynamic Characterization of CH3C Variants

This example describes pharmacokinetic/pharmacodynamic (PK/PD) characterization of CH3C variant polypeptides of the present invention in mouse plasma and brain tissue.

Pharmacokinetics of CH3C Variants in Wild-Type Mouse Plasma

Pharmacokinetics (PK) were tested for several CH3C variants in wild-type mice to demonstrate in vivo stability in a model lacking TfR-mediated clearance, as the polypeptide-Fab fusions bind only human TfR and not murine TfR. The study design is shown in Table 12 below. 6-8 week-old C57B16 mice were intravenously dosed and in-life bleeds were taken via submandibular-bleeds, at time points as indicated in Table 12. Blood was collected in EDTA plasma tubes, spun at 14,000 rpm for 5 minutes, and then plasma was isolated for subsequent analysis.

TABLE 12

PK study design

| Group | Polypeptide | Time points | N | Dose (IV) |
|---|---|---|---|---|
| 1A/1B | Ab122 | A = 30 min, 24 h, 4 d<br>B = 4 h, 2 d, 7 d | A = 2<br>B = 3 | 12.3 mg/kg |
| 2A/2B | Ab153 | A = 30 min, 24 h, 4 d<br>B = 4 h, 2 d, 7 d | A = 2<br>B = 3 | 11.4 mg/kg |
| 3A/3B | CH3C.35.163 mono (Ab153 fusion) | A = 30 min, 24 h, 4 d<br>B = 4 h, 2 d, 7 d | A = 2<br>B = 3 | 11.4 mg/kg |
| 4A/4B | CH3C.3.2-19 (Ab153 fusion) | A = 30 min, 24 h, 4 d<br>B = 4 h, 2 d, 7 d | A = 2<br>B = 3 | 11.0 mg/kg |
| 5A/5B | CH3C.3.2-5 (Ab153 fusion) | A = 30 min, 24 h, 4 d<br>B = 4 h, 2 d, 7 d | A = 2<br>B = 3 | 10.5 mg/kg |
| 6A/6B | CH3C.3.2-1 (Ab153 fusion) | A = 30 min, 24 h, 4 d<br>B = 4 h, 2 d, 7 d | A = 2<br>B = 3 | 10.0 mg/kg |

Ab122 served as an anti-RSV control that has normal PK in mice. Ab153 served as an anti-BACE1 control that has normal PK in mice. The Fab arms of Ab153 were fused to the modified Fc polypeptides in this study.

Figure 30:
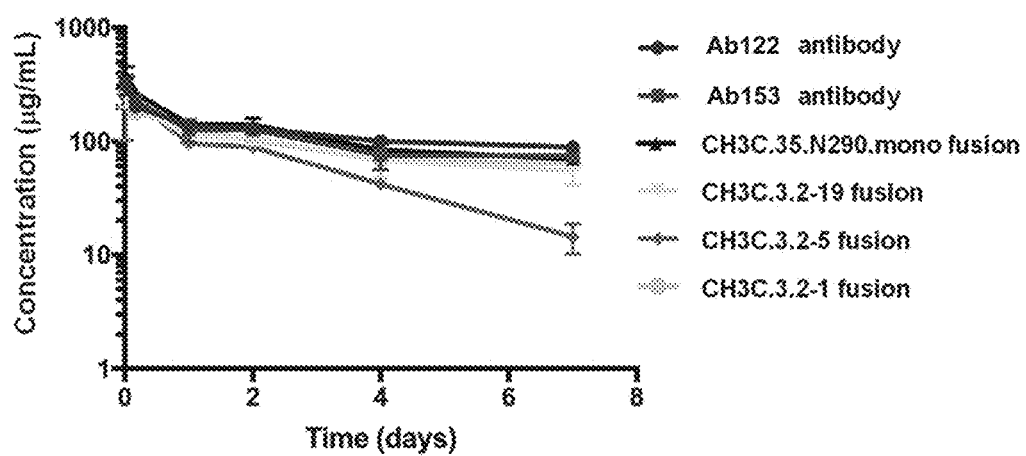

Polypeptide concentrations in mouse plasma were quantified using a generic human IgG assay (MSD® human IgG kit #K150JLD-4) following the manufacturer's instructions. Briefly, precoated plates were blocked for 30 minutes with MSD® Blocker A. Plasma samples were diluted 1:2,500 using a Hamilton® NIMBUS liquid handler and added in duplicate to the blocked plates. Dosing solutions were also analyzed on the same plate to confirm the correct dosage. The standard curve, 0.78-200 ng/mL IgG, was fit using a four-parameter logistic regression. FIG. 30 and Table 13 show the analysis of these data. All of the CH3C polypeptide variants had clearance and half-life values comparable to the standard Ab122, except for CH3C.3.2-5, which had substantially faster clearance and a shorter half-life. Interestingly, this variant was a point mutant of CH3C.3.2-19 (N163D), the latter of which had a normal PK profile.

TABLE 13

PK parameters for CH3C polypeptide-Fab fusions

| Polypeptide | Clearance (mg/day/kg) | Half-life (days) |
|---|---|---|
| Ab122 | 6.12 | 9.12 |
| Ab153 | 9.11 | 4.74 |
| CH3C.35.N163 mono (Ab153 fusion) | 8.44 | 5.35 |
| CH3C.3.2-19 (Ab153 fusion) | 10.3 | 5.42 |
| CH3C.3.2-5 (Ab153 fusion) | 21.0 | 1.90 |
| CH3C.3.2-1 (Ab153 fusion) | 9.25 | 4.65 |

Additional PK Study in Wild-Type Mouse

A second PK study was conducted in wild-type mice according to the study design in Table 14 below (all polypeptide-Fab fusions to Ab153 Fab):

TABLE 14

| Polypeptide | Dose (mg/kg) | Timepoint | n/group |
|---|---|---|---|
| Ab153 | 10 | 0.5 h, 1 d, 4 d, 7 d | 3 |
| CH3C.35.21.mono | 10 | 0.5 h, 1 d, 4 d, 7 d | 3 |
| CH3C.35.24.mono | 10 | 0.5 h, 1 d, 4 d, 7 d | 3 |
| CH3C.35.21.16.mono | 10 | 0.5 h, 1 d, 4 d, 7 d | 3 |
| CH3C.35.21.17.mono | 10 | 0.5 h, 1 d, 4 d, 7 d | 3 |
| CH3C.35.20.bi | 10 | 0.5 h, 1 d, 4 d, 7 d | 3 |
| CH3C.35.21.bi | 10 | 0.5 h, 1 d, 4 d, 7 d | 3 |

Mice and samples were processed as described in the previous study. Data is provided in Table 15.

TABLE 15

Clearance values for CH3C.35 polypeptide-Fab fusions

| Test polypeptide | Clearance (mL/day/kg) |
|---|---|
| Ab153 | 9.53 |
| CH3C.35.21.mono | 8.99 |
| CH3C.35.24.mono | 9.00 |
| CH3C.35.21.16.mono | 11.6 |
| CH3C.35.21.17.mono | 10.9 |
| CH3C.35.20.bi | 7.13 |
| CH3C.35.21.bi | 11.6 |

As is apparent from the clearance values, these polypeptide-Fab fusions exhibited similar clearance in wild-type mice as compared with a standard control antibody.

PK/PD Evaluation of Monovalent CH3C.35.N163 in Wild-Type Mouse Brain Tissue

Transgenic mice expressing human Tfrc apical domain within the murine Tfrc gene were generated using CRISPR/Cas9 technology. The resulting chimeric TfR was expressed in vivo under the control of the endogenous promoter.

Chimeric huTfR$^{apical}$ heterozygous mice (n=4/group) were intravenously dosed with 42 mg/kg of either Ab153 or monovalent CH3C.35.N163, and wild-type mice (n=3) were dosed intravenously with 50 mg/kg of control human IgG1. Ab153 served as a control that has normal PK in mice. All mice were perfused with PBS 24 hours post-dose. Prior to perfusion, blood was collected in EDTA plasma tubes via cardiac puncture and spun at 14,000 rpm for 5 minutes. Plasma was then isolated for subsequent PK and PD analysis. Brains were extracted after perfusion and hemi-brains were isolated for homogenization in 10× by tissue weight of 1% NP-40 in PBS (for PK) or 5 M GuHCl (for PD).

Figure 31:
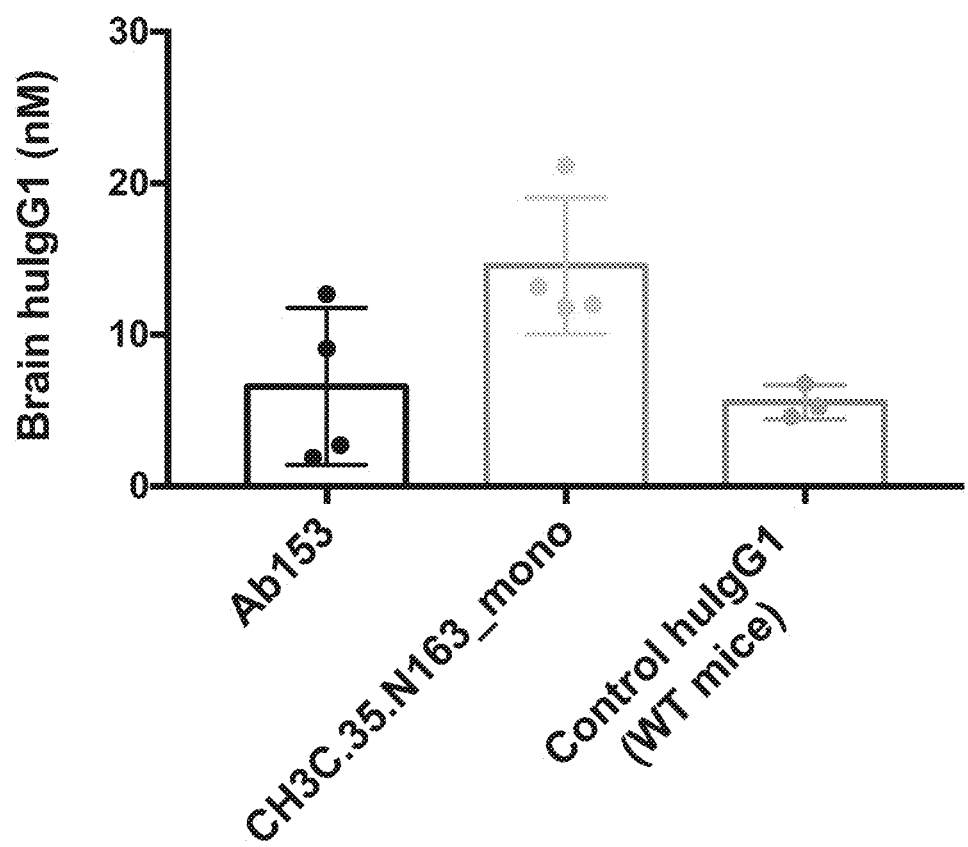

FIG. 31 shows the results of the brain PK study. Uptake was greater in the monovalent CH3C.35.N163 group than the Ab153 and control human IgG1 groups.

Brain and Plasma PKPD of Polypeptide-Fab Fusions in hTfR$^{apical+/+}$ Mice: CH3C.35.21 and CH3C.35.N153

Homozygous hTfR$^{apical+/+}$ mice were intravenously injected with 50 mg/kg of either anti-BACE1 antibody Ab153, anti-TfR/BACE1 bispecific antibody Ab116, CH3C.35.21.mono fused to Ab153 Fab, or CH3C.35.N153.mono fused to Ab153 Fab, as indicated in the study design in Table 16. In this study, all Fc's had LALAPG mutations to remove effector functions.

TABLE 16

Study design for single point brain and plasma PKPD study

| Polypeptide | hTfR affinity (nM) | Dose (mg/kg) | Timepoint (day) | n/group |
|---|---|---|---|---|
| Ab153 | n/a | 50 | 1 | 8 |
| Ab116 | 330 | 50 | 1 | 8 |
| CH3C.35.21.mono | 160 | 50 | 1 | 8 |
| CH3C.35.N153.mono | 370 | 50 | 1 | 8 |

After 24 hours, blood was collected via cardiac puncture and the mice were perfused with PBS. Brain tissue was homogenized in 10× tissue weight of lysis buffer containing 1% NP-40 in PBS. Blood was collected in EDTA tubes to prevent clotting and spun at 14,000 rpm for 7 minutes to isolate plasma. Polypeptide concentrations in mouse plasma and brain lysates were quantified using a generic human IgG assay (MSD human IgG kit #K150JLD) following the manufacturer's instructions. Briefly, pre-coated plates were blocked for 30 minutes with MSD Blocker A. Plasma samples were diluted 1:10,000 using a Hamilton Nimbus liquid handler and added in duplicate to the blocked plates. Brain samples were homogenized in 1% NP40 lysis buffer and lysates diluted 1:10 for PK analysis. Dosing solutions were also analyzed on the same plate to confirm the correct dosage. The standard curve, 0.78-200 ng/mL IgG, was fit using a four-parameter logistic regression.

Figure 32B:
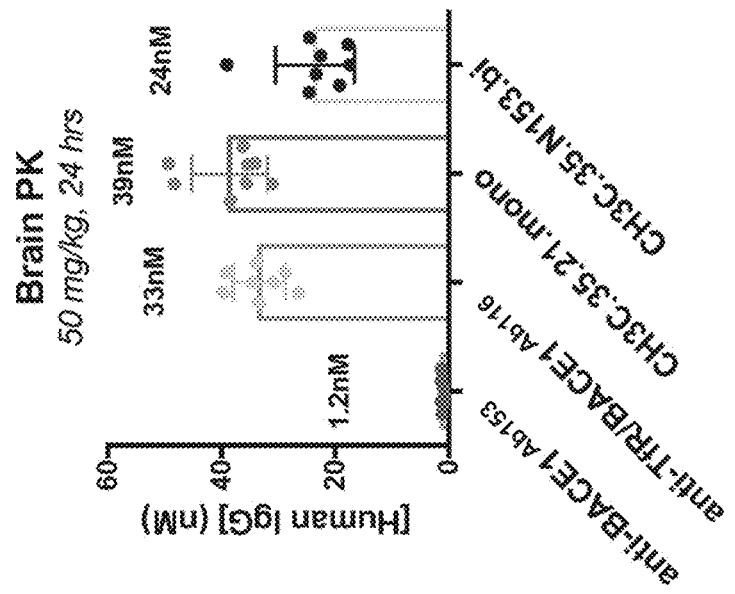
Figure 32A:
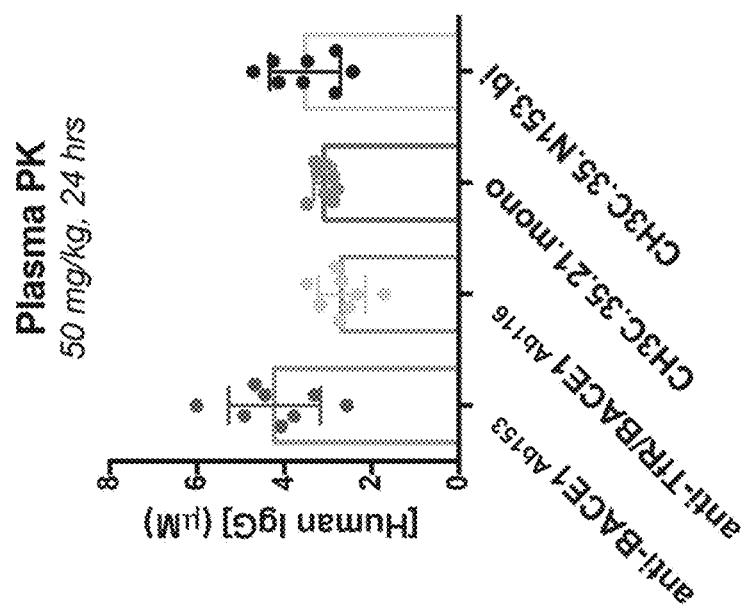

After 24 hours, the plasma levels of TfR-binding polypeptides were lower than the levels for anti-BACE1, likely due to clearance of this antibody via binding to peripherally-expressed $hTfR^{apical}$ (FIG. 32A). In brain, there was a significant increase in the concentration of anti-TfR/BACE1 compared to anti-BACE1 (FIG. 32B). The greatest increase was observed for CH3C.35.21.mono, but brain uptake was also significantly improved as compared to anti-BACE with CH3C35.N153.bi. The significant accumulation of the engineered TfR-binding polypeptides was due to TfR-mediated transcytosis at the BBB, thus validating the utility of engineering TfR binding into the Fc region.

BACE1 inhibition of amyloid precursor protein APP cleavage was used as a pharmacodynamic readout of antibody activity in plasma and brain. Brain tissue was homogenized in 10× tissue weight of 5 M guanidine-HCl and then diluted 1:10 in 0.25% casein buffer in PBS. Mouse Aβ340 levels in plasma and brain lysate were measured using a sandwich ELISA. A 384-well MaxiSorp plate was coated overnight with a polyclonal capture antibody specific for the C-terminus of the Aβ340 peptide (Millipore #ABN240). Casein-diluted guanidine brain lysates were further diluted 1:2 on the ELISA plate and added concurrently with the detection antibody, biotinylated M3.2. Plasma was analyzed at a 1:5 dilution. Samples were incubated overnight at 4° C. prior to addition of streptavidin-HRP followed by TMB substrate. The standard curve, 0.78-50 pg/mL msAβ340, was fit using a four-parameter logistic regression.

Figure 33A:
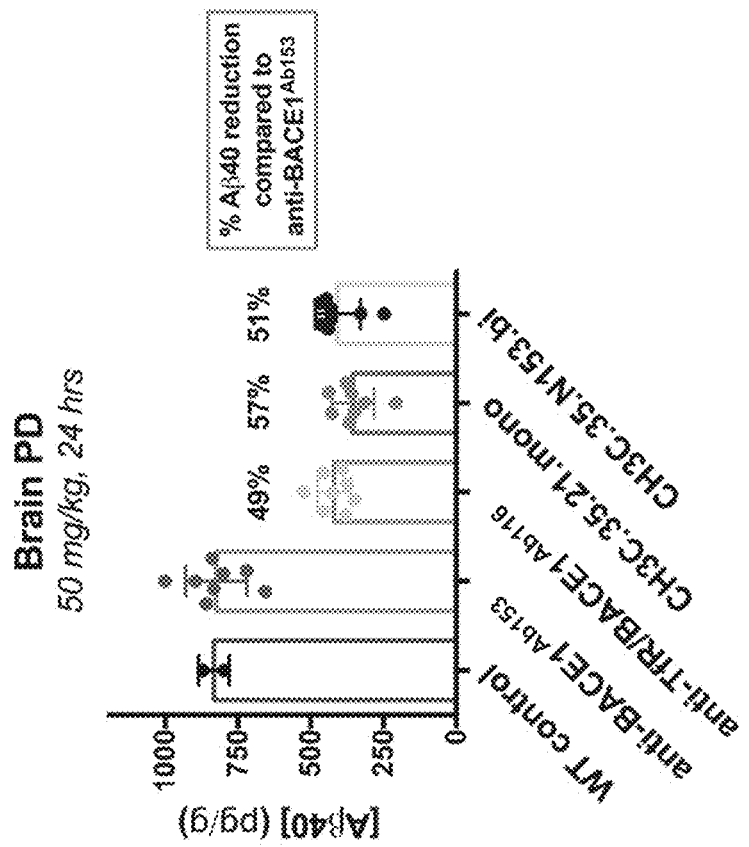
Figure 33B:
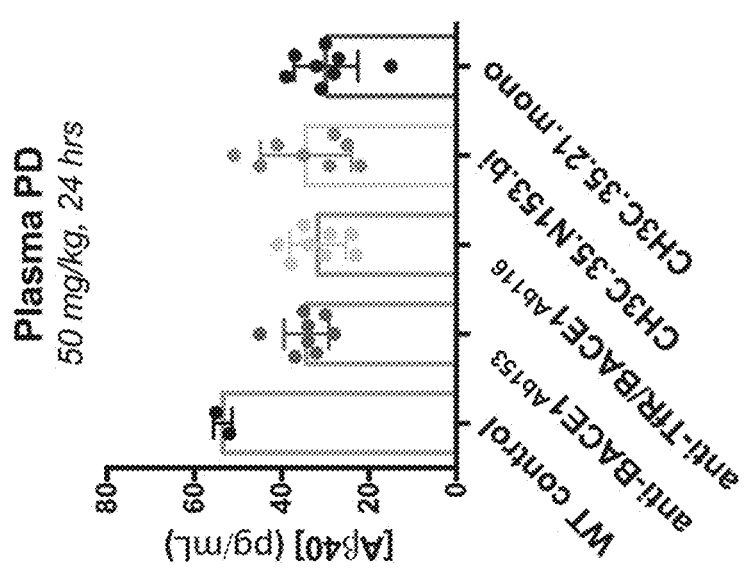

Plasma amyloid beta-protein (Abeta) was reduced to a similar extent for all polypeptides, as compared to untreated wild-type mice (FIG. 33A), due to the presence of anti-BACE1 Fab arms on all polypeptides. Compared to anti-BACE1, treatment with TfR-binding polypeptides resulted in an increased reduction of Abeta in $hTfR^{apical+/+}$ mice, indicating BACE1 target engagement in the brain was achieved (FIG. 33B). The level of target engagement in brain was similar for the engineering polypeptide fusions and the anti-TfR/BACE1 bispecific antibody.

Brain and Plasma PKPD of Polypeptide-Fab Fusions in $hTfR^{apical+/+}$ Mice: CH3C.35.21, CH3C.35.20, CH3C.35, CH3C.35.23, CH3C.35.23.3

Figure 44A:
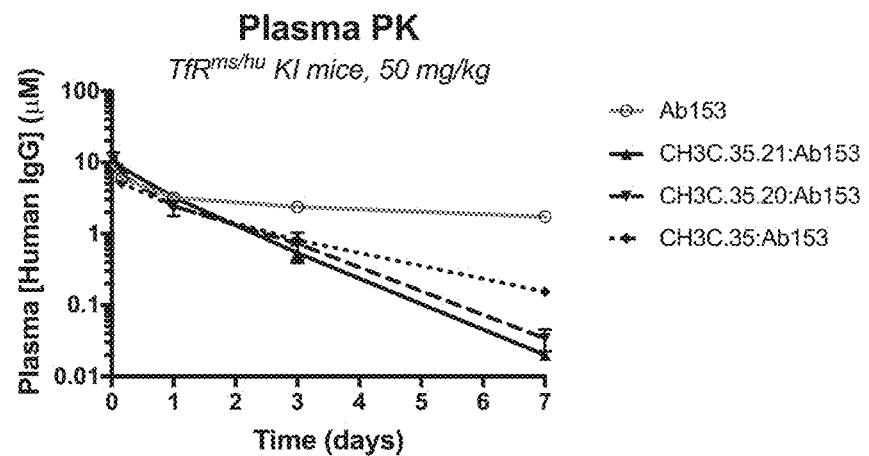
FIGS. 44A and 44B depict huIgG1 concentrations in plasma (FIG. 44A) and brain lysates (FIG. 44B) of hTfRapical+/+ knock-in (KI) mice after a single 50 mg/kg systemic injection of anti-BACE1_Ab153, CH3C35.21:Ab153, CH3C35.20:Ab153, or CH3C35:Ab153 polypeptide fusion (mean±SEM, n=5 per group).
Figure 44B:
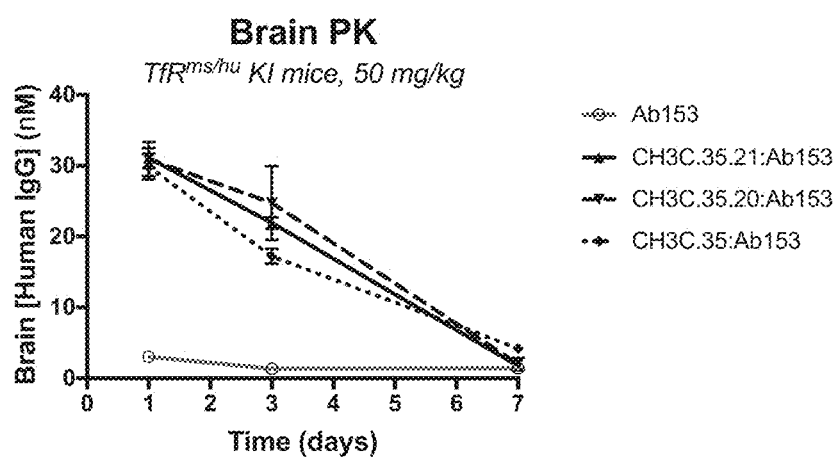
Figure 44C:
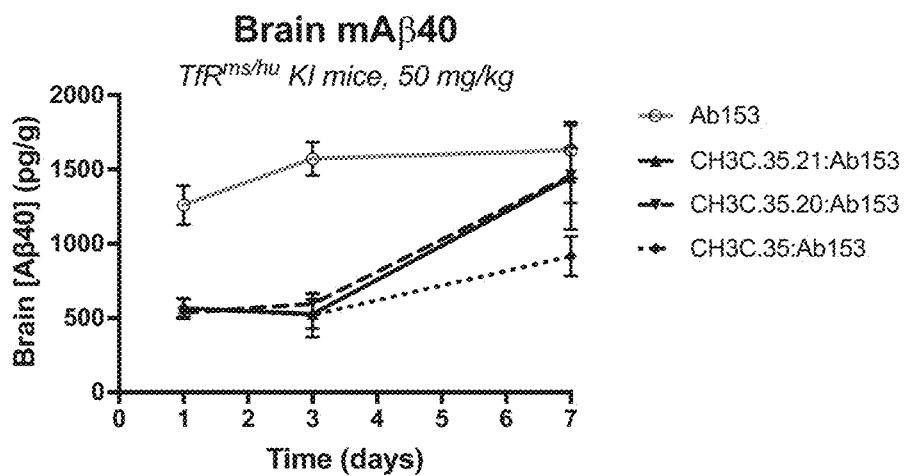
FIG. 44C depicts endogenous mouse Aβ concentration in brain lysate of hTfRapical+/+ KI mice after a single 50 mg/kg systemic injection of anti-BACE1_Ab153, CH3C35.21: Ab153, CH3C35.20:Ab153, or CH3C35:Ab153 polypeptide fusion (mean±SEM, n=5 per group).
Figure 44D:
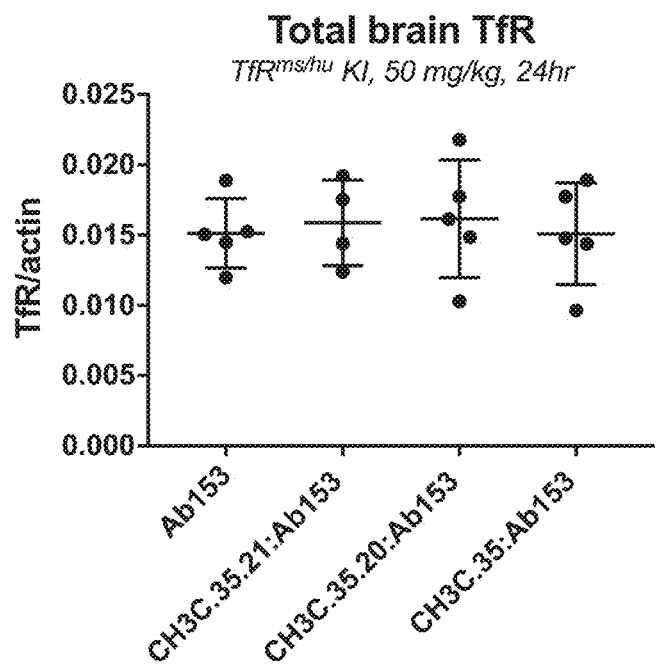
FIG. 44D depicts Western blot quantification of brain TfR protein normalized to actin in brain lysate of hTfRapical+/+ KI mice after a single 50 mg/kg systemic injection of anti-BACE1_Ab153, CH3C35.21:Ab153, CH3C35.20: Ab153, or CH3C35:Ab153 polypeptide fusion (mean±SEM, n=5 per group).

To evaluate the impact of TfR binding affinity for PK and brain uptake, anti-BACE1 Ab153 and TfR-binding polypeptide fusions (CH3C.35.21:Ab153, CH3C.35.20:Ab153, CH3C.35:Ab153 fusions) were generated that differed in their binding affinity to apical human TfR as measured by Biacore. The binding affinities of CH3C.35.21:Ab153, CH3C.35.20:Ab153, CH3C.35:Ab153 fusions to human TfR are 100 nM, 170 nM and 620 nM, respectively. $hTfRapical^{+/+}$ knock-in mice were systemically administered either Ab153 or the polypeptide-Fab fusions at 50 mg/kg, and plasma PK and brain PKPD was evaluated at 1, 3, and 7 days post-dose. Brain and plasma PKPD analysis was conducted as described in the previous section. Due to expression of TfR on peripheral tissues, CH3C.35.21:Ab153, CH3C.35.20:Ab153, and CH3C.35:Ab153 fusions exhibited faster clearance in plasma as compared to Ab153 alone, consistent with target-mediated clearance and indicative of in vivo TfR binding (FIG. 44A). Impressively, brain concentrations of CH3C.35.21:Ab153, CH3C.35.20:Ab153, and CH3C.35:Ab153 fusions were significantly increased compared to Ab153, achieving a maximum brain concentration of more than 30 nM at 1 day post-dose, compared to only about 3 nM for Ab153 at this same time point (FIG. 44B). The increase in brain exposure of CH3C.35.21:Ab153, CH3C.35.20:Ab153, and CH3C.35:Ab153 fusions resulted in about 55-60% lower endogenous mouse Aβ levels in brains of mice compared to Aβ levels in mice dosed with Ab153 (FIG. 44C). The lower brain Aβ levels were sustained while concentrations of CH3C.35.21:Ab153, CH3C.35.20:Ab153, and CH3C.35:Ab153 fusions remained elevated in brain, and returned to levels similar to Ab153 treated mice at when exposure was reduced by day 7. The reduction in brain exposure over time correlated with a reduction in peripheral exposure of CH3C.35.21:Ab153, CH3C.35.20:Ab153, and CH3C.35:Ab153 fusions, providing a clear PK/PD relationship in vivo (compare FIGS. 44A and 44C). Additionally, total brain TfR levels were comparable for Ab153-treated and polypeptide-Fab fusion-treated mice after this single high dose, indicating no significant impact of increased brain exposure of the polypeptide-Fab fusions to TfR expression in brain (FIG. 44D).

Figure 45A:
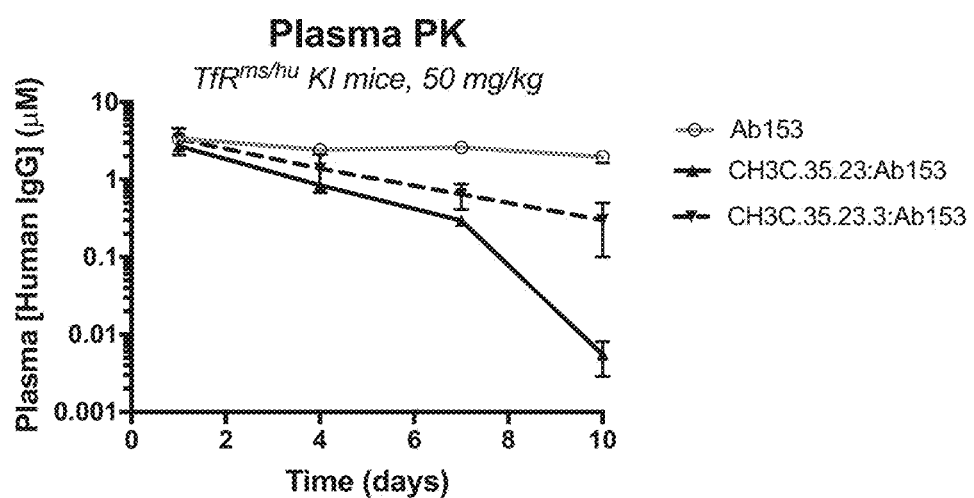
FIGS. 45A and 45B depict huIgG1 concentrations in plasma (FIG. 45A) and brain lysates (FIG. 45B) of hTfR$^{apical+/+}$ KI mice after a single 50 mg/kg systemic injection of anti-BACE1_Ab153, CH3C.35.23:Ab153, or CH3C.35.23.3:Ab153 polypeptide fusion (mean±SEM, n=5 per group).
Figure 45B:
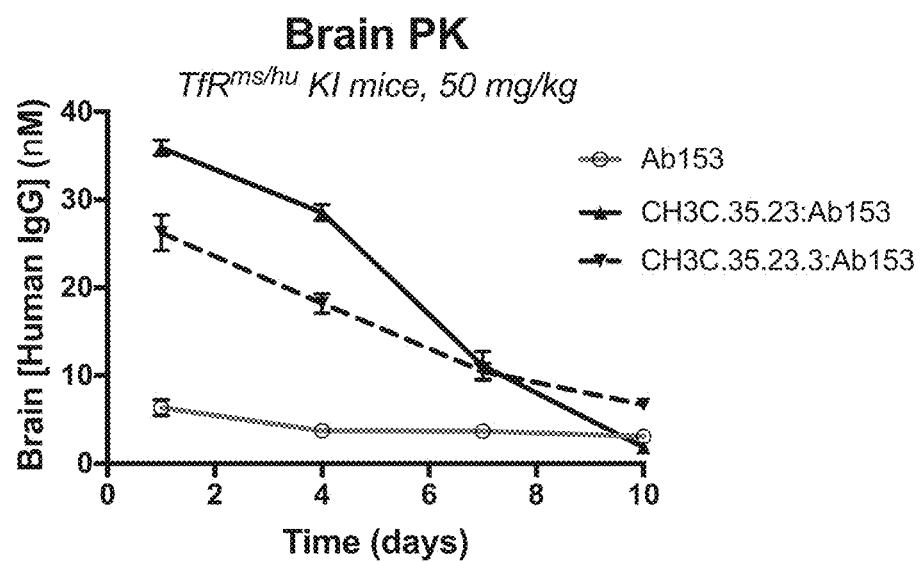
Figure 45C:
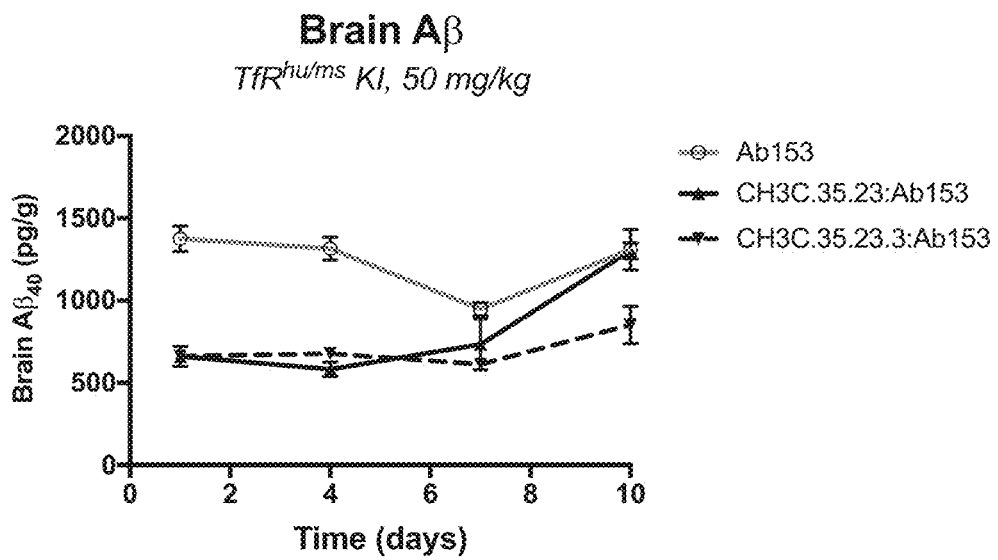
FIG. 45C depicts endogenous mouse Aβ concentration in brain lysate of hTfR$^{apical+/+}$ KI mice after a single 50 mg/kg systemic injection of anti-BACE1_Ab153, CH3C.35.23: Ab153, or CH3C.35.23.3:Ab153 polypeptide fusion (mean±SEM, n=5 per group).
Figure 45D:
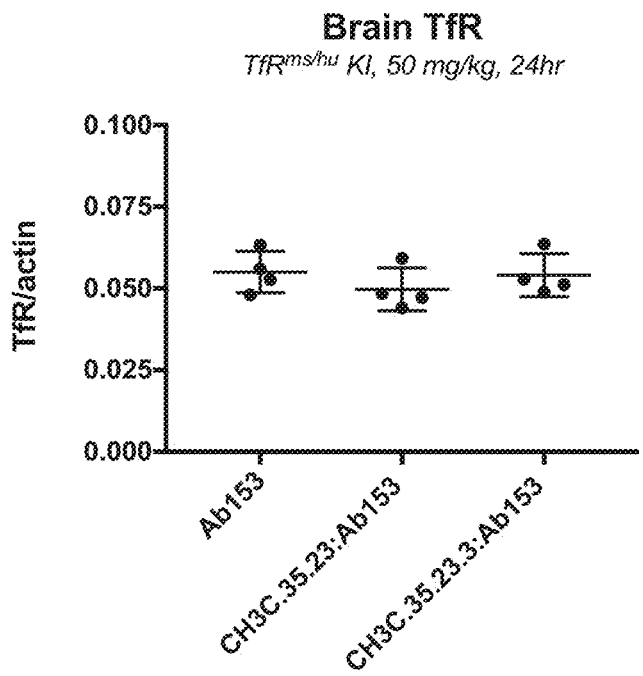
FIG. 45D depicts Western blot quantification of brain TfR protein normalized to actin in brain lysate of hTfR$^{apical+/+}$ KI mice after a single 50 mg/kg systemic injection of anti-BACE1_Ab153, CH3C.35.23:Ab153, or CH3C.35.23.3:Ab153 polypeptide fusion (mean±SEM, n=4 per group).

To further evaluate the relationship between PK and brain uptake with a wider affinity range of TfR-binding polypeptide-Fab fusions, additional fusions with a wider affinity range for hTfR binding was generated. The binding affinities of CH3C.35.23:Ab153 and CH3C.35.23.3:Ab153 fusions to human TfR are 420 nM and 1440 nM, respectively. $hTfRapical^{+/+}$ knock-in mice were dosed as described above. Plasma PK and brain PKPD were evaluated at 1, 4, 7, and 10 days post-dose. Peripheral PK of the polypeptide-Fab fusions were hTfR affinity-dependent, where the higher affinity CH3C.35.23:Ab153 fusion exhibited faster clearance compared to the much lower affinity CH3C.35.23.3:Ab153 fusion (FIG. 45A). Both CH3C.35.23:Ab153 and CH3C.35.23.3:Ab153 fusions had significantly greater brain exposure than compared to Ab153 alone, with CH3C.35.23:Ab153 achieving about 36 nM in brain at 1 day post-dose (FIG. 45B). Despite similar plasma concentrations, this maximum brain uptake of CH3C.35.23.3:Ab153 fusion was lower than that of CH3.35.23:Ab153 fusion, likely due to the about 3.5-fold lower affinity of the latter fusion for hTfR. Interestingly, because the lower affinity fusion provided a more sustained peripheral exposure by day 10, its brain exposure was also higher than that of the higher affinity CH3C.35.23:Ab153 fusion. This illustrates a trade-off of lower brain $C_{max}$ but more sustained PK over time for lower affinity TfR-binding polypeptide-Fab Fusions. Significantly lower concentrations of Aβ340 was observed in brains of mice dosed with the anti-BACE1 polypeptide fusions compared to anti-BACE1 alone (FIG. 45C). This duration of Aβ340 reduction was consistent with levels of huIgG1 exposure in brain over time (FIG. 45B). Impressively, mice dosed with CH3C.35:Ab153 fusion exhibited a prolonged brain Aβ340 reduction out to 7-10 days after a single dose. Total brain TfR levels were comparable between mice dosed with Ab153 versus CH3C.35:Ab153 fusion at 1 day post-dose (FIG. 45D). Together these data demonstrate that TfR-binding polypeptide fusion can increase brain exposure of anti-BACE1 to significantly reduce brain Aβ340 after a single dose.

Example 6. CH3C.18 Fc and Transferrin Receptor Apical Domain Crystallization

This example describes the crystallization and analysis of the binding interface between CH3C.18 and the apical domain of the transferrin receptor (TfR-AD).

Expression

The apical domain of human transferrin receptor (TfR-AD) and an engineered human Fc (CH3C.18 Fc) were expressed (SEQ ID NOS:301 and 302, respectively) in Expi293 cells at the initial cell density of 2.5×10⁶ cells/mL. Expressions were performed in volumes of 200 mL or more, as necessary. Kifunensine, a glycosylation inhibitor, was added 20 hours post transfection at a final concentration of 25 µM. Expression cultures were collected 3 to 4 days post transfection, when cell viability had significantly decreased.

Purification

Expressed TfR-AD and CH3C.18 Fc were purified with protein A and Ni-NTA resins, respectively, followed by size-exclusion chromatography on a Superdex200 26/60 gel filtration column. The following buffers were used:
Protein A wash buffer: 20 mM Hepes pH 7.4, 100 mM NaCl;
Protein A elution buffer: 30 mM glycine pH 2.5 (the eluate was collected into a tube containing 1 M Tris, pH 9.0 to immediately neutralize the eluate);
Ni-NTA wash buffer: 30 mM Tris pH, 10 mM imidazole, and 200 mM NaCl;
Ni-NTA elution buffer: 30 mM Tris pH 8.0, 200 mM NaCl, and 250 mM imidazole; and
Size-exclusion buffer (SEC): 30 mM HEPES pH 7.5, 200 mM NaCl, and 3% glycerol.

Complex Formation and Purification

Figure 34:
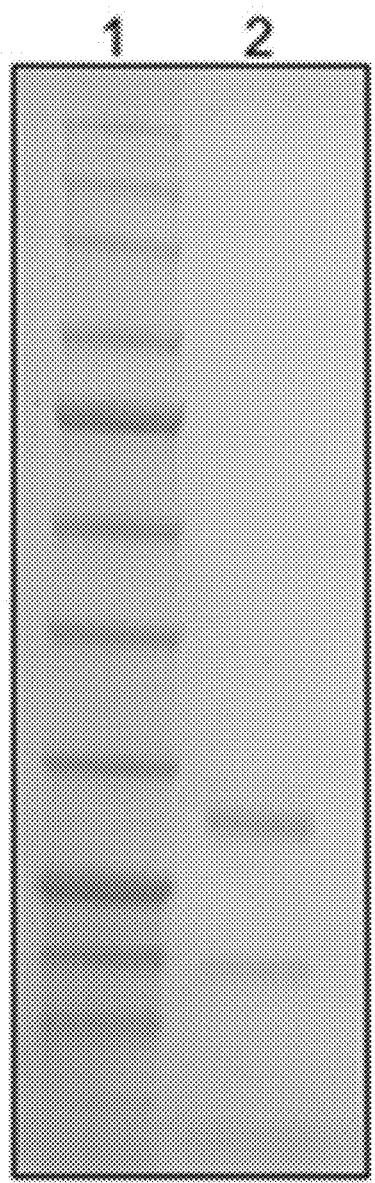
Figure 35A:
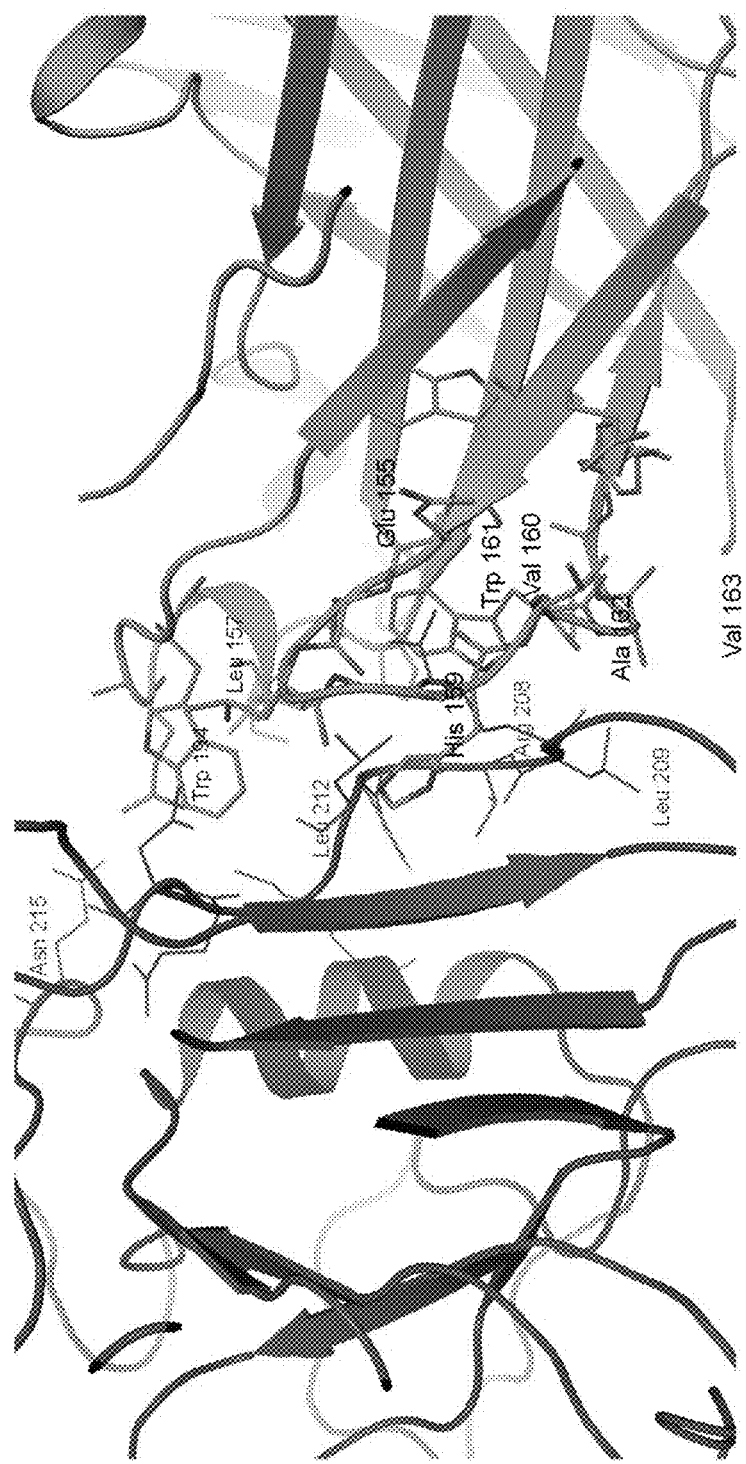
Figure 35B:
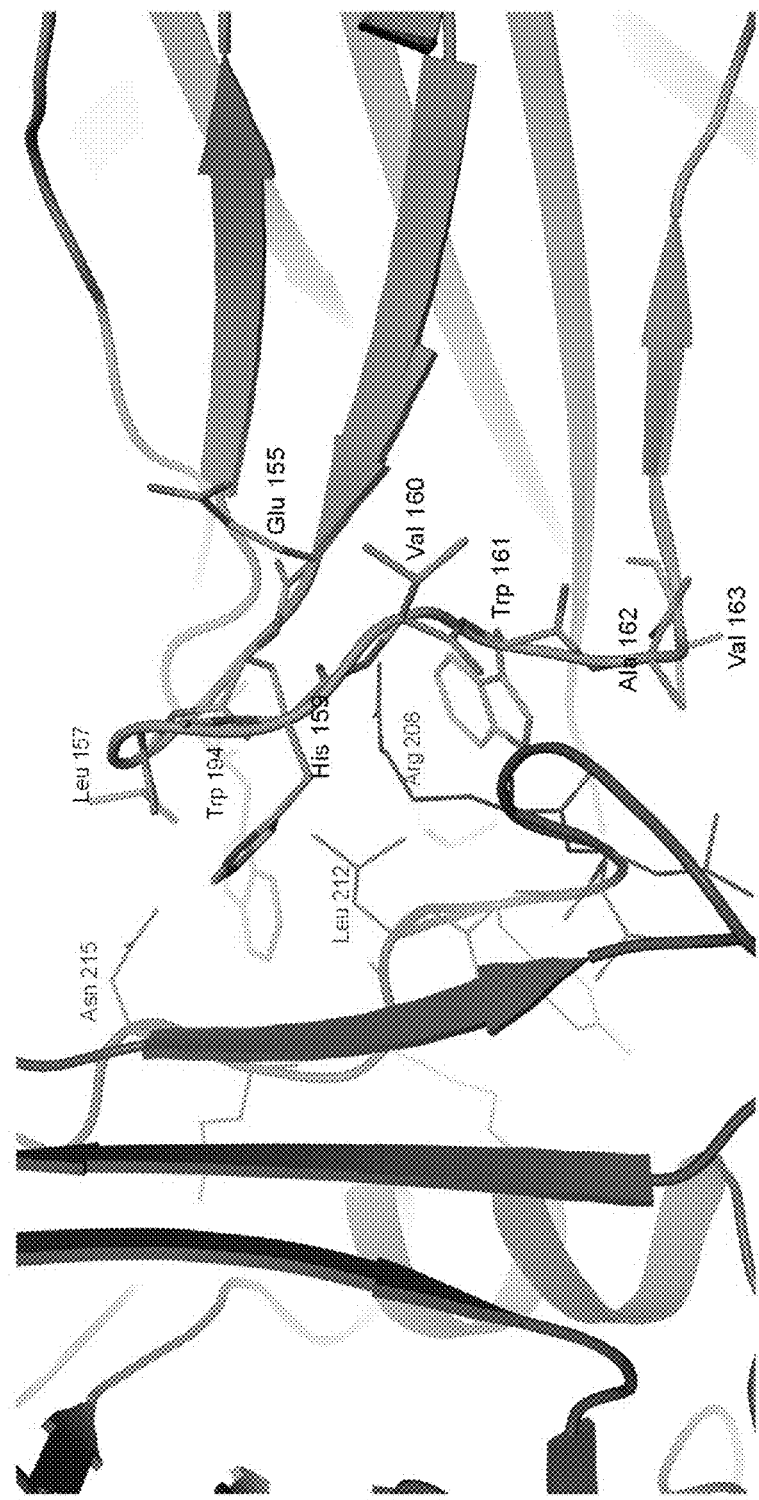

Purified TfR-AD and CH3C.18 Fc were mixed with an excess of apical domain, incubated at room temperature for 1 hour, and the complex was purified using size-exclusion chromatography on a Superdex200 26/60 gel-filtration column using the previously mentioned SEC buffer. The sizing gave two major peaks as expected; one corresponded to the complex (retention volume=180 ml) and the other one corresponded to the excess apical domain (retention volume=240 ml). The peak fractions were analyzed by Coomassie stained SDS-PAGE gel (FIG. 34).

Crystallization

Initial crystallization screening of the complex was performed by the sitting drop vapor diffusion method at 15° C. and room temperature (RT) at 8.5 mg/mL protein concentration. Showers of thin needles of crystals were observed in the condition that contained 25% PEG 3350, 0.1 M Tris pH 8.5 and 0.2 M MgCl₂. These crystals were used to seed in the same condition but at 20% PEG 3350 to produce single thin needles of mountable size.

X-Ray Data Collection

Crystals were flash-cooled by direct immersion in liquid nitrogen using the crystallization mother liquor supplemented with 20% (v/v) ethylene glycol. X-ray intensity data were collected at the SER-CAT beam line of the Advanced Photon Source (APS) using a Rayonix 300 high speed detector. Crystals were diffracted to 3.6 Å, and belonged to the hexagonal space group P64 with two complex molecules in the asymmetric unit (Table 17). Data were indexed, integrated, and scaled using the program HKL2000. Data collected from two crystals were merged to produce 3.6 Å data.

TABLE 17

Crystal data for CH3C.18 Fc-TfR-AD complex structure

| Name/code | | CH3C.18 Fc-TfR-AD complex |
|---|---|---|
| Cell dimensions | a (Å) | 124.3 |
| | b | 124.3 |
| | c | 113.1 |
| | α(°) | 90.0 |
| | β | 90.0 |
| | γ | 120.0 |
| Space group | | P6₄ |
| Resolution range (Å) | Overall | 50-3.6 |
| | Last shell | 3.71-3.6 |
| Number of unique reflections | | 11,259 |
| Completeness (%) | (Overall/Last shell) | 95.9/74.1 |
| $R_{merge}$¹ | (Overall/Last shell) | 20/93 |
| Refinement Statistics | Resolution (Å) | 50-3.6 |
| | R factor²/Rfree (%) | 30/39 |

¹$R_{merge} = \Sigma_j(|I_h - <I>_h|)/\Sigma I_h$, where $<I_h>$ is the average intensity over symmetry equivalents
²R-factor = $\Sigma|F_{obs} - F_{calc}|/\Sigma|F_{obs}|$ Structure Determination and Refinement The crystal structure of the complex was determined by molecular replacement with PHASER using the CH3C.18 Fc dimer and TFR-AD monomer as the initial search models. The model was refined by rigid-body refinement followed by restrained refinement using REFMAC. All crystallographic calculations were performed with the CCP4 suite of programs (www.ccp4.ac.uk/). Model building of the complex into the electron density was done using the graphics program COOT. The electron density for the complex molecule was good, especially at the CH3C.18 Fc-TfF-AD interface (2Fo-Fc map contoured to 1.2 sigma level). After iterative model building and refinement, high R and freeR (R/freeR=0.30/0.39) were noticed due to the low resolution of the data and disordered CH2 domain. The disorder of the CH2, as found in other available Fc structures, was due to the flexible elbow angle between the CH2 and CH3 domains.

Binding Interface Interactions

Figure 37A:
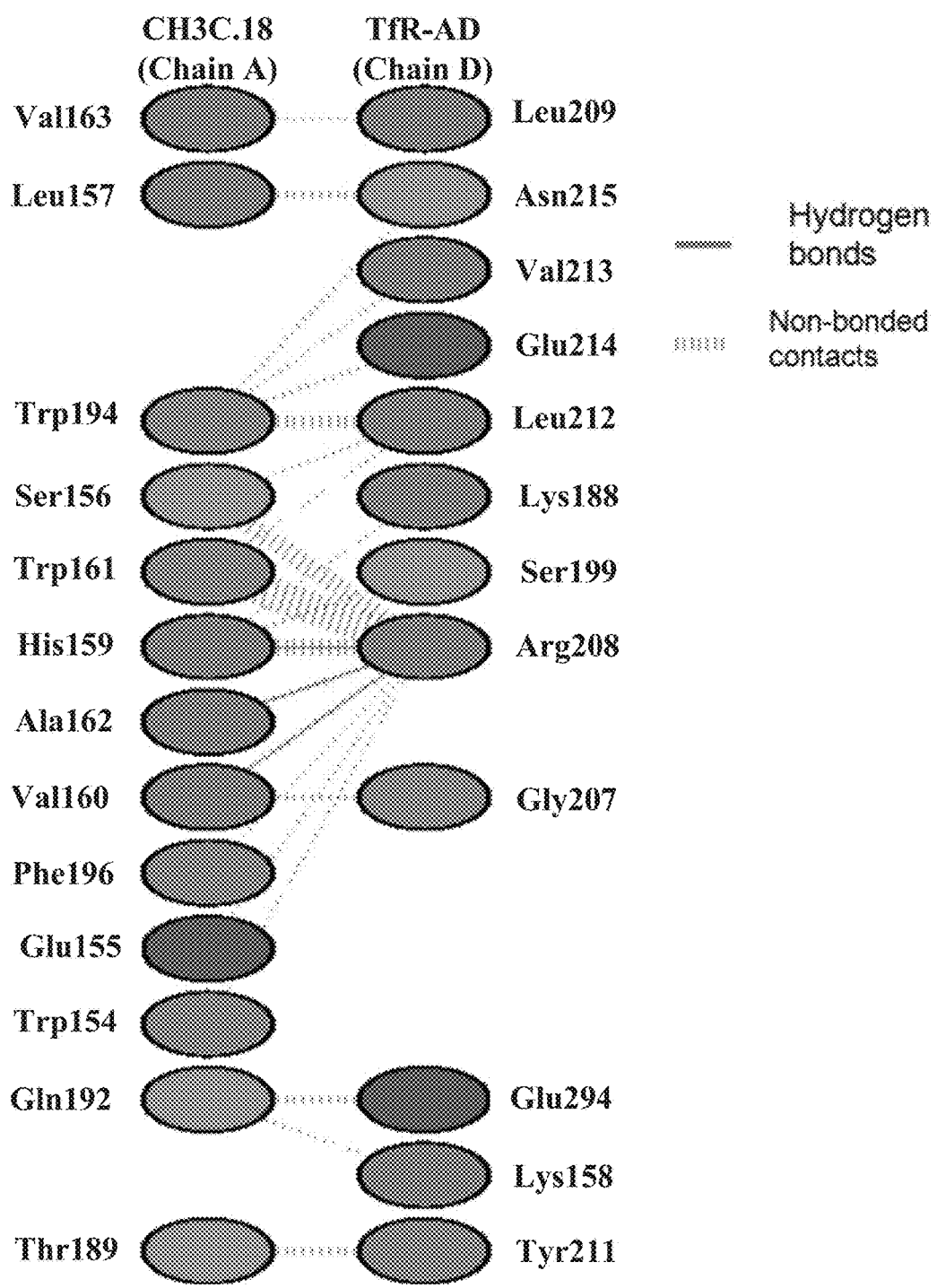
FIG. 37B depicts hydrogen bonds and non-bonded contacts between residues in clone CH3C.18 (Chain B) and the apical domain of the transferrin receptor (Chain C).
Figure 39A:
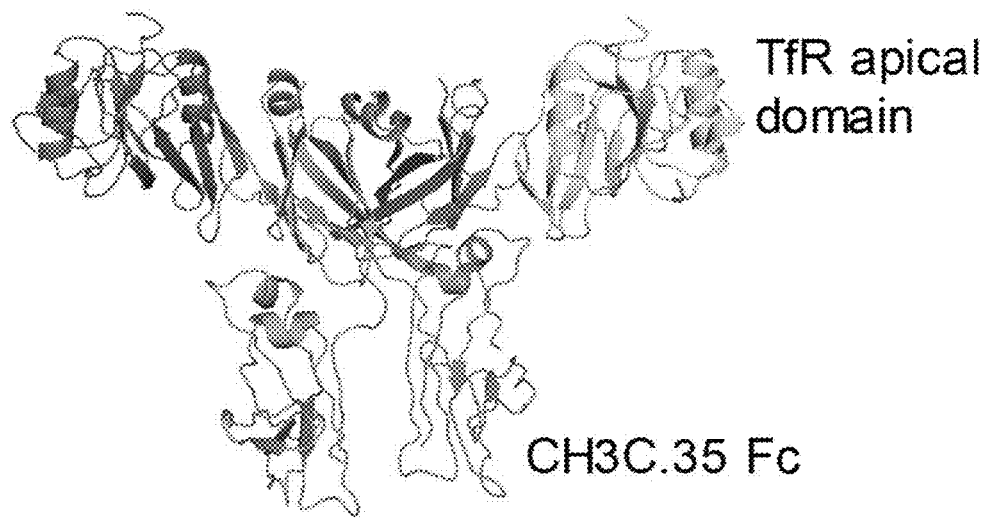
FIGS. 39A-39C depict binding between polypeptides of the present invention and the transferrin receptor.
Figure 39B:
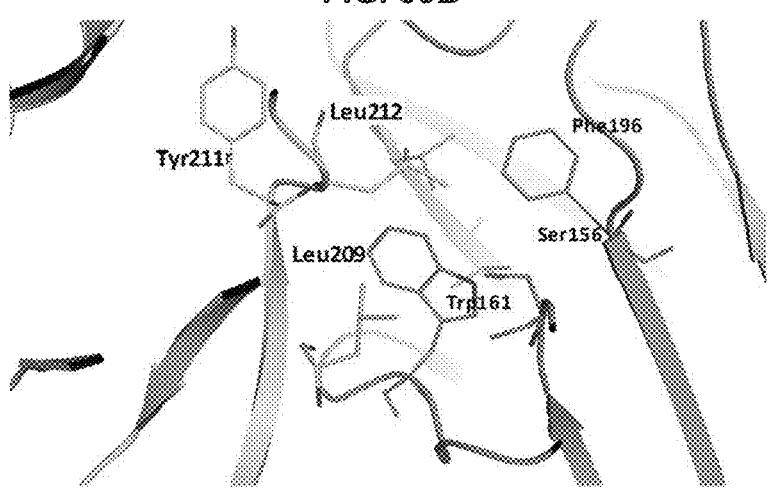
Figure 39C:
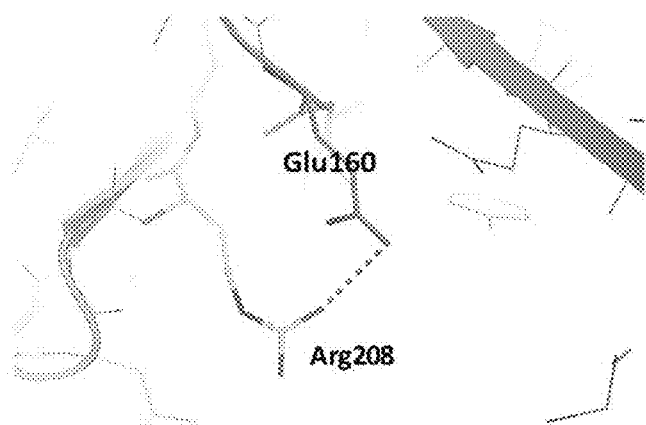
Figure 40A:
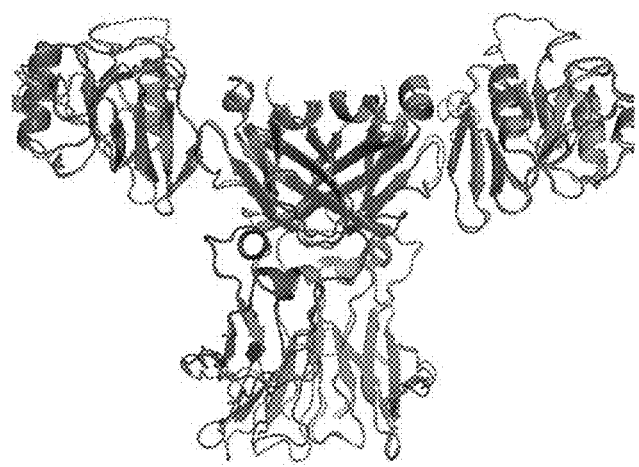
FIG. 40A depicts an overlaid structure between the CH3C.35 Fc and TfR-AD complex and the CH3C.18 Fc and TfR-AD complex.
Figure 40B:
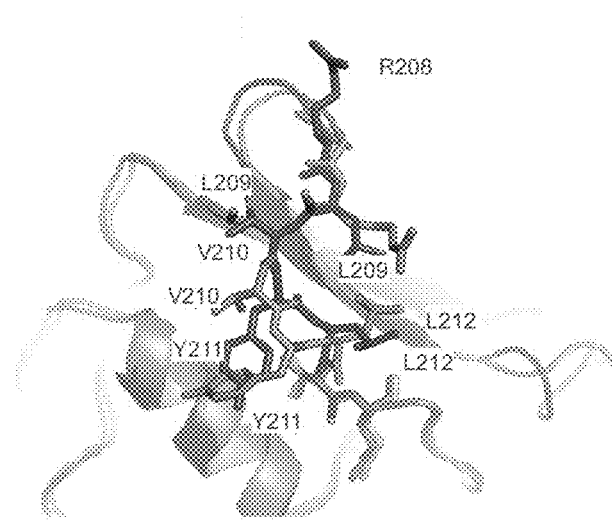
FIG. 40B depicts an enlarged view of the overlaid structure in FIG. 40A.

The binding interface between CH3C.18 Fc and TfR-AD is depicted in FIGS. 35A-35B and FIGS. 36A-36B. As shown in FIGS. 37A-37B, interactions were observed between:

Trp154 of CH3C.18 and Arg208 of TfR-AD;
Glu155 of CH3C.18 and Arg208 of TfR-AD;
Ser156 of CH3C.18 and Arg208 and Leu212 of TfR-AD;
Leu157 of CH3C.18 and Ser 199 and Asn215 of TfR-AD;
His159 of CH3C.18 and Lys188, Ser199, and Arg208 of TfR-AD;
Val160 of CH3C.18 and Gly207 and Arg208 of TfR-AD;
Trp161 of CH3C.18 and Arg208, Val210, and Leu212 of TfR-AD;
Ala162 of CH3C.18 and Arg208 of TfR-AD;
Val163 of CH3C.18 and Leu209 of TfR-AD;
Ser188 of CH3C.18 and Tyr211 of TfR-AD;
Thr189 of CH3C.18 and Tyr211 and Leu212 of TfR-AD;
Gln192 of CH3C.18 and Lys158 and Glu294 of TfR-AD;
Trp194 of CH3C.18 and Leu212, Val213, Glu214, and Asn215 of TfR-AD; and
Phe196 of CH3C.18 and Arg208 of TfR-AD.

Furthermore, as described in the section titled "Paratope Mapping" of Example 2 and as shown in FIGS. 37A-37B, several positions outside of the CH3C register also participate in binding to TfR.

Determination of Level of Conservation of Epitope and Three-Dimensional Structure Between Permuted TfR Apical Domain Construct and Native, Full-Length TfR A 3.6 Å X-ray crystal structure of CH3C.18 Fc polypeptide bound to permuted TfR apical domain (SEQ ID NO:301) was solved as described above. Structural alignment of permuted TfR apical domain with apical domain of a representative, full-length TfR structure (PDB code: 3KAS) revealed a conserved fold (outside the permuted amino acids). Root mean square deviation (RMSD) between the two structures was determined to be 1.24 Å. TfR residues 194-297, and 326-379 were aligned with corresponding residues in the permuted structure to calculate RMSD. Structural alignment and RMSD calculations were performed in MOE v2016.0802 (Chemical Computing Group). The low RMSD of 1.24 Å reflects the conserved apical domain three-dimensional structure, and demonstrates that the permuted structure maintained the native fold and was able to present a conserved epitope or antigen for binding.

Example 7. CH3C.35 Fc and Transferrin Receptor Apical Domain Crystallization

This example describes the crystallization and analysis of the binding interface between CH3C.35 and the apical domain of the transferrin receptor (TfR-AD).

Expression

The apical domain of human transferrin receptor (TfR-AD) and an engineered human Fc (CH3C.35 Fc) were expressed (SEQ ID NOS:301 and 421, respectively) in CHO cells at an initial cell density of 2.5×10$^6$ cells/mL. Expressions were performed in volumes of 500 mL or more, as necessary. Expression cultures were collected 3 to 4 days post transfection, when cell viability had significantly decreased.

Purification

Expressed TfR-AD and CH3C.35 Fc were purified with protein A (Genescript) and Ni-NTA (Sigma) resins, respectively, followed by size-exclusion chromatography on a Superdex200 26/60 gel filtration column. The following buffers were used:

Protein A elution buffer: 30 mM glycine pH 2.5 (the eluate was collected into a tube containing 1 M Tris, pH 9.0 to immediately neutralize the eluate);

Ni-NTA elution buffer: 30 mM Tris pH 8.0, 200 mM NaCl, and 250 mM imidazole; and Size-exclusion buffer (SEC): 30 mM HEPES pH 7.5, 150 mM NaCl, 50 mM KCl, 3% glycerol, and 0.01% sodium azide.

Complex Formation and Purification

Purified TfR-AD and CH3C.35 Fc were mixed with an excess of apical domain, incubated at room temperature for 1 hour, and the complex was purified using size-exclusion chromatography on a Superdex200 26/60 gel filtration column using the previously mentioned SEC buffer.

Crystallization

Initial crystallization screening of the complex was performed by the sitting drop vapor diffusion method at 4° C., 15° C., and room temperature (RT). Showers of thin needles of crystals were observed in the condition that contained 25% PEG 3350, 0.1 M Bis-Tris pH 6.5, and 0.2 M $LiSO_4$. These crystals were used to seed in the same condition but at 20% PEG 3350 to produce single thin needles and the seeding was repeated sequentially four times to produce crystals of mountable size.

X-Ray Data Collection

Crystals were flash-cooled by direct immersion in liquid nitrogen using the crystallization mother liquor supplemented with 20% (v/v) ethylene glycol. X-ray intensity data were collected at 104 beam line of the Diamond Light Source (DLS) using PILATUS detector. Micro focus beam of size 5 micron was used for the data collection. Crystals were diffracted to 3.38 Å, and belonged to the hexagonal space group P64 with two complex molecules in the asymmetric unit (Table 18). Data were indexed, integrated, and scaled using the CCP4 suite programs (Xia2-XDS and XSCALE).

TABLE 18

Crystal data for CH3C.35 Fc-TfR-AD complex structure

| Name/code | | CH3C.35 Fc-TfR-AD complex |
|---|---|---|
| Cell dimensions | a (Å) | 126.4 |
| | b | 126.4 |
| | c | 113.8 |
| | α(°) | 90.0 |
| | β | 90.0 |
| | γ | 120.0 |
| Space group | | $P6_4$ |
| Resolution range (Å) | Overall | 50-3.38 |
| | Last shell | 3.44-3.38 |
| Number of unique reflections | | 14,541 |
| Completeness (%) | (Overall/Last shell) | 100/99.7 |
| $R_{merge}$[1] | (Overall/Last shell) | 31/152 |
| Refinement Statistics | Resolution (Å) | 50-3.38 |
| | R factor[2]/Rfree (%) | 27/35 |

[1]$R_{merge} = \Sigma_j(|I_h - \langle I \rangle_h|)/\Sigma I_h$, where $\langle I_h \rangle$ is the average intensity over symmetry equivalents
[2]R-factor = $\Sigma|F_{obs} - F_{calc}|/\Sigma|F_{obs}|$ Structure Determination and Refinement The crystal structure of the complex was determined by molecular replacement with PHASER using the CH3C.35 Fc-AD TfR complex as the search model. The model was refined by rigid-body refinement followed by restrained refinement using REFMAC. All crystallographic calculations were performed with the CCP4 suite of programs. Model building of the complex into the electron density was done using the graphics program COOT. The electron density for the complex molecule was good, especially at the CH3C.35 Fc-TfF-AD interface.

Binding Interface Interactions

The binding interface between CH3C.35 Fc and TfR-AD is depicted in FIGS. 39A-39C. FIG. 39A shows the complex of CH3C.35 Fc and TfR-AD at 3.4 Å. FIG. 39B shows residue W161 in CH3C.35 Fc is stabilized by residues L209, L212, and Y211 in TfR-AD. FIG. 39C shows a salt bridge between residue E160 in CH3C.35 Fc and residue R208 in TfR-AD as a central binding interaction, which may partially account for the difference in binding affinity of the modified Fc polypeptide to human TfR (Arg at position 208) and to cynomolgus TfR (Gly at position 208). FIG. 40A shows an overlaid structure between the CH3C.35 Fc and TfR-AD complex and the CH3C. 18 Fc and TfR-AD complex (described in Example 6), demonstrating that there is no significant Fc backbone conformational change between CH3C.35 and CH3C. 18. FIG. 40B shows an enlarged view of the overlaid structure in FIG. 40A. Residues 206-212 in TfR-AD of the CH3C.35 Fc/TfR-AD complex adopted different conformations from the residues in the TfR-AD of the CH3C.18 Fc/TfR-AD complex. Residue R208 in TfR-AD appeared buried in surface of the CH3C.18 Fc/TfR-AD complex, but appeared solvent exposed in the CH3C.35 Fc/TfR-AD complex. Further, residue L209 in TfR-AD of the CH3C.35 Fc/TfR-AD complex appeared rotated 180° and bound to the surface, but appeared away from the surface in the in the CH3C.18 Fc/TfR-AD complex.

Figure 41B:
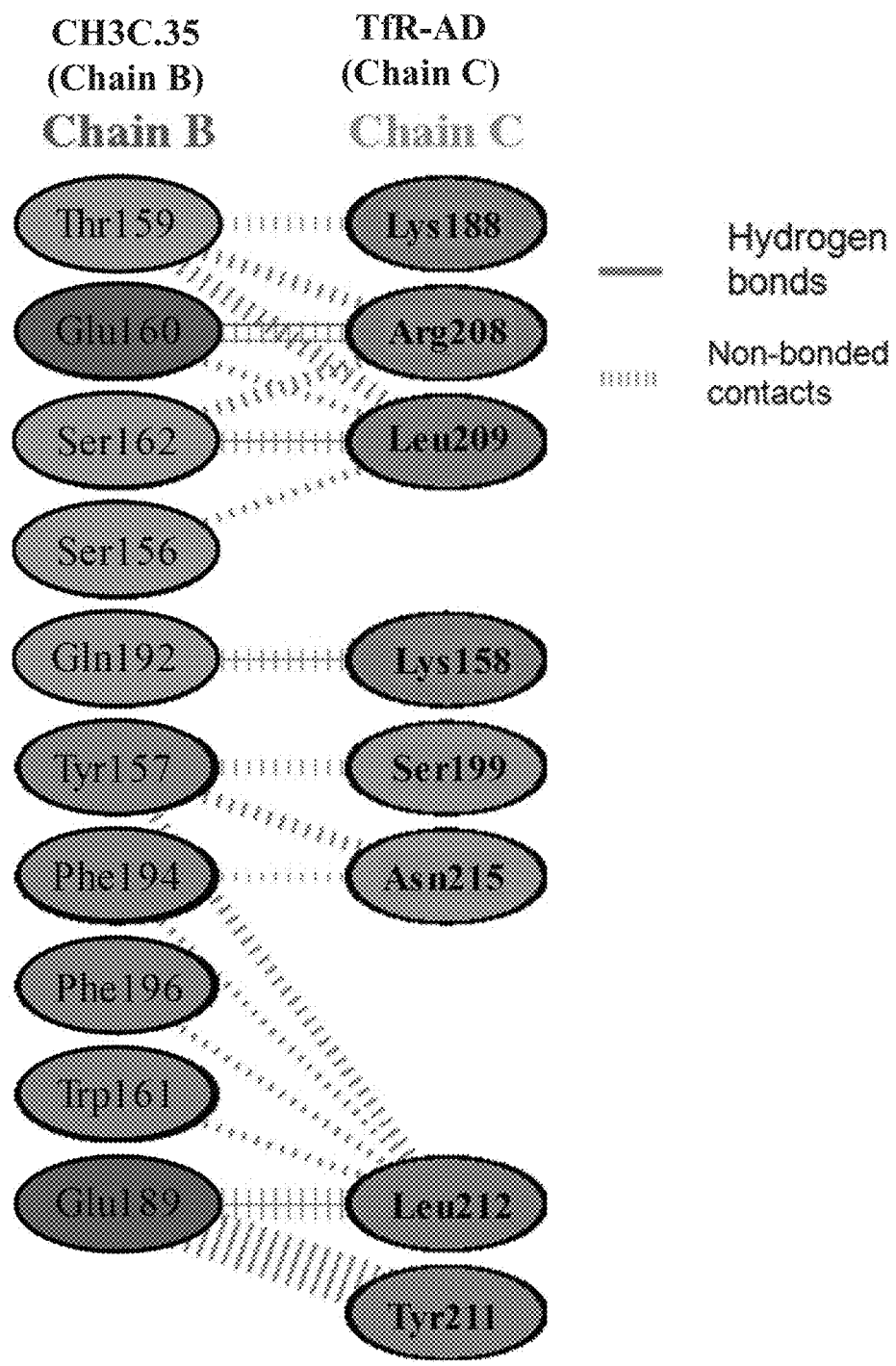

As shown in FIGS. 41A and 41B, interactions were observed between:

Thr159 of CH3C.35 and Gly207, Arg208, Lys188, and Leu209 of TfR-AD;

Glu160 of CH3C.35 and Arg208 and Leu209 of TfR-AD;

Ser162 of CH3C.35 and Arg208 and Leu209 of TfR-AD;

Ser156 of CH3C.35 and Leu209 of TfR-AD;

Trp161 of CH3C.35 and Leu209, Tyr211, and Leu212 of TfR-AD;

Glu189 of CH3C.35 and Tyr211 and Leu212 of TfR-AD;

Phe194 of CH3C.35 and Leu212, Asn215, and Val213 of TfR-AD;

Tyr157 of CH3C.35 and Leu212, Asn215, and Ser199 of TfR-AD;

Gln192 of CH3C.35 and Val213 and Lys158 of TfR-AD; and

Phe196 of CH3C.35 and Val213 and Leu212 of TfR-AD.

Furthermore, as described in the section titled "Paratope Mapping" of Example 2 and as shown in FIGS. 41A and 41B, several positions outside of the CH3C register also participate in binding to TfR.

Example 8. Pharmacokinetic/Pharmacodynamic Studies of Fc-Fab Fusion Polypeptides Comprising CH3C Variants in Cynomolgus Monkeys This example describes pharmacokinetic/pharmacodynamic (PK/PD) characterization of Fc-Fab fusions comprising CH3C variant polypeptides of the present invention in cynomolgus monkeys.

Study Design

A single 30 mg/kg dose of Ab122 (an anti-RSV antibody as control IgG), Ab153 (an anti-BACE1 antibody), Ab210 (anti-TfR/BACE1 bispecific antibody), or Fc-Fab fusion polypeptides comprising CH3C variant polypeptides fused to the Fab domain of Ab153 were intravenously administered in male cynomolgus monkeys 2-4 years old to evaluate plasma PK, plasma PD (Aβ340), and cerebrospinal fluid (CSF) PD (A1340) over the course of 29 days (n=4/group). To establish baseline, pre-dose CSF and blood samples were taken from each animal 7 days prior to dosing. After dosing, CSF was collected via an IT-L catheter at 12, 24, 48, 72, and 96 hours post-dose, and on study days 8, 11, 15, 18, 22, 25, and 29 for PD analysis. Blood samples were collected for plasma and serum PK at 0.25, 1, 6, 12, 24, 72 hours post-dose, and on study days 8, 11, 15, 18, 22, 25, and 29.

Table 19 shows an outline of the study design. "CH3C.35.21.16:Ab153" is a monovalent Fc-Fab fusion polypeptide comprising clone CH3C.35.21.16 fused to the Ab153 Fab domain. "CH3C.35.21:Ab153" is a monovalent Fc-Fab fusion polypeptide comprising clone CH3C.35.21 fused to the Ab153 Fab domain. "CH3C.35.9:Ab153" is a bivalent Fc-Fab fusion polypeptide comprising clone CH3C.35.21 fused to the Ab153 Fab domain. "CH3C.35.8:Ab153" is a bivalent Fc-Fab fusion polypeptide comprising clone CH3C.35.20 fused to the Ab153 Fab domain. "LALAPG" indicates that the antibody or Fc-Fab fusion polypeptide contains the mutations L7A, L8A, and P102G in the Fc sequence (as numbered with reference to SEQ ID NO:1). "LALAPG.YTE" indicates that the Fc-Fab fusion polypeptide contains the mutations L7A, L8A, P102G, M25Y, S27T, and T29E in the Fc sequence (as numbered with reference to SEQ ID NO: 1).

TABLE 19

| Treatment | Isotype | Cyno TfR full-length affinity (nM) | Cyno TfR apical affinity (nM) | Dose | N | Material (mg) |
| --- | --- | --- | --- | --- | --- | --- |
| Ab122 (control IgG) | huIgG1.LALAPG | — | | 30 | 4 | 750 |
| Ab153 | huIgG1.LALAPG | — | | 30 | 4 | 750 |
| Ab210 | huIgG1.LALAPG | 52 | 140 | 30 | 4 | 750 |
| CH3C.35.21.16:Ab153 (monovalent) | huIgG1.LALAPG | 1800 | 1900 | 30 | 4 | 750 |
| CH3C.35.21.16:Ab153 (monovalent) | huIgG1.LALAPG.YTE | 1800 | 1900 | 30 | 4 | 750 |
| CH3C.35.21:Ab153 (monovalent) | huIgG1.LALAPG.YTE | 2100 | 2200 | 30 | 4 | 750 |
| CH3C.35.9:Ab153 (bivalent) | huIgG1.LALAPG.YTE | 700 | | 30 | 4 | 750 |
| CH3C.35.8:Ab153 (bivalent) | huIgG1.LALAPG.YTE | 1700 | | 30 | 4 | 750 |

Methods

Human IgG PK Assay

Antibody or Fc-Fab fusion polypeptide concentrations in cyno serum were quantified using a human IgG-specific sandwich ELISA. A 384-well MaxiSorp plate was coated overnight with an antibody specific for the Fc of human IgG. Serum samples were diluted 1:100, 1:1,000, 1:10,000, and 1:100,000 and added to the blocked plates. The detection antibody was a polyclonal anti-human IgG monkey-absorbed antibody. The standard curves were prepared for each antibody or Fc-Fab fusion polypeptide individually (48-200, 000 pg/mL IgG) and the assay has a lower limit of quantification (LLOQ) in serum of 20 ng/mL.

PD Assays

Soluble APPα/β levels in cyno CSF were measured using a MesoScale Discovery (MSD) multiplex kit (MSD #K15120E). Two different antibodies specifically captured either sAPPα or sAPPβ, and then both analytes were detected with a SULFO-tag labeled anti-APP mouse monoclonal antibody. Cyno Aβ340 levels were measured using a MSD ultra-sensitive kit (MSD #K151FTE). This assay used the huAβ-specific 6E10 antibody as the capture and an anti-Aβ340 antibody specific for the C-terminus of the peptide as the detection molecule. Both assays were run according to the manufacturer's instructions. Briefly, pre-coated plates were blocked for 1 hour with MSD Blocker A. CSF samples were diluted 1:5 and added in duplicate to the blocked plates followed by an overnight incubation at 4° C. Next, the respective detection antibodies were added and the plates read on a Sector S600 instrument. The standard curves, 0.92-3750 pg/mL huAβ340 and 0.1-100 ng/mL for both sAPPα/β, were fit using a four-parameter logistic regression. The assays had a LLOQ of 73 pg/mL for Aβ340 and 0.5 ng/mL for sAPPα/β.

Results

Figure 42A:
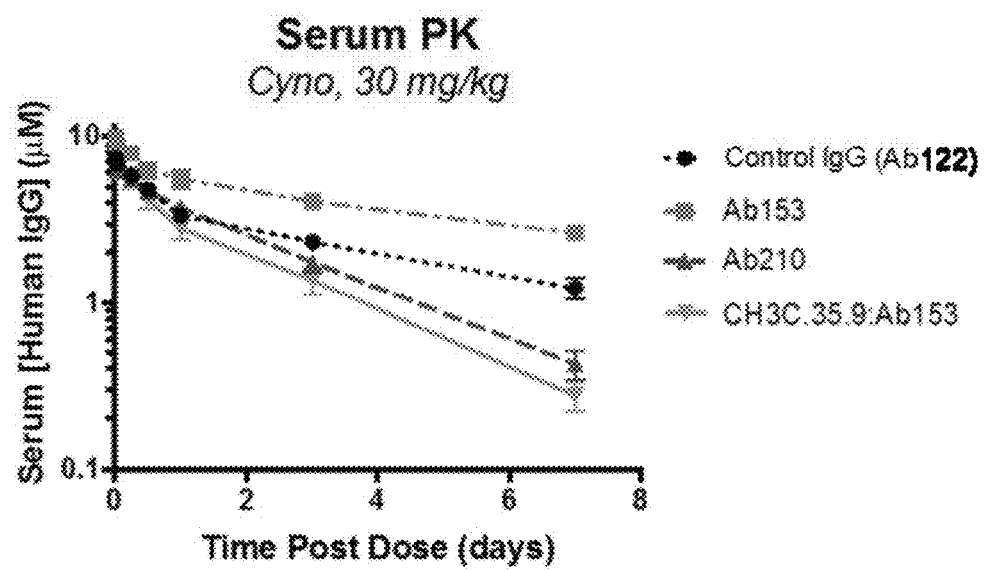
FIGS. 42A and 42B depict plasma PK and Aβ340 reduction for an Fc-Fab fusion polypeptide comprising a CH3C variant fused to the Ab153 Fab domain in cynomolgus monkeys.
Figure 42B:
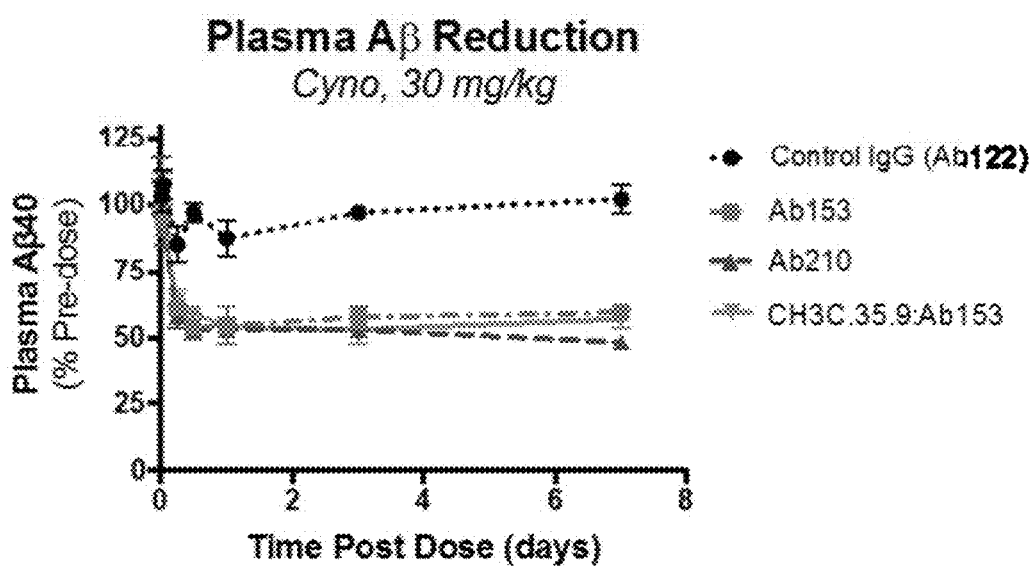
Figure 43A:
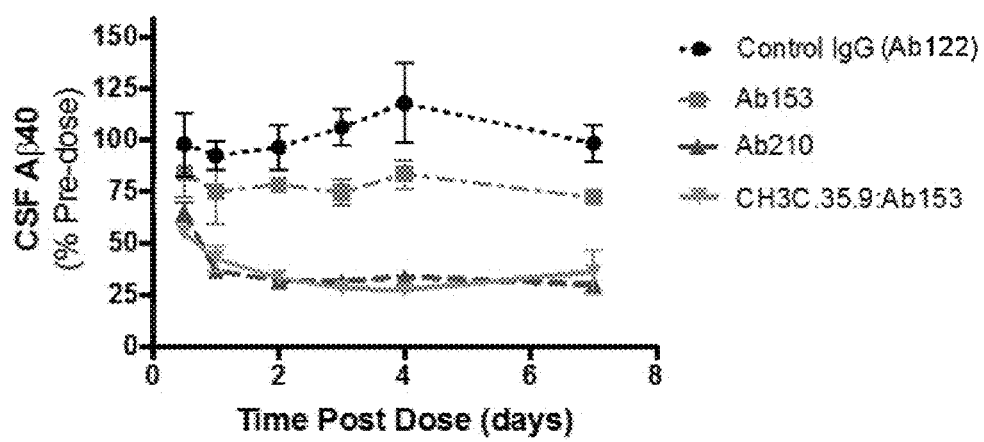
FIGS. 43A and 43B depict significant cerebrospinal fluid (CSF) Aβ and sAPPβ/sAPPα reduction with an Fc-Fab fusion polypeptide comprising a CH3C variant fused to the Ab153 Fab domain in cynomolgus monkeys.
Figure 43B:
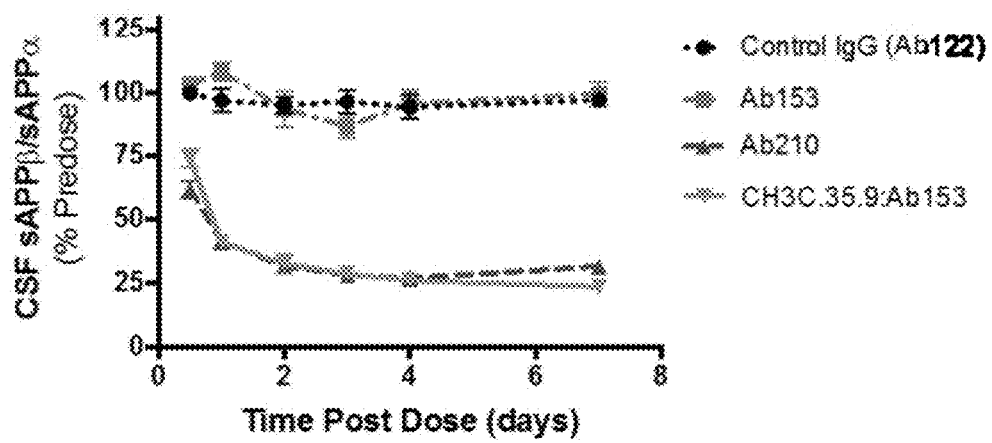

Interim serum PK from the first 7 days post-dose showed the expected target-mediated clearance for Ab210 and CH3C.35.9:Ab153 due to their binding to TfR in the periphery (FIG. 42A). Both Ab153 and Ab210 antibodies, as well as CH3C.35.9:Ab153, resulted in a significant and sustained reduction in plasma Aβ340 compared to control IgG (FIG. 42B), confirming all three molecules were able to inhibit BACE1 activity in vivo to a similar extent. In the CSF, both Ab210 and CH3C.35.9:Ab153 were able to reduce CSF Aβ340 and sAPPβ/sAPPα ratio to about 70% and about 75%, respectively, compared to control IgG (FIGS. 43A and 43B). Ab153, an anti-BACE1 antibody that does not bind TfR, showed minimal impact on CSF Aβ340 and sAPPβ/sAPPα ratio compared to control IgG. These results demonstrate that binding to TfR with a CH3C variant polypeptide (e.g., clone CH3C.35.9) enhances CNS penetration of an Fc-Fab fusion comprising the CH3C variant polypeptide fused to the Fab domain of an anti-BACE1 antibody (e.g., CH3C.35.9:Ab153) to inhibit CSF Aβ340 and sAPPβ/sAPPα production.

Figure 46A:
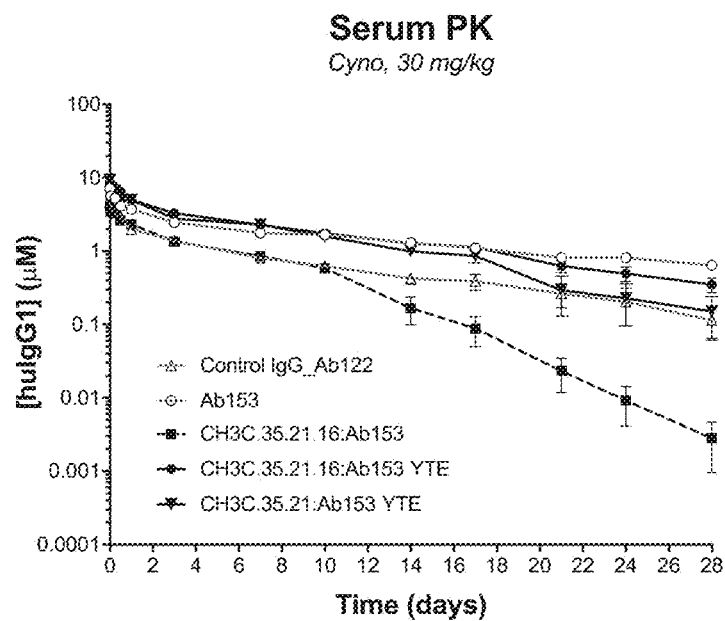
FIGS. 46A-46D depict 28-day PKPD study in cynomolgus monkeys after a single 30 mg/kg dose of the indicated proteins.
Figure 46B:
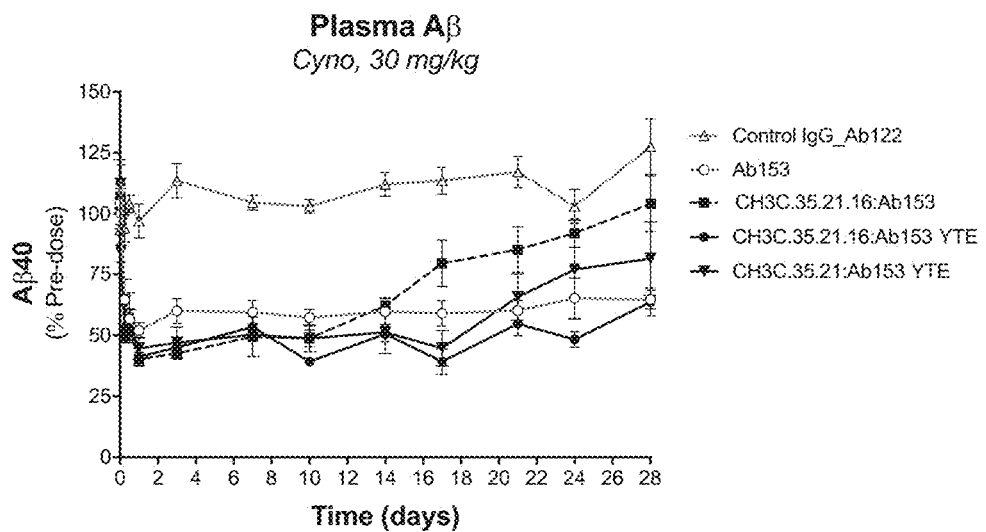
Figure 46C:
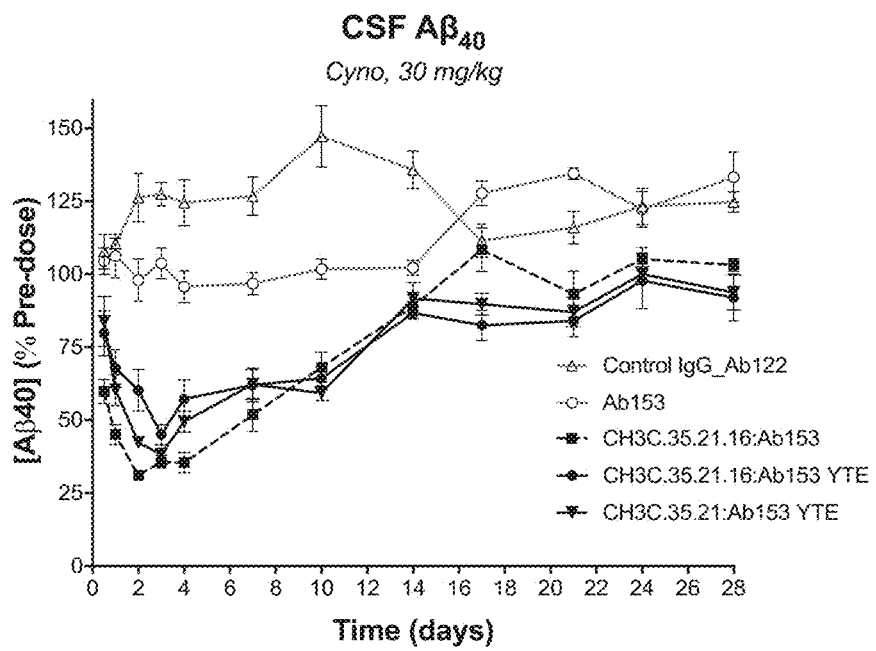
Figure 46D:
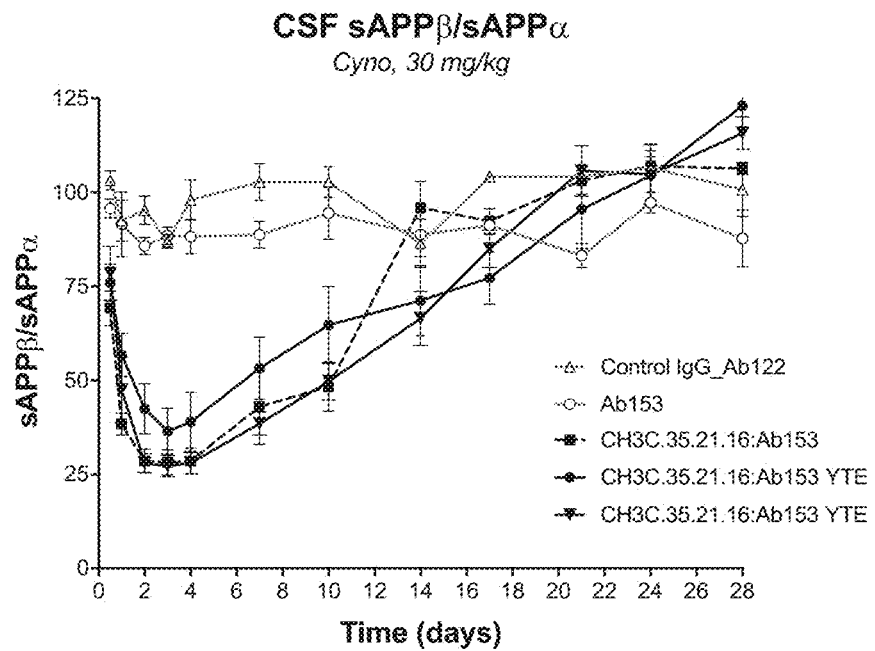

Serum PK, plasma Aβ, and CSF Aβ levels were also evaluated for four weeks following a single dose. Similar to what was observed in mouse, peripheral serum PK of TfR-binding Fc-Fab fusions (CH3C.35.21.16:Ab153 LALAPG, CH3C.35.21.16:Ab153 LALAPGYTE, and CH3C.35.21:Ab153 LALAPGYTE) exhibited faster clearance compared to Ab122 and Ab153 due to binding to TfR on peripheral tissues (FIG. 46A). Both Ab153 and CH3C:Ab153 fusion reduced plasma Aβ levels by greater than about 50% compared to control IgG Ab122 (FIG. 46B). The maximum Aβ was similar between Ab153 and CH3C:Ab153 fusion, indicating that the Fc modifications did not affect ability of anti-BACE1 Fab to inhibit APP cleavage in vivo (FIG. 46B). The duration of plasma Aβ correlated with the exposure of Ab153 and CH3C:Ab153 over time. In the CSF, all three Fc-Fab fusions were able to significantly reduce both Aβ340 and sAPPβ/sAPPα ratio to about 70% compared to control IgGAb122, whereas no significant reduction was observed in animals dosed with Ab153 (FIGS. 46C and 46D). These results demonstrate that binding to TfR with a CH3C variant polypeptide (e.g., clone CH3C.35.21.16 and CH3C.35.21) enhances CNS penetration of an Fc-Fab fusion comprising the CH3C variant polypeptide fused to the Fab domain of an anti-BACE1 antibody (e.g., CH3C.35.21.16: Ab153 and CH3C.35.21:Ab153) to inhibit CSF Aβ340 and sAPPβ/sAPPα production.

Figure 47A:
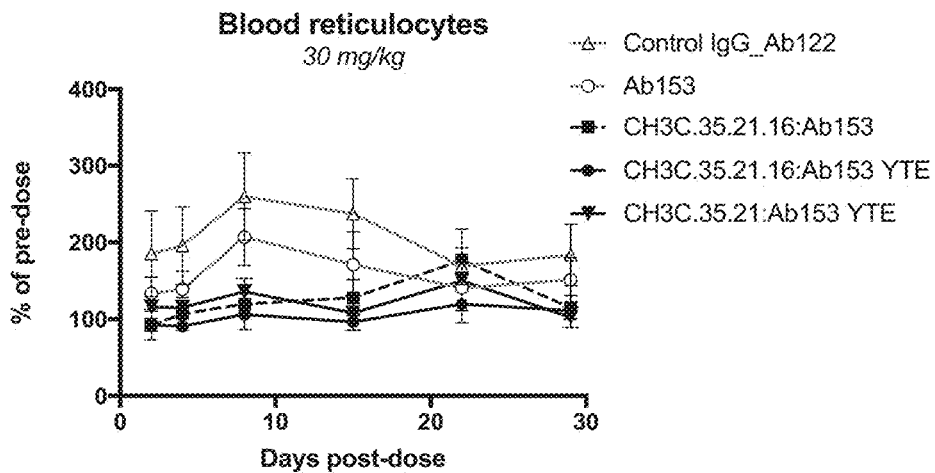
FIGS. 47A-47C depict blood reticulocyte relative to predose levels (FIG. 47A), absolute serum iron levels (FIG. 47B), and absolute red blood cell count (FIG. 47C) in peripheral blood in cynomolgus monkeys after a single 30 mg/kg dose of the indicated proteins (mean±SEM, n=4-5 per group).
Figure 47B:
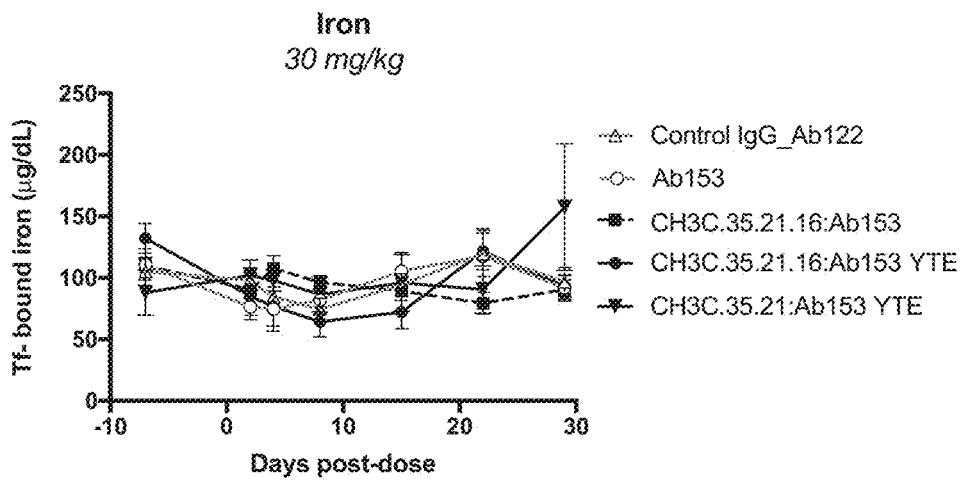
Figure 47C:
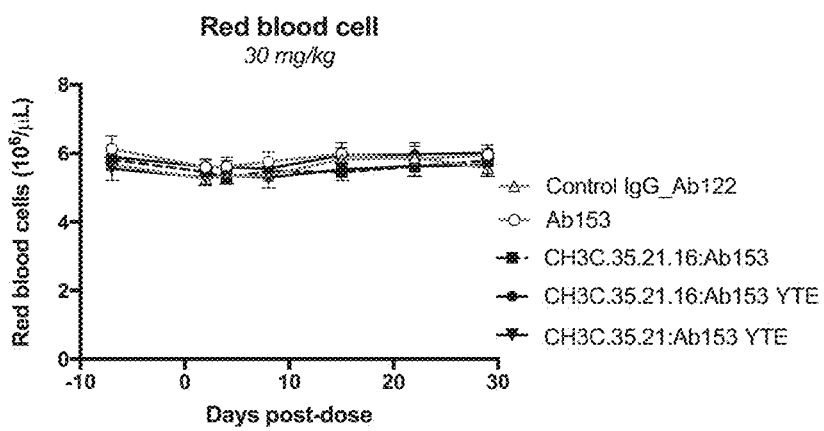

Because of the high level of TfR expression on immature red blood cells, peripheral blood clinical pathology was evaluated throughout the course of the study to evaluate reticulocyte number, serum iron, and red blood cell count. The assessment of serum iron levels utilized a variation of the method using TPTZ [2,4,6-Tri-(2-pyridyl)-5-triazine] as the chromogen. In an acidic medium, transferrin-bound iron dissociated into free ferric ions and apo transferrin. Hydrochloric acid and sodium ascorbate reduced the ferric ions to the ferrous state. The ferrous ions then reacted with TPTZ to form a blue colored complex that was measured bichromatically at 600/800 nm. The increase in absorbance was directly proportional to the amount of transferrin bound iron present. This is performed on the Beckman/Olympus AU640e chemistry analyzer. Absolute reticulocytes and RBC morphology were analyzed by the Siemens Advia 120 automated hematology system. Fc-Fab fusions had no impact on reticulocyte number, as compared to their pre-dose values (FIG. 47A). Additionally, serum iron as well as red blood cell number were also not impacted (FIGS. 47B and 47C). Together these data indicate that modified TfR-binding Fc polypeptide-Fab fusions can safely and effectively increase brain exposure of antibodies in non-human primates to produce a robust pharmacodynamic response (i.e., CSF Aβ reduction).

Example 9. Pharmacokinetic Analysis of CH3C.35 Containing M201L and N207S Mutations This example describes that mutations M201L and N207S are compatible with CH3C.35.

Figures 48A, 48B:
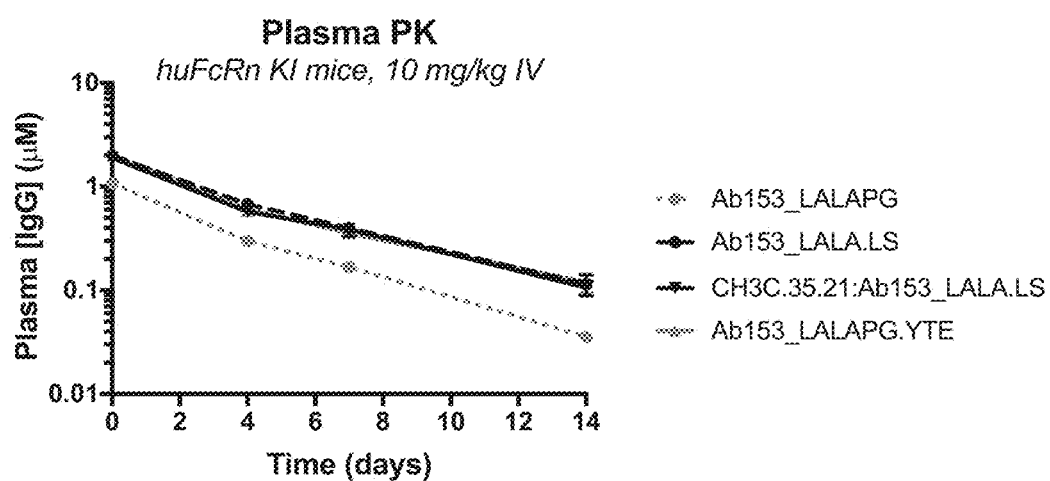
FIGS. 48A and 48B depict peripheral PK analysis (plasma huIgG1 concentrations (FIG. 48A) and clearance values (FIG. 48B)) of indicated proteins in hFcRn knock-in mice after a single 10 mg/kg intravenous injection over 14 days (mean±SEM, n=3 per group).

In order to evaluate whether mutations that increase serum stability, M201L and N207S as numbered with reference to SEQ ID NO:1 (M428L/N434S according to EU numbering; also referred to as "LS" mutations), are compatible with TfR-binding Fc modifications, human FcRn knock-in mice were dosed with Ab153_LALAPG, Ab153_LALA.LS, CH3C.35.21:Ab153_LALA.LS, or Ab153_LALAPG.YTE at 10 mg/kg. Plasma PK evaluation over 14 days showed a similar about 2-fold improvement for Ab153_LALA.LS, CH3C.35.21:Ab153_LALA.LS, and Ab153_LALAPG.YTE compared to Ab153_LALAPG without any serum stability mutations (FIGS. 48A and 48B). This indicates that the additional Fc mutations for TfR binding do not impact the ability of the LS mutations to improve huIgG1 half-life in vivo.

Example 10. Engineering TfR Construct

This example describes the expression and purification of a TfR construct comprising a first polypeptide having the sequence of SEQ ID NO:449 and a second polypeptide having the sequence of SEQ ID NO:450.

A DNA fragment encoding a TfR construct, His10-Smt3-Avi-TfR, was synthesized and inserted into pET28 vector. The sequence of SEQ ID NO:468 encodes His10-Smt3-Avi-TfR having human TfR sequences (the first polypeptide having the sequence of SEQ ID NO:449 and the second polypeptide having the sequence of SEQ ID NO:450). The sequence of SEQ ID NO:469 encodes His10-Smt3-Avi-TfR having cynomolgus monkey TfR sequences (the first polypeptide having the sequence of SEQ ID NO:451 and the second polypeptide having the sequence of SEQ ID NO:452). For co-expression of the TfR construct and *Escherichia coli* biotin ligase BirA, plasmid pACYC-BirA was transformed with pET28-His10-Smt3-Avi-PreScission-TfR into *E. coli* BL21(DE3) (Novagen). Cultures were inoculated and maintained in logarithmic growth at 37° C. in LB medium containing kanamycin (50 µg/ml) and chloramphenicol (35 µg/ml). When the A600 of the cultures reached 0.6-0.8, the cultures were chilled for 30 min on ice, IPTG was added to a final concentration of 1.0 mM, and the cultures were incubated for 16 hours at 18° C. with constant shaking. Cells were harvested by centrifugation and stored at −80 OC.

All subsequent operations were performed at 4° C. The cell pellets from a 6-L LB culture were suspended in 200 ml of buffer A (50 mM Tris-HCl, pH 7.5, 500 mM NaCl, 10% glycerol), and benzonase (Sigma) was added with 1:20000 dilutions. The suspension was mixed gently for at least 1 hour. The lysate was applied to a microfluidizer, and the insoluble material was removed by centrifugation for 45 min at 14,000 rpm in a Sorvall SS34 rotor. The soluble cytosol fraction was loaded onto 5-ml HisTrap (GE Healthcare) equilibrated in buffer A. The column was washed with 25 mM imidazole and 50 mM imidazole in buffer A with at least 20 column volumes (CV) and 3 CV, respectively. Bound TfR construct was eluted with a gradient of 100-500 mM imidazole in buffer A with 8 CV. Peak fractions containing the TfR construct were pooled, and divided into 2 portions. Half of the pooled fractions was used to further purify the TfR construct, and the other was used to cleave the His10-Smt3 tag and purify Avi-TfR.

For the tag cleavage, Smt3 specific protease Ulp 1 (Sumo fusion:protease) was added at the molar ratio of 100:1, incubated and dialyzed against buffer C (50 mM HEPES, pH 7.5, 150 mM NaCl, 1 mM DTT) at 4° C. overnight. The protein mixture was filtered (0.22 m), and loaded again onto 5-ml HisTrap (GE Healthcare), which was equilibrated in buffer C. The cleaved His10-Smt3 tag and Ulp1 protease were removed by loading onto 5-ml HisTrap (GE Healthcare) equilibrated in buffer C, and the flow through which contains cleaved Avi-TfR was collected and concentrated. Each of His10-Smt3 fused and tag cleaved human TfR was applied to a HiLoad Superdex 200 26/60 and Superdex 75 16/60 (GE Healthcare), respectively. Both columns were equilibrated and run with buffer C. The purity of the preparation was monitored by SDS-PAGE analysis and staining with Instant Blue staining (Expedeon). The protein concentration was determined by UV reading using extinction coefficient determined by the sequence of each target protein. In vivo biotinylation of the target protein was confirmed by Western blot probed with streptavidin-HRP (Sigma).

XIV. Examplary Embodiments

Exemplary embodiments provided in accordance with the presently disclosed subject matter include, but are not limited to, the claims and the following embodiments:

1. A polypeptide that is capable of being actively transported across the blood brain barrier (BBB) comprising:
(a) a modified Fc polypeptide, or fragment thereof;
(b) a first site within the modified Fc polypeptide or fragment that specifically binds to a BBB receptor; and
(c) a second site that binds to a neonatal Fc receptor (FcRn).
2. The polypeptide of embodiment 1, wherein the second site is a native FcRn binding site.
3. The polypeptide of embodiment 1, wherein the FcRn binding site comprises amino acid changes relative to the native Fc sequence that extend serum half-life.
4. The polypeptide of embodiment 3, wherein the amino acid changes comprise substitutions of Tyr at position 25, Thr at position 27, and Glu at position 29, wherein the positions of the residues are determined with reference to SEQ ID NO: 1.
5. The polypeptide of embodiment 3, wherein the amino acid changes comprise substitutions of Leu at position 201 and Ser at position 207, wherein the positions of the residues are determined with reference to SEQ ID NO:1.
6. The polypeptide of embodiment 3, wherein the amino acid changes comprise a substitution of Ser or Ala at position 207, wherein the position of the residue is determined with reference to SEQ ID NO:1.
7. The polypeptide of any one of embodiments 1 to 6, wherein the modified Fc polypeptide or fragment comprises at least 50 amino acids that correspond to a native Fc polypeptide amino acid sequence.
8. The polypeptide of embodiment 7, wherein the at least 50 amino acids are contiguous.
9. The polypeptide of embodiment 7, wherein the modified Fc polypeptide or fragment comprises at least 100 amino acids that correspond to a native Fc polypeptide amino acid sequence.
10. The polypeptide of any one of embodiments 1 to 9, wherein the first site comprises at least one modified amino acid in a β-sheet of the Fc polypeptide.
11. The polypeptide of embodiment 10, wherein the β-sheet is in the CH2 domain.
12. The polypeptide of embodiment 10, wherein the β-sheet is in the CH3 domain.
13. The polypeptide of any one of embodiments 1 to 12, wherein the first site includes a substitution of at least one solvent-exposed amino acid.
14. The polypeptide of embodiment 13, wherein the first site includes substitutions in at least two solvent-exposed amino acids in a loop region or in a β-sheet, wherein the two solvent-exposed residues are not in the same loop region or the same β-sheet.
15. The polypeptide of any one of embodiments 1 to 14, wherein the modified Fc polypeptide or fragment sequence comprises a modified CH2 domain sequence.
16. The polypeptide of embodiment 15, wherein the modified CH2 domain sequence is derived from a human IgG1, IgG2, IgG3, or IgG4 CH2 domain sequence.
17. The polypeptide of embodiment 15 or 16, wherein the modifications to the CH2 domain comprise at least two substitutions of amino acids in a set of amino acids selected from the group consisting of:
(a) residues 47, 49, 56, 58, 59, 60, 61, 62, and 63;
(b) residues 39, 40, 41, 42, 43, 44, 68, 70, 71, and 72;
(c) residues 41, 42, 43, 44, 45, 65, 66, 67, 69, and 73; and
(d) residues 45, 47, 49, 95, 97, 99, 102, 103, and 104;
wherein positions of the residues are determined with reference to SEQ ID NO: 1.
18. The polypeptide of any one of embodiments 1 to 14, wherein the modified Fc polypeptide or fragment sequence comprises a modified CH3 domain sequence.
19. The polypeptide of embodiment 18, wherein the modified CH3 domain sequence is derived from a human IgG1, IgG2, IgG3, or IgG4 CH3 domain sequence.
20. The polypeptide of embodiment 18 or 19, wherein the modifications to the CH3 domain comprise at least two substitutions of amino acids in a set of amino acids selected from the group consisting of:
(a) residues 157, 159, 160, 161, 162, 163, 186, 189, and 194; and
(b) residues 118, 119, 120, 122, 210, 211, 212, and 213;
wherein positions of the residues are determined with reference to SEQ ID NO: 1.
21. The polypeptide of any one of embodiments 1 to 20, wherein the modified Fc polypeptide or fragment has an amino acid sequence identity of at least 75% as compared to the corresponding wild-type Fc polypeptide or fragment.
22. The polypeptide of embodiment 21, wherein the identity is at least 80%, 90%, 92%, or 95%.
23. The polypeptide of any one of embodiments 1 to 22, wherein the modified Fc polypeptide or fragment has effector function.
24. The polypeptide of any one of embodiments 1 to 22, wherein the modified Fc polypeptide or fragment does not have effector function.
25. The polypeptide of embodiment 24, wherein the modified Fc polypeptide or fragment comprises a modification that reduces effector function.
26. The polypeptide of embodiment 25, wherein the modification comprises substitutions of Leu at position 7 and Leu at position 8, wherein the positions of the residues are determined with reference to SEQ ID NO:1.

27. The polypeptide of embodiment 26, wherein the modification further comprises substitution of Pro at position 102, wherein the position of the residue is determined with reference to SEQ ID NO:1.

28. A dimeric protein comprising the polypeptide or fragment of any one of embodiments 1 to 27.

29. The dimeric protein of embodiment 28, which is a heterodimer comprising a first and a second polypeptide chain, wherein the first polypeptide chain comprises the first site that specifically binds to a BBB receptor.

30. The dimeric protein of embodiment 29, wherein the second polypeptide chain does not comprise a site that specifically binds to a BBB receptor.

31. The dimeric protein of embodiment 28, which is a homodimer comprising a first and a second polypeptide chain, wherein the first and second polypeptide chains each comprise a site that specifically binds to a BBB receptor.

32. The polypeptide of any one of embodiments 1 to 27, wherein the BBB receptor is selected from the group consisting of transferrin receptor (TfR), insulin receptor, insulin-like growth factor receptor (IGF-R), low density lipoprotein receptor (LDLR), low density lipoprotein receptor-related protein 1 (LRP1), low density lipoprotein receptor-related protein 2 (LRP2), low density lipoprotein receptor-related protein 8 (LRP8), GLUT1, basigin, diphtheria toxin receptor, membrane-bound precursor of heparin binding epidermal growth factor-like growth factor (HB-EGF), melanotransferrin, and vasopressin receptor.

33. The polypeptide of embodiment 32, wherein the BBB receptor is TfR.

34. The polypeptide of embodiment 32, wherein the BBB receptor is IGF-R.

35. The polypeptide of any one of embodiments 1 to 27 and 32 to 34, wherein the polypeptide specifically binds to the BBB receptor without competing for binding with an endogenous ligand of the receptor.

36. The polypeptide of embodiment 35, wherein the BBB receptor is transferrin receptor and the endogenous ligand is transferrin.

37. The polypeptide of any one of embodiments 1 to 27 and 32 to 36, further comprising a biologically active polypeptide.

38. The polypeptide of embodiment 37, wherein the biologically active polypeptide is a therapeutically active polypeptide.

39. The polypeptide of embodiment 37 or 38, wherein uptake into brain of the biologically active polypeptide is at least ten-fold greater as compared to uptake of the biologically active polypeptide when the modified Fc polypeptide or fragment is not present.

40. A protein that is capable of being actively transported across the BBB, the protein comprising:
(a) an antibody variable region sequence that is capable of binding an antigen, or antigen-binding fragment thereof, and
(b) a polypeptide comprising a modified Fc polypeptide, or a fragment thereof, wherein the modified Fc polypeptide or fragment contains a first binding site that specifically binds to a BBB receptor; and a second binding site that binds to a neonatal Fc receptor (FcRn).

41. The protein of embodiment 40, wherein the antibody variable region sequence comprises a Fab domain.

42. The protein of embodiment 40 or 41, wherein the antibody variable region sequence comprises two antibody variable region heavy chains and two antibody variable region light chains, or respective fragments thereof.

43. The protein of any one of embodiments 40 to 42, comprising a single modified Fc polypeptide or fragment that binds to the BBB receptor.

44. The protein of any one of embodiments 40 to 42, comprising two modified Fc polypeptides or fragments that binds to the BBB receptor.

45. The protein of any one of embodiments 40 to 44, wherein the uptake of the protein into the brain is at least 10-fold greater as compared either to (a) the same protein without the polypeptide comprising a modified Fc polypeptide or fragment or (b) the same protein with the polypeptide comprising an Fc polypeptide or Fc polypeptide fragment that does not contain the modifications that result in BBB receptor binding.

46. A conjugate comprising (a) a polypeptide of any one of embodiments 1 to 27 and 32 to 39; and (b) therapeutic or diagnostic agent; wherein the conjugate is capable of being transported across the blood-brain barrier.

47. The conjugate of embodiment 46, wherein uptake of the therapeutic or diagnostic agent to the brain is increased by at least 10-, 20-, 30-, 40-, or 50-fold relative to the uptake of the therapeutic or diagnostic agent absent the polypeptide.

The amino acid substitutions for each clone described in the Tables (e.g., Table 9) dictate the amino acid substitutions at the register positions of that clone over the amino acids found in the sequence set forth in the Sequence Listing, in case of discrepancy.

It is understood that the examples and embodiments described herein are for illustrative purposes only and that various modifications or changes in light thereof will be suggested to persons skilled in the art and are to be included within the spirit and purview of this application and scope of the appended claims. The sequences of the sequence accession numbers cited herein are hereby incorporated by reference.

TABLE 1

CH2A2 Register Positions and Mutations

| Sequence name | Seq. group | 47 | 48 | 49 | . . . | 56 | 57 | 58 | 59 | 60 | 61 | 62 | 63 |
|---|---|---|---|---|---|---|---|---|---|---|---|---|---|
| Wild-type | n/a | K | F | N | . . . | E | V | H | N | A | K | T | K |
| CH2A2.1 | 1 | E | F | I | . . . | D | V | R | Y | E | W | Q | L |
| CH2A2.2 | 1 | G | F | V | . . . | P | V | S | W | E | W | Y | W |
| CH2A2.3 | 1 | Q | F | D | . . . | M | V | R | R | E | W | H | R |
| CH2A2.4 | 1 | S | F | E | . . . | P | V | R | W | E | W | Q | W |
| CH2A2.5 | 1 | A | F | T | . . . | P | V | R | W | E | W | Q | N |
| CH2A2.6 | 1 | N | F | D | . . . | L | V | R | R | E | W | H | R |
| CH2A2.7 | 1 | Q | F | V | . . . | A | V | R | W | E | W | I | R |
| CH2A2.8 | 1 | E | F | I | . . . | E | V | A | W | E | W | F | W |

TABLE 1-continued CH2A2 Register Positions and Mutations

| Sequence name | Seq. group | 47 | 48 | 49 | ... | 56 | 57 | 58 | 59 | 60 | 61 | 62 | 63 |
|---|---|---|---|---|---|---|---|---|---|---|---|---|---|
| CH2A2.9 | 1 | G | F | A | ... | N | V | R | V | E | W | Q | Y |
| CH2A2.10 | 1 | G | F | V | ... | E | V | R | R | E | W | V | R |
| CH2A2.11 | 1 | S | F | D | ... | L | V | R | R | E | W | Q | R |
| CH2A2.12 | 1 | E | F | T | ... | D | V | R | Y | E | W | Y | Y |
| CH2A2.13 | 1 | Q | F | T | ... | D | V | R | Y | E | W | V | R |
| CH2A2.14 | 1 | Q | F | Y | ... | N | V | R | R | E | W | H | R |
| CH2A2.15 | 1 | Y | F | D | ... | M | V | R | R | E | W | H | R |
| CH2A2.16 | 2 | W | F | E | ... | F | V | G | V | A | Y | D | V |

TABLE 2

CH2C Register Positions and Mutations

| Sequence name | Seq. group | 39 | 40 | 41 | 42 | 43 | 44 | ... | 68 | 69 | 70 | 71 | 72 |
|---|---|---|---|---|---|---|---|---|---|---|---|---|---|
| Wild-type | n/a | V | S | H | E | D | P | ... | Q | Y | N | S | T |
| CH2C.1 | 1 | P | Q | T | P | P | W | ... | E | Y | Y | T | Y |
| CH2C.2 | 1 | P | P | S | P | P | W | ... | E | Y | Y | S | N |
| CH2C.3 | 1 | P | Q | T | P | P | W | ... | E | Y | Y | S | N |
| CH2C.4 | 1 | F | R | G | P | P | W | ... | E | Y | Y | H | D |
| CH2C.5 | 1 | P | Q | T | V | P | W | ... | E | Y | Y | S | N |
| CH2C.6 | 1 | P | K | M | P | P | W | ... | E | Y | Y | T | Y |
| CH2C.7 | 1 | P | P | V | P | P | W | ... | E | Y | Y | S | N |
| CH2C.8 | 1 | P | A | F | P | P | W | ... | E | Y | Y | Q | Y |
| CH2C.9 | 1 | A | I | W | P | P | W | ... | E | Y | Y | S | N |
| CH2C.10 | 1 | P | P | V | A | P | W | ... | E | Y | Y | S | S |
| CH2C.11 | 1 | P | Q | M | P | P | Q | ... | E | Y | Y | S | N |
| CH2C.12 | 1 | P | Q | T | A | P | W | ... | E | Y | Y | T | Y |
| CH2C.13 | 1 | P | Q | T | P | P | Q | ... | E | Y | Y | S | N |
| CH2C.14 | 1 | P | Q | T | P | P | W | ... | E | Y | Y | T | Y |
| CH2C.15 | 1 | P | R | V | P | P | W | ... | E | Y | Y | Q | N |
| CH2C.16 | 1 | P | S | V | P | P | W | ... | E | Y | Y | S | N |
| CH2C.17 | 2 | M | L | W | P | V | P | ... | V | Y | H | R | P |
| CH2C.18 | 2 | M | L | W | P | V | P | ... | T | Y | H | N | P |
| CH2C.19 | 2 | M | E | W | P | V | T | ... | T | Y | H | H | P |
| CH2C.20 | 2 | M | L | W | P | V | P | ... | T | Y | H | H | P |
| CH2C.21 | 3 | D | D | L | T | F | Q | ... | V | Y | V | T | P |
| CH2C.22 | 3 | D | D | L | T | F | Q | ... | L | Y | V | T | P |
| CH2C.23 | 4 | A | Y | G | D | P | E | ... | W | Y | D | V | P |

TABLE 3

CH2D Register Positions and Mutations

| Sequence name | Seq. group | 41 | 42 | 43 | 44 | 45 | ... | 65 | 66 | 67 | 68 | 69 | 70 | 71 | 72 | 73 |
|---|---|---|---|---|---|---|---|---|---|---|---|---|---|---|---|---|
| Wild-type | n/a | H | E | D | P | E | ... | R | E | E | Q | Y | N | S | T | Y |
| CH2D.1 | 1 | V | P | P | R | M | ... | L | T | S | Q | H | N | S | T | V |
| CH2D.2 | 1 | V | P | P | W | M | ... | L | T | S | Q | H | N | S | T | V |
| CH2D.3 | 2 | D | M | W | E | Y | ... | W | V | K | Q | L | N | S | T | W |
| CH2D.4 | 2 | D | D | W | T | W | ... | W | I | A | Q | P | N | S | T | W |
| CH2D.5 | 2 | D | D | W | E | W | ... | W | K | L | Q | L | N | S | T | W |

TABLE 4

CH2E3 Register Positions and Mutations

| Sequence name | Seq. group | 45 | 46 | 47 | 48 | 49 | ... | 95 | 96 | 97 | 98 | 99 | 100 | 101 | 102 | 103 | 104 |
|---|---|---|---|---|---|---|---|---|---|---|---|---|---|---|---|---|---|
| Wild-type | n/a | E | V | K | F | N | ... | K | V | S | N | K | A | L | P | A | P |
| CH2E3.1 | 1 | W | V | W | F | Y | ... | S | V | V | N | I | A | L | W | W | S |

TABLE 4-continued

CH2E3 Register Positions and Mutations

| Sequence name | Seq. group | 45 | 46 | 47 | 48 | 49 | ... | 95 | 96 | 97 | 98 | 99 | 100 | 101 | 102 | 103 | 104 |
|---|---|---|---|---|---|---|---|---|---|---|---|---|---|---|---|---|---|
| CH2E3.2 | 2 | V | V | G | F | R | ... | R | V | S | N | S | A | L | T | W | K |
| CH2E3.3 | 2 | V | V | G | F | R | ... | R | V | S | N | S | A | L | S | W | R |
| CH2E3.4 | 2 | I | V | G | F | R | ... | R | V | S | N | S | A | L | R | W | R |
| CH2E3.5 | 3 | A | V | G | F | E | ... | Q | V | F | N | W | A | L | D | W | V |

TABLE 5

CH3B Register Positions and Mutations

| Sequence name | Seq. group | 118 | 119 | 120 | 121 | 122 | ... | 210 | 211 | 212 | 213 |
|---|---|---|---|---|---|---|---|---|---|---|---|
| Wild-type | n/a | E | P | Q | V | Y | ... | T | Q | K | S |
| CH3B.1 | 1 | F | D | Y | V | T | ... | G | F | H | D |
| CH3B.2 | 1 | F | D | M | V | T | ... | G | F | H | D |
| CH3B.3 | 1 | F | E | Y | V | T | ... | G | F | H | D |
| CH3B.4 | 1 | F | E | M | V | T | ... | G | F | H | D |
| CH3B.5 | 1 | F | E | L | V | T | ... | G | F | H | D |
| CH3B.6 | 1 | F | E | I | V | T | ... | G | F | H | D |
| CH3B.7 | 1 | F | D | I | V | T | ... | G | F | H | D |
| CH3B.8 | 1 | F | D | Y | V | T | ... | G | F | H | D |
| CH3B.9 | 1 | F | G | M | V | T | ... | G | F | H | D |
| CH3B.10 | 1 | F | A | D | V | T | ... | G | F | Y | D |
| CH3B.11 | 1 | F | G | L | V | T | ... | G | F | H | D |
| CH3B.12 | 1 | F | D | Y | V | T | ... | G | F | S | D |
| CH3B.13 | 1 | I | D | Y | V | T | ... | G | F | S | D |
| CH3B.14 | 1 | F | K | D | V | T | ... | G | F | F | D |
| CH3B.15 | 1 | F | D | L | V | T | ... | G | F | Y | D |
| CH3B.16 | 1 | I | D | Y | V | T | ... | G | F | S | D |
| CH3B.17 | 1 | F | E | L | V | A | ... | G | F | H | D |

TABLE 6

CH3C Register Positions and Mutations

| Sequence name | Seq. group | 157 | 158 | 159 | 160 | 161 | 162 | 163 | 164 | ... | 186 | 187 | 188 | 189 | 190 | 191 | 192 | 193 | 194 |
|---|---|---|---|---|---|---|---|---|---|---|---|---|---|---|---|---|---|---|---|
| Wild-type | n/a | N | G | Q | P | E | N | N | Y | ... | D | K | S | R | W | Q | Q | G | N |
| CH3C.1 | | L | G | L | V | W | V | G | Y | ... | A | K | S | T | W | Q | Q | G | W |
| CH3C.2 | | Y | G | T | V | W | S | H | Y | ... | S | K | S | E | W | Q | Q | G | Y |
| CH3C.3 | | Y | G | T | E | W | S | Q | Y | ... | E | K | S | D | W | Q | Q | G | H |
| CH3C.4 | | V | G | T | P | W | A | L | Y | ... | L | K | S | E | W | Q | Q | G | W |
| CH3C.17 | 2 | Y | G | T | V | W | S | K | Y | ... | S | K | S | E | W | Q | Q | G | F |
| CH3C.18 | 1 | L | G | H | V | W | A | V | Y | ... | P | K | S | T | W | Q | Q | G | W |
| CH3C.21 | 1 | L | G | L | V | W | V | G | Y | ... | P | K | S | T | W | Q | Q | G | W |
| CH3C.25 | 1 | M | G | H | V | W | V | G | Y | ... | D | K | S | T | W | Q | Q | G | W |
| CH3C.34 | 1 | L | G | L | V | W | V | F | S | ... | P | K | S | T | W | Q | Q | G | W |
| CH3C.35 | 2 | Y | G | T | E | W | S | S | Y | ... | T | K | S | E | W | Q | Q | G | F |
| CH3C.44 | 2 | Y | G | T | E | W | S | N | Y | ... | S | K | S | E | W | Q | Q | G | F |
| CH3C.51 | 1/2 | L | G | H | V | W | V | G | Y | ... | S | K | S | E | W | Q | Q | G | W |
| CH3C.3.1-3 | 1 | L | G | H | V | W | V | A | T | ... | P | K | S | T | W | Q | Q | G | W |
| CH3C.3.1-9 | 1 | L | G | P | V | W | V | H | T | ... | P | K | S | T | W | Q | Q | G | W |
| CH3C.3.2-5 | 1 | L | G | H | V | W | V | D | Q | ... | P | K | S | T | W | Q | Q | G | W |
| CH3C.3.2-19 | 1 | L | G | H | V | W | V | N | Q | ... | P | K | S | T | W | Q | Q | G | W |
| CH3C.3.2-1 | 1 | L | G | H | V | W | V | N | F | ... | P | K | S | T | W | Q | Q | G | W |

TABLE 9

Exploration of Acceptable Diversity Within Register and Hot Spot Positions for CH3C.35.21

| | 151 | 152 | 153 | 154 | 155 | 156 | 157 | 158 | 159 | 160 | 161 | 162 | 163 | 164 |
|---|---|---|---|---|---|---|---|---|---|---|---|---|---|---|
| Wild-type | A | V | E | W | E | S | N | G | Q | P | E | N | N | Y |
| CH3C.35.20.1 | . | . | . | . | . | . | F | . | T | E | W | S | S | . |
| CH3C.35.20.2 | . | . | . | . | . | . | Y | . | T | E | W | A | S | . |

TABLE 9-continued

Exploration of Acceptable Diversity Within Register and Hot Spot Positions for CH3C.35.21

| | | | | | | | | | | | | | | |
|---|---|---|---|---|---|---|---|---|---|---|---|---|---|---|
| CH3C.35.20.3 | . | . | . | . | . | . | Y | . | T | E | W | V | S | . |
| CH3C.35.20.4 | . | . | . | . | . | . | Y | . | T | E | W | S | S | . |
| CH3C.35.20.5 | . | . | . | . | . | . | F | . | T | E | W | A | S | . |
| CH3C.35.20.6 | . | . | . | . | . | . | F | . | T | E | W | V | S | . |
| CH3C.35.21.a.1 | . | . | W | . | . | . | F | . | T | E | W | S | S | . |
| CH3C.35.21.a.2 | . | . | W | . | . | . | Y | . | T | E | W | A | S | . |
| CH3C.35.21.a.3 | . | . | W | . | . | . | Y | . | T | E | W | V | S | . |
| CH3C.35.21.a.4 | . | . | W | . | . | . | Y | . | T | E | W | S | S | . |
| CH3C.35.21.a.5 | . | . | W | . | . | . | F | . | T | E | W | A | S | . |
| CH3C.35.21.a.6 | . | . | W | . | . | . | F | . | T | E | W | V | S | . |
| CH3C.35.23.1 | . | . | . | . | . | . | F | . | T | E | W | S | . | . |
| CH3C.35.23.2 | . | . | . | . | . | . | Y | . | T | E | W | A | . | . |
| CH3C.35.23.3 | . | . | . | . | . | . | Y | . | T | E | W | V | . | . |
| CH3C.35.23.4 | . | . | . | . | . | . | Y | . | T | E | W | S | . | . |
| CH3C.35.23.5 | . | . | . | . | . | . | F | . | T | E | W | A | . | . |
| CH3C.35.23.6 | . | . | . | . | . | . | F | . | T | E | W | V | . | . |
| CH3C.35.24.1 | . | . | W | . | . | . | F | . | T | E | W | S | . | . |
| CH3C.35.24.2 | . | . | W | . | . | . | Y | . | T | E | W | A | . | . |
| CH3C.35.24.3 | . | . | W | . | . | . | Y | . | T | E | W | V | . | . |
| CH3C.35.24.4 | . | . | W | . | . | . | Y | . | T | E | W | S | . | . |
| CH3C.35.24.5 | . | . | W | . | . | . | F | . | T | E | W | A | . | . |
| CH3C.35.24.6 | . | . | W | . | . | . | F | . | T | E | W | V | . | . |
| CH3C.35.21.17.1 | . | . | L | . | . | . | F | . | T | E | W | S | S | . |
| CH3C.35.21.17.2 | . | . | L | . | . | . | Y | . | T | E | W | A | S | . |
| CH3C.35.21.17.3 | . | . | L | . | . | . | Y | . | T | E | W | V | S | . |
| CH3C.35.21.17.4 | . | . | L | . | . | . | Y | . | T | E | W | S | S | . |
| CH3C.35.21.17.5 | . | . | L | . | . | . | F | . | T | E | W | A | S | . |
| CH3C.35.21.17.6 | . | . | L | . | . | . | F | . | T | E | W | V | S | . |
| CH3C.35.20 | . | . | . | . | . | . | Y | . | T | E | W | S | S | . |
| CH3C.35.21 | . | . | W | . | . | . | Y | . | T | E | W | S | S | . |
| CH3C.35.22 | . | . | W | . | . | . | Y | . | T | E | W | S | . | . |
| CH3C.35.23 | . | . | . | . | . | . | Y | . | T | E | W | S | . | . |
| CH3C.35.24 | . | . | W | . | . | . | Y | . | T | E | W | S | . | . |
| CH3C.35.21.17 | . | . | L | . | . | . | Y | . | T | E | W | S | S | . |
| CH3C.35.N390 | . | . | . | . | . | . | Y | . | T | E | W | S | . | . |

| | 165 | 184 | 185 | 186 | 187 | 188 | 189 | 190 | 191 | 192 | 193 | 194 | 195 | 196 |
|---|---|---|---|---|---|---|---|---|---|---|---|---|---|---|
| Wild-type | K | T | V | D | K | S | R | W | Q | Q | G | N | V | F |
| CH3C.35.20.1 | . | . | . | T | . | E | E | . | . | . | . | F | . | . |
| CH3C.35.20.2 | . | . | . | T | . | E | E | . | . | . | . | F | . | . |
| CH3C.35.20.3 | . | . | . | T | . | E | E | . | . | . | . | F | . | . |
| CH3C.35.20.4 | . | . | . | S | . | E | E | . | . | . | . | F | . | . |
| CH3C.35.20.5 | . | . | . | T | . | E | E | . | . | . | . | F | . | . |
| CH3C.35.20.6 | . | . | . | T | . | E | E | . | . | . | . | F | . | . |
| CH3C.35.21.a.1 | . | . | . | T | . | E | E | . | . | . | . | F | . | . |
| CH3C.35.21.a.2 | . | . | . | T | . | E | E | . | . | . | . | F | . | . |
| CH3C.35.21.a.3 | . | . | . | T | . | E | E | . | . | . | . | F | . | . |
| CH3C.35.21.a.4 | . | . | . | S | . | E | E | . | . | . | . | F | . | . |
| CH3C.35.21.a.5 | . | . | . | T | . | E | E | . | . | . | . | F | . | . |
| CH3C.35.21.a.6 | . | . | . | T | . | E | E | . | . | . | . | F | . | . |
| CH3C.35.23.1 | . | . | . | T | . | E | E | . | . | . | . | F | . | . |
| CH3C.35.23.2 | . | . | . | T | . | E | E | . | . | . | . | F | . | . |
| CH3C.35.23.3 | . | . | . | T | . | E | E | . | . | . | . | F | . | . |
| CH3C.35.23.4 | . | . | . | S | . | E | E | . | . | . | . | F | . | . |
| CH3C.35.23.5 | . | . | . | T | . | E | E | . | . | . | . | F | . | . |
| CH3C.35.23.6 | . | . | . | T | . | E | E | . | . | . | . | F | . | . |
| CH3C.35.24.1 | . | . | . | T | . | E | E | . | . | . | . | F | . | . |
| CH3C.35.24.2 | . | . | . | T | . | E | E | . | . | . | . | F | . | . |
| CH3C.35.24.3 | . | . | . | T | . | E | E | . | . | . | . | F | . | . |
| CH3C.35.24.4 | . | . | . | S | . | E | E | . | . | . | . | F | . | . |
| CH3C.35.24.5 | . | . | . | T | . | E | E | . | . | . | . | F | . | . |
| CH3C.35.24.6 | . | . | . | T | . | E | E | . | . | . | . | F | . | . |
| CH3C.35.21.17.1 | . | . | . | T | . | E | E | . | . | . | . | F | . | . |
| CH3C.35.21.17.2 | . | . | . | T | . | E | E | . | . | . | . | F | . | . |
| CH3C.35.21.17.3 | . | . | . | T | . | E | E | . | . | . | . | F | . | . |
| CH3C.35.21.17.4 | . | . | . | S | . | E | E | . | . | . | . | F | . | . |
| CH3C.35.21.17.5 | . | . | . | T | . | E | E | . | . | . | . | F | . | . |
| CH3C.35.21.17.6 | . | . | . | T | . | E | E | . | . | . | . | F | . | . |
| CH3C.35.20 | . | . | . | T | . | E | E | . | . | . | . | F | . | . |
| CH3C.35.21 | . | . | . | T | . | E | E | . | . | . | . | F | . | . |
| CH3C.35.22 | . | . | . | T | . | . | E | . | . | . | . | F | . | . |
| CH3C.35.23 | . | . | . | T | . | E | E | . | . | . | . | F | . | . |
| CH3C.35.24 | . | . | . | T | . | E | E | . | . | . | . | F | . | . |
| CH3C.35.21.17 | . | . | . | T | . | E | E | . | . | . | . | F | . | . |
| CH3C.35.N390 | . | . | . | T | . | . | E | . | . | . | . | F | . | . |

| SEQ ID NO: | Sequence | Description |
|---|---|---|
| 1 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Wild-type human Fc sequence amino acids 1-3 (PCP) are from a hinge region |
| 2 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAK | CH2 domain sequence, including three amino acids (PCP) at the N-terminus from the hinge region |
| 3 | GQPREPQVYTLPPSRDELTKNQVSLTCLVKGFYPSDIAVEWESNGQP ENNYKTTPPVLDSDGSFFLYSKLTVDKSRWQQGNVFSCSVMHEALH NHYTQKSLSLSPGK | CH3 domain sequence |
| 4 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGLVWVGYKTTPPVLDSDGSFFLYSKLTVAK STWQQGWVFSCSVMHEALHNHYTQKSLSLSPGK | Clone CH3C.1 |
| 5 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTVWSHYKTTPPVLDSDGSFFLYSKLTVSK SEWQQGYVFSCSVMHEALHNHYTQKSLSLSPGK | Clone CH3C.2 |
| 6 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSQYKTTPPVLDSDGSFFLYSKLTVEK SDWQQGHVFSCSVMHEALHNHYTQKSLSLSPGK | Clone CH3C.3 |
| 7 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESVGTPWALYKTTPPVLDSDGSFFLYSKLTVLK SEWQQGWVFSCSVMHEALHNHYTQKSLSLSPGK | Clone CH3C.4 |
| 8 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTVWSKYKTTPPVLDSDGSFFLYSKLTVSK SEWQQGFVFSCSVMHEALHNHYTQKSLSLSPGK | Clone CH3C.17 |
| 9 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGHVWAVYKTTPPVLDSDGSFFLYSKLTVPK STWQQGWVFSCSVMHEALHNHYTQKSLSLSPGK | Clone CH3C.18 |
| 10 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGLVWVGYKTTPPVLDSDGSFFLYSKLTVPK STWQQGWVFSCSVMHEALHNHYTQKSLSLSPGK | Clone CH3C.21 |
| 11 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESMGHVWVGYKTTPPVLDSDGSFFLYSKLTVD KSTWQQGWVFSCSVMHEALHNHYTQKSLSLSPGK | Clone CH3C.25 |
| 12 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGLVWVFSKTTPPVLDSDGSFFLYSKLTVPKS TWQQGWVFSCSVMHEALHNHYTQKSLSLSPGK | Clone CH3C.34 |
| 13 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSSYKTTPPVLDSDGSFFLYSKLTVTKS EWQQGFVFSCSVMHEALHNHYTQKSLSLSPGK | Clone CH3C.35 |

| SEQ ID NO: | Sequence | Description |
|---|---|---|
| 14 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESYGTEWSNYKTTPPVLDSDGSFFLYSKLTVSK<br>SEWQQGFVFSCSVMHEALHNHYTQKSLSLSPGK | Clone CH3C.44 |
| 15 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVGYKTTPPVLDSDGSFFLYSKLTVSK<br>SEWQQGWVFSCSVMHEALHNHYTQKSLSLSPGK | Clone CH3C.51 |
| 16 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVATKTTPPVLDSDGSFFLYSKLTVPK<br>STWQQGWVFSCSVMHEALHNHYTQKSLSLSPGK | Clone CH3C.3.1-3 |
| 17 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGPVWVHTKTTPPVLDSDGSFFLYSKLTVPK<br>STWQQGWVFSCSVMHEALHNHYTQKSLSLSPGK | Clone CH3C.3.1-9 |
| 18 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVDQKTTPPVLDSDGSFFLYSKLTVPK<br>STWQQGWVFSCSVMHEALHNHYTQKSLSLSPGK | Clone CH3C.3.2-5 |
| 19 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVNQKTTPPVLDSDGSFFLYSKLTVPK<br>STWQQGWVFSCSVMHEALHNHYTQKSLSLSPGK | Clone CH3C.3.2-19 |
| 20 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVNFKTTPPVLDSDGSFFLYSKLTVPK<br>STWQQGWVFSCSVMHEALHNHYTQKSLSLSPGK | Clone CH3C.3.2-1 |
| 21 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESLGHVWAVYKTTPPVLDSDGSFFLYSKLTVP<br>KSTWQQGWVFSCSVMHEALHNHYTQKSLSLSPGK | Clone CH3C.18.E153W (CH3C.35.13) |
| 22 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWAVYQTTPPVLDSDGSFFLYSKLTVPK<br>STWQQGWVFSCSVMHEALHNHYTQKSLSLSPGK | Clone CH3C.18.K165Q (CH3C.35.14) |
| 23 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESLGHVWAVYQTTPPVLDSDGSFFLYSKLTVP<br>KSTWQQGWVFSCSVMHEALHNHYTQKSLSLSPGK | Clone CH3C.18.E153W. K165Q(CH3C.35.15) |
| 24 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESYGTEWSSYKTTPPVLDSDGSFFLYSKLTVTK<br>SEWQQGFVFSCSVMHEALHNHYTQKSLSLSPGK | Clone CH3C.35.E153W (CH3C.35.19) |
| 25 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESYGTEWSSYKTTPPVLDSDGSFFLYSKLTVTK<br>EEWQQGFVFSCSVMHEALHNHYTQKSLSLSPGK | Clone CH3C.35.S188E (CH3C.35.20) |
| 26 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY | Clone CH3C.35.E153W. S188E(CH3C.35.21) |

INFORMAL SEQUENCE LISTING

| SEQ ID NO: | Sequence | Description |
|---|---|---|
| | KCKVSNKALPAPIEKTISKAKGQPREPQVYTLPPSRDELTKNQVSLTC LVKGFYPSDIAVWWESYGTEWSSYKTTPPVLDSDGSFFLYSKLTVTK EEWQQGFVFSCSVMHEALHNHYTQKSLSLSPGK | |
| 27 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSNYKTTPPVLDSDGSFFLYSKLTVTK SEWQQGFVFSCSVMHEALHNHYTQKSLSLSPGK | Clone CH3C.35.N163 |
| 28 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSSYQTTPPVLDSDGSFFLYSKLTVTKS EWQQGFVFSCSVMHEALHNHYTQKSLSLSPGK | Clone CH3C.35.K165Q |
| 29 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSNYQTTPPVLDSDGSFFLYSKLTVTK SEWQQGFVFSCSVMHEALHNHYTQKSLSLSPGK | Clone CH3C.35.N163.K165Q |
| 30 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.1 |
| 31 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDMVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.2 |
| 32 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFEYVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.3 |
| 33 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFEMVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.4 |
| 34 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFELVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.5 |
| 35 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFEIVTTLPPSRDELTKNQVSLTCL VKGFYPSDIAVEWESNGQPENNYKTTPPVLDSDGSFFLYSKLTVDKS RWQQGNVFSCSVMHEALHNHYGFHDLSLSPGK | Clone CH3B.6 |
| 36 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDIVTTLPPSRDELTKNQVSLTCL VKGFYPSDIAVEWESNGQPENNYKTTPPVLDSDGSFFLYSKLTVDKS RWQQGNVFSCSVMHEALHNHYGFHDLSLSPGK | Clone CH3B.7 |
| 37 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYVTTLPPSRDELTKNQVSLTC LVKGFYPSDIAVEWESNGQPENNYKTTPPVLDSDGSFFLYSKLTVDK SRWQQGNVFSCSVMHEALHNHYGFHDLSLSPGK | Clone CH3B.8 |
| 38 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFGMVTTLPPSRDELTKNQVSLTC | Clone CH3B.9 |

| SEQ ID NO: | Sequence | Description |
|---|---|---|
| | LVKGFYPSDIAVEWESNGQPENNYKTTPPVLDSDGSFFLYSKLTVDK<br>SRWQQGNVFSCSVMHEALHNHYGFHDLSLSPGK | |
| 39 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFADVTILPPSRDELTKNQVSLTC<br>LVKGFYPSDIAVEWESNGQPENNYKTTPPVLDSDGSFFLYSKLTVDK<br>SRWQQGNVFSCSVMHEALHNHYGFYDLSLSPGK | Clone CH3B.10 |
| 40 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFGLVTTLPPSRDELTKNQVSLTC<br>LVKGFYPSDIAVEWESNGQPENNYKTTPPVLDSDGSFFLYSKLTVDK<br>SRWQQGNVFSCSVMHEALHNHYGFHDLSLSPGK | Clone CH3B.11 |
| 41 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFDYVTTLPPSRDELTKNQVSLTC<br>LVKGFYPSDIAVEWESNGQPENNYKTTPPVLDSDGSFFLYSKLTVDK<br>SRWQQGNVFSCSVMHEALHNHYGFSDLSLSPGK | Clone CH3B.12 |
| 42 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRIDYVTTLPPSRDELTKNQVSLTC<br>LVKGFYPSDIAVEWESNGQPENNYKTTPPVLDSDGSFFLYSKLTVDK<br>SRWQQGNVFSCSVMHEALHNHYGFSDLSLSPGK | Clone CH3B.13 |
| 43 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFKDVTILPPSRDELTKNQVSLTC<br>LVKGFYPSDIAVEWESNGQPENNYKTTPPVLDSDGSFFLYSKLTVDK<br>SRWQQGNVFSCSVMHEALHNHYGFFDLSLSPGK | Clone CH3B.14 |
| 44 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFDLVTILPPSRDELTKNQVSLTCL<br>VKGFYPSDIAVEWESNGQPENNYKTTPPVLDSDGSFFLYSKLTVDKS<br>RWQQGNVFSCSVMHEALHNHYGFYDLSLSPGK | Clone CH3B.15 |
| 45 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRIDYVTTLPPSRDELTKNQVSLTC<br>LVKGFYPSDIAVEWESNGQPENNYKTTPPVLDSDGSFFLYSKLTVDK<br>SRWQQGNVFSCSVMHEALHNHYGFSDLSLSPGK | Clone CH3B.16 |
| 46 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPRFELVATLPPSRDELTKNQVSLTC<br>LVKGFYPSDIAVEWESNGQPENNYKTTPPVLDSDGSFFLYSKLTVDK<br>SRWQQGNVFSCSVMHEALHNHYGFHDLSLSPGK | Clone CH3B.17 |
| 47 | PCPAPELLGGPSVFLFPPKPKDTLMISRTPEVTCVVVDVSHEDPEVEFI<br>WYVDGVDVRYEWQLPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK | Clone CH2A2.1 |
| 48 | PCPAPELLGGPSVFLFPPKPKDTLMISRTPEVTCVVVDVSHEDPEVGF<br>VVVYVDGVPVSWEWYWPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2A2.2 |
| 49 | PCPAPELLGGPSVFLFPPKPKDTLMISRTPEVTCVVVDVSHEDPEVQF<br>DWYVDGVMVRREWHRPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2A2.3 |
| 50 | PCPAPELLGGPSVFLFPPKPKDTLMISRTPEVTCVVVDVSHEDPEVSFE<br>WYVDGVPVRWEWQWPREEQYNSTYRVVSVLTVLHQDWLNGKEYK<br>CKVSNKALPAPIEKTISKAKGQPREPQVYTLPPSRDELTKNQVSLTCL<br>VKGFYPSDIAVEWESNGQPENNYKTTPPVLDSDGSFFLYSKLTVDKS<br>RWQQGNVFSCSVMHEALHNHYTQKSLSLSPGK | Clone CH2A2.4 |

| INFORMAL SEQUENCE LISTING | | |
|---|---|---|
| SEQ ID NO: | Sequence | Description |
| 51 | PCPAPELLGGPSVFLFPPKPKDTLMISRTPEVTCVVVDVSHEDPEVAF TWYVDGVPVRWEWQNPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.5 |
| 52 | PCPAPELLGGPSVFLFPPKPKDTLMISRTPEVTCVVVDVSHEDPEVNF DWYVDGVLVRREWHRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.6 |
| 53 | PCPAPELLGGPSVFLFPPKPKDTLMISRTPEVTCVVVDVSHEDPEVQF VVVYVDGVAVRWEWIRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.7 |
| 54 | PCPAPELLGGPSVFLFPPKPKDTLMISRTPEVTCVVVDVSHEDPEVEFI WYVDGVEVAWEWFWPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK | Clone CH2A2.8 |
| 55 | PCPAPELLGGPSVFLFPPKPKDTLMISRTPEVTCVVVDVSHEDPEVGF AWYVDGVNVRVEWQYPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.9 |
| 56 | PCPAPELLGGPSVFLFPPKPKDTLMISRTPEVTCVVVDVSHEDPEVGF VVVYVDGVEVRREWVRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.10 |
| 57 | PCPAPELLGGPSVFLFPPKPKDTLMISRTPEVTCVVVDVSHEDPEVSF DWYVDGVLVRREWQRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.11 |
| 58 | PCPAPELLGGPSVFLFPPKPKDTLMISRTPEVTCVVVDVSHEDPEVEFT WYVDGVDVRYEWYYPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK | Clone CH2A2.12 |
| 59 | PCPAPELLGGPSVFLFPPKPKDTLMISRTPEVTCVVVDVSHEDPEVQF TWYVDGVDVRYEWVRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.13 |
| 60 | PCPAPELLGGPSVFLFPPKPKDTLMISRTPEVTCVVVDVSHEDPEVQF YWYVDGVNVRREWHRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.14 |
| 61 | PCPAPELLGGPSVFLFPPKPKDTLMISRTPEVTCVVVDVSHEDPEVYF DWYVDGVMVRREWHRPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.15 |
| 62 | PCPAPELLGGPSVFLFPPKPKDTLMISRTPEVTCVVVDVSHEDPEVWF EWYVDGVFVGVAYDVPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2A2.16 |

| SEQ ID NO: | Sequence | Description |
|---|---|---|
| 63 | PCPAPELLGGPSVFLFPPKPKDTLMISRTPEVTCVVVDPQTPPWEVKF NWYVDGVEVHNAKTKPREEEYYTYYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.1 |
| 64 | PCPAPELLGGPSVFLFPPKPKDTLMISRTPEVTCVVVDPPSPPWEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.2 |
| 65 | PCPAPELLGGPSVFLFPPKPKDTLMISRTPEVTCVVVDPQTPPWEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.3 |
| 66 | PCPAPELLGGPSVFLFPPKPKDTLMISRTPEVTCVVVDFRGPPWEVKF NWYVDGVEVHNAKTKPREEEYYHDYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.4 |
| 67 | PCPAPELLGGPSVFLFPPKPKDTLMISRTPEVTCVVVDPQTVPWEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.5 |
| 68 | PCPAPELLGGPSVFLFPPKPKDTLMISRTPEVTCVVVDPKMPPWEVKF NWYVDGVEVHNAKTKPREEEYYTYYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.6 |
| 69 | PCPAPELLGGPSVFLFPPKPKDTLMISRTPEVTCVVVDPPVPPWEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.7 |
| 70 | PCPAPELLGGPSVFLFPPKPKDTLMISRTPEVTCVVVDPAFPPWEVKF NWYVDGVEVHNAKTKPREEEYYQNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.8 |
| 71 | PCPAPELLGGPSVFLFPPKPKDTLMISRTPEVTCVVVDAIWPPWEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDSFFLYSKLTVDK SRWQQGNVFSCSVMHEALHNHYTQKSLSLSPGK | Clone CH2C.9 |
| 72 | PCPAPELLGGPSVFLFPPKPKDTLMISRTPEVTCVVVDPPVAPWEVKF NWYVDGVEVHNAKTKPREEEYYSSYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK | Clone CH2C.10 |
| 73 | PCPAPELLGGPSVFLFPPKPKDTLMISRTPEVTCVVVDPQMPPQEVKF NWYVDGVEVHNAKTKPREEEYYSNYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.11 |
| 74 | PCPAPELLGGPSVFLFPPKPKDTLMISRTPEVTCVVVDPQTAPWEVKF NWYVDGVEVHNAKTKPREEEYYTYYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2C.12 |

| SEQ ID NO: | Sequence | Description |
|---|---|---|
| 75 | PCPAPELLGGPSVFLFPPKPKDTLMISRTPEVTCVVVDPQTPPQEVKF<br>NWYVDGVEVHNAKTKPREEEYYSNYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.13 |
| 76 | PCPAPELLGGPSVFLFPPKPKDTLMISRTPEVTCVVVDPQTPPWEVKF<br>NWYVDGVEVHNAKTKPREEEYYTYYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.14 |
| 77 | PCPAPELLGGPSVFLFPPKPKDTLMISRTPEVTCVVVDPRVPPWEVKF<br>NWYVDGVEVHNAKTKPREEEYYQNYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.15 |
| 78 | PCPAPELLGGPSVFLFPPKPKDTLMISRTPEVTCVVVDPSVPPWEVKF<br>NWYVDGVEVHNAKTKPREEEYYSNYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.16 |
| 79 | PCPAPELLGGPSVFLFPPKPKDTLMISRTPEVTCVVVDMLWPVPEVKF<br>NWYVDGVEVHNAKTKPREEVYHRPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.17 |
| 80 | PCPAPELLGGPSVFLFPPKPKDTLMISRTPEVTCVVVDMLWPVPEVKF<br>NWYVDGVEVHNAKTKPREETYHNPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.18 |
| 81 | PCPAPELLGGPSVFLFPPKPKDTLMISRTPEVTCVVVDMEWPVTEVKF<br>NWYVDGVEVHNAKTKPREETYHNPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.19 |
| 82 | PCPAPELLGGPSVFLFPPKPKDTLMISRTPEVTCVVVDMLWPVPEVKF<br>NWYVDGVEVHNAKTKPREETYHHPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.20 |
| 83 | PCPAPELLGGPSVFLFPPKPKDTLMISRTPEVTCVVVDDDLTFQEVKF<br>NWYVDGVEVHNAKTKPREEVYVTPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.21 |
| 84 | PCPAPELLGGPSVFLFPPKPKDTLMISRTPEVTCVVVDDDLTFQEVKF<br>NWYVDGVEVHNAKTKPREELYVTPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.22 |
| 85 | PCPAPELLGGPSVFLFPPKPKDTLMISRTPEVTCVVVDAYGDPEEVKF<br>NWYVDGVEVHNAKTKPREEWYDVPYRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2C.23 |
| 86 | PCPAPELLGGPSVFLFPPKPKDTLMISRTPEVTCVVVDVSVPPRMVKF<br>NWYVDGVEVHNAKTKSLTSQHNSTVRVVSVLTVLHQDWLNGKEY<br>KCKVSNKALPAPIEKTISKAKGQPREPQVYTLPPSRDELTKNQVSLTC<br>LVKGFYPSDIAVEWESNGQPENNYKTTPPVLDSDGSFFLYSKLTVDK<br>SRWQQGNVFSCSVMHEALHNHYTQKSLSLSPGK | Clone CH2D.1 |

-continued

INFORMAL SEQUENCE LISTING

| SEQ ID NO: | Sequence | Description |
|---|---|---|
| 87 | PCPAPELLGGPSVFLFPPKPKDTLMISRTPEVTCVVVDVSVPPWMVKF NWYVDGVEVHNAKTKSLTSQHNSTVRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2D.2 |
| 88 | PCPAPELLGGPSVFLFPPKPKDTLMISRTPEVTCVVVDVSDMWEYVK FNWYVDGVEVHNAKTKPWVKQLNSTWRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK | Clone CH2D.3 |
| 89 | PCPAPELLGGPSVFLFPPKPKDTLMISRTPEVTCVVVDVSDDWTWVK FNWYVDGVEVHNAKTKPWIAQPNSTWRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK | Clone CH2D.4 |
| 90 | PCPAPELLGGPSVFLFPPKPKDTLMISRTPEVTCVVVDVSDDWEWVK FNWYVDGVEVHNAKTKPWKLQLNSTWRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK | Clone CH2D.5 |
| 91 | PCPAPELLGGPSVFLFPPKPKDTLMISRTPEVTCVVVDVSHEDPWVW FYWYVDGVEVHNAKTKPREEQYNSTYRVVSVLTVLHQDWLNGKEY KCSVVNIALWWSIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2E3.1 |
| 92 | PCPAPELLGGPSVFLFPPKPKDTLMISRTPEVTCVVVDVSHEDPVVGF RWYVDGVEVHNAKTKPREEQYNSTYRVVSVLTVLHQDWLNGKEY KCRVSNSALTWKIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2E3.2 |
| 93 | PCPAPELLGGPSVFLFPPKPKDTLMISRTPEVTCVVVDVSHEDPVVGF RWYVDGVEVHNAKTKPREEQYNSTYRVVSVLTVLHQDWLNGKEY KCRVSNSALSWRIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | Clone CH2E3.3 |
| 94 | PCPAPELLGGPSVFLFPPKPKDTLMISRTPEVTCVVVDVSHEDPIVGFR WYVDGVEVHNAKTKPREEQYNSTYRVVSVLTVLHQDWLNGKEYK CRVSNSALRWRIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK | Clone CH2E3.4 |
| 95 | PCPAPELLGGPSVFLFPPKPKDTLMISRTPEVTCVVVDVSHEDPAVGF EWYVDGVEVHNAKTKPREEQYNSTYRVVSVLTVLHQDWLNGKEY KCQVFNWALDWVIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK | Clone CH2E3.5 |
| 96 | PCPAPELLGGPSVFLFPPKPKDTLMISRTPEVTCVVVDVSHEDPEVXF XWYVDGVXVXXXXXXPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | CH2A2 library (X denotes randomized amino acid position) |
| 97 | PCPAPELLGGPSVFLFPPKPKDTLMISRTPEVTCVVVDXXXXXXXEVKF NWYVDGVEVHNAKTKPREEXYXXXYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | CH2C library (X denotes randomized amino acid position) |
| 98 | PCPAPELLGGPSVFLFPPKPKDTLMISRTPEVTCVVVDVSXXXXXVKF NWYVDGVEVHNAKTKPXXXQXNSTXRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK | CH2D library (X denotes randomized amino acid position) |

| SEQ ID NO: | Sequence | Description |
|---|---|---|
| 99 | PCPAPELLGGPSVFLFPPKPKDTLMISRTPEVTCVVVDVSHEDPXVXF XWYVDGVEVHNAKTKPREEQYNSTYRVVSVLTVLHQDWLNGKEY KCXVXNXALXXXIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK | CH2E3 library (X denotes randomized amino acid position) |
| 100 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRXXXVXTLPPSRDELTKNQVSLTC LVKGFYPSDIAVEWESNGQPENNYKTTPPVLDSDGSFFLYSKLTVDK SRWQQGNVFSCSVMHEALHNHYXXXXLSLSPGK | CH3B library (X denotes randomized amino acid position) |
| 101 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYVTTLPPXXXEXXXXQVSLT CLVKGFYPSDIAVEWESNGQPENNYKTTPPVLDSDGSFFLYSKLTVD KSRWQQGNVFSCSVMHEALHNHYGFSDLSLSPGK | CH3B-patch1 library (X denotes randomized amino acid position) |
| 102 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYXTTLPPSRDELTKNQVSLTC LVKGFYPSDIAVEWESNGQPENNYKTTPPVLDSDGSFFLYSKLTVDK SRWQQGNVFSCSVMHEALXXHXGFSDLSLSPGK | CH3B-patch2 library (X denotes randomized amino acid position) |
| 103 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYVTTLXPSRDELTKNQVSLTC LVKGFYPSDIAVEWESNGQPENNYKTTPPVLDSDGSFFLYSKLTVDK SRWQQGNVFSCSVMHEALHNHYGFSDXSLXXXX | CH3B-patch3 library (X denotes randomized amino acid position) |
| 104 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGXPXFDYVTTLPPSRDELTKNQVSLTC LVXGFYPSDIAVEWESNGQPENNYKTTPPVLDSXGXFFLYSKLTVDK SRWQQGNVFSCSVMHEALHNHYGFSDLSLSPGK | CH3B-patch4 library (X denotes randomized amino acid position) |
| 105 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPRFDYVTTLPPSRDELTKNQVSLTC LVKGFYPSDIAVEWXSXXQPENNYKTTPPVLDSDGSFFLYSKLTVDK SRWQQXXXFSCSVMHEALHNHYGFSDLSLSPGK | CH3B-patch5 library (X denotes randomized amino acid position) |
| 106 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESXGXXXXXYKTTPPVLDSDGSFFLYSKLTVXK XXWQQGXVFSCSVMHEALHNHYTQKSLSLSPGK | CH3C library (X denotes randomized amino acid position) |
| 107 | NSVIIVDKNGRLVYLVENPGGYVAYSKAATVTGKLVHANFGTKKDF EDLYTPVNGSIVIVRAGKITFAEKVANAESLNAIGVLIYMDQTKFPIV NAELSFFGHAHLGTDPYTPGFPSFNHTQFPPSRSSGLPNIPVQTISRA AAEKLFGNMEGDCPSDWKTDSTCRMVTSESKNVKLTVS | Human TfR apical domain |
| 108 | NSVIIVDKNGGLVYLVENPGGYVAYSKAATVTGKLVHANFGTKKDF EDLDSPVNGSIVIVRAGKITFAEKVANAESLNAIGVLIYMDQTKFPIV KADLSFFGHAHLGTDPYTPGFPSFNHTQFPPSQSSGLPNIPVQTISRA AAEKLFGNMEGDCPSDWKTDSTCKMVTSENKSVKLTVS | Cynomolgus TfR apical domain |
| 109 | SSGLPNIPVQTISRAAAEKLFGNMEGDCPSDWKTDSTCRMVTSESKN VKLTVSNDSAQNSVIIVDKNGRLVYLVENPGGYVAYSKAATVTGKL VHANFGTKKDFEDLYTPVNGSIVIVRAGKITFAEKVANAESLNAIGVL IYMDQTKFPIVNAELSGP | Loop-truncated human TfR apical domain displayed on phage |
| 110 | SSGLPNIPVQTISRAAAEKLFGNMEGDCPSDWKTDSTCKMVTSENKS VKLTVSNDSAQNSVIIVDKNGGLVYLVENPGGYVAYSKAATVTGKL VHANFGTKKDFEDLDSPVNGSIVIVRAGKITFAEKVANAESLNAIGVL IYMDQTKFPIVKADLSGP | Loop-truncated cynomolgus TfR apical domain displayed on phage |
| 111 | VPPXM | CH2D conserved sequence |
| 112 | SLTS | CH2D conserved sequence |
| 113 | WESXGXXXXXYK | First portion CH3C register |

-continued

| SEQ ID NO: | Sequence | Description |
|---|---|---|
| 114 | TVXKXXWQQGXV | Second portion CH3C register |
| 115 | YGTEW | CH3C conserved sequence |
| 116 | LGLVWVG | CH3C modified binding sequence |
| 117 | YGTVWSH | CH3C modified binding sequence |
| 118 | YGTEWSQ | CH3C modified binding sequence |
| 119 | VGTPWAL | CH3C modified binding sequence |
| 120 | YGTVWSK | CH3C modified binding sequence |
| 121 | LGHVWAV | CH3C modified binding sequence |
| 122 | MGHVWVG | CH3C modified binding sequence |
| 123 | LGLVGVF | CH3C modified binding sequence |
| 124 | YGTEWSS | CH3C modified binding sequence |
| 125 | YGTEWSN | CH3C modified binding sequence |
| 126 | LGHVWVG | CH3C modified binding sequence |
| 127 | LGHVWVA | CH3C modified binding sequence |
| 128 | LGPVWVH | CH3C modified binding sequence |
| 129 | LGHVWVD | CH3C modified binding sequence |
| 130 | LGHVWVN | CH3C modified binding sequence |
| 131 | AKSTWQQGW | CH3C modified binding sequence |
| 132 | SKSEWQQGY | CH3C modified binding sequence |
| 133 | EKSDWQQGH | CH3C modified binding sequence |
| 134 | LKSEWQQGW | CH3C modified binding sequence |
| 135 | SKSEWQQGF | CH3C modified binding sequence |
| 136 | PKSTWQQGW | CH3C modified binding sequence |
| 137 | DKSTWQQGW | CH3C modified binding sequence |
| 138 | TKSEWQQGF | CH3C modified binding sequence |

-continued

INFORMAL SEQUENCE LISTING

| SEQ ID NO: | Sequence | Description |
|---|---|---|
| 139 | SKSEWQQGW | CH3C modified binding sequence |
| 140 | FDYVT | CH3B modified binding sequence |
| 141 | FDMVT | CH3B modified binding sequence |
| 142 | FEYVT | CH3B modified binding sequence |
| 143 | FEMVT | CH3B modified binding sequence |
| 144 | FELVT | CH3B modified binding sequence |
| 145 | FEIVT | CH3B modified binding sequence |
| 146 | FDIVT | CH3B modified binding sequence |
| 147 | FGMVT | CH3B modified binding sequence |
| 148 | FADVT | CH3B modified binding sequence |
| 149 | FGLVT | CH3B modified binding sequence |
| 150 | IDYVT | CH3B modified binding sequence |
| 151 | FKDVT | CH3B modified binding sequence |
| 152 | FDLVT | CH3B modified binding sequence |
| 153 | FELVA | CH3B modified binding sequence |
| 154 | GHFD | CH3B modified binding sequence |
| 155 | GFYD | CH3B modified binding sequence |
| 156 | GFSD | CH3B modified binding sequence |
| 157 | GFFD | CH3B modified binding sequence |
| 158 | EFI | CH2A2 modified binding sequence |
| 159 | GFV | CH2A2 modified binding sequence |
| 160 | QFD | CH2A2 modified binding sequence |
| 161 | SFE | CH2A2 modified binding sequence |
| 162 | AFT | CH2A2 modified binding sequence |

| INFORMAL SEQUENCE LISTING | | |
|---|---|---|
| SEQ ID NO: | Sequence | Description |
| 163 | NFD | CH2A2 modified binding sequence |
| 164 | QFV | CH2A2 modified binding sequence |
| 165 | GFA | CH2A2 modified binding sequence |
| 166 | SFD | CH2A2 modified binding sequence |
| 167 | EFT | CH2A2 modified binding sequence |
| 168 | QFT | CH2A2 modified binding sequence |
| 169 | QFY | CH2A2 modified binding sequence |
| 170 | YFD | CH2A2 modified binding sequence |
| 171 | WFE | CH2A2 modified binding sequence |
| 172 | DVRYEWQL | CH2A2 modified binding sequence |
| 173 | PVSWEWYW | CH2A2 modified binding sequence |
| 174 | MVRREWHR | CH2A2 modified binding sequence |
| 175 | PVRWEWQW | CH2A2 modified binding sequence |
| 176 | PVRWEWQN | CH2A2 modified binding sequence |
| 177 | LVRREWHR | CH2A2 modified binding sequence |
| 178 | AVRWEWIR | CH2A2 modified binding sequence |
| 179 | EVAWEWFW | CH2A2 modified binding sequence |
| 180 | NVRVEWQY | CH2A2 modified binding sequence |
| 181 | EVRREWVR | CH2A2 modified binding sequence |
| 182 | LVRREWQR | CH2A2 modified binding sequence |
| 183 | DVRYEWYY | CH2A2 modified binding sequence |
| 184 | DVRYEWVR | CH2A2 modified binding sequence |
| 185 | NVRREWHR | CH2A2 modified binding sequence |
| 186 | FVGVAYDV | CH2A2 modified binding sequence |

-continued

| SEQ ID NO: | Sequence | Description |
|---|---|---|
| 187 | PQTPPW | CH2C modified binding sequence |
| 188 | PPSPPW | CH2C modified binding sequence |
| 189 | FRGPPW | CH2C modified binding sequence |
| 190 | PQTVPW | CH2C modified binding sequence |
| 191 | PKMPPW | CH2C modified binding sequence |
| 192 | PPVPPW | CH2C modified binding sequence |
| 193 | PAFPPW | CH2C modified binding sequence |
| 194 | AIWPPW | CH2C modified binding sequence |
| 195 | PPVAPW | CH2C modified binding sequence |
| 196 | PQMPPQ | CH2C modified binding sequence |
| 197 | PQTAPW | CH2C modified binding sequence |
| 198 | PQTPPQ | CH2C modified binding sequence |
| 199 | PRVPPW | CH2C modified binding sequence |
| 200 | PSVPPW | CH2C modified binding sequence |
| 201 | MLWPVP | CH2C modified binding sequence |
| 202 | MEWPVT | CH2C modified binding sequence |
| 203 | DDLTFQ | CH2C modified binding sequence |
| 204 | AYGDPE | CH2C modified binding sequence |
| 205 | EYYTY | CH2C modified binding sequence |
| 206 | EYYSN | CH2C modified binding sequence |
| 207 | EYYHD | CH2C modified binding sequence |
| 208 | EYYQN | CH2C modified binding sequence |
| 209 | EYYSS | CH2C modified binding sequence |
| 210 | VYHRP | CH2C modified binding sequence |

| INFORMAL SEQUENCE LISTING | | |
|---|---|---|
| SEQ ID NO: | Sequence | Description |
| 211 | TYHNP | CH2C modified binding sequence |
| 212 | TYHHP | CH2C modified binding sequence |
| 213 | VYVTP | CH2C modified binding sequence |
| 214 | LYVTP | CH2C modified binding sequence |
| 215 | WYDVP | CH2C modified binding sequence |
| 216 | VPPRM | CH2D modified binding sequence |
| 217 | VPPWM | CH2D modified binding sequence |
| 218 | DMWEY | CH2D modified binding sequence |
| 219 | DDWTW | CH2D modified binding sequence |
| 220 | DDWEW | CH2D modified binding sequence |
| 221 | LTSQHNSTV | CH2D modified binding sequence |
| 222 | WVKQLNSTW | CH2D modified binding sequence |
| 223 | WIAQPNSTW | CH2D modified binding sequence |
| 224 | WKLQLNSTW | CH2D modified binding sequence |
| 225 | WVWFY | CH2E3 modified binding sequence |
| 226 | VVGFR | CH2E3 modified binding sequence |
| 227 | IVGFR | CH2E3 modified binding sequence |
| 228 | AVGFE | CH2E3 modified binding sequence |
| 229 | SVVNIALWWS | CH2E3 modified binding sequence |
| 230 | RVSNSALTWK | CH2E3 modified binding sequence |
| 231 | RVSNSALSWR | CH2E3 modified binding sequence |
| 232 | RVSNSALRWR | CH2E3 modified binding sequence |
| 233 | QVFNWALDWV | CH2E3 modified binding sequence |
| 234 | EPKSCDKTHTCPPCP | Human IgG1 hinge amino acid sequence |

INFORMAL SEQUENCE LISTING

| SEQ ID NO: | Sequence | Description |
|---|---|---|
| 235 | MMDQARSAFSNLFGGEPLSYTRFSLARQVDGDNSHVEMKLAVDEEE NADNNTKANVTKPKRCSGSICYGTIAVIVFFLIGFMIGYLGYCKGVEP KTECERLAGTESPVREEPGEDFPAARRLYWDDLKRKLSEKLDSTDFT GTIKLLNENSYVPREAGSQKDENLALYVENQFREFKLSKVWRDQHF VKIQVKDSAQNSVIIVDKNGRLVYLVENPGGYVAYSKAATVTGKLV HANFGTKKDFEDLYTPVNGSIVIVRAGKITFAEKVANAESLNAIGVLI YMDQTKFPIVNAELSFFGHAHLGTGDPYTPGFPSFNHTQFPPSRSSGL PNIPVQTISRAAAEKLFGNMEGDCPSDWKTDSTCRMVTSESKNVKLT VSNVLKEIKILNIFGVIKGFVEPDHYVVVGAQRDAWGPGAAKSGVGT ALLLKLAQMFSDMVLKDGFQPSRSIIFASWSAGDFGSVGATEWLEGY LSSLHLKAFTYINLDKAVLGTSNFKVSASPLLYTLIEKTMQNVKHPVT GQFLYQDSNWASKVEKLTLDNAAFPFLAYSGIPAVSFCFCEDTDYPY LGTTMDTYKELIERIPELNKVARAAAEVAGQFVIKLTHDVELNLDYE RYNSQLLSFVRDLNQYRADIKEMGLSLQWLYSARGDFFRATSRLTTD FGNAEKTDRFVMKKLNDRVMRVEYHFLSPYVSPKESPFRHVFWGSG SHTLPALLENLKLRKQNNGAFNETLFRNQLALATWTIQGAANALSG DVWDIDNEF | Human transferrin receptor protein 1 (TFR1) |
| 236 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYKTTPPVLDSDGSFFLYSKLTVTK SEWQQGFVFSCSVMHEALHNHYTQKSLSLSPGK | Clone CH3C.35.19 |
| 237 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSSYKTTPPVLDSDGSFFLYSKLTVTK EEWQQGFVFSCSVMHEALHNHYTQKSLSLSPGK | Clone CH3C.35.20 |
| 238 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYKTTPPVLDSDGSFFLYSKLTVTK EEWQQGFVFSCSVMHEALHNHYTQKSLSLSPGK | Clone CH3C.35.21 |
| 239 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGIEWSNYKTTPPVLDSDGSFFLYSKLTVTK SEWQQGFVFSCSVMHEALHNHYTQKSLSLSPGK | Clone CH3C.35.22 |
| 240 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSNYKTTPPVLDSDGSFFLYSKLTVTK EEWQQGFVFSCSVMHEALHNHYTQKSLSLSPGK | Clone CH3C.35.23 |
| 241 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGIEWSNYKTTPPVLDSDGSFFLYSKLTVTK EEWQQGFVFSCSVMHEALHNHYTQKSLSLSPGK | Clone CH3C.35.24 |
| 242 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESLGHVWAVYKTTPPVLDSDGSFFLYSKLTVP KSTWQQGWVFSCSVMHEALHNHYTQKSLSLSPGK | CH3C.18 variant |
| 243 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESLGHVWAVYKTTPPVLDSDGSFFLYSKLTVPK STWQQGWVFSCSVMHEALHNHYTQKSLSLSPGK | CH3C.18 variant |
| 244 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVYWESLGHVWAVYKTTPPVLDSDGSFFLYSKLTVPK STWQQGWVFSCSVMHEALHNHYTQKSLSLSPGK | CH3C.18 variant |
| 245 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY | CH3C.18 variant |

INFORMAL SEQUENCE LISTING

| SEQ ID NO: | Sequence | Description |
|---|---|---|
| | KCKVSNKALPAPIEKTISKAKGQPREPQVYTLPPSRDELTKNQVSLTC LVKGFYPSDIAVEWESLGHVWAVYQTTPPVLDSDGSFFLYSKLTVPK STWQQGWVFSCSVMHEALHNHYTQKSLSLSPGK | |
| 246 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGHVWAVYFTTPPVLDSDGSFFLYSKLTVPK STWQQGWVFSCSVMHEALHNHYTQKSLSLSPGK | CH3C.18 variant |
| 247 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESLGHVWAVYHTTPPVLDSDGSFFLYSKLTVPK STWQQGWVFSCSVMHEALHNHYTQKSLSLSPGK | CH3C.18 variant |
| 248 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYKTTPPVLDSDGSFFLYSKLTVTKS EWQQGFVFSCSVMHEALHNHYTQKSLSLSPGK | Clone CH3C.35.21.1 |
| 249 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTKS EWQQGFVFSCSVMHEALHNHYTQKSLSLSPGK | Clone CH3C.35.21.2 |
| 250 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTRE EWQQGFVFSCSVMHEALHNHYTQKSLSLSPGK | Clone CH3C.35.21.3 |
| 251 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTGE EWQQGFVFSCSVMHEALHNHYTQKSLSLSPGK | Clone CH3C.35.21.4 |
| 252 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTRE EWQQGFVFSCWVMHEALHNHYTQKSLSLSPGK | Clone CH3C.35.21.5 |
| 253 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTKE EWQQGFVFSCWVMHEALHNHYTQKSLSLSPGK | Clone CH3C.35.21.6 |
| 254 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTRE EWQQGFVFTCWVMHEALHNHYTQKSLSLSPGK | Clone CH3C.35.21.7 |
| 255 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTRE EWQQGFVFTCGVMHEALHNHYTQKSLSLSPGK | Clone CH3C.35.21.8 |
| 256 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTRE EWQQGFVFECWVMHEALHNHYTQKSLSLSPGK | Clone CH3C.35.21.9 |
| 257 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC | Clone CH3C.35.21.10 |

| SEQ ID NO: | Sequence | Description |
|---|---|---|
|  | LVKGFYPSDIAVLWESYGTEWSSYRTTPPVLDSDGSFFLYSKLTVTRE EWQQGFVFKCWVMHEALHNHYTQKSLSLSPGK |  |
| 258 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTPE EWQQGFVFKCWVMHEALHNHYTQKSLSLSPGK | Clone CH3C.35.21.11 |
| 259 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYRTTPPVLDSDGSFFLYSKLTVTR EEWQQGFVFSCSVMHEALHNHYTQKSLSLSPGK | Clone CH3C.35.21.12 |
| 260 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYRTTPPVLDSDGSFFLYSKLTVTG EEWQQGFVFSCSVMHEALHNHYTQKSLSLSPGK | Clone CH3C.35.21.13 |
| 261 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYRTTPPVLDSDGSFFLYSKLTVTR EEWQQGFVFTCWVMHEALHNHYTQKSLSLSPGK | Clone CH3C.35.21.14 |
| 262 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYRTTPPVLDSDGSFFLYSKLTVTG EEWQQGFVFTCWVMHEALHNHYTQKSLSLSPGK | Clone CH3C.35.21.15 |
| 263 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYRTTPPVLDSDGSFFLYSKLTVTR EEWQQGFVFTCGVMHEALHNHYTQKSLSLSPGK | Clone CH3C.35.21.16 |
| 264 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYKTTPPVLDSDGSFFLYSKLTVTK EEWQQGFVFSCSVMHEALHNHYTQKSLSLSPGK | Clone CH3C.35.21.17 |
| 265 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVLWESYGTEWSSYRTTPPVLDSDGSFFLYSKLTVTKE EWQQGFVFSCSVMHEALHNHYTQKSLSLSPGK | Clone CH3C.35.21.18 |
| 266 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESFGTEWSSYKTTPPVLDSDGSFFLYSKLTVTKE EWQQGFVFSCSVMHEALHNHYTQKSLSLSPGK | Clone CH3C.35.20.1 |
| 267 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWASYKTTPPVLDSDGSFFLYSKLTVTK EEWQQGFVFSCSVMHEALHNHYTQKSLSLSPGK | Clone CH3C.35.20.2 |
| 268 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWVSYKTTPPVLDSDGSFFLYSKLTVTK EEWQQGFVFSCSVMHEALHNHYTQKSLSLSPGK | Clone CH3C.35.20.3 |
| 269 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSSYKTTPPVLDSDGSFFLYSKLTVSKE EWQQGFVFSCSVMHEALHNHYTQKSLSLSPGK | Clone CH3C.35.20.4 |

| INFORMAL SEQUENCE LISTING | | |
|---|---|---|
| SEQ ID NO: | Sequence | Description |
| 270 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESFGTEWASYKTTPPVLDSDGSFFLYSKLTVTK EEWQQGFVFSCSVMHEALHNHYTQKSLSLSPGK | Clone CH3C.35.20.5 |
| 271 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESFGTEWVSYKTTPPVLDSDGSFFLYSKLTVTK EEWQQGFVFSCSVMHEALHNHYTQKSLSLSPGK | Clone CH3C.35.20.6 |
| 272 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESFGTEWSSYKTTPPVLDSDGSFFLYSKLTVTK EEWQQGFVFSCSVMHEALHNHYTQKSLSLSPGK | Clone CH3C35.21.a.1 |
| 273 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWASYKTTPPVLDSDGSFFLYSKLTVTK EEWQQGFVFSCSVMHEALHNHYTQKSLSLSPGK | Clone CH3C.35.21.a.2 |
| 274 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWVSYKTTPPVLDSDGSFFLYSKLTVTK EEWQQGFVFSCSVMHEALHNHYTQKSLSLSPGK | Clone CH3C.35.21.a.3 |
| 275 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESYGTEWSSYKTTPPVLDSDGSFFLYSKLTVSK EEWQQGFVFSCSVMHEALHNHYTQKSLSLSPGK | Clone CH3C.35.21.a.4 |
| 276 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESFGTEWASYKTTPPVLDSDGSFFLYSKLTVTK EEWQQGFVFSCSVMHEALHNHYTQKSLSLSPGK | Clone CH3C.35.21.a.5 |
| 277 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVWWESFGTEWVSYKTTPPVLDSDGSFFLYSKLTVTK EEWQQGFVFSCSVMHEALHNHYTQKSLSLSPGK | Clone CH3C.35.21.a.6 |
| 278 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESFGTEWSNYKTTPPVLDSDGSFFLYSKLTVTK EEWQQGFVFSCSVMHEALHNHYTQKSLSLSPGK | Clone CH3C.35.23.1 |
| 279 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWANYKTTPPVLDSDGSFFLYSKLTVTK EEWQQGFVFSCSVMHEALHNHYTQKSLSLSPGK | Clone CH3C.35.23.2 |
| 280 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWVNYKTTPPVLDSDGSFFLYSKLTVTK EEWQQGFVFSCSVMHEALHNHYTQKSLSLSPGK | Clone CH3C.35.23.3 |
| 281 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESYGTEWSNYKTTPPVLDSDGSFFLYSKLTVSK EEWQQGFVFSCSVMHEALHNHYTQKSLSLSPGK | Clone CH3C.35.23.4 |

INFORMAL SEQUENCE LISTING

| SEQ ID NO: | Sequence | Description |
|---|---|---|
| 282 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESFGTEWANYKTTPPVLDSDGSFFLYSKLTVTK<br>EEWQQGFVFSCSVMHEALHNHYTQKSLSLSPGK | Clone CH3C.35.23.5 |
| 283 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESFGTEWVNYKTTPPVLDSDGSFFLYSKLTVTK<br>EEWQQGFVFSCSVMHEALHNHYTQKSLSLSPGK | Clone CH3C.35.23.6 |
| 284 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESFGTEWSNYKTTPPVLDSDGSFFLYSKLTVTK<br>EEWQQGFVFSCSVMHEALHNHYTQKSLSLSPGK | Clone CH3C.35.24.1 |
| 285 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESYGTEWANYKTTPPVLDSDGSFFLYSKLTVT<br>KEEWQQGFVFSCSVMHEALHNHYTQKSLSLSPGK | Clone CH3C.35.24.2 |
| 286 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESYGTEWVNYKTTPPVLDSDGSFFLYSKLTVT<br>KEEWQQGFVFSCSVMHEALHNHYTQKSLSLSPGK | Clone CH3C.35.24.3 |
| 287 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESYGIEWSNYKTTPPVLDSDGSFFLYSKLTVSK<br>EEWQQGFVFSCSVMHEALHNHYTQKSLSLSPGK | Clone CH3C.35.24.4 |
| 288 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESFGTEWANYKTTPPVLDSDGSFFLYSKLTVTK<br>EEWQQGFVFSCSVMHEALHNHYTQKSLSLSPGK | Clone CH3C.35.24.5 |
| 289 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESFGTEWVNYKTTPPVLDSDGSFFLYSKLTVTK<br>EEWQQGFVFSCSVMHEALHNHYTQKSLSLSPGK | Clone CH3C.35.24.6 |
| 290 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVLWESFGTEWSSYKTTPPVLDSDGSFFLYSKLTVTKE<br>EWQQGFVFSCSVMHEALHNHYTQKSLSLSPGK | Clone CH3C.35.21.17.1 |
| 291 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVLWESYGTEWASYKTTPPVLDSDGSFFLYSKLTVTK<br>EEWQQGFVFSCSVMHEALHNHYTQKSLSLSPGK | Clone CH3C.35.21.17.2 |
| 292 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVLWESYGTEWVSYKTTPPVLDSDGSFFLYSKLTVTK<br>EEWQQGFVFSCSVMHEALHNHYTQKSLSLSPGK | Clone CH3C.35.21.17.3 |
| 293 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVLWESYGTEWSSYKTTPPVLDSDGSFFLYSKLTVSKE<br>EWQQGFVFSCSVMHEALHNHYTQKSLSLSPGK | Clone CH3C.35.21.17.4 |
| 294 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY | Clone CH3C.35.21.17.5 |

| SEQ ID NO: | Sequence | Description |
|---|---|---|
| | KCKVSNKALPAPIEKTISKAKGQPREPQVYTLPPSRDELTKNQVSLTC<br>LVKGFYPSDIAVLWESFGTEWASYKTTPPVLDSDGSFFLYSKLTVTK<br>EEWQQGFVFSCSVMHEALHNHYTQKSLSLSPGK | |
| 295 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVLWESFGTEWVSYKTTPPVLDSDGSFFLYSKLTVTK<br>EEWQQGFVFSCSVMHEALHNHYTQKSLSLSPGK | Clone CH3C.35.21.17.6 |
| 296 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESYGTEWSNYKTTPPVLDSDGSFFLYSKLTVTK<br>SEWQQGFVFSCSVMHEALHNHYTQKSLSLSPGK | Clone CH3C.35.N390 |
| 297 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESLGHVWVNQKTTPPVLDSDGSFFLYSKLTVP<br>KSTWQQGWVFSCSVMHEALHNHYTQKSLSLSPGK | Clone CH3C.35.16 |
| 298 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVEWESLGHVWVNQQTTPPVLDSDGSFFLYSKLTVPK<br>STWQQGWVFSCSVMHEALHNHYTQKSLSLSPGK | Clone CH3C.35.17 |
| 299 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLTC<br>LVKGFYPSDIAVWWESLGHVWVNQQTTPPVLDSDGSFFLYSKLTVP<br>KSTWQQGWVFSCSVMHEALHNHYTQKSLSLSPGK | Clone CH3C.35.18 |
| 300 | MMDQARSAFSNLFGGEPLSYTRFSLARQVDGDNSHVEMKLGVDEEE<br>NTDNNTKANGTKPKRCGGNICYGTIAVIIFFLIGFMIGYLGYCKGVEP<br>KTECERLAGTESPAREEPEEDFPAAPRLYWDDLKRKLSEKLDTTDFT<br>STIKLLNENLYVPREAGSQKDENLALYIENQFREFKLSKVWRDQHFV<br>KIQVKDSAQNSVIIVDKNGGLVYLVENPGGYVAYSKAATVTGKLVH<br>ANFGTKKDFEDLDSPVNGSIVIVRAGKITFAEKVANAESLNAIGVLIY<br>MDQTKFPIVKADLSFFGHAHLGTGDPYTPGFPSFNHTQFPPSQSSGLP<br>NIPVQTISRAAAEKLFGNMEGDCPSDWKTDSTCKMVTSENKSVKLT<br>VSNVLKETKILNIFGVIKGFVEPDHYVVVGAQRDAWGPGAAKSSVG<br>TALLLKLAQMFSDMVLKDGFQPSRSIIFASWSAGDFGSVGATEWLEG<br>YLSSLHLKAFTYINLDKAVLGTSNFKVSASPLLYTLIEKTMQDVKHP<br>VTGRSLYQDSNWASKVEKLTLDNAAFPPLAYSGIPAVSFCFCEDTDY<br>PYLGTTMDTYKELVERIPELNKVARAAAEVAGQFVIKLTHDTELNLD<br>YERYNSQLLLFLRDLNQYRADVKEMGLSLQWLYSARGDFFRATSRL<br>TTDPRNAEKRDKFVMKKLNDRVMRVEYYFLSPYVSPKESPFRHVFW<br>GSGSHTLSALLESLKLRRQNNSAFNETLFRNQLALATWTIQGAANAL<br>SGDVWDIDNEF | Cyno TfR |
| 301 | MGWSCIILFLVATATGAYAGTSSGLPNIPVQTISRAAAEKLFGNMEG<br>DCPSDWKTDSTCRMVTSESKNVKLTVSNDSAQNSVIIVDKNGRLVY<br>LVENPGGYVAYSKAATVTGKLVHANFGTKKDFEDLYTPVNGSIVIV<br>RAGKITFAEKVANAESLNAIGVLIYMDQTKFPIVNAELSASHHHHHH | His-tagged permuted TfR apical domain |
| 302 | METDTLLLWVLLLWVPGSTGDKTHTCPPCPAPEAAGGPSVFLFPPKP<br>KDTLYITREPEVTCVVVDVSHEDPEVKFNWYVDGVEVHNAKTKPRE<br>EQYNSTYRVVSVLTVLHQDWLNGKEYKCKVSNKALGAPIEKTISKA<br>KGQPREPQVYTLPPSRDELTKNQVSLTCLVKGFYPSDIAVEWESLGH<br>VWAVYKTTPPVLDSDGSFFLYSKLTVPKSTWQQGWVFSCSVMHEAL<br>HNHYTQKSLSLSPGK | Expressed CH3C.18 Fc sequence |
| 303 | EWESFGTEWSS | CH3C modified binding sequence |
| 304 | EWESYGTEWAS | CH3C modified binding sequence |
| 305 | EWESYGTEWVS | CH3C modified binding sequence |

-continued

| INFORMAL SEQUENCE LISTING | | |
|---|---|---|
| SEQ ID NO: | Sequence | Description |
| 306 | EWESYGTEWSS | CH3C modified binding sequence |
| 307 | EWESFGTEWAS | CH3C modified binding sequence |
| 308 | EWESFGTEWVS | CH3C modified binding sequence |
| 309 | WWESFGTEWSS | CH3C modified binding sequence |
| 310 | WWESYGTEWAS | CH3C modified binding sequence |
| 311 | WWESYGTEWVS | CH3C modified binding sequence |
| 312 | WWESYGTEWSS | CH3C modified binding sequence |
| 313 | WWESFGTEWAS | CH3C modified binding sequence |
| 314 | WWESFGTEWVS | CH3C modified binding sequence |
| 315 | EWESFGTEWSN | CH3C modified binding sequence |
| 316 | EWESYGTEWAN | CH3C modified binding sequence |
| 317 | EWESYGTEWVN | CH3C modified binding sequence |
| 318 | EWESYGTEWSN | CH3C modified binding sequence |
| 319 | EWESFGTEWAN | CH3C modified binding sequence |
| 320 | EWESFGTEWVN | CH3C modified binding sequence |
| 321 | WWESFGTEWSN | CH3C modified binding sequence |
| 322 | WWESYGTEWAN | CH3C modified binding sequence |
| 323 | WWESYGTEWVN | CH3C modified binding sequence |
| 324 | WWESYGTEWSN | CH3C modified binding sequence |
| 325 | WWESFGTEWAN | CH3C modified binding sequence |
| 326 | WWESFGTEWVN | CH3C modified binding sequence |
| 327 | LWESFGTEWSS | CH3C modified binding sequence |
| 328 | LWESYGTEWAS | CH3C modified binding sequence |
| 329 | LWESYGTEWVS | CH3C modified binding sequence |
| 330 | LWESYGTEWSS | CH3C modified binding sequence |

-continued

INFORMAL SEQUENCE LISTING

| SEQ ID NO: | Sequence | Description |
|---|---|---|
| 331 | LWESFGTEWAS | CH3C modified binding sequence |
| 332 | LWESFGTEWVS | CH3C modified binding sequence |
| 333 | WWESLGHVWAV | CH3C modified binding sequence |
| 334 | EWESLGHVWAV | CH3C modified binding sequence |
| 335 | LWESLGHVWAV | CH3C modified binding sequence |
| 336 | YWESLGHVWAV | CH3C modified binding sequence |
| 337 | EWESLGLVWVF | CH3C modified binding sequence |
| 338 | WWESLGHVWVN | CH3C modified binding sequence |
| 339 | EWESLGHVWVN | CH3C modified binding sequence |
| 340 | TKEEWQQGF | CH3C modified binding sequence |
| 341 | SKEEWQQGF | CH3C modified binding sequence |
| 342 | PKTSWQQGW | CH3C modified binding sequence |
| 343 | TREEWQQGF | CH3C modified binding sequence |
| 344 | TPEEWQQGF | CH3C modified binding sequence |
| 345 | TGEEWQQGF | CH3C modified binding sequence |
| 346 | TVXKXXWQQGXV | Second portion CH3C register |
| 347 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLTC LVKGFYPSDIAVEWESYGTEWSSYKTTPPVLDSDGSFFLYSKLTVTK EEWQQGFVFSCSVMHEALHNHYTQKSLSLSPGK | Clone CH3C.35.8 (Clone CH3C.35.20 with YTE and LALAPG mutations) |
| 348 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLTC LVKGFYPSDIAVEWESFGTEWSSYKTTPPVLDSDGSFFLYSKLTVTKE EWQQGFVFSCSVMHEALHNHYTQKSLSLSPGK | Clone CH3C.35.9 (Clone CH3C.35.21 with YTE and LALAPG mutations) |
| 349 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob mutation |
| 350 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob and LALA mutations |

INFORMAL SEQUENCE LISTING

| SEQ ID NO: | Sequence | Description |
|---|---|---|
| 351 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob and LALAPG mutations |
| 352 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob and YTE mutations |
| 353 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob, LALA, and YTE mutations |
| 354 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVEWESFGTEWSSYKTTPPVLDSDGSFFLYSKLTVTK EEWQQGFVFSCSVMHEALHNHYTQKSLSLSPGK | Clone CH3C.35.20.1 with knob, LALAPG, and YTE mutations |
| 355 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole mutations |
| 356 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole and LALA mutations |
| 357 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole and LALAPG mutations |
| 358 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole and YTE mutations |
| 359 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole, LALA, and YTE mutations |
| 360 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole, LALAPG, and YTE mutations |
| 361 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGIEWANYKTTPPVLDSDGSFFLYSKLTVT KEEWQQGFVFSCSVMHEALHNHYTQKSLSLSPGK | Clone CH3C.35.23.2 with knob mutation |
| 362 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGTEWANYKTTPPVLDSDGSFFLYSKLTVT KEEWQQGFVFSCSVMHEALHNHYTQKSLSLSPGK | Clone CH3C.35.23.2 with knob and LALA mutations |
| 363 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY | Clone CH3C.35.23.2 with knob and LALAPG |

| SEQ ID NO: | Sequence | Description |
|---|---|---|
|  | KCKVSNKALGAPIEKTISKAKGQPREPQVYTLPPSRDELTKNQVSLW<br>CLVKGFYPSDIAVEWESYGTEWANYKTTPPVLDSDGSFFLYSKLTVT<br>KEEWQQGFVFSCSVMHEALHNHYTQKSLSLSPGK | mutations |
| 364 | PCPAPELLGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWANYKTTPPVLDSDGSFFLYSKLTVT<br>KEEWQQGFVFSCSVMHEALHNHYTQKSLSLSPGK | Clone CH3C.35.23.2 with knob and YTE mutations |
| 365 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWANYKTTPPVLDSDGSFFLYSKLTVT<br>KEEWQQGFVFSCSVMHEALHNHYTQKSLSLSPGK | Clone CH3C.35.23.2 with knob, LALA, and YTE mutations |
| 366 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLW<br>CLVKGFYPSDIAVEWESYGTEWANYKTTPPVLDSDGSFFLYSKLTVT<br>KEEWQQGFVFSCSVMHEALHNHYTQKSLSLSPGK | Clone CH3C.35.23.2 with knob, LALAPG, and YTE mutations |
| 367 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole mutations |
| 368 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole and LALA mutations |
| 369 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole and LALAPG mutations |
| 370 | PCPAPELLGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole and YTE mutations |
| 371 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole, LALA, and YTE mutations |
| 372 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLSC<br>AVKGFYPSDIAVEWESYGTEWANYKTTPPVLDSDGSFFLVSKLTVTK<br>EEWQQGFVFSCSVMHEALHNHYTQKSLSLSPGK | Clone CH3C.35.23.2 with hole, LALAPG, and YTE mutations |
| 373 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWVNYKTTPPVLDSDGSFFLYSKLTVT<br>KEEWQQGFVFSCSVMHEALHNHYTQKSLSLSPGK | Clone CH3C.35.23.3 with knob mutation |
| 374 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWVNYKTTPPVLDSDGSFFLYSKLTVT<br>KEEWQQGFVFSCSVMHEALHNHYTQKSLSLSPGK | Clone CH3C.35.23.3 with knob and LALA mutations |
| 375 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLW | Clone CH3C.35.23.3 with knob and LALAPG mutations |

INFORMAL SEQUENCE LISTING

| SEQ ID NO: | Sequence | Description |
|---|---|---|
| | CLVKGFYPSDIAVEWESYGTEWVNYKTTPPVLDSDGSFFLYSKLTVT<br>KEEWQQGFVFSCSVMHEALHNHYTQKSLSLSPGK | |
| 376 | PCPAPELLGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWVNYKTTPPVLDSDGSFFLYSKLTVT<br>KEEWQQGFVFSCSVMHEALHNHYTQKSLSLSPGK | Clone CH3C.35.23.3 with knob and YTE mutations |
| 377 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWVNYKTTPPVLDSDGSFFLYSKLTVT<br>KEEWQQGFVFSCSVMHEALHNHYTQKSLSLSPGK | Clone CH3C.35.23.3 with knob, LALA, and YTE mutations |
| 378 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLW<br>CLVKGFYPSDIAVEWESYGTEWVNYKTTPPVLDSDGSFFLYSKLTVT<br>KEEWQQGFVFSCSVMHEALHNHYTQKSLSLSPGK | Clone CH3C.35.23.3 with knob, LALAPG, and YTE mutations |
| 379 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole mutations |
| 380 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole and LALA mutations |
| 381 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole and LALAPG mutations |
| 382 | PCPAPELLGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole and YTE mutations |
| 383 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole, LALA, and YTE mutations |
| 384 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLSC<br>AVKGFYPSDIAVEWESYGTEWVNYKTTPPVLDSDGSFFLVSKLTVTK<br>EEWQQGFVFSCSVMHEALHNHYTQKSLSLSPGK | Clone CH3C.35.23.3 with hole, LALAPG, and YTE mutations |
| 385 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWSNYKTTPPVLDSDGSFFLYSKLTVS<br>KEEWQQGFVFSCSVMHEALHNHYTQKSLSLSPGK | Clone CH3C.35.23.4 with knob mutation |
| 386 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWSNYKTTPPVLDSDGSFFLYSKLTVS<br>KEEWQQGFVFSCSVMHEALHNHYTQKSLSLSPGK | Clone CH3C.35.23.4 with knob and LALA mutations |
| 387 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLW<br>CLVKGFYPSDIAVEWESYGTEWSNYKTTPPVLDSDGSFFLYSKLTVS<br>KEEWQQGFVFSCSVMHEALHNHYTQKSLSLSPGK | Clone CH3C.35.23.4 with knob and LALAPG mutations |

| INFORMAL SEQUENCE LISTING | | |
|---|---|---|
| SEQ ID NO: | Sequence | Description |
| 388 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGTEWSNYKTTPPVLDSDGSFFLYSKLTVS KEEWQQGFVFSCSVMHEALHNHYTQKSLSLSPGK | Clone CH3C.35.23.4 with knob and YTE mutations |
| 389 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGTEWSNYKTTPPVLDSDGSFFLYSKLTVS KEEWQQGFVFSCSVMHEALHNHYTQKSLSLSPGK | Clone CH3C.35.23.4 with knob, LALA, and YTE mutations |
| 390 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVEWESYGTEWSNYKTTPPVLDSDGSFFLYSKLTVS KEEWQQGFVFSCSVMHEALHNHYTQKSLSLSPGK | Clone CH3C.35.23.4 with knob, LALAPG, and YTE mutations |
| 391 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole mutations |
| 392 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole and LALA mutations |
| 393 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole and LALAPG mutations |
| 394 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole and YTE mutations |
| 395 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole, LALA, and YTE mutations |
| 396 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVEWESYGTEWSNYKTTPPVLDSDGSFFLVSKLTVSK EEWQQGFVFSCSVMHEALHNHYTQKSLSLSPGK | Clone CH3C.35.23.4 with hole, LALAPG, and YTE mutations |
| 397 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob mutation |
| 398 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob and LALA mutations |
| 399 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob and LALAPG mutations |

| SEQ ID NO: | Sequence | Description |
|---|---|---|
| 400 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob and YTE mutations |
| 401 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob, LALA, and YTE mutations |
| 402 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVLWESYGTEWASYKTTPPVLDSDGSFFLYSKLTVT KEEWQQGFVFSCSVMHEALHNHYTQKSLSLSPGK | Clone CH3C.35.21.17.2 with knob, LALAPG, and YTE mutations |
| 403 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.3521.17.2 with hole mutations |
| 404 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.35.21.17.2 with hole and LALA mutations |
| 405 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.35.21.17.2 with hole and LALAPG mutations |
| 406 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.35.21.17.2 with hole and YTE mutations |
| 407 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.35.21.17.2 with hole, LALA, and YTE mutations |
| 408 | PCPAPEAAGGPSVFLFPPKPKDTLYITREPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLSC AVKGFYPSDIAVLWESYGTEWASYKTTPPVLDSDGSFFLVSKLTVTK EEWQQGFVFSCSVMHEALHNHYTQKSLSLSPGK | Clone CH3C.35.21.17.2 with hole, LALAPG, and Y1Emutations |
| 409 | PCPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGTEWSNYKTTPPVLDSDGSFFLYSKLTVT KEEWQQGFVFSCSVMHEALHNHYTQKSLSLSPGK | Clone CH3C.35.23 with knob mutation |
| 410 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLW CLVKGFYPSDIAVEWESYGTEWSNYKTTPPVLDSDGSFFLYSKLTVT KEEWQQGFVFSCSVMHEALHNHYTQKSLSLSPGK | Clone CH3C.35.23 with knob and LALA mutations |
| 411 | PCPAPEAAGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALGAPIEKTISKAKGQPREPQVYTLPPSRDELTKNQVSLW CLVKGFYPSDIAVEWESYGTEWSNYKTTPPVLDSDGSFFLYSKLTVT KEEWQQGFVFSCSVMHEALHNHYTQKSLSLSPGK | Clone CH3C.35.23 with knob and LALAPG mutations |
| 412 | PCPAPELLGGPSVFLFPPKPKDTLYITREPEVTCVVVDVSHEDPEVKF NWYVDGVEVHNAKTKPREEQYNSTYRVVSVLTVLHQDWLNGKEY | Clone CH3C.35.23 with knob and YTE mutations |

INFORMAL SEQUENCE LISTING

| SEQ ID NO: | Sequence | Description |
|---|---|---|
| | KCKVSNKALPAPIEKTISKAKGQPREPQVYTLPPSRDELTKNQVSLW<br>CLVKGFYPSDIAVEWESYGTEWSNYKTTPPVLDSDGSFFLYSKLTVT<br>KEEWQQGFVFSCSVMHEALHNHYTQKSLSLSPGK | |
| 413 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLW<br>CLVKGFYPSDIAVEWESYGTEWSNYKTTPPVLDSDGSFFLYSKLTVT<br>KEEWQQGFVFSCSVMHEALHNHYTQKSLSLSPGK | Clone CH3C.35.23 with knob, LALA, and YTE mutations |
| 414 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLW<br>CLVKGFYPSDIAVEWESYGTEWSNYKTTPPVLDSDGSFFLYSKLTVT<br>KEEWQQGFVFSCSVMHEALHNHYTQKSLSLSPGK | Clone CH3C.35.23 with knob, LALAPG, and YTE mutations |
| 415 | PCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole mutations |
| 416 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole and LALA mutations |
| 417 | PCPAPEAAGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole and LALAPG mutations |
| 418 | PCPAPELLGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole and YTE mutations |
| 419 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALPAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole, LALA, and YTE mutations |
| 420 | PCPAPEAAGGPSVFLFPPKPKDTLYITREPEVTCVVVDVSHEDPEVKF<br>NWYVDGVEVHNAKTKPREEQYNSTYRVVSVLTVLHQDWLNGKEY<br>KCKVSNKALGAPIEKTISKAKGQPREPQVYTLPPSRDELTKNQVSLC<br>AVKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole, LALAPG, and YTE mutations |
| 421 | METDTLLLWVLLLWVPGSTGDKTHTCPPCPAPEAAGGPSVFLFPPKP<br>KDTLYITREPEVTCVVVDVSHEDPEVKFNWYVDGVEVHNAKTKPRE<br>EQYNSTYRVVSVLTVLHQDWLNGKEYKCKVSNKALGAPIEKTISKA<br>KGQPREPQVYTLPPSRDELTKNQVSLTCLVKGFYPSDIAVEWESYGT<br>EWSSYKTTPPVLDSDGSFFLYSKLTVTKSEWQQGFVFSCSVMHEALH<br>NHYTQKSLSLSPGK | Expressed CH3C.35 Fc sequence |
| 422 | NSVIIVDKNGRLVYLVENPGGYVAYSKAATVTGKLVHANFGTKKDF<br>EDLDSPVNGSIVIVRAGKITFAEKVANAESLNAIGVLIYMDQTKFPIV<br>NAXLSFFGHAHLGTGDPYTPGFPSFNHTQFPPSRSSGLPNIPVQTISRA<br>AAEKLFGNMEGDCPSDWKTDSTCRMVTSENKNVKLTVS<br>X is D or E | Consensus sequence between human and cyno TfR |
| 423 | ASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLT<br>VLHQDWLNGKEYKCKVSNKALPAPIEKTISKAKGQPREPQVYTLPPS<br>RDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGK | IGHG1_P01857 |

| SEQ ID NO: | Sequence | Description |
|---|---|---|
| 424 | ASTKGPSVFPLAPCSRSTSESTAALGCLVKDYFPEPVTVSWNSGALTS GVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVV DVSHEDPEVQFNWYVDGVEVHNAKTKPREEQFNSTFRVVSVLTVVH QDWLNGKEYKCKVSNKGLPAPIEKTISKTKGQPREPQVYTLPPSREE MTKNQVSLTCLVKGFYPSDISVEWESNGQPENNYKTTPPMLDSDGSF FLYSKLTVDKSRWQQGNVFSCSVMHEALHNHYTQKSLSLSPGK | IGHG2_P01859 |
| 425 | ASTKGPSVFPLAPCSRSTSGGTAALGCLVKDYFPEPVTVSWNSGALT SGVHTFPAVLQSSGLYSLSSVVTVPSSSLGTQTYTCNVNHKPSNTKV DKRVELKTPLGDTTHTCPRCPEPKSCDTPPPCPRCPEPKSCDTPPPCPR CPEPKSCDTPPPCPRCPAPELLGGPSVFLFPPKPKDTLMISRTPEVTCV VVDVSHEDPEVQFKWYVDGVEVHNAKTKPREEQYNSTFRVVSVLT VLHQDWLNGKEYKCKVSNKALPAPIEKTISKTKGQPREPQVYTLPPS REEMTKNQVSLTCLVKGFYPSDIAVEWESSGQPENNYNTTPPMLDSD GSFFLYSKLTVDKSRWQQGNIFSCSVMHEALHNRFTQKSLSLSPGK | IGHG3_P01860 |
| 426 | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPSCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGSF FLYSRLTVDKSRWQEGNVFSCSVMHEALHNHYTQKSLSLSLGK | IGHG4_P01861 |
| 427 | TISRAAAEKLFGNMEGDCPSDWKTDSTCRMVTSE | polypeptide_1 |
| 428 | DKNGRLVYLVENPGGYVAYSKAATVTGKLVHANFGTKKDFEDLYT PVNGSIVIVRAGKITFAEKVANAESLNAIGVLIYMDQT | polypeptide_2 |
| 429 | SKNVKLTVSNVLKEIKILNIFGVIK | polypeptide_3 |
| 430 | SKNVK | polypeptide_4 |
| 431 | SKNVKLTVSN | polypeptide_5 |
| 432 | SKNVKLTVSNVLKEI | polypeptide_6 |
| 433 | SKNVKLTVSNVLKEIKILNI | polypeptide_7 |
| 434 | KFPIVNAELSFFGHAHLGTGDPYTP | polypeptide_8 |
| 435 | KFPIV | polypeptide_9 |
| 436 | KFPIVNAELS | polypeptide_10 |
| 437 | KFPIVNAELSFFGHA | polypeptide_11 |
| 438 | KFPIVNAELSFFGHAHLGTG | polypeptide_12 |
| 439 | GFPSFNHTQFPPSRSSGLPNIPVQ | polypeptide_13 |
| 440 | NIPVQ | polypeptide_14 |
| 441 | SSGLPNIPVQ | polypeptide_15 |
| 442 | FPPSRSSGLPNIPVQ | polypeptide_16 |
| 443 | FNHTQFPPSRSSGLPNIPVQ | polypeptide_17 |
| 444 | SKVWRDQHFVKIQVKDSAQNSVIIV | polypeptide_18 |
| 445 | SVIIV | polypeptide_19 |
| 446 | DSAQNSVIIV | polypeptide_20 |
| 447 | KIQVKDSAQNSVIIV | polypeptide_21 |
| 448 | DQHFVKIQVKDSAQNSVIIV | polypeptide_22 |
| 449 | SSGLPNIPVQTISRAAAEKLFGNMEGDCPSDWKTDSTCRMVTSESKN VKLTVSN | polypeptide_23 |

INFORMAL SEQUENCE LISTING

| SEQ ID NO: | Sequence | Description |
|---|---|---|
| 450 | DSAQNSVIIVDKNGRLVYLVENPGGYVAYSKAATVTGKLVHANFGT KKDFEDLYTPVNGSIVIVRAGKITFAEKVANAESLNAIGVLIYMDQTK FPIVNAELS | polypeptide_24 |
| 451 | SSGLPNIPVQTISRAAAEKLFGNMEGDCPSDWKTDSTCKMVTSENKS VKLTVSN | polypeptide_25 |
| 452 | DSAQNSVIIVDKNGGLVYLVENPGGYVAYSKAATVTGKLVHANFGT KKDFEDLDSPVNGSIVIVRAGKITFAEKVANAESLNAIGVLIYMDQTK FPIVKADLS | polypeptide_26 |
| 453 | GGGG | Linker_1 |
| 454 | GSGS | Linker_2 |
| 455 | SGGG | Linker_3 |
| 456 | GSGG | Linker_4 |
| 457 | GGSG | Linker_5 |
| 458 | GGGS | Linker_6 |
| 459 | HHHHHH | Purification peptide_1 |
| 460 | HHHHHHHHHH | Purification peptide_2 |
| 461 | GLNDIFEAQKIEWHE | Purification peptide_3 |
| 462 | DYKDDDDK | Purification peptide_4 |
| 463 | EQKLISEEDL | Purification peptide_5 |
| 464 | YPYDVPDYA | Purification peptide_6 |
| 465 | MSDSEVNQEAKPEVKPEVKPETHINLKVSDGSSEIFFKIKKTTPLRRL MEAFAKRQGKEMDSLRFLYDGIRIQADQTPEDLDMEDNDIIEAHREQ IGGS | Smt3 |
| 466 | ENLYFQS | TEV cleavage sequence |
| 467 | DEMEECSQ | NS3 HCV cleavage sequence |
| 468 | MGHHHHHHHHHHSSGHIEGRHMASMSDSEVNQEAKPEVKPEVKPE THINLKVSDGSSEIFFKIKKTTPLRRLMEAFAKRQGKEMDSLRFLYDG IRIQADQTPEDLDMEDNDIIEAHREQIGGSGLNDIFEAQKIEWHELEVL FQGPSSGLPNIPVQTISRAAAEKLFGNMEGDCPSDWKTDSTCRMVTS ESKNVKLTVSNDSAQNSVIIVDKNGRLVYLVENPGGYVAYSKAATV TGKLVHANFGTKKDFEDLYTPVNGSIVIVRAGKITFAEKVANAESLN AIGVLIYMDQTKFPIVNAELS | Human TfR construct |
| 469 | MGHHHHHHHHHHSSGHIEGRHMASMSDSEVNQEAKPEVKPEVKPE THINLKVSDGSSEIFFKIKKTTPLRRLMEAFAKRQGKEMDSLRFLYDG IRIQADQTPEDLDMEDNDIIEAHREQIGGSGLNDIFEAQKIEWHELEVL FQGPSSGLPNIPVQTISRAAAEKLFGNMEGDCPSDWKTDSTCRMVTS ENKSVKLTVSNDSAQNSVIIVDKNGGLVYLVENPGGYVAYSKAATV TGKLVHANFGTKKDFEDLDSPVNGSIVIVRAGKITFAEKVANAESLN AIGVLIYMDQTKFPIVKADLS | Cynomolgus monkey TfR construct |
| 470 | TXWSX | Clone motif |
| 471 | KDSAQNS | N-terminal sequence |
| 472 | DSAQN | N-terminal sequence |
| 473 | LTVSN | C-terminal sequence |
| 474 | MGWSCIILFLVATATGAYAG | Signal peptide of TfR apical domain construct of SEQ ID NO: 301 |

What is claimed is:

1. A transferrin receptor (TfR) construct comprising from N- to C-terminus:
   (a) a first polypeptide comprising a C-terminal fragment of a TfR apical domain;
   (b) an optional linker; and
   (c) a second polypeptide comprising an N-terminal fragment of the TfR apical domain,
   wherein the first polypeptide, the optional linker, and the second polypeptide are fused in a tandem series.

2. The TfR construct of claim 1, wherein the last amino acid of the first polypeptide is fused to the first amino acid of the second polypeptide.

3. The TfR construct of claim 1, wherein the first polypeptide comprises a sequence having at least 90% sequence identity or up to seven amino acid changes relative to the sequence of SEQ ID NO:427.

4. The TfR construct of claim 1, wherein the second polypeptide comprises a sequence having at least 90% sequence identity or up to sixteen amino acid changes relative to the sequence of SEQ ID NO:428.

5. The TfR construct of claim 1, wherein the TfR apical domain comprises the sequence of SEQ ID NO:107 or SEQ ID NO:108.

6. The TfR construct of claim 1, comprising:
   (a) the first polypeptide comprising a sequence having at least 90% sequence identity or up to seven amino acid changes relative to the sequence of SEQ ID NO:427;
   (b) the optional linker; and
   (c) the second polypeptide comprising a sequence having at least 90% sequence identity or up to sixteen amino acid changes relative to the sequence of SEQ ID NO:428.

7. The TfR construct of claim 6, wherein the first polypeptide at the C-terminus further comprises a sequence having at least 90% sequence identity or up to five amino acid changes relative to the sequence of SEQ ID NO:429 or a fragment thereof.

8. The TfR construct of claim 6, wherein the second polypeptide at the C-terminus further comprises a sequence having at least 90% sequence identity or up to five amino acid changes relative to the sequence of SEQ ID NO:434 or a fragment thereof.

9. The TfR construct of claim 6, wherein the first polypeptide at the N-terminus further comprises a sequence having at least 90% sequence identity or up to five amino acid changes relative to the sequence of SEQ ID NO:439 or a fragment thereof.

10. The TfR construct of claim 6, wherein the second polypeptide at the N-terminus further comprises a sequence having at least 90% sequence identity or up to five amino acid changes relative to the sequence of SEQ ID NO:444 or a fragment thereof.

11. The TfR construct of claim 6, wherein the first polypeptide at the C-terminus further comprises the sequence of SEQ ID NO:431 and/or the first polypeptide at the N-terminus further comprises the sequence of SEQ ID NO:441.

12. The TfR construct of claim 6, wherein the second polypeptide at the C-terminus further comprises the sequence of SEQ ID NO:436 and/or wherein the second polypeptide at the N-terminus further comprises the sequence of SEQ ID NO:446.

13. The TfR construct of claim 1, wherein the first polypeptide comprises a sequence having at least 90% sequence identity or up to ten amino acid changes relative to the sequence of SEQ ID NO:449.

14. The TfR construct of claim 1, wherein the second polypeptide comprises a sequence having at least 90% sequence identity or up to twenty amino acid changes relative to the sequence of SEQ ID NO:450.

15. The TfR construct of claim 1, wherein the TfR construct comprises the first polypeptide having the sequence of SEQ ID NO:449 or SEQ ID NO:451, and the second polypeptide having the sequence of SEQ ID NO:450 or SEQ ID NO:452, wherein the C-terminus of the first polypeptide is fused to the N-terminus of the second polypeptide.

16. The TfR construct of claim 1, wherein the linker is 1 to 10 amino acids in length or comprises a protein loop domain.

17. The TfR construct of claim 16, wherein the N- and C-termini of the protein loop domain are less than 5 Å apart.

18. The TfR construct of claim 1, wherein the TfR construct further comprises a purification peptide and/or a cleavage peptide.

19. The TfR construct of claim 1, wherein the TfR construct is soluble.

20. An isolated, recombinant TfR apical domain construct comprising an amino acid sequence having at least about 90% identity to any one of SEQ ID NOS:109, 110, 301, 468, and 469.

21. The TfR apical domain construct of claim 20, wherein the TfR apical domain construct comprises the amino acid sequence of any one of SEQ ID NOS:109, 110, 301, 468, and 469.

22. An isolated polynucleotide comprising a nucleotide sequence encoding the TfR construct of claim 1.

23. A vector comprising the polynucleotide of claim 22.

24. A method of identifying an agent that binds the apical domain of a TfR, comprising:
 (a) contacting the TfR construct of claim 1 with the agent; and
 (b) determining whether the agent binds to the TfR construct.

25. The method of claim 24, wherein the agent is a polypeptide or a protein.

26. The method of claim 24, wherein the agent is a modified Fc polypeptide, a modified Fc polypeptide dimer, or an antibody.

27. The TfR construct of claim 1, wherein the C-terminal fragment of the TfR apical domain comprises 25 to 55 amino acids.

28. The TfR construct of claim 1, wherein the N-terminal fragment of the TfR apical domain comprises 75 to 120 amino acids.

29. The TfR construct of claim 27, wherein the N-terminal fragment of the TfR apical domain comprises 75 to 120 amino acids.

* * * * *